(12) United States Patent
Burns et al.

(10) Patent No.: US 10,676,471 B2
(45) Date of Patent: *Jun. 9, 2020

(54) CYCLOALKYL-LINKED DIHETEROCYCLE DERIVATIVES

(71) Applicant: Pfizer Inc., New York, NY (US)

(72) Inventors: Aaron Craig Burns, San Diego, CA (US); Michael Raymond Collins, San Diego, CA (US); Samantha Elizabeth Greasley, San Diego, CA (US); Robert Louis Hoffman, Carlsbad, CA (US); Peter Qinhua Huang, San Diego, CA (US); Robert Steven Kania, Solana Beach, CA (US); Pei-Pei Kung, San Diego, CA (US); Maria Angelica Linton, San Diego, CA (US); Lakshmi Sourirajan Narasimhan, San Diego, CA (US); Paul Francis Richardson, San Diego, CA (US); Daniel Tyler Richter, San Diego, CA (US); Graham Smith, San Diego, CA (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/416,997

(22) Filed: May 20, 2019

(65) Prior Publication Data

US 2019/0270737 A1 Sep. 5, 2019

Related U.S. Application Data

(63) Continuation of application No. 16/157,618, filed on Oct. 11, 2018, now abandoned, which is a continuation of application No. 15/826,027, filed on Nov. 29, 2017, now Pat. No. 10,125,130, which is a continuation of application No. 15/306,979, filed as application No. PCT/IB2015/052833 on Apr. 17, 2015, now abandoned.

(60) Provisional application No. 61/986,876, filed on Apr. 30, 2014.

(51) Int. Cl.

| C07D 417/14 | (2006.01) |
| C07D 401/14 | (2006.01) |
| C07D 417/08 | (2006.01) |
| A61K 31/427 | (2006.01) |
| A61K 31/4439 | (2006.01) |
| A61K 31/444 | (2006.01) |
| A61K 31/501 | (2006.01) |
| A61K 31/506 | (2006.01) |
| A61K 45/06 | (2006.01) |
| C07D 277/46 | (2006.01) |

(52) U.S. Cl.
CPC ......... *C07D 417/14* (2013.01); *C07D 417/08* (2013.01); *A61K 31/427* (2013.01); *A61K 31/444* (2013.01); *A61K 31/4439* (2013.01); *A61K 31/501* (2013.01); *A61K 31/506* (2013.01); *A61K 45/06* (2013.01); *C07D 277/46* (2013.01); *C07D 401/14* (2013.01)

(58) Field of Classification Search
CPC .......................... C07D 417/14; C07D 401/14
See application file for complete search history.

(56) References Cited

U.S. PATENT DOCUMENTS

| 5,702,637 | A | 12/1997 | Johnson et al. |
| 5,972,241 | A | 10/1999 | Johnson et al. |
| 9,029,531 | B2 | 5/2015 | Lemieux et al. |
| 9,783,533 | B2 | 10/2017 | Bhavar et al. |
| 10,125,130 | B2 * | 11/2018 | Burns .................. C07D 417/08 |
| 2002/0115698 | A1 | 8/2002 | Newcomb et al. |
| 2002/0170125 | A1 | 11/2002 | Goettel et al. |
| 2004/0164275 | A1 | 8/2004 | Spawn et al. |
| 2006/0124898 | A1 | 6/2006 | Spawn et al. |
| 2008/0015202 | A1 | 1/2008 | Inoue et al. |
| 2008/0280925 | A1 | 11/2008 | Wahhab et al. |

(Continued)

FOREIGN PATENT DOCUMENTS

| DE | 2037257 | 2/1972 |
| JP | 9104838 | 4/1997 |

(Continued)

OTHER PUBLICATIONS

Gross, M., et al., "Antitumor Activity of the Glutaminase Inhibitor CB-839 in Triple-Negative Breast Cancer," Molecular Cancer Therapeutics, 2014, 890-901, vol. 13, No. 4.

(Continued)

*Primary Examiner* — Matthew P Coughlin
(74) *Attorney, Agent, or Firm* — James T. Wasicak

(57) ABSTRACT

The present invention relates to compounds of formula (I)

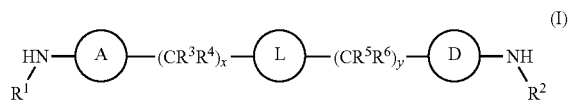

or pharmaceutically acceptable salts thereof, wherein A, L, D, $R^1$-$R^{15}$, w, x, y, and z are defined herein. The novel cycloalkyl-linked diheterocycle derivatives that are useful in the treatment of abnormal cell growth, such as cancer, in mammals. The present invention also relates to pharmaceutical compositions containing the compounds and to methods of using the compounds and compositions in the treatment of abnormal cell growth in mammals.

2 Claims, No Drawings

(56) References Cited

U.S. PATENT DOCUMENTS

| | | |
|---|---|---|
| 2013/0157998 A1 | 6/2013 | Li et al. |
| 2014/0050699 A1 | 2/2014 | Li et al. |
| 2014/0057914 A1 | 2/2014 | Jones et al. |
| 2014/0142081 A1 | 5/2014 | Lemieux et al. |
| 2014/0142146 A1 | 5/2014 | Lemieux et al. |
| 2014/0194421 A1 | 7/2014 | Li et al. |
| 2014/0369961 A1 | 12/2014 | Li et al. |
| 2015/0299152 A1 | 10/2015 | Lemieux et al. |
| 2016/0297761 A1 | 10/2016 | Bhavar et al. |
| 2016/0318921 A1 | 11/2016 | Bhavar et al. |
| 2017/0050958 A1 | 2/2017 | Burns et al. |
| 2017/0137414 A1 | 5/2017 | Cianchetta et al. |
| 2018/0148441 A1 | 5/2018 | Burns et al. |

FOREIGN PATENT DOCUMENTS

| | | |
|---|---|---|
| WO | 9633251 | 10/1996 |
| WO | 2004076589 | 9/2004 |
| WO | 2013078123 | 5/2013 |
| WO | 2014078645 | 5/2014 |
| WO | 2014079011 | 5/2014 |
| WO | 2014079136 | 5/2014 |
| WO | 2014079150 | 5/2014 |
| WO | 2014089048 | 6/2014 |
| WO | 2015048246 | 4/2015 |
| WO | 2015061432 | 4/2015 |
| WO | 2015101957 | 7/2015 |
| WO | 2015101958 | 7/2015 |
| WO | 2015138902 | 9/2015 |
| WO | 2015143340 | 9/2015 |
| WO | 2015192014 | 12/2015 |
| WO | 2016014890 | 1/2016 |
| WO | 2016160980 | 10/2016 |
| WO | 2016164401 | 10/2016 |

OTHER PUBLICATIONS

International Search Report for Int'l Appln. No. PCT/IB2015/052833 completed on Aug. 7, 2015.

International Preliminary Report on Patentability for Int'l Appln. No. PCT/IB2015/052833 completed on Aug. 7, 2015.

Shukla, K., et al., "Design, Synthesis, and Pharmacological Evaluation of Bis-2-(5-phenylacetamido-1,2,4-thiadiazol-2-yl)ethyl Sulfide 3 (BPTES) Analogs as Glutaminase Inhibitors," Journal of Medicinal Chemistry, 2012, 10551-10563, vol. 55, No. 23.

Parvin, K., "Synthesis and Pharmacological Evaluation of Some Novel Imidazo[2,1-b][1,3,4]thiadiazole Derivatives", Chinese Journal of Chemistry, 2010, 250-254, vol. 28, No. 2.

* cited by examiner

CYCLOALKYL-LINKED DIHETEROCYCLE DERIVATIVES

CROSS-REFERENCE TO RELATED APPLICATIONS

This application is a continuation application of U.S. application Ser. No. 16/157,618, filed Oct. 11, 2018, which is a continuation application of U.S. application Ser. No. 15/826,027, filed Nov. 29, 2017, now U.S. patent Ser. No. 10/125,130, issued on Nov. 13, 2018, which is a continuation of U.S. application Ser. No. 15/306,979, filed Oct. 26, 2016, which is a § 371 filing of PCT/IB2015/052833 filed Apr. 17, 2015, which claims the benefit of priority to U.S. Provisional Application No. 61/986,876 filed Apr. 30, 2014; the entire contents of which are incorporated herein by reference.

FIELD OF THE INVENTION

The present invention relates to novel cycloalkyl-linked diheterocycle derivatives that are useful in the treatment of abnormal cell growth, such as cancer, in mammals. The present invention also relates to pharmaceutical compositions containing the compounds and to methods of using the compounds and compositions in the treatment of abnormal cell growth in mammals.

BACKGROUND OF THE INVENTION

Tumor cells require nutrients to generate ATP and macromolecules to sustain survival and proliferation. (Ward P. S., et al., "Metabolic Reprogramming: a Cancer Hallmark even Warburg did not Anticipate", *Cancer Cell.* 21(3) (2012), pp. 297-308.) Glucose and glutamine are two major sources of nutrients that tumor cells depend on. Tumor cells prefer to use glycolysis pathways, even under aerobic conditions, to metabolize glucose to produce lactic acid and ATP, the so-called Warburg's effect. In addition to glucose, many tumor cells are addicted to glutamine ("Gln") for survival (DeBerardinis R. J., et al., "Q's Next: The Diverse Functions of Glutamine in Metabolism, Cell Biology and Cancer", *Oncogene.* 29(3) (2010), pp. 313-24; Shanware N. P., et al., "Glutamine: Pleiotropic Roles in Tumor Growth and Stress Resistance", *J Mol Med (Berl).* 89(3) (2011), pp. 229-36.). This amino acid can be metabolized to generate intermediates of tricarboxylic acid cycle for ATP production, as well as building blocks such as lipids and nucleotides to sustain the cell proliferation. Gln metabolism in cancer cells is regulated and cross-talks with multiple oncogenic pathways (Gao P, et al., "c-Myc Suppression of miR-23a/b Enhances Mitochondrial Glutaminase Expression and Glutamine Metabolism", *Nature.* 458(7239) (2009), pp. 762-5; Duran R V, et al. "Glutaminolysis Activates Rag-mTORC1 Signaling", *Mol Cell.* 47(3) (2012), pp. 349-58; Thangavelu K, et al., "Structural Basis for the Allosteric Inhibitory mechanism of Human Kidney-Type Glutaminase (KGA) and its Regulation by Raf-Mek-Erk Signaling in Cancer Cell Metabolism", *J. Proc Natl Acad Sci USA.* 109(20) (2012), pp. 7705-10; Son J, et al., "Glutamine supports pancreatic cancer growth through a KRAS-regulated metabolic pathway", 496(7443) *Nature.* (2013), pp. 101-5.). (GLS1) is an essential enzyme that catalyzes the first step in glutamine metabolism, leading to the generation of glutamate and ammonia. Glutamate is also the critical substrate for glutathione synthesis, which plays important role in redox homeostasis. GLS1 is overexpressed across many tumor types, and myc up-regulates GLS1 protein level through transcriptional repression of miR-23a and miR-23b. Suppression of GLS1 with selective small molecule inhibitors may be valuable to treat different types of cancers (Wise D. R., et al., "Glutamine Addiction: a New Therapeutic Target in Cancer", *Trends Biochem Sci.* 35(8) 2010, pp. 427-33; Shukla K, et al., "Design, Synthesis, and Pharmacological Evaluation of Bis-2-(5-phenylacetamido-1,2,4-thiadiazol-2-yl)ethyl sulfide 3 (BPTES) Analogs as Glutaminase Inhibitors", *J Med Chem.* 55(23) (2012), pp. 10551-63.).

Thus, there is a need for compounds that inhibit GLS1.

SUMMARY OF THE INVENTION

Each of the embodiments described below can be combined with any other embodiment described herein not inconsistent with the embodiment with which it is combined. The phrase "or a pharmaceutically acceptable salt thereof" is implicit in the description of all compounds described herein; however, in one aspect of any of the embodiments herein, the compound is in the form of a free base.

Embodiments described herein relate to a compound of formula (I)

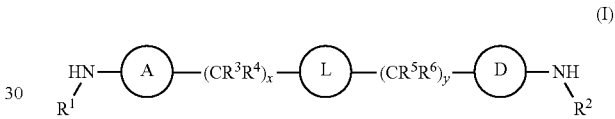

wherein

A and D are independently 5 or 6-membered heteroaryl optionally substituted by one or two $R^7$ groups;

L is —($C_4$-$C_{10}$ cycloalkyl)- optionally substituted by one to three substituents selected from the group consisting of halogen, cyano, $C_1$-$C_4$ alkyl, hydroxy, and $C_1$-$C_4$ alkoxy;

$R^1$ is hydrogen, $C_1$-$C_4$ alkyl, $C_3$-$C_6$ cycloalkyl, —C(O)$R^{10a}$, or 5-6 membered heteroaryl, wherein the $C_3$-$C_6$ cycloalkyl and the 5-6 membered heteroaryl are independently optionally substituted by one or two $R^{15}$ groups;

$R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups;

$R^3$, $R^4$, $R^5$ and $R^6$ are each independently hydrogen, halogen, $C_1$-$C_4$ alkyl, $C_1$-$C_4$ alkoxy or $C_3$-$C_6$ cycloalkyl;

each $R^7$ is each independently hydrogen, halogen, cyano, $C_1$-$C_2$ alkyl, hydroxy, $C_1$-$C_2$ alkoxy, or —N($R^{11}$)($R^{12}$), wherein the $C_1$-$C_2$ alkyl and the $C_1$-$C_2$ alkoxy are each independently optionally substituted by halogen or hydroxy;

$R^{10a}$ and $R^{10b}$ are each independently hydrogen, $C_1$-$C_4$ alkyl, —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl), wherein the $C_1$-$C_4$ alkyl, the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —($CH_2$)$_w$—N($R^{11}$)($R^{12}$), —($CH_2$)$_w$—C(O)N($R^{11}$)($R^{12}$), —C(O)O$R^{11}$, —N($R^{11}$)C(O)$R^{12}$, —S(O)$_2$$R^{11}$, or —S(O)N($R^{11}$)($R^{12}$) groups;

each $R^{11}$, $R^{12}$, $R^{13}$, $R^{14}$ and $R^{15}$ is independently hydrogen, $C_1$-$C_4$ alkyl, $C_1$-$C_4$ alkoxy, $C_3$-$C_6$ cycloalkyl, or 3-6 membered heterocycloalkyl, wherein the $C_1$-$C_4$ alkyl, the $C_3$-$C_6$ cycloalkyl, and the 3-6 membered heterocycloalkyl are each independently optionally substituted by one, two or three substituents selected from the group consisting of halogen, cyano, hydroxy, and methoxy;

w is 0, 1, 2 or 3;
x is 0 or 1;
y is 0 or 1, provided that at least one of x and y is 0; and
z is 0, 1, 2 or 3;
or a pharmaceutically acceptable salt thereof.

Embodiments described herein relate to a compound of formula (I), or a pharmaceutically acceptable salt thereof, wherein A and D are independently thiadiazolyl, pyridazinyl optionally substituted by one or two $R^7$ groups, and 1,2,4-triazinyl optionally substituted by $R^7$.

Embodiments described herein relate to a compound of formula (I), or a pharmaceutically acceptable salt thereof, wherein at least one of A and D is

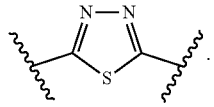 [SMILES: *c1nnc(*)s1]

Embodiments described herein relate to a compound of formula (I), or a pharmaceutically acceptable salt thereof, wherein y is 0.

Embodiments described herein relate to a compound of formula (I), or a pharmaceutically acceptable salt thereof, wherein D is

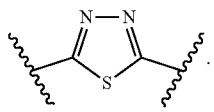 [SMILES: *c1nnc(*)s1]

Embodiments described herein relate to a compound of formula (I), or a pharmaceutically acceptable salt thereof, wherein A is pyridazinyl optionally substituted by one or two $R^7$ groups.

Embodiments described herein relate to a compound of formula (I), or a pharmaceutically acceptable salt thereof, wherein A is

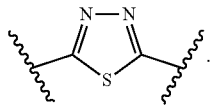 [SMILES: *c1nnc(*)s1]

Embodiments described herein relate to a compound of formula (I), or a pharmaceutically acceptable salt thereof, wherein x is 0 and y is 0 or 1.

Embodiments described herein relate to a compound of formula (I), or a pharmaceutically acceptable salt thereof, wherein x is 1 and y is 0.

Embodiments described herein relate to a compound of formula (I), or a pharmaceutically acceptable salt thereof, wherein L is

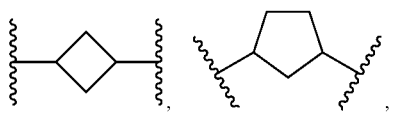

-continued

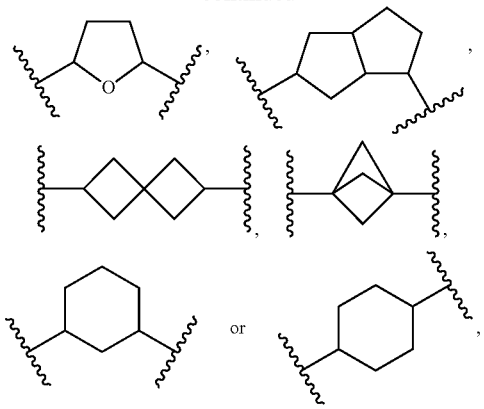

optionally substituted by one to three substituents selected from the group consisting of halogen, cyano, $C_1$-$C_4$ alkyl, hydroxy, and $C_1$-$C_4$ alkoxy.

Embodiments described herein relate to a compound of formula (I), or a pharmaceutically acceptable salt thereof, wherein L is

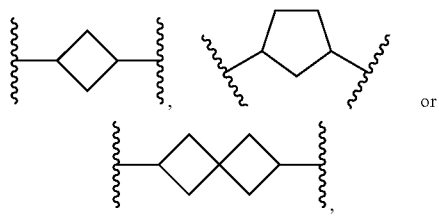

optionally substituted by one to three substituents selected from the group consisting of halogen, cyano, $C_1$-$C_4$ alkyl, hydroxy, and $C_1$-$C_4$ alkoxy.

Embodiments described herein relate to a compound of formula (I), or a pharmaceutically acceptable salt thereof, wherein
$R^1$ is —C(O)$R^{10a}$ and $R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or
$R^2$ is —C(O)$R^{10b}$ and $R^1$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or
$R^1$ is —C(O)$R^{10a}$ and $R^2$ is —C(O)$R^{10b}$.

Embodiments described herein relate to a compound of formula (I), or a pharmaceutically acceptable salt thereof, wherein $R^{10a}$ is $C_1$-$C_4$ alkyl and $R^{10b}$ is $C_1$-$C_4$ alkyl.

Embodiments described herein relate to a compound of formula (I), or a pharmaceutically acceptable salt thereof, wherein $R^1$ is —C(O)$R^{10a}$ and $R^2$ is —C(O)$R^{10b}$.

Embodiments described herein relate to a compound of formula (I), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)

$-(R^{14})]_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, $-(CH_2)_w-N(R^{11})(R^{12})$, $-(CH_2)_w-C(O)N(R^{11})(R^{12})$, $-C(O)OR^{11}$, $-N(R^{11})C(O)R^{12}$, $-S(O)_2R^{11}$, or $-S(O)N(R^{11})(R^{12})$ groups.

Embodiments described herein relate to a compound of formula (I), or a pharmaceutically acceptable salt thereof, wherein $R^{10a}$ is $-[C(R^{13})(R^{14})]_z-(C_6$ aryl) or $-[C(R^{13})(R^{14})]_z$-(5-6 membered heteroaryl) and $R^{10b}$ is $-[C(R^{13})(R^{14})]_z-(C_6$ aryl) or $-[C(R^{13})(R^{14})]_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (I), or a pharmaceutically acceptable salt thereof, wherein at least one of $R^1$ and $R^2$ is $C_1$-$C_4$ alkyl.

Embodiments described herein relate to a compound of formula (I), or a pharmaceutically acceptable salt thereof, wherein $R^1$ and $R^2$ each independently $C_1$-$C_4$ alkyl.

Embodiments described herein relate to a compound of formula (I), or a pharmaceutically acceptable salt thereof, wherein at least one of $R^1$ and $R^2$ is hydrogen.

Embodiments described herein relate to a compound of formula (I), or a pharmaceutically acceptable salt thereof, wherein at least one of $R^1$ and $R^2$ is $C_3$-$C_6$ cycloalkyl optionally substituted by one or two $R^{15}$ groups.

Embodiments described herein relate to a compound of formula (I), or a pharmaceutically acceptable salt thereof, wherein at least one of $R^1$ and $R^2$ is 5-6 membered heteroaryl optionally substituted by one or two $R^{15}$ groups.

Embodiments described herein relate to a compound of formula (I), or a pharmaceutically acceptable salt thereof, wherein L is

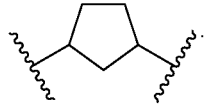 [SMILES: *C1CCC(*)C1]

Embodiments described herein relate to a compound of formula (I), or a pharmaceutically acceptable salt thereof, wherein
$R^1$ is $-C(O)R^{10a}$ and $R^2$ is hydrogen, $C_1$-$C_4$ alkyl, $C_3$-$C_6$ cycloalkyl, $-C(O)R^{10b}$, or 5-6 membered heteroaryl, wherein the $C_3$-$C_6$ cycloalkyl and the 5-6 membered heteroaryl are independently optionally substituted by one or two $R^{15}$ groups; or
$R^2$ is $-C(O)R^{10b}$ and $R^1$ is hydrogen, $C_1$-$C_4$ alkyl, $C_3$-$C_6$ cycloalkyl, $-C(O)R^{10b}$, or 5-6 membered heteroaryl, wherein the $C_3$-$C_6$ cycloalkyl and the 5-6 membered heteroaryl are independently optionally substituted by one or two $R^{15}$ groups; or
$R^1$ is $-C(O)R^{10a}$ and $R^2$ is $-C(O)R^{10b}$.

Embodiments described herein relate to a compound of formula (I), or a pharmaceutically acceptable salt thereof, wherein $R^1$ is $-C(O)R^{10a}$ and $R^2$ is $-C(O)R^{10b}$.

Embodiments described herein relate to a compound of formula (I), or a pharmaceutically acceptable salt thereof, wherein $R^{10a}$ is $-[C(R^{13})(R^{14})]_z-(C_4$-$C_{10}$ cycloalkyl), $-[C(R^{13})(R^{14})]_z$-(4-6 membered heterocycloalkyl), $-[C(R^{13})(R^{14})]-(C_6$-$C_{10}$ aryl), or $-[C(R^{13})(R^{14})]_z$-(5-10 membered heteroaryl) and $R^{10b}$ is $-[C(R^{13})(R^{14})]_z-(C_4$-$C_{10}$ cycloalkyl), $-[C(R^{13})(R^{14})]_z$-(4-6 membered heterocycloalkyl), $-[C(R^{13})(R^{14})]_z-(C_6$-$C_{10}$ aryl), or $-[C(R^{13})(R^{14})]_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, $-(CH_2)_w-N(R^{11})(R^{12})$, $-(CH_2)_w-C(O)N(R^{11})(R^{12})$, $-C(O)OR^{11}$, $-N(R^{11})C(O)R^{12}$, $-S(O)_2R^{11}$, or $-S(O)N(R^{11})(R^{12})$ groups.

Embodiments described herein relate to a compound of formula (I), or a pharmaceutically acceptable salt thereof, wherein $R^{10a}$ is $-[C(R^{13})(R^{14})]_z-(C_6$ aryl) or $-[C(R^{13})(R^{14})]_z$-(5-6 membered heteroaryl) and $R^{10b}$ is $-[C(R^{13})(R^{14})]_z-(C_6$ aryl), or $-[C(R^{13})(R^{14})]_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (I), or a pharmaceutically acceptable salt thereof, wherein $R^{10a}$ is $-[C(R^{13})(R^{14})]_z$-(5-6 membered heteroaryl) and $R^{10b}$ is $-[C(R^{13})(R^{14})]_z$-(5-6 membered heteroaryl), wherein the aryl and the heteroaryl in $R^{10a}$ and $R^{10b}$ are each independently optionally substituted by one or two $C_1$-$C_4$ alkyl groups.

Embodiments described herein relate to a compound of formula (I), or a pharmaceutically acceptable salt thereof, wherein each $R^{13}$ and $R^{14}$ is hydrogen and each z is 1.

Embodiments described herein relate to a compound of formula (I), or a pharmaceutically acceptable salt thereof, wherein $R^{10a}$ is $-CH_2$-pyridinyl and $R^{10b}$ is $-CH_2$-pyridinyl, wherein each pyridinyl is optionally substituted by one or two $C_1$-$C_4$ alkyl groups.

Embodiments described herein relate to a compound of formula (I), or a pharmaceutically acceptable salt thereof, wherein $R^{10a}$ is $-CH_2$-pyridinyl optionally substituted by one or two $C_1$-$C_4$ alkyl groups and $R^{10b}$ is $-CH_2$-pyrazolyl optionally substituted by one or two $C_1$-$C_4$ alkyl groups.

Embodiments described herein relate to a compound of formula (I), or a pharmaceutically acceptable salt thereof, wherein $R^{10a}$ is $-[C(R^{13})(R^{14})]_z-(C_4$-$C_{10}$ cycloalkyl), $-[C(R^{13})(R^{14})]_z$-(4-6 membered heterocycloalkyl), $-[C(R^{13})(R^{14})]-(C_6$-$C_{10}$ aryl), or $-[C(R^{13})(R^{14})]_z$-(5-10 membered heteroaryl) and $R^{10b}$ is $-[C(R^{13})(R^{14})]_z-(C_4$-$C_{10}$ cycloalkyl), $-[C(R^{13})(R^{14})]_z$-(4-6 membered heterocycloalkyl), $-[C(R^{13})(R^{14})]-(C_6$-$C_{10}$ aryl), or $-[C(R^{13})(R^{14})]_z$-(5-10 membered heteroaryl), and $R^{10b}$ is $C_1$-$C_4$ alkyl, wherein the $C_1$-$C_4$ alkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, $-(CH_2)_w-N(R^{11})(R^{12})$, $-(CH_2)_w-C(O)N(R^{11})(R^{12})$, $-C(O)OR^{11}$, $-N(R^{11})C(O)R^{12}$, $-S(O)_2R^{11}$, or $-S(O)N(R^{11})(R^{12})$ groups.

Embodiments described herein relate to a compound of formula (I), or a pharmaceutically acceptable salt thereof, wherein $R^{10a}$ is $-[C(R^{13})(R^{14})]_z-(C_6$ aryl) or $-[C(R^{13})(R^{14})]_z$-(5-6 membered heteroaryl), wherein the $C_6$ aryl and the 5-6 membered heteroaryl in $R^{10a}$ are each independently optionally substituted by one or two halogen or $C_1$-$C_4$ alkyl groups, and $R^{10b}$ is $C_1$-$C_4$ alkyl optionally substituted by $C_1$-$C_6$ alkoxy.

Embodiments described herein relate to a compound of formula (I), or a pharmaceutically acceptable salt thereof, wherein each $R^{13}$ and $R^{14}$ is hydrogen and each z is 1.

Embodiments described herein relate to a compound of formula (I), or a pharmaceutically acceptable salt thereof, wherein $R^{10a}$ is —(CH$_2$)-(5-6 membered heteroaryl) optionally substituted by one or two C$_1$-C$_4$ alkyl groups and $R^{10b}$ is C$_1$-C$_4$ alkyl optionally substituted by C$_1$-C$_2$ alkoxy.

Embodiments described herein relate to a compound of formula (I), or a pharmaceutically acceptable salt thereof, wherein $R^{10a}$ is —CH$_2$-pyridinyl and $R^{10b}$ is —CH$_2$CH$_2$—O—CH$_3$.

Embodiments described herein relate to a compound of formula (I), or a pharmaceutically acceptable salt thereof, wherein $R^1$ is —C(O)R$^{10a}$ and $R^2$ is C$_3$-C$_6$ cycloalkyl optionally substituted by one or two $R^{15}$ groups.

Embodiments described herein relate to a compound of formula (I), or a pharmaceutically acceptable salt thereof, wherein $R^{10a}$ is —[C(R$^{13}$)(R$^{14}$)]$_z$—(C$_4$-C$_{10}$ cycloalkyl), —[C(R$^{13}$)(R$^{14}$)]$_z$-(4-6 membered heterocycloalkyl), —[C(R$^{13}$)(R$^{14}$)]$_z$—(C$_6$-C$_{10}$ aryl), or —[C(R$^{13}$)(R$^{14}$)]$_z$-(5-10 membered heteroaryl) and $R^{10b}$ is —[C(R$^{13}$)(R$^{14}$)]$_z$—(C$_4$-C$_{10}$ cycloalkyl), —[C(R$^{13}$)(R$^{14}$)]$_z$-(4-6 membered heterocycloalkyl), —[C(R$^{13}$)(R$^{14}$)]—(C$_6$-C$_{10}$ aryl), or —[C(R$^{13}$)(R$^{14}$)]$_z$-(5-10 membered heteroaryl), wherein the C$_4$-C$_{10}$ cycloalkyl, the 4-6 membered heterocycloalkyl, the C$_6$-C$_{10}$ aryl, and the 5-10 membered heteroaryl in $R^{10a}$ are each independently optionally substituted by one, two or three halogen, cyano, C$_1$-C$_6$ alkyl, hydroxy, C$_1$-C$_6$ alkoxy, —(CH$_2$)$_w$—N(R$^{11}$)(R$^{12}$), —(CH$_2$)$_w$—C(O)N(R$^{11}$)(R$^{12}$), —C(O)OR$^{11}$, —N(R$^{11}$)C(O)R$^{12}$, —S(O)$_2$R$^{11}$, or —S(O)N(R$^{11}$)(R$^{12}$) groups.

Embodiments described herein relate to a compound of formula (I), or a pharmaceutically acceptable salt thereof, wherein each $R^{13}$ and $R^{14}$ is hydrogen and each z is 1.

Embodiments described herein relate to a compound of formula (I), or a pharmaceutically acceptable salt thereof, wherein $R^{10a}$ is —CH$_2$-(5-6 membered heteroaryl) optionally substituted by one or two halogen or C$_1$-C$_4$ alkyl groups.

Embodiments described herein relate to a compound of formula (I), or a pharmaceutically acceptable salt thereof, wherein $R^{10a}$ is —CH$_2$-pyridinyl optionally substituted by one or two C$_1$-C$_4$ alkyl groups and $R^2$ is cyclopropyl.

Embodiments described herein relate to a compound of formula (I), or a pharmaceutically acceptable salt thereof, wherein L is

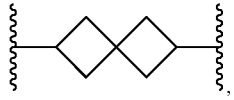

x is 0 and y is 0.

Embodiments described herein relate to a compound of formula (I), or a pharmaceutically acceptable salt thereof, wherein $R^1$ is —C(O)R$^{10a}$ and $R^2$ is hydrogen, C$_1$-C$_4$ alkyl, C$_3$-C$_6$ cycloalkyl, —C(O)R$^{10b}$, or 5-6 membered heteroaryl, wherein the C$_3$-C$_6$ cycloalkyl and the 5-6 membered heteroaryl are independently optionally substituted by one or two $R^{15}$ groups; or $R^2$ is —C(O)R$^{10b}$ and $R^1$ is hydrogen, C$_1$-C$_4$ alkyl, C$_3$-C$_6$ cycloalkyl, —C(O)R$^{10b}$, or 5-6 membered heteroaryl, wherein the C$_3$-C$_6$ cycloalkyl and the 5-6 membered heteroaryl are independently optionally substituted by one or two $R^{15}$ groups; or $R^1$ is —C(O)R$^{10a}$ and $R^2$ is —C(O)R$^{10b}$.

Embodiments described herein relate to a compound of formula (I), or a pharmaceutically acceptable salt thereof, wherein $R^1$ is —C(O)R$^{10a}$ and $R^2$ is —C(O)R$^{10b}$.

Embodiments described herein relate to a compound of formula (I), or a pharmaceutically acceptable salt thereof, wherein $R^{10a}$ is —[C(R$^{13}$)(R$^{14}$)]$_z$—(C$_4$-C$_{10}$ cycloalkyl), —[C(R$^{13}$)(R$^{14}$)]$_z$-(4-6 membered heterocycloalkyl), —[C(R$^{13}$)(R$^{14}$)]$_z$—(C$_6$-C$_{10}$ aryl), or —[C(R$^{13}$)(R$^{14}$)]$_z$-(5-10 membered heteroaryl) and $R^{10b}$ is —[C(R$^{13}$)(R$^{14}$)]$_z$—(C$_4$-C$_{10}$ cycloalkyl), —[C(R$^{13}$)(R$^{14}$)]$_z$-(4-6 membered heterocycloalkyl), —[C(R$^{13}$)(R$^{14}$)]—(C$_6$-C$_{10}$ aryl), or —[C(R$^{13}$)(R$^{14}$)]$_z$-(5-10 membered heteroaryl), wherein the C$_4$-C$_{10}$ cycloalkyl, the 4-6 membered heterocycloalkyl, the C$_6$-C$_{10}$ aryl, and the 5-10 membered heteroaryl in $R^{10a}$ and $R^{10b}$ are each independently optionally substituted by one, two or three halogen, cyano, C$_1$-C$_6$ alkyl, hydroxy, C$_1$-C$_6$ alkoxy, —(CH$_2$)$_w$—N(R$^{11}$)(R$^{12}$), —(CH$_2$)$_w$—C(O)N(R$^{11}$)(R$^{12}$), —C(O)OR$^{11}$, —N(R$^{11}$)C(O)R$^{12}$, —S(O)$_2$R$^{11}$, or —S(O)N(R$^{11}$)(R$^{12}$) groups.

Embodiments described herein relate to a compound of formula (I), or a pharmaceutically acceptable salt thereof, wherein $R^{10a}$ is —[C(R$^{13}$)(R$^{14}$)]$_z$—(C$_6$ aryl) or —[C(R$^{13}$)(R$^{14}$)]$_z$-(5-6 membered heteroaryl) and $R^{10b}$ is —[C(R$^{13}$)(R$^{14}$)]—(C$_6$ aryl) or —[C(R$^{13}$)(R$^{14}$)]$_z$-(5-6 membered heteroaryl), wherein the C$_6$ aryl and the 5-6 membered heteroaryl in $R^{10a}$ and $R^{10b}$ are each independently optionally substituted by one or two halogen or C$_1$-C$_4$ alkyl groups.

Embodiments described herein relate to a compound of formula (I), or a pharmaceutically acceptable salt thereof, wherein $R^{10a}$ is —[C(R$^{13}$)(R$^{14}$)]$_z$-(5-6 membered heteroaryl) optionally substituted by one or two C$_1$-C$_4$ alkyl groups and $R^{10b}$ is —[C(R$^{13}$)(R$^{14}$)]$_z$-(5-6 membered heteroaryl) optionally substituted by one or two C$_1$-C$_4$ alkyl groups.

Embodiments described herein relate to a compound of formula (I), or a pharmaceutically acceptable salt thereof, wherein $R^{10a}$ is —CH$_2$-pyrazolyl optionally substituted by one or two C$_1$-C$_4$ alkyl groups and $R^{10b}$ is —CH$_2$-pyrazolyl optionally substituted by one or two C$_1$-C$_4$ alkyl groups.

Embodiments described herein relate to a compound of formula (I), or a pharmaceutically acceptable salt thereof, wherein L is

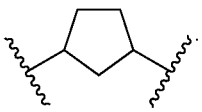 [SMILES: *C1CCC(*)C1]

Embodiments described herein relate to a compound of formula (I), or a pharmaceutically acceptable salt thereof, wherein $R^1$ is —C(O)R$^{10a}$ and $R^2$ is hydrogen, C$_1$-C$_4$ alkyl, C$_3$-C$_6$ cycloalkyl, —C(O)R$^{10b}$, or 5-6 membered heteroaryl, wherein the C$_3$-C$_6$ cycloalkyl and the 5-6 membered heteroaryl are independently optionally substituted by one or two $R^{15}$ groups; or $R^2$ is —C(O)R$^{10b}$ and $R^1$ is hydrogen, C$_1$-C$_4$ alkyl, C$_3$-C$_6$ cycloalkyl, —C(O)R$^{10b}$, or 5-6 membered heteroaryl, wherein the C$_3$-C$_6$ cycloalkyl and the 5-6 membered heteroaryl are independently optionally substituted by one or two $R^{15}$ groups; or $R^1$ is —C(O)R$^{10a}$ and $R^2$ is —C(O)R$^{10b}$.

Embodiments described herein relate to a compound of formula (I), or a pharmaceutically acceptable salt thereof, wherein $R^1$ is —C(O)R$^{10a}$ and $R^2$ is —C(O)R$^{10b}$.

Embodiments described herein relate to a compound of formula (I), or a pharmaceutically acceptable salt thereof, wherein $R^{10a}$ is —[C(R$^{13}$)(R$^{14}$)]$_z$—(C$_4$-C$_{10}$ cycloalkyl), —[C(R$^{13}$)(R$^{14}$)]$_z$-(4-6 membered heterocycloalkyl), —[C(R$^{13}$)(R$^{14}$)]$_z$—(C$_6$-C$_{10}$ aryl), or —[C(R$^{13}$)(R$^{14}$)]$_z$-(5-10 membered heteroaryl) and R$^{10b}$ is —[C(R$^{13}$)(R$^{14}$)]$_z$—(C$_4$-C$_{10}$ cycloalkyl), —[C(R$^{13}$)(R$^{14}$)]$_z$-(4-6 membered heterocycloalkyl), —[C(R$^{13}$)(R$^{14}$)]$_z$—(C$_6$-C$_{10}$ aryl), or —[C(R$^{13}$)(R$^{14}$)]$_z$-(5-10 membered heteroaryl), wherein the C$_4$-C$_{10}$ cycloalkyl, the 4-6 membered heterocycloalkyl, the C$_6$-C$_{10}$ aryl, and the 5-10 membered heteroaryl in R$^{10a}$ and R$^{10b}$ are each independently optionally substituted by one, two or three halogen, cyano, C$_1$-C$_6$ alkyl, hydroxy, C$_1$-C$_6$ alkoxy, —(CH$_2$)$_w$—N(R$^{11}$)(R$^{12}$), —(CH$_2$)$_w$—C(O)N(R$^{11}$)(R$^{12}$), —C(O)OR$^{11}$, —N(R$^{11}$)C(O)R$^{12}$, —S(O)$_2$R$^{11}$, or —S(O)N(R$^{11}$)(R$^{12}$) groups.

Embodiments described herein relate to a compound of formula (I), or a pharmaceutically acceptable salt thereof, wherein R$^{10a}$ is —[C(R$^{13}$)(R$^{14}$)]$_z$—(C$_6$ aryl) or —[C(R$^{13}$)(R$^{14}$)]$_z$-(5-6 membered heteroaryl) and R$^{10b}$ is —[C(R$^{13}$)(R$^{14}$)]—(C$_6$ aryl) or —[C(R$^{13}$)(R$^{14}$)]$_z$-(5-6 membered heteroaryl), wherein the C$_6$ aryl and the 5-6 membered heteroaryl in R$^{10a}$ and R$^{10b}$ are each independently optionally substituted by one or two halogen or C$_1$-C$_4$ alkyl groups.

Embodiments described herein relate to a compound of formula (I), or a pharmaceutically acceptable salt thereof, wherein R$^{10a}$ is —[C(R$^{13}$)(R$^{14}$)]$_z$-(5-6 membered heteroaryl) and R$^{10b}$ is —[C(R$^{13}$)(R$^{14}$)]$_z$-(5-6 membered heteroaryl), wherein the 5-6 membered heteroaryl in R$^{10a}$ and R$^{10b}$ are each independently optionally substituted by one or two C$_1$-C$_4$ alkyl groups.

Embodiments described herein relate to a compound of formula (I), or a pharmaceutically acceptable salt thereof, wherein each R$^{13}$ and R$^{14}$ is hydrogen and each z is 1.

Embodiments described herein relate to a compound of formula (I), or a pharmaceutically acceptable salt thereof, wherein R$^{10a}$ is —CH$_2$-pyridinyl optionally substituted by one or two C$_1$-C$_4$ alkyl groups and R$^{10b}$ is —CH$_2$-pyridinyl optionally substituted by one or two C$_1$-C$_4$ alkyl groups.

Embodiments described herein relate to a compound of formula (I), or a pharmaceutically acceptable salt thereof, wherein L is

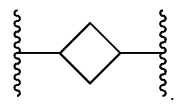

Embodiments described herein relate to a compound of formula (I), or a pharmaceutically acceptable salt thereof, wherein R$^1$ is —C(O)R$^{10a}$ and R$^2$ is hydrogen, C$_1$-C$_4$ alkyl, C$_3$-C$_6$ cycloalkyl, —C(O)R$^{10b}$, or 5-6 membered heteroaryl, wherein the C$_3$-C$_6$ cycloalkyl and the 5-6 membered heteroaryl are independently optionally substituted by one or two R$^{15}$ groups; or R$^2$ is —C(O)R$^{10b}$ and R$^1$ is hydrogen, C$_1$-C$_4$ alkyl, C$_3$-C$_6$ cycloalkyl, —C(O)R$^{10b}$, or 5-6 membered heteroaryl, wherein the C$_3$-C$_6$ cycloalkyl and the 5-6 membered heteroaryl are independently optionally substituted by one or two R$^{15}$ groups; or R$^1$ is —C(O)R$^{10a}$ and R$^2$ is —C(O)R$^{10b}$.

Embodiments described herein relate to a compound of formula (I), or a pharmaceutically acceptable salt thereof, wherein R$^1$ is —C(O)R$^{10a}$ and R$^2$ is —C(O)R$^{10b}$.

Embodiments described herein relate to a compound of formula (I), or a pharmaceutically acceptable salt thereof, wherein R$^{10a}$ is —[C(R$^{13}$)(R$^{14}$)]$_z$—(C$_4$-C$_{10}$ cycloalkyl), —[C(R$^{13}$)(R$^{14}$)]$_z$-(4-6 membered heterocycloalkyl), —[C(R$^{13}$)(R$^{14}$)]$_z$—(C$_6$-C$_{10}$ aryl), or —[C(R$^{13}$)(R$^{14}$)]$_z$-(5-10 membered heteroaryl) and R$^{10b}$ is —[C(R$^{13}$)(R$^{14}$)]$_z$—(C$_4$-C$_{10}$ cycloalkyl), —[C(R$^{13}$)(R$^{14}$)]$_z$-(4-6 membered heterocycloalkyl), —[C(R$^{13}$)(R$^{14}$)]$_z$—(C$_6$-C$_{10}$ aryl), or —[C(R$^{13}$)(R$^{14}$)]$_z$-(5-10 membered heteroaryl), wherein the C$_4$-C$_{10}$ cycloalkyl, the 4-6 membered heterocycloalkyl, the C$_6$-C$_{10}$ aryl, and the 5-10 membered heteroaryl in R$^{10a}$ and R$^{10b}$ are each independently optionally substituted by one, two or three halogen, cyano, C$_1$-C$_6$ alkyl, hydroxy, C$_1$-C$_6$ alkoxy, —(CH$_2$)$_w$—N(R$^{11}$)(R$^{12}$), —(CH$_2$)$_w$—C(O)N(R$^{11}$)(R$^{12}$), —C(O)OR$^{11}$, —N(R$^{11}$)C(O)R$^{12}$, —S(O)$_2$R$^{11}$, or —S(O)N(R$^{11}$)(R$^{12}$) groups.

Embodiments described herein relate to a compound of formula (I), or a pharmaceutically acceptable salt thereof, wherein R$^{10a}$ is —[C(R$^{13}$)(R$^{14}$)]$_z$—(C$_6$ aryl) or —[C(R$^{13}$)(R$^{14}$)]$_z$-(5-6 membered heteroaryl) and R$^{10b}$ is —[C(R$^{13}$)(R$^{14}$)]$_z$—(C$_6$ aryl), or —[C(R$^{13}$)(R$^{14}$)]$_z$-(5-6 membered heteroaryl), wherein the C$_6$ aryl and the 5-6 membered heteroaryl in R$^{10a}$ and R$^{10b}$ are each independently optionally substituted by one or two halogen or C$_1$-C$_4$ alkyl groups.

Embodiments described herein relate to a compound of formula (I), or a pharmaceutically acceptable salt thereof, wherein R$^{10a}$ is —[C(R$^{13}$)(R$^{14}$)]$_z$-(5-6 membered heteroaryl) and R$^{10b}$ is —[C(R$^{13}$)(R$^{14}$)]$_z$-(5-6 membered heteroaryl), wherein the 5-6 membered heteroaryl in R$^{10a}$ and R$^{10b}$ are each independently optionally substituted by one or two C$_1$-C$_4$ alkyl groups.

Embodiments described herein relate to a compound of formula (I), or a pharmaceutically acceptable salt thereof, wherein each R$^{13}$ and R$^{14}$ is hydrogen and each z is 1.

Embodiments described herein relate to a compound of formula (I), or a pharmaceutically acceptable salt thereof, wherein R$^{10a}$ is —CH$_2$-pyridinyl optionally substituted by one or two C$_1$-C$_4$ alkyl groups and R$^{10b}$ is —CH$_2$-pyridinyl optionally substituted by one or two C$_1$-C$_4$ alkyl groups.

Embodiments described herein relate to a compound of formula (II)

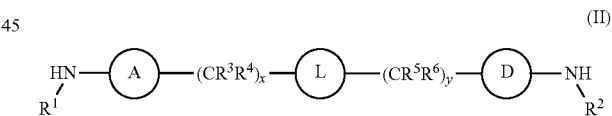

wherein

A and D are independently

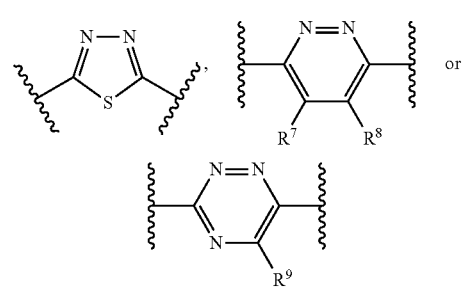

provided that at least one of A and D is

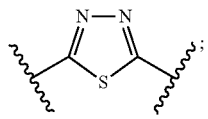

L is —($C_4$-$C_{10}$ cycloalkyl)- optionally substituted by one to three substituents selected from the group consisting of halogen, cyano, $C_1$-$C_4$ alkyl, hydroxy, and $C_1$-$C_4$ alkoxy;

$R^1$ is hydrogen, $C_1$-$C_4$ alkyl, $C_3$-$C_6$ cycloalkyl, —C(O)$R^{10a}$, or 5-6 membered heteroaryl, wherein the $C_3$-$C_6$ cycloalkyl and the 5-6 membered heteroaryl are independently optionally substituted by one or two $R^{15}$ groups;

$R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups;

$R^3$, $R^4$, $R^5$ and $R^6$ are each independently hydrogen, halogen, $C_1$-$C_4$ alkyl, $C_1$-$C_4$ alkoxy or $C_3$-$C_6$ cycloalkyl;

$R^7$, $R^8$ and $R^9$ are each independently hydrogen, halogen, cyano, $C_1$-$C_2$ alkyl, hydroxy, $C_1$-$C_2$ alkoxy, or —N($R^{11}$)($R^{12}$), wherein the $C_1$-$C_2$ alkyl and the $C_1$-$C_2$ alkoxy are each independently optionally substituted by halogen or hydroxy;

$R^{10a}$ and $R^{10b}$ are each independently hydrogen, $C_1$-$C_4$ alkyl, —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]—($C_6$-$C_{10}$ aryl), or —[C($R^{13}$)($R^{14}$)]$_z$-(5-10 membered heteroaryl), wherein the $C_1$-$C_4$ alkyl, the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —(CH$_2$)$_w$—N($R^{11}$)($R^{12}$), —(CH$_2$)$_w$—C(O)N($R^{11}$)($R^{12}$), —C(O)O$R^{11}$, —N($R^{11}$)C(O)$R^{12}$, —S(O)$_2R^{11}$, or —S(O)N($R^{11}$)($R^{12}$) groups;

each $R^{11}$, $R^{12}$, $R^{13}$, $R^{14}$ and $R^{15}$ is independently hydrogen, $C_1$-$C_4$ alkyl, $C_1$-$C_4$ alkoxy, $C_3$-$C_6$ cycloalkyl, or 3-6 membered heterocycloalkyl, wherein the $C_1$-$C_4$ alkyl, the $C_3$-$C_6$ cycloalkyl, and the 3-6 membered heterocycloalkyl are each independently optionally substituted by one, two or three substituents selected from the group consisting of halogen, cyano, hydroxy, and methoxy;

w is 0, 1, 2 or 3;
x is 0 or 1;
y is 0 or 1, provided that at least one of x and y is 0; and
z is 0, 1, 2 or 3;
or a pharmaceutically acceptable salt thereof.

Embodiments described herein relate to a compound of formula (II), or a pharmaceutically acceptable salt thereof, wherein y is 0.

Embodiments described herein relate to a compound of formula (II), or a pharmaceutically acceptable salt thereof, wherein D is

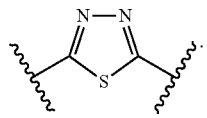 [SMILES: *c1nnc(*)s1]

Embodiments described herein relate to a compound of formula (II), or a pharmaceutically acceptable salt thereof, wherein A is

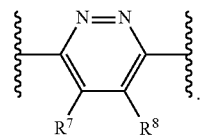

Embodiments described herein relate to a compound of formula (II), or a pharmaceutically acceptable salt thereof, wherein A is

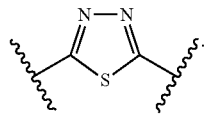 [SMILES: *c1nnc(*)s1]

Embodiments described herein relate to a compound of formula (II), or a pharmaceutically acceptable salt thereof, wherein x is 0 and y is 0 or 1.

Embodiments described herein relate to a compound of formula (II), or a pharmaceutically acceptable salt thereof, wherein x is 1 and y is 0.

Embodiments described herein relate to a compound of formula (II), or a pharmaceutically acceptable salt thereof, wherein L is

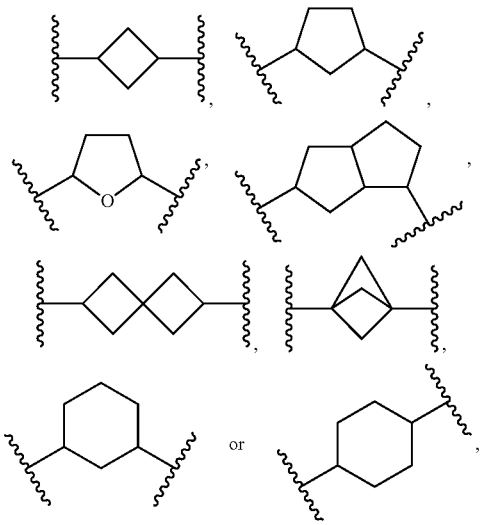

optionally substituted by one to three substituents selected from the group consisting of halogen, cyano, $C_1$-$C_4$ alkyl, hydroxy, and $C_1$-$C_4$ alkoxy.

Embodiments described herein relate to a compound of formula (II), or a pharmaceutically acceptable salt thereof, wherein L is

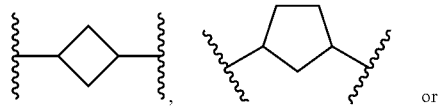

or

-continued

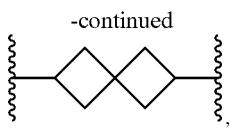

optionally substituted by one to three substituents selected from the group consisting of halogen, cyano, $C_1$-$C_4$ alkyl, hydroxy, and $C_1$-$C_4$ alkoxy.

Embodiments described herein relate to a compound of formula (II), or a pharmaceutically acceptable salt thereof, wherein $R^1$ is —C(O)$R^{10a}$ and $R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^2$ is —C(O)$R^{10b}$ and $R^1$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^1$ is —C(O)$R^{10a}$ and $R^2$ is —C(O)$R^{10b}$.

Embodiments described herein relate to a compound of formula (II), or a pharmaceutically acceptable salt thereof, wherein $R^{10a}$ is $C_1$-$C_4$ alkyl and $R^{10b}$ is $C_1$-$C_4$ alkyl.

Embodiments described herein relate to a compound of formula (II), or a pharmaceutically acceptable salt thereof, wherein $R^1$ is —C(O)$R^{10a}$ and $R^2$ is —C(O)$R^{10b}$.

Embodiments described herein relate to a compound of formula (II), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —(CH$_2$)$_w$—N($R^{11}$)($R^{12}$), —(CH$_2$)$_w$—C(O)N($R^{11}$)($R^{12}$), —C(O)O$R^{11}$, —N($R^{11}$)C(O)$R^{12}$, —S(O)$_2$$R^{11}$, or —S(O)N($R^{11}$)($R^{12}$) groups.

Embodiments described herein relate to a compound of formula (II), or a pharmaceutically acceptable salt thereof, wherein $R^{10a}$ is —[C($R^{13}$)($R^{14}$)]$_z$—($C_6$ aryl) or —[C($R^{13}$)($R^{14}$)]$_z$-(5-6 membered heteroaryl) and $R^{10b}$ is —[C($R^{13}$)($R^{14}$)]$_z$—($C_6$ aryl) or —[C($R^{13}$)($R^{14}$)]$_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (II), or a pharmaceutically acceptable salt thereof, wherein at least one of $R^1$ and $R^2$ is $C_1$-$C_4$ alkyl.

Embodiments described herein relate to a compound of formula (II), or a pharmaceutically acceptable salt thereof, wherein $R^1$ and $R^2$ each independently $C_1$-$C_4$ alkyl.

Embodiments described herein relate to a compound of formula (II), or a pharmaceutically acceptable salt thereof, wherein at least one of $R^1$ and $R^2$ is hydrogen.

Embodiments described herein relate to a compound of formula (II), or a pharmaceutically acceptable salt thereof, wherein at least one of $R^1$ and $R^2$ is $C_3$-$C_6$ cycloalkyl optionally substituted by one or two $R^{15}$ groups.

Embodiments described herein relate to a compound of formula (II), or a pharmaceutically acceptable salt thereof, wherein at least one of $R^1$ and $R^2$ is 5-6 membered heteroaryl optionally substituted by one or two $R^{15}$ groups.

Embodiments described herein relate to a compound of formula (II), or a pharmaceutically acceptable salt thereof, wherein L is

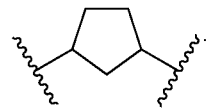 [SMILES: *C1CCC(*)C1]

Embodiments described herein relate to a compound of formula (II), or a pharmaceutically acceptable salt thereof, wherein $R^1$ is —C(O)$R^{10a}$ and $R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^2$ is —C(O)$R^{10b}$ and $R^1$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^1$ is —C(O)$R^{10a}$ and $R^2$ is —C(O)$R^{10b}$.

Embodiments described herein relate to a compound of formula (II), or a pharmaceutically acceptable salt thereof, wherein $R^1$ is —C(O)$R^{10a}$ and $R^2$ is —C(O)$R^{10b}$.

Embodiments described herein relate to a compound of formula (II), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —(CH$_2$)$_w$—N($R^{11}$)($R^{12}$), —(CH$_2$)$_w$—C(O)N($R^{11}$)($R^{12}$), —C(O)O$R^{11}$, —N($R^{11}$)C(O)$R^{12}$, —S(O)$_2$$R^{11}$, or —S(O)N($R^{11}$)($R^{12}$) groups.

Embodiments described herein relate to a compound of formula (II), or a pharmaceutically acceptable salt thereof, wherein $R^{10a}$ is —[C($R^{13}$)($R^{14}$)]$_z$—($C_6$ aryl) or —[C($R^{13}$)($R^{14}$)]$_z$-(5-6 membered heteroaryl) and $R^{10b}$ is —[C($R^{13}$)($R^{14}$)]$_z$—($C_6$ aryl), or —[C($R^{13}$)($R^{14}$)]$_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (II), or a pharmaceutically acceptable salt thereof, wherein $R^{10a}$ is —[C($R^{13}$)($R^{14}$)]$_z$-(5-6 membered heteroaryl) and $R^{10b}$ is —[C($R^{13}$)($R^{14}$)]$_z$-(5-6 membered heteroaryl), wherein the aryl and the heteroaryl in $R^{10a}$ and $R^{10b}$ are each independently optionally substituted by one or two $C_1$-$C_4$ alkyl groups.

Embodiments described herein relate to a compound of formula (II), or a pharmaceutically acceptable salt thereof, wherein each $R^{13}$ and $R^{14}$ is hydrogen and each z is 1.

Embodiments described herein relate to a compound of formula (II), or a pharmaceutically acceptable salt thereof, wherein $R^{10a}$ is —$CH_2$-pyridinyl and $R^{10b}$ is —$CH_2$-pyridinyl, wherein each pyridinyl is optionally substituted by one or two $C_1$-$C_4$ alkyl groups.

Embodiments described herein relate to a compound of formula (II), or a pharmaceutically acceptable salt thereof, wherein $R^{10a}$ is —$CH_2$-pyridinyl optionally substituted by one or two $C_1$-$C_4$ alkyl groups and $R^{10b}$ is —$CH_2$-pyrazolyl optionally substituted by one or two $C_1$-$C_4$ alkyl groups.

Embodiments described herein relate to a compound of formula (II), or a pharmaceutically acceptable salt thereof, wherein $R^{10a}$ is —$[C(R^{13})(R^{14})]_z$—($C_4$-$C_{10}$ cycloalkyl), —$[C(R^{13})(R^{14})]_z$-(4-6 membered heterocycloalkyl), —$[C(R^{13})(R^{14})]$—($C_6$-$C_{10}$ aryl), or —$[C(R^{13})(R^{14})]_z$-(5-10 membered heteroaryl) and $R^{10b}$ is —$[C(R^{13})(R^{14})]_z$—($C_4$-$C_{10}$ cycloalkyl), —$[C(R^{13})(R^{14})]_z$-(4-6 membered heterocycloalkyl), —$[C(R^{13})(R^{14})]$—($C_6$-$C_{10}$ aryl), or —$[C(R^{13})(R^{14})]_z$-(5-10 membered heteroaryl), and $R^{10b}$ is $C_1$-$C_4$ alkyl, wherein the $C_1$-$C_4$ alkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —$(CH_2)_w$—$N(R^{11})(R^{12})$, —$(CH_2)_w$—$C(O)N(R^{11})(R^{12})$, —$C(O)OR^{11}$, —$N(R^{11})C(O)R^{12}$, —$S(O)_2R^{11}$, or —$S(O)N(R^{11})(R^{12})$ groups.

Embodiments described herein relate to a compound of formula (II), or a pharmaceutically acceptable salt thereof, wherein is —$[C(R^{13})(R^{14})]_z$—($C_6$ aryl) or —$[C(R^{13})(R^{14})]_z$-(5-6 membered heteroaryl), wherein the $C_6$ aryl and the 5-6 membered heteroaryl in $R^{10a}$ are each independently optionally substituted by one or two halogen or $C_1$-$C_4$ alkyl groups, and $R^{10b}$ is $C_1$-$C_4$ alkyl optionally substituted by $C_1$-$C_6$ alkoxy.

Embodiments described herein relate to a compound of formula (II), or a pharmaceutically acceptable salt thereof, wherein each $R^{13}$ and $R^{14}$ is hydrogen and each z is 1.

Embodiments described herein relate to a compound of formula (II), or a pharmaceutically acceptable salt thereof, wherein $R^{10a}$ is —$(CH_2)$-(5-6 membered heteroaryl) optionally substituted by one or two $C_1$-$C_4$ alkyl groups and $R^{10b}$ is $C_1$-$C_4$ alkyl optionally substituted by $C_1$-$C_2$ alkoxy.

Embodiments described herein relate to a compound of formula (II), or a pharmaceutically acceptable salt thereof, wherein $R^{10a}$ is —$CH_2$-pyridinyl and $R^{10b}$ is —$CH_2CH_2$—O—$CH_3$.

Embodiments described herein relate to a compound of formula (II), or a pharmaceutically acceptable salt thereof, wherein $R^1$ is —$C(O)R^{10a}$ and $R^2$ is $C_3$-$C_6$ cycloalkyl optionally substituted by one or two $R^{15}$ groups.

Embodiments described herein relate to a compound of formula (II), or a pharmaceutically acceptable salt thereof, wherein $R^{10a}$ is —$[C(R^{13})(R^{14})]_z$—($C_4$-$C_{10}$ cycloalkyl), —$[C(R^{13})(R^{14})]_z$-(4-6 membered heterocycloalkyl), —$[C(R^{13})(R^{14})]_z$—($C_6$-$C_{10}$ aryl), or —$[C(R^{13})(R^{14})]_z$-(5-10 membered heteroaryl) and $R^{10b}$ is —$[C(R^{13})(R^{14})]_z$—($C_4$-$C_{10}$ cycloalkyl), —$[C(R^{13})(R^{14})]_z$-(4-6 membered heterocycloalkyl), —$[C(R^{13})(R^{14})]$—($C_6$-$C_{10}$ aryl), or —$[C(R^{13})(R^{14})]_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ are each independently optionally substituted by one, two or three halogen, cyano, $C_1$-$C_6$ alkyl, hydroxy, $C_1$-$C_6$ alkoxy, —$(CH_2)_w$—$N(R^{11})(R^{12})$, —$(CH_2)_w$—$C(O)N(R^{11})(R^{12})$, —$C(O)OR^{11}$, —$N(R^{11})C(O)R^{12}$, —$S(O)_2R^{11}$, or —$S(O)N(R^{11})(R^{12})$ groups.

Embodiments described herein relate to a compound of formula (II), or a pharmaceutically acceptable salt thereof, wherein each $R^{13}$ and $R^{14}$ is hydrogen and each z is 1.

Embodiments described herein relate to a compound of formula (II), or a pharmaceutically acceptable salt thereof, wherein $R^{10a}$ is —$CH_2$-(5-6 membered heteroaryl) optionally substituted by one or two halogen or $C_1$-$C_4$ alkyl groups.

Embodiments described herein relate to a compound of formula (II), or a pharmaceutically acceptable salt thereof, wherein $R^{10a}$ is —$CH_2$-pyridinyl optionally substituted by one or two $C_1$-$C_4$ alkyl groups and $R^2$ is cyclopropyl.

Embodiments described herein relate to a compound of formula (II), or a pharmaceutically acceptable salt thereof, wherein L is

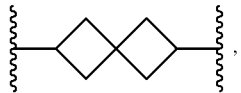

x is 0 and y is 0.

Embodiments described herein relate to a compound of formula (II), or a pharmaceutically acceptable salt thereof, wherein $R^1$ is —$C(O)R^{10a}$ and $R^2$ is hydrogen, $C_1$-$C_4$ alkyl, $C_3$-$C_6$ cycloalkyl, —$C(O)R^{10b}$, or 5-6 membered heteroaryl, wherein the $C_3$-$C_6$ cycloalkyl and the 5-6 membered heteroaryl are independently optionally substituted by one or two $R^{15}$ groups; or $R^2$ is —$C(O)R^{10b}$ and $R^1$ is hydrogen, $C_1$-$C_4$ alkyl, $C_3$-$C_6$ cycloalkyl, —$C(O)R^{10b}$, or 5-6 membered heteroaryl, wherein the $C_3$-$C_6$ cycloalkyl and the 5-6 membered heteroaryl are independently optionally substituted by one or two $R^{15}$ groups; or $R^1$ is —$C(O)R^{10a}$ and $R^2$ is —$C(O)R^{10b}$.

Embodiments described herein relate to a compound of formula (II), or a pharmaceutically acceptable salt thereof, wherein $R^1$ is —$C(O)R^{10a}$ and $R^2$ is —$C(O)R^{10b}$.

Embodiments described herein relate to a compound of formula (II), or a pharmaceutically acceptable salt thereof, wherein $R^{10a}$ is —$[C(R^{13})(R^{14})]_z$—($C_4$-$C_{10}$ cycloalkyl), —$[C(R^{13})(R^{14})]_z$-(4-6 membered heterocycloalkyl), —$[C(R^{13})(R^{14})]_z$—($C_6$-$C_{10}$ aryl), or —$[C(R^{13})(R^{14})]_z$-(5-10 membered heteroaryl) and $R^{10b}$ is —$[C(R^{13})(R^{14})]_z$—($C_4$-$C_{10}$ cycloalkyl), —$[C(R^{13})(R^{14})]_z$-(4-6 membered heterocycloalkyl), —$[C(R^{13})(R^{14})]$—($C_6$-$C_{10}$ aryl), or —$[C(R^{13})(R^{14})]_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —$(CH_2)_w$—$N(R^{11})(R^{12})$, —$(CH_2)_w$—$C(O)N(R^{11})(R^{12})$, —$C(O)OR^{11}$, —$N(R^{11})C(O)R^{12}$, —$S(O)_2R^{11}$, or —$S(O)N(R^{11})(R^{12})$ groups.

Embodiments described herein relate to a compound of formula (II), or a pharmaceutically acceptable salt thereof, wherein $R^{10a}$ is —$[C(R^{13})(R^{14})]_z$—($C_6$ aryl) or —$[C(R^{13})(R^{14})]_z$-(5-6 membered heteroaryl) and $R^{10b}$ is —$[C(R^{13})(R^{14})]_z$—($C_6$ aryl) or —$[C(R^{13})(R^{14})]_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (II), or a pharmaceutically acceptable salt thereof, wherein $R^{10a}$ is —$[C(R^{13})(R^{14})]_z$-(5-6 membered heteroaryl) optionally substituted by one or two $C_1$-$C_4$ alkyl groups and $R^{10b}$ is —[C($R^{13}$)($R^{14}$)]$_z$-(5-6 membered heteroaryl) optionally substituted by one or two $C_1$-$C_4$ alkyl groups.

Embodiments described herein relate to a compound of formula (II), or a pharmaceutically acceptable salt thereof, wherein $R^{10a}$ is —CH$_2$-pyrazolyl optionally substituted by one or two $C_1$-$C_4$ alkyl groups and $R^{10b}$ is —CH$_2$-pyrazolyl optionally substituted by one or two $C_1$-$C_4$ alkyl groups.

Embodiments described herein relate to a compound of formula (II), or a pharmaceutically acceptable salt thereof, wherein L is

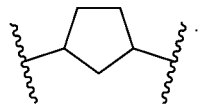 [SMILES: *C1CCC(*)C1]

Embodiments described herein relate to a compound of formula (II), or a pharmaceutically acceptable salt thereof, wherein $R^1$ is —C(O)$R^{10a}$ and $R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^2$ is —C(O)$R^{10b}$ and $R^1$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^1$ is —C(O)$R^{10a}$ and $R^2$ is —C(O)$R^{10b}$.

Embodiments described herein relate to a compound of formula (II), or a pharmaceutically acceptable salt thereof, wherein $R^1$ is —C(O)$R^{10a}$ and $R^2$ is —C(O)$R^{10b}$.

Embodiments described herein relate to a compound of formula (II), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —(CH$_2$)$_w$—N($R^{11}$)($R^{12}$), —(CH$_2$)$_w$—C(O)N($R^{11}$)($R^{12}$), —C(O)O$R^{11}$, —N($R^{11}$)C(O)$R^{12}$, —S(O)$_2R^{11}$, or —S(O)N($R^{11}$)($R^{12}$) groups.

Embodiments described herein relate to a compound of formula (II), or a pharmaceutically acceptable salt thereof, wherein $R^{10a}$ is —[C($R^{13}$)($R^{14}$)]$_z$—($C_6$ aryl) or —[C($R^{13}$)($R^{14}$)]$_z$-(5-6 membered heteroaryl) and $R^{10b}$ is —[C($R^{13}$)($R^{14}$)]—($C_6$ aryl) or —[C($R^{13}$)($R^{14}$)]$_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (II), or a pharmaceutically acceptable salt thereof, wherein $R^{10a}$ is —[C($R^{13}$)($R^{14}$)]$_z$-(5-6 membered heteroaryl) and $R^{10b}$ is —[C($R^{13}$)($R^{14}$)]$_z$-(5-6 membered heteroaryl), wherein the 5-6 membered heteroaryl in $R^{10a}$ and $R^{10b}$ are each independently optionally substituted by one or two $C_1$-$C_4$ alkyl groups.

Embodiments described herein relate to a compound of formula (II), or a pharmaceutically acceptable salt thereof, wherein each $R^{13}$ and $R^{14}$ is hydrogen and each z is 1.

Embodiments described herein relate to a compound of formula (II), or a pharmaceutically acceptable salt thereof, wherein $R^{10a}$ is —CH$_2$-pyridinyl optionally substituted by one or two $C_1$-$C_4$ alkyl groups and $R^{10b}$ is —CH$_2$-pyridinyl optionally substituted by one or two $C_1$-$C_4$ alkyl groups.

Embodiments described herein relate to a compound of formula (II), or a pharmaceutically acceptable salt thereof, wherein, wherein L is

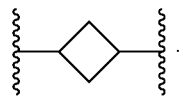 [SMILES: *C1CC(*)C1]

Embodiments described herein relate to a compound of formula (II), or a pharmaceutically acceptable salt thereof, wherein $R^1$ is —C(O)$R^{10a}$ and $R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^2$ is —C(O)$R^{10b}$ and $R^1$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^1$ is —C(O)$R^{10a}$ and $R^2$ is —C(O)$R^{10b}$.

Embodiments described herein relate to a compound of formula (II), or a pharmaceutically acceptable salt thereof, wherein $R^1$ is —C(O)$R^{10a}$ and $R^2$ is —C(O)$R^{10b}$.

Embodiments described herein relate to a compound of formula (II), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —(CH$_2$)$_w$—N($R^{11}$)($R^{12}$), —(CH$_2$)$_w$—C(O)N($R^{11}$)($R^{12}$), —C(O)O$R^{11}$, —N($R^{11}$)C(O)$R^{12}$, —S(O)$_2R^{11}$, or —S(O)N($R^{11}$)($R^{12}$) groups.

Embodiments described herein relate to a compound of formula (II), or a pharmaceutically acceptable salt thereof, wherein $R^{10a}$ is —[C($R^{13}$)($R^{14}$)]$_z$—($C_6$ aryl) or —[C($R^{13}$)($R^{14}$)]$_z$-(5-6 membered heteroaryl) and $R^{10b}$ is —[C($R^{13}$)($R^{14}$)]$_z$—($C_6$ aryl), or —[C($R^{13}$)($R^{14}$)]$_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (II), or a pharmaceutically acceptable salt thereof, wherein $R^{10a}$ is —[C($R^{13}$)($R^{14}$)]$_z$-(5-6 membered heteroaryl) and $R^{10b}$ is —[C($R^{13}$)($R^{14}$)]$_z$-(5-6 membered heteroaryl), wherein the 5-6 membered heteroaryl in $R^{10a}$ and $R^{10b}$ are each independently optionally substituted by one or two $C_1$-$C_4$ alkyl groups.

Embodiments described herein relate to a compound of formula (II), or a pharmaceutically acceptable salt thereof, wherein each $R^{13}$ and $R^{14}$ is hydrogen and each z is 1.

Embodiments described herein relate to a compound of formula (II), or a pharmaceutically acceptable salt thereof, wherein $R^{10a}$ is —$CH_2$-pyridinyl optionally substituted by one or two $C_1$-$C_4$ alkyl groups and $R^{10b}$ is —$CH_2$-pyridinyl optionally substituted by one or two $C_1$-$C_4$ alkyl groups.

Embodiments described herein relate to a compound of formula (III)

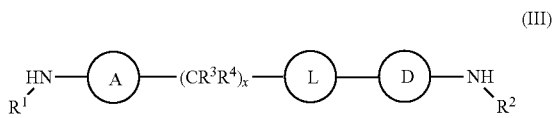

(III)

wherein
A and D are independently

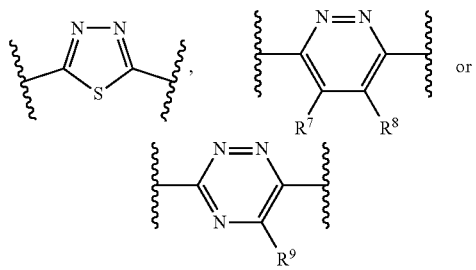

provided that at least one of A and D is

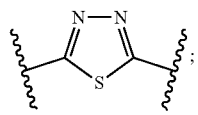 [SMILES: *c1nnc(*)s1]

L is —($C_4$-$C_{10}$ cycloalkyl)- optionally substituted by one to three substituents selected from the group consisting of halogen, cyano, $C_1$-$C_4$ alkyl, hydroxy, and $C_1$-$C_4$ alkoxy;

$R^1$ is hydrogen, $C_1$-$C_4$ alkyl, $C_3$-$C_6$ cycloalkyl, —C(O)$R^{10a}$, or 5-6 membered heteroaryl, wherein the $C_3$-$C_6$ cycloalkyl and the 5-6 membered heteroaryl are independently optionally substituted by one or two $R^{15}$ groups;

$R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups;

$R^3$ and $R^4$ are each independently hydrogen, halogen, $C_1$-$C_4$ alkyl, $C_1$-$C_4$ alkoxy, or $C_3$-$C_6$ cycloalkyl;

$R^7$, $R^8$ and $R^9$ are each independently hydrogen, halogen, cyano, $C_1$-$C_2$ alkyl, hydroxy, $C_1$-$C_2$ alkoxy, or —N($R^{11}$)($R^{12}$), wherein the $C_1$-$C_2$ alkyl and the $C_1$-$C_2$ alkoxy are each independently optionally substituted by halogen or hydroxy;

$R^{10a}$ and $R^{10b}$ are each independently hydrogen, $C_1$-$C_4$ alkyl, —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl), wherein the $C_1$-$C_4$ alkyl, the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —($CH_2$)$_w$—N($R^{11}$)($R^{12}$), —($CH_2$)$_w$—C(O)N($R^{11}$)($R^{12}$), —C(O)O$R^{11}$, —N($R^{11}$)C(O)$R^{12}$, —S(O)$_2R^{11}$, or —S(O)N($R^{11}$)($R^{12}$) groups;

each $R^{11}$, $R^{12}$, $R^{13}$, $R^{14}$ and $R^{15}$ is independently hydrogen, $C_1$-$C_4$ alkyl, $C_1$-$C_4$ alkoxy, $C_3$-$C_6$ cycloalkyl, or 3-6 membered heterocycloalkyl, wherein the $C_1$-$C_4$ alkyl, the $C_3$-$C_6$ cycloalkyl, and the 3-6 membered heterocycloalkyl are each independently optionally substituted by one, two or three substituents selected from the group consisting of halogen, cyano, hydroxy, and methoxy;

w is 0, 1, 2 or 3;

x is 0 or 1; and z is 0, 1, 2 or 3;

or a pharmaceutically acceptable salt thereof.

Embodiments described herein relate to a compound of formula (III), or a pharmaceutically acceptable salt thereof, wherein D is

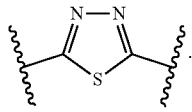 [SMILES: *c1nnc(*)s1]

Embodiments described herein relate to a compound of formula (III), or a pharmaceutically acceptable salt thereof, wherein A is

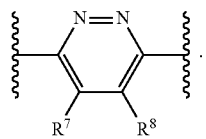

Embodiments described herein relate to a compound of formula (III), or a pharmaceutically acceptable salt thereof, wherein A is

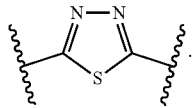 [SMILES: *c1nnc(*)s1]

Embodiments described herein relate to a compound of formula (III), or a pharmaceutically acceptable salt thereof, wherein x is 0.

Embodiments described herein relate to a compound of formula (III), or a pharmaceutically acceptable salt thereof, wherein x is 1.

Embodiments described herein relate to a compound of formula (III), or a pharmaceutically acceptable salt thereof, wherein L is

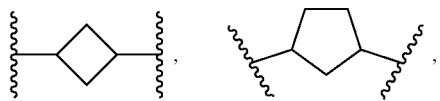

-continued

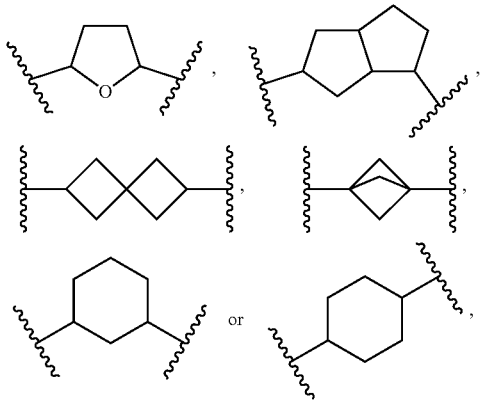

optionally substituted by one to three substituents selected from the group consisting of halogen, cyano, $C_1$-$C_4$ alkyl, hydroxy, and $C_1$-$C_4$ alkoxy.

Embodiments described herein relate to a compound of formula (III), or a pharmaceutically acceptable salt thereof, wherein L is

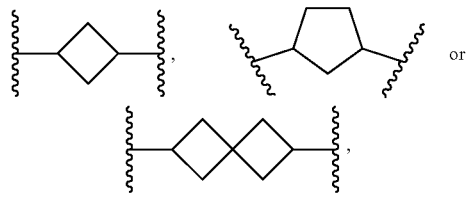

optionally substituted by one to three substituents selected from the group consisting of halogen, cyano, $C_1$-$C_4$ alkyl, hydroxy, and $C_1$-$C_4$ alkoxy.

Embodiments described herein relate to a compound of formula (III), or a pharmaceutically acceptable salt thereof, wherein $R^1$ is —C(O)$R^{10a}$ and $R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^2$ is —C(O)$R^{10b}$ and $R^1$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^1$ is —C(O)$R^{10a}$ and $R^2$ is —C(O)$R^{10b}$.

Embodiments described herein relate to a compound of formula (III), or a pharmaceutically acceptable salt thereof, wherein $R^{10a}$ is $C_1$-$C_4$ alkyl and $R^{10b}$ is $C_1$-$C_4$ alkyl.

Embodiments described herein relate to a compound of formula (III), or a pharmaceutically acceptable salt thereof, wherein $R^1$ is —C(O)$R^{10a}$ and $R^2$ is —C(O)$R^{10b}$.

Embodiments described herein relate to a compound of formula (III), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —(CH$_2$)$_w$—N($R^{11}$)($R^{12}$), —(CH$_2$)$_w$—C(O)N($R^{11}$)($R^{12}$), —C(O)O$R^{11}$, —N($R^{11}$)C(O)$R^{12}$, —S(O)$_2$$R^{11}$, or —S(O)N($R^{11}$)($R^{12}$) groups.

Embodiments described herein relate to a compound of formula (III), or a pharmaceutically acceptable salt thereof, wherein $R^{10a}$ is —[C($R^{13}$)($R^{14}$)]$_z$—($C_6$ aryl) or —[C($R^{13}$)($R^{14}$)]$_z$-(5-6 membered heteroaryl) and $R^{10b}$ is —[C($R^{13}$)($R^{14}$)]$_z$—($C_6$ aryl) or —[C($R^{13}$)($R^{14}$)]$_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (III), or a pharmaceutically acceptable salt thereof, wherein at least one of $R^1$ and $R^2$ is $C_1$-$C_4$ alkyl.

Embodiments described herein relate to a compound of formula (III), or a pharmaceutically acceptable salt thereof, wherein $R^1$ and $R^2$ each independently $C_1$-$C_4$ alkyl.

Embodiments described herein relate to a compound of formula (III), or a pharmaceutically acceptable salt thereof, wherein at least one of $R^1$ and $R^2$ is hydrogen.

Embodiments described herein relate to a compound of formula (III), or a pharmaceutically acceptable salt thereof, wherein at least one of $R^1$ and $R^2$ is $C_3$-$C_6$ cycloalkyl optionally substituted by one or two $R^{15}$ groups.

Embodiments described herein relate to a compound of formula (III), or a pharmaceutically acceptable salt thereof, wherein at least one of $R^1$ and $R^2$ is 5-6 membered heteroaryl optionally substituted by one or two $R^{15}$ groups.

Embodiments described herein relate to a compound of formula (III), or a pharmaceutically acceptable salt thereof, wherein L is

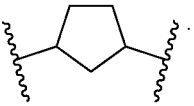 [SMILES: *C1CCC(*)C1]

Embodiments described herein relate to a compound of formula (III), or a pharmaceutically acceptable salt thereof, wherein $R^1$ is —C(O)$R^{10a}$ and $R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^2$ is —C(O)$R^{10b}$ and $R^1$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^1$ is —C(O)$R^{10a}$ and $R^2$ is —C(O)$R^{10b}$.

Embodiments described herein relate to a compound of formula (III), or a pharmaceutically acceptable salt thereof, wherein $R^1$ is —C(O)$R^{10a}$ and $R^2$ is —C(O)$R^{10b}$.

Embodiments described herein relate to a compound of formula (III), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—(C$_6$-C$_{10}$ aryl), or —[C($R^{13}$)($R^{14}$)]$_z$-(5-10 membered heteroaryl), wherein the C$_4$-C$_{10}$ cycloalkyl, the 4-6 membered heterocycloalkyl, the C$_6$-C$_{10}$ aryl, and the 5-10 membered heteroaryl in $R^{10a}$ and $R^{10b}$ are each independently optionally substituted by one, two or three halogen, cyano, C$_1$-C$_6$ alkyl, hydroxy, C$_1$-C$_6$ alkoxy, —(CH$_2$)$_w$—N($R^{11}$)($R^{12}$), —(CH$_2$)$_w$—C(O)N($R^{11}$)($R^{12}$), —C(O)O$R^{11}$, —N($R^{11}$)C(O)$R^{12}$, —S(O)$_2$$R^{11}$, or —S(O)N($R^{11}$)($R^{12}$) groups.

Embodiments described herein relate to a compound of formula (III), or a pharmaceutically acceptable salt thereof, wherein $R^{10a}$ is —[C($R^{13}$)($R^{14}$)]$_z$—(C$_6$ aryl) or —[C($R^{13}$)($R^{14}$)]$_z$-(5-6 membered heteroaryl) and $R^{10b}$ is —[C($R^{13}$)($R^{14}$)]$_z$—(C$_6$ aryl), or —[C($R^{13}$)($R^{14}$)]$_z$-(5-6 membered heteroaryl), wherein the C$_6$ aryl and the 5-6 membered heteroaryl in $R^{10a}$ and $R^{10b}$ are each independently optionally substituted by one or two halogen or C$_1$-C$_4$ alkyl groups.

Embodiments described herein relate to a compound of formula (III), or a pharmaceutically acceptable salt thereof, wherein $R^{10a}$ is —[C($R^{13}$)($R^{14}$)]$_z$-(5-6 membered heteroaryl) and $R^{10b}$ is —[C($R^{13}$)($R^{14}$)]$_z$-(5-6 membered heteroaryl), wherein the aryl and the heteroaryl in $R^{10a}$ and $R^{10b}$ are each independently optionally substituted by one or two C$_1$-C$_4$ alkyl groups.

Embodiments described herein relate to a compound of formula (III), or a pharmaceutically acceptable salt thereof, wherein each $R^{13}$ and $R^{14}$ is hydrogen and each z is 1.

Embodiments described herein relate to a compound of formula (III), or a pharmaceutically acceptable salt thereof, wherein $R^{10a}$ is —CH$_2$-pyridinyl and $R^{10b}$ is —CH$_2$-pyridinyl, wherein each pyridinyl is optionally substituted by one or two C$_1$-C$_4$ alkyl groups.

Embodiments described herein relate to a compound of formula (III), or a pharmaceutically acceptable salt thereof, wherein $R^{10a}$ is —CH$_2$-pyridinyl optionally substituted by one or two C$_1$-C$_4$ alkyl groups and $R^{10b}$ is —CH$_2$-pyrazolyl optionally substituted by one or two C$_1$-C$_4$ alkyl groups.

Embodiments described herein relate to a compound of formula (III), or a pharmaceutically acceptable salt thereof, wherein $R^{10a}$ is —[C($R^{13}$)($R^{14}$)]$_z$—(C$_4$-C$_{10}$ cycloalkyl), —[C($R^{13}$)($R^{14}$)]$_z$-(4-6 membered heterocycloalkyl), —[C($R^{13}$)($R^{14}$)]—(C$_6$-C$_{10}$ aryl), or —[C($R^{13}$)($R^{14}$)]$_z$-(5-10 membered heteroaryl) and $R^{10b}$ is —[C($R^{13}$)($R^{14}$)]$_z$—(C$_4$-C$_{10}$ cycloalkyl), —[C($R^{13}$)($R^{14}$)]$_z$-(4-6 membered heterocycloalkyl), —[C($R^{13}$)($R^{14}$)]—(C$_6$-C$_{10}$ aryl), or —[C($R^{13}$)($R^{14}$)]$_z$-(5-10 membered heteroaryl), and $R^{10b}$ is C$_1$-C$_4$ alkyl, wherein the C$_1$-C$_4$ alkyl, the 4-6 membered heterocycloalkyl, the C$_6$-C$_{10}$ aryl, and the 5-10 membered heteroaryl in $R^{10a}$ and $R^{10b}$ are each independently optionally substituted by one, two or three halogen, cyano, C$_1$-C$_6$ alkyl, hydroxy, C$_1$-C$_6$ alkoxy, —(CH$_2$)$_w$—N($R^{11}$)($R^{12}$), —(CH$_2$)$_w$—C(O)N($R^{11}$)($R^{12}$), —C(O)O$R^{11}$, —N($R^{11}$)C(O)$R^{12}$, —S(O)$_2$$R^{11}$, or —S(O)N($R^{11}$)($R^{12}$) groups.

Embodiments described herein relate to a compound of formula (III), or a pharmaceutically acceptable salt thereof, wherein $R^{10a}$ is —[C($R^{13}$)($R^{14}$)]$_z$—(C$_6$ aryl) or —[C($R^{13}$)($R^{14}$)]$_z$-(5-6 membered heteroaryl), wherein the C$_6$ aryl and the 5-6 membered heteroaryl in $R^{10a}$ are each independently optionally substituted by one or two halogen or C$_1$-C$_4$ alkyl groups, and $R^{10b}$ is C$_1$-C$_4$ alkyl optionally substituted by C$_1$-C$_6$ alkoxy.

Embodiments described herein relate to a compound of formula (III), or a pharmaceutically acceptable salt thereof, wherein each $R^{13}$ and $R^{14}$ is hydrogen and each z is 1.

Embodiments described herein relate to a compound of formula (III), or a pharmaceutically acceptable salt thereof, wherein $R^{10a}$ is —(CH$_2$)-(5-6 membered heteroaryl) optionally substituted by one or two C$_1$-C$_4$ alkyl groups and $R^{10b}$ is C$_1$-C$_4$ alkyl optionally substituted by C$_1$-C$_2$ alkoxy.

Embodiments described herein relate to a compound of formula (III), or a pharmaceutically acceptable salt thereof, wherein $R^{10a}$ is —CH$_2$-pyridinyl and $R^{10b}$ is —CH$_2$CH$_2$—O—CH$_3$.

Embodiments described herein relate to a compound of formula (III), or a pharmaceutically acceptable salt thereof, wherein $R^1$ is —C(O)$R^{10a}$ and $R^2$ is C$_3$-C$_6$ cycloalkyl optionally substituted by one or two $R^{15}$ groups.

Embodiments described herein relate to a compound of formula (III), or a pharmaceutically acceptable salt thereof, wherein $R^{10a}$ is —[C($R^{13}$)($R^{14}$)]$_z$—(C$_4$-C$_{10}$ cycloalkyl), —[C($R^{13}$)($R^{14}$)]$_z$-(4-6 membered heterocycloalkyl), —[C($R^{13}$)($R^{14}$)]$_z$—(C$_6$-C$_{10}$ aryl), or —[C($R^{13}$)($R^{14}$)]$_z$-(5-10 membered heteroaryl) and $R^{10b}$ is —[C($R^{13}$)($R^{14}$)]$_z$—(C$_4$-C$_{10}$ cycloalkyl), —[C($R^{13}$)($R^{14}$)]$_z$-(4-6 membered heterocycloalkyl), —[C($R^{13}$)($R^{14}$)]$_z$—(C$_6$-C$_{10}$ aryl), or —[C($R^{13}$)($R^{14}$)]$_z$-(5-10 membered heteroaryl), wherein the C$_4$-C$_{10}$ cycloalkyl, the 4-6 membered heterocycloalkyl, the C$_6$-C$_{10}$ aryl, and the 5-10 membered heteroaryl in $R^{10a}$ are each independently optionally substituted by one, two or three halogen, cyano, C$_1$-C$_6$ alkyl, hydroxy, C$_1$-C$_6$ alkoxy, —(CH$_2$)$_w$—N($R^{11}$)($R^{12}$), —(CH$_2$)$_w$—C(O)N($R^{11}$)($R^{12}$), —C(O)O$R^{11}$, —N($R^{11}$)C(O)$R^{12}$, —S(O)$_2$$R^{11}$, or —S(O)N($R^{11}$)($R^{12}$) groups.

Embodiments described herein relate to a compound of formula (III), or a pharmaceutically acceptable salt thereof, wherein each $R^{13}$ and $R^{14}$ is hydrogen and each z is 1.

Embodiments described herein relate to a compound of formula (III), or a pharmaceutically acceptable salt thereof, wherein $R^{10a}$ is —CH$_2$-(5-6 membered heteroaryl) optionally substituted by one or two halogen or C$_1$-C$_4$ alkyl groups.

Embodiments described herein relate to a compound of formula (III), or a pharmaceutically acceptable salt thereof, wherein $R^{10a}$ is —CH$_2$-pyridinyl optionally substituted by one or two C$_1$-C$_4$ alkyl groups and $R^2$ is cyclopropyl.

Embodiments described herein relate to a compound of formula (III), or a pharmaceutically acceptable salt thereof, wherein wherein L is

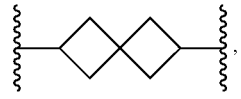 [SMILES: *C1CC2(C1)CC(*)C2]

x is 0 and y is 0.

Embodiments described herein relate to a compound of formula (III), or a pharmaceutically acceptable salt thereof, wherein $R^1$ is —C(O)$R^{10a}$ and $R^2$ is hydrogen, C$_1$-C$_4$ alkyl, C$_3$-C$_6$ cycloalkyl, —C(O)$R^{10b}$, or 5-6 membered heteroaryl, wherein the C$_3$-C$_6$ cycloalkyl and the 5-6 membered heteroaryl are independently optionally substituted by one or two $R^{15}$ groups; or $R^2$ is —C(O)$R^{10b}$ and $R^1$ is hydrogen, C$_1$-C$_4$ alkyl, C$_3$-C$_6$ cycloalkyl, —C(O)$R^{10b}$, or 5-6 membered heteroaryl, wherein the C$_3$-C$_6$ cycloalkyl and the 5-6 membered heteroaryl are independently optionally substituted by one or two $R^{15}$ groups; or $R^1$ is —C(O)$R^{10a}$ and $R^2$ is —C(O)$R^{10b}$.

Embodiments described herein relate to a compound of formula (III), or a pharmaceutically acceptable salt thereof, wherein $R^1$ is —C(O)$R^{10a}$ and $R^2$ is —C(O)$R^{10b}$.

Embodiments described herein relate to a compound of formula (III), or a pharmaceutically acceptable salt thereof, wherein $R^{10a}$ is —[C($R^{13}$)($R^{14}$)]$_z$—(C$_4$-C$_{10}$ cycloalkyl), —[C($R^{13}$)($R^{14}$)]$_z$-(4-6 membered heterocycloalkyl), —[C($R^{13}$)($R^{14}$)]$_z$—(C$_6$-C$_{10}$ aryl), or —[C($R^{13}$)($R^{14}$)]$_z$-(5-10 membered heteroaryl) and $R^{10b}$ is —[C($R^{13}$)($R^{14}$)]$_z$—(C$_4$-C$_{10}$ cycloalkyl), —[C($R^{13}$)($R^{14}$)]$_z$-(4-6 membered heterocycloalkyl), —[C($R^{13}$)($R^{14}$)]—(C$_6$-C$_{10}$ aryl), or —[C($R^{13}$)($R^{14}$)]$_z$-(5-10 membered heteroaryl), wherein the C$_4$-C$_{10}$ cycloalkyl, the 4-6 membered heterocycloalkyl, the C$_6$-C$_{10}$ aryl, and the 5-10 membered heteroaryl in $R^{10a}$ and $R^{10b}$ are each independently optionally substituted by one, two or three halogen, cyano, C$_1$-C$_6$ alkyl, hydroxy, C$_1$-C$_6$ alkoxy, —(CH$_2$)$_w$—N($R^{11}$)($R^{12}$), —(CH$_2$)$_w$—C(O)N($R^{11}$)($R^{12}$), —C(O)O$R^{11}$, —N($R^{11}$)C(O)$R^{12}$, —S(O)$_2$$R^{11}$, or —S(O)N($R^{11}$)($R^{12}$) groups.

Embodiments described herein relate to a compound of formula (III), or a pharmaceutically acceptable salt thereof, wherein $R^{10a}$ is —[C($R^{13}$)($R^{14}$)]$_z$—(C$_6$ aryl) or —[C($R^{13}$)($R^{14}$)]$_z$-(5-6 membered heteroaryl) and $R^{10b}$ is —[C($R^{13}$)($R^{14}$)]—(C$_6$ aryl) or —[C($R^{13}$)($R^{14}$)]$_z$-(5-6 membered heteroaryl), wherein the C$_6$ aryl and the 5-6 membered heteroaryl in $R^{10a}$ and $R^{10b}$ are each independently optionally substituted by one or two halogen or C$_1$-C$_4$ alkyl groups.

Embodiments described herein relate to a compound of formula (III), or a pharmaceutically acceptable salt thereof, wherein $R^{10a}$ is —[C($R^{13}$)($R^{14}$)]$_z$-(5-6 membered heteroaryl) optionally substituted by one or two C$_1$-C$_4$ alkyl groups and $R^{10b}$ is —[C($R^{13}$)($R^{14}$)]$_z$-(5-6 membered heteroaryl) optionally substituted by one or two C$_1$-C$_4$ alkyl groups.

Embodiments described herein relate to a compound of formula (III), or a pharmaceutically acceptable salt thereof, wherein $R^{10a}$ is —CH$_2$-pyrazolyl optionally substituted by one or two C$_1$-C$_4$ alkyl groups and $R^{10b}$ is —CH$_2$-pyrazolyl optionally substituted by one or two C$_1$-C$_4$ alkyl groups.

Embodiments described herein relate to a compound of formula (III), or a pharmaceutically acceptable salt thereof, wherein L is

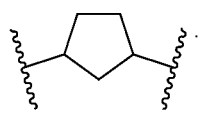 [SMILES: *C1CCC(*)C1]

Embodiments described herein relate to a compound of formula (III), or a pharmaceutically acceptable salt thereof, wherein $R^1$ is —C(O)$R^{10a}$ and $R^2$ is hydrogen, C$_1$-C$_4$ alkyl, C$_3$-C$_6$ cycloalkyl, —C(O)$R^{10b}$, or 5-6 membered heteroaryl, wherein the C$_3$-C$_6$ cycloalkyl and the 5-6 membered heteroaryl are independently optionally substituted by one or two $R^{15}$ groups; or $R^2$ is —C(O)$R^{10b}$ and $R^1$ is hydrogen, C$_1$-C$_4$ alkyl, C$_3$-C$_6$ cycloalkyl, —C(O)$R^{10b}$, or 5-6 membered heteroaryl, wherein the C$_3$-C$_6$ cycloalkyl and the 5-6 membered heteroaryl are independently optionally substituted by one or two $R^{15}$ groups; or $R^1$ is —C(O)$R^{10a}$ and $R^2$ is —C(O)$R^{10b}$.

Embodiments described herein relate to a compound of formula (III), or a pharmaceutically acceptable salt thereof, wherein $R^1$ is —C(O)$R^{10a}$ and $R^2$ is —C(O)$R^{10b}$.

Embodiments described herein relate to a compound of formula (III), or a pharmaceutically acceptable salt thereof, wherein $R^{10a}$ is —[C($R^{13}$)($R^{14}$)]$_z$—(C$_4$-C$_{10}$ cycloalkyl), —[C($R^{13}$)($R^{14}$)]$_z$-(4-6 membered heterocycloalkyl), —[C($R^{13}$)($R^{14}$)]$_z$—(C$_6$-C$_{10}$ aryl), or —[C($R^{13}$)($R^{14}$)]$_z$-(5-10 membered heteroaryl) and $R^{10b}$ is —[C($R^{13}$)($R^{14}$)]$_z$—(C$_4$-C$_{10}$ cycloalkyl), —[C($R^{13}$)($R^{14}$)]$_z$-(4-6 membered heterocycloalkyl), —[C($R^{13}$)($R^{14}$)]$_z$—(C$_6$-C$_{10}$ aryl), or —[C($R^{13}$)($R^{14}$)]$_z$-(5-10 membered heteroaryl), wherein the C$_4$-C$_{10}$ cycloalkyl, the 4-6 membered heterocycloalkyl, the C$_6$-C$_{10}$ aryl, and the 5-10 membered heteroaryl in $R^{10a}$ and $R^{10b}$ are each independently optionally substituted by one, two or three halogen, cyano, C$_1$-C$_6$ alkyl, hydroxy, C$_1$-C$_6$ alkoxy, —(CH$_2$)$_w$—N($R^{11}$)($R^{12}$), —(CH$_2$)$_w$—C(O)N($R^{11}$)($R^{12}$), —C(O)O$R^{11}$, —N($R^{11}$)C(O)$R^{12}$, —S(O)$_2$$R^{11}$, or —S(O)N($R^{11}$)($R^{12}$) groups.

Embodiments described herein relate to a compound of formula (III), or a pharmaceutically acceptable salt thereof, wherein $R^{10a}$ is —[C($R^{13}$)($R^{14}$)]$_z$—(C$_6$ aryl) or —[C($R^{13}$)($R^{14}$)]$_z$-(5-6 membered heteroaryl) and $R^{10b}$ is —[C($R^{13}$)($R^{14}$)]—(C$_6$ aryl) or —[C($R^{13}$)($R^{14}$)]$_z$-(5-6 membered heteroaryl), wherein the C$_6$ aryl and the 5-6 membered heteroaryl in $R^{10a}$ and $R^{10b}$ are each independently optionally substituted by one or two halogen or C$_1$-C$_4$ alkyl groups.

Embodiments described herein relate to a compound of formula (III), or a pharmaceutically acceptable salt thereof, wherein $R^{10a}$ is —[C($R^{13}$)($R^{14}$)]$_z$-(5-6 membered heteroaryl) and $R^{10b}$ is —[C($R^{13}$)($R^{14}$)]$_z$-(5-6 membered heteroaryl), wherein the 5-6 membered heteroaryl in $R^{10a}$ and $R^{10b}$ are each independently optionally substituted by one or two C$_1$-C$_4$ alkyl groups.

Embodiments described herein relate to a compound of formula (III), or a pharmaceutically acceptable salt thereof, wherein each $R^{13}$ and $R^{14}$ is hydrogen and each z is 1.

Embodiments described herein relate to a compound of formula (III), or a pharmaceutically acceptable salt thereof, wherein $R^{10a}$ is —CH$_2$-pyridinyl optionally substituted by one or two C$_1$-C$_4$ alkyl groups and $R^{10b}$ is —CH$_2$-pyridinyl optionally substituted by one or two C$_1$-C$_4$ alkyl groups.

Embodiments described herein relate to a compound of formula (III), or a pharmaceutically acceptable salt thereof, wherein, wherein L is

Embodiments described herein relate to a compound of formula (III), or a pharmaceutically acceptable salt thereof, wherein $R^1$ is —C(O)$R^{10a}$ and $R^2$ is hydrogen, C$_1$-C$_4$ alkyl, C$_3$-C$_6$ cycloalkyl, —C(O)$R^{10b}$, or 5-6 membered heteroaryl, wherein the C$_3$-C$_6$ cycloalkyl and the 5-6 membered heteroaryl are independently optionally substituted by one or two $R^{15}$ groups; or $R^2$ is —C(O)$R^{10b}$ and $R^1$ is hydrogen, C$_1$-C$_4$ alkyl, C$_3$-C$_6$ cycloalkyl, —C(O)$R^{10b}$, or 5-6 membered heteroaryl, wherein the C$_3$-C$_6$ cycloalkyl and the 5-6 membered heteroaryl are independently optionally substituted by one or two $R^{15}$ groups; or $R^1$ is —C(O)$R^{10a}$ and $R^2$ is —C(O)$R^{10b}$.

Embodiments described herein relate to a compound of formula (III), or a pharmaceutically acceptable salt thereof, wherein $R^1$ is —C(O)$R^{10a}$ and $R^2$ is —C(O)$R^{10b}$.

Embodiments described herein relate to a compound of formula (III), or a pharmaceutically acceptable salt thereof, wherein $R^{10a}$ is —[C($R^{13}$)($R^{14}$)]$_z$—(C$_4$-C$_{10}$ cycloalkyl), —[C($R^{13}$)($R^{14}$)]$_z$-(4-6 membered heterocycloalkyl), —[C($R^{13}$)($R^{14}$)]$_z$—(C$_6$-C$_{10}$ aryl), or —[C($R^{13}$)($R^{14}$)]$_z$-(5-10 membered heteroaryl) and $R^{10b}$ is —[C($R^{13}$)($R^{14}$)]$_z$—(C$_4$-

$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —(CH$_2$)$_w$—N($R^{11}$)($R^{12}$), —(CH$_2$)$_w$—C(O)N($R^{11}$)($R^{12}$), —C(O)O$R^{11}$, —N($R^{11}$)C(O)$R^{12}$, —S(O)$_2$$R^{11}$, or —S(O)N($R^{11}$)($R^{12}$) groups.

Embodiments described herein relate to a compound of formula (III), or a pharmaceutically acceptable salt thereof, wherein $R^{10a}$ is —[C($R^{13}$)($R^{14}$)]$_z$—($C_6$ aryl) or —[C($R^{13}$)($R^{14}$)]$_z$-(5-6 membered heteroaryl) and $R^{10b}$ is —[C($R^{13}$)($R^{14}$)]$_z$—($C_6$ aryl), or —[C($R^{13}$)($R^{14}$)]$_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (III), or a pharmaceutically acceptable salt thereof, wherein $R^{10a}$ is —[C($R^{13}$)($R^{14}$)]$_z$-(5-6 membered heteroaryl) and $R^{10b}$ is —[C($R^{13}$)($R^{14}$)]$_z$-(5-6 membered heteroaryl), wherein the 5-6 membered heteroaryl in $R^{10a}$ and $R^{10b}$ are each independently optionally substituted by one or two $C_1$-$C_4$ alkyl groups.

Embodiments described herein relate to a compound of formula (III), or a pharmaceutically acceptable salt thereof, wherein each $R^{13}$ and $R^{14}$ is hydrogen and each z is 1.

Embodiments described herein relate to a compound of formula (III), or a pharmaceutically acceptable salt thereof, wherein $R^{10a}$ is —CH$_2$-pyridinyl optionally substituted by one or two $C_1$-$C_4$ alkyl groups and $R^{10b}$ is —CH$_2$-pyridinyl optionally substituted by one or two $C_1$-$C_4$ alkyl groups.

Embodiments described herein relate to a compound of formula (IV)

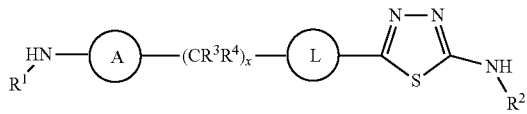

(IV)

wherein
A is

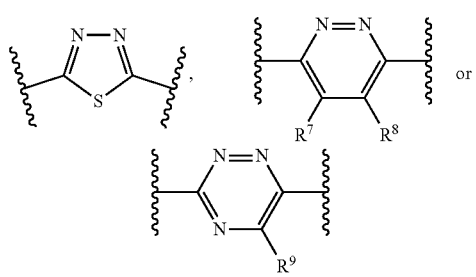

L is —($C_4$-$C_{10}$ cycloalkyl)- optionally substituted by one to three substituents selected from the group consisting of halogen, cyano, $C_1$-$C_4$ alkyl, hydroxy, and $C_1$-$C_4$ alkoxy;

$R^1$ is hydrogen, $C_1$-$C_4$ alkyl, $C_3$-$C_6$ cycloalkyl, —C(O)$R^{10a}$, or 5-6 membered heteroaryl, wherein the $C_3$-$C_6$ cycloalkyl and the 5-6 membered heteroaryl are independently optionally substituted by one or two $R^{15}$ groups;

$R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups;

$R^3$ and $R^4$ are each independently hydrogen, halogen, $C_1$-$C_4$ alkyl, $C_1$-$C_4$ alkoxy, or $C_3$-$C_6$ cycloalkyl;

$R^7$, $R^8$ and $R^9$ are each independently hydrogen, halogen, cyano, $C_1$-$C_2$ alkyl, hydroxy, $C_1$-$C_2$ alkoxy, or —N($R^{11}$)($R^{12}$), wherein the $C_1$-$C_2$ alkyl and the $C_1$-$C_2$ alkoxy are each independently optionally substituted by halogen or hydroxy;

$R^{10a}$ and $R^{11b}$ are each independently hydrogen, $C_1$-$C_4$ alkyl, —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl), wherein the $C_1$-$C_4$ alkyl, the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —(CH$_2$)$_w$—N($R^{11}$)($R^{12}$), —(CH$_2$)$_w$—C(O)N($R^{11}$)($R^{12}$), —C(O)O$R^{11}$, —N($R^{11}$)C(O)$R^{12}$, —S(O)$_2$$R^{11}$, or —S(O)N($R^{11}$)($R^{12}$) groups; each $R^{11}$, $R^{12}$, $R^{13}$, $R^{14}$ and $R^{15}$ is independently hydrogen, $C_1$-$C_4$ alkyl, $C_1$-$C_4$ alkoxy, $C_3$-$C_6$ cycloalkyl, or 3-6 membered heterocycloalkyl, wherein the $C_1$-$C_4$ alkyl, the $C_3$-$C_6$ cycloalkyl, and the 3-6 membered heterocycloalkyl are each independently optionally substituted by one, two or three substituents selected from the group consisting of halogen, cyano, hydroxy, and methoxy;

w is 0, 1, 2 or 3;
x is 0 or 1; and
z is 0, 1, 2 or 3;
or a pharmaceutically acceptable salt thereof.

Embodiments described herein relate to a compound of formula (IV), or a pharmaceutically acceptable salt thereof, wherein A is

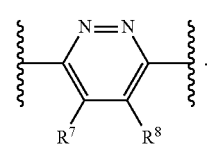

Embodiments described herein relate to a compound of formula (IV), or a pharmaceutically acceptable salt thereof, wherein A is

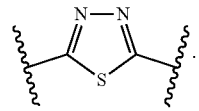

Embodiments described herein relate to a compound of formula (IV), or a pharmaceutically acceptable salt thereof, wherein x is 0.

Embodiments described herein relate to a compound of formula (IV), or a pharmaceutically acceptable salt thereof, wherein x is 1.

Embodiments described herein relate to a compound of formula (IV), or a pharmaceutically acceptable salt thereof, wherein L is

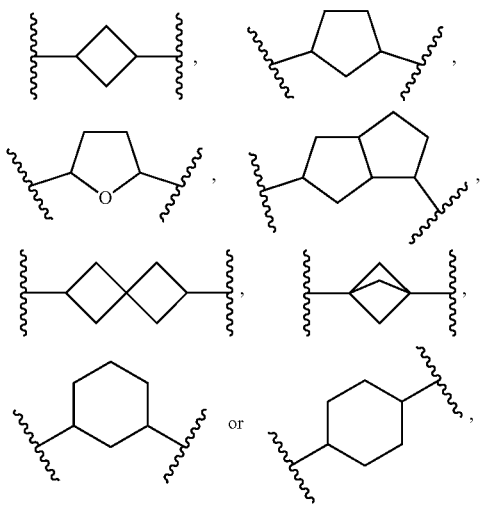

optionally substituted by one to three substituents selected from the group consisting of halogen, cyano, $C_1$-$C_4$ alkyl, hydroxy, and $C_1$-$C_4$ alkoxy.

Embodiments described herein relate to a compound of formula (IV), or a pharmaceutically acceptable salt thereof, wherein L is

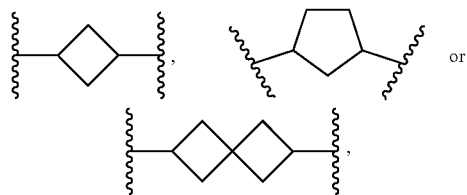

optionally substituted by one to three substituents selected from the group consisting of halogen, cyano, $C_1$-$C_4$ alkyl, hydroxy, and $C_1$-$C_4$ alkoxy.

Embodiments described herein relate to a compound of formula (IV), or a pharmaceutically acceptable salt thereof, wherein $R^1$ is —C(O)$R^{10a}$ and $R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^2$ is —C(O)$R^{10b}$ and $R^1$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^1$ is —C(O)$R^{10a}$ and $R^2$ is —C(O)$R^{10b}$.

Embodiments described herein relate to a compound of formula (IV), or a pharmaceutically acceptable salt thereof, wherein $R^{10a}$ is $C_1$-$C_4$ alkyl and $R^{10b}$ is $C_1$-$C_4$ alkyl.

Embodiments described herein relate to a compound of formula (IV), or a pharmaceutically acceptable salt thereof, wherein $R^1$ is —C(O)$R^{10a}$ and $R^2$ is —C(O)$R^{10b}$.

Embodiments described herein relate to a compound of formula (IV), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]—($C_6$-$C_{10}$ aryl), or —[C($R^{13}$)($R^{14}$)]$_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —(CH$_2$)$_w$—N($R^{11}$)($R^{12}$), —(CH$_2$)$_w$—C(O)N($R^{11}$)($R^{12}$), —C(O)O$R^{11}$, —N($R^{11}$)C(O)$R^{12}$, —S(O)$_2$$R^{11}$, or —S(O)N($R^{11}$)($R^{12}$) groups.

Embodiments described herein relate to a compound of formula (IV), or a pharmaceutically acceptable salt thereof, wherein $R^{10a}$ is —[C($R^{13}$)($R^{14}$)]$_z$—($C_6$ aryl) or —[C($R^{13}$)($R^{14}$)]$_z$-(5-6 membered heteroaryl) and $R^{10b}$ is —[C($R^{13}$)($R^{14}$)]$_z$—($C_6$ aryl) or —[C($R^{13}$)($R^{14}$)]$_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (IV), or a pharmaceutically acceptable salt thereof, wherein at least one of $R^1$ and $R^2$ is $C_1$-$C_4$ alkyl.

Embodiments described herein relate to a compound of formula (IV), or a pharmaceutically acceptable salt thereof, wherein $R^1$ and $R^2$ each independently $C_1$-$C_4$ alkyl.

Embodiments described herein relate to a compound of formula (IV), or a pharmaceutically acceptable salt thereof, wherein at least one of $R^1$ and $R^2$ is hydrogen.

Embodiments described herein relate to a compound of formula (IV), or a pharmaceutically acceptable salt thereof, wherein at least one of $R^1$ and $R^2$ is $C_3$-$C_6$ cycloalkyl optionally substituted by one or two $R^{15}$ groups.

Embodiments described herein relate to a compound of formula (IV), or a pharmaceutically acceptable salt thereof, wherein at least one of $R^1$ and $R^2$ is 5-6 membered heteroaryl optionally substituted by one or two $R^{15}$ groups.

Embodiments described herein relate to a compound of formula (IV), or a pharmaceutically acceptable salt thereof, wherein L is

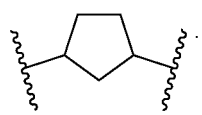

Embodiments described herein relate to a compound of formula (IV), or a pharmaceutically acceptable salt thereof, wherein $R^1$ is —C(O)$R^{10a}$ and $R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^2$ is —C(O)$R^{10b}$ and $R^1$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^1$ is —C(O)$R^{10a}$ and $R^2$ is —C(O)$R^{10b}$.

Embodiments described herein relate to a compound of formula (IV), or a pharmaceutically acceptable salt thereof, wherein $R^1$ is —C(O)$R^{10a}$ and $R^2$ is —C(O)$R^{10b}$.

Embodiments described herein relate to a compound of formula (IV), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C $(R^{13})(R^{14})]_z$—$(C_6$-$C_{10}$ aryl), or —$[C(R^{13})(R^{14})]_z$-(5-10 membered heteroaryl) and $R^{10b}$ is —$[C(R^{13})(R^{14})]_z$—$(C_4$-$C_{10}$ cycloalkyl), —$[C(R^{13})(R^{14})]_z$-(4-6 membered heterocycloalkyl), —$[C(R^{13})(R^{14})]_z$—$(C_6$-$C_{10}$ aryl), or —$[C(R^{13})(R^{14})]_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —$(CH_2)_w$—$N(R^{11})(R^{12})$, —$(CH_2)_w$—$C(O)N(R^{11})(R^{12})$, —$C(O)OR^{11}$, —$N(R^{11})C(O)R^{12}$, —$S(O)_2R^{11}$, or —$S(O)N(R^{11})(R^{12})$ groups.

Embodiments described herein relate to a compound of formula (IV), or a pharmaceutically acceptable salt thereof, wherein $R^{10a}$ is —$[C(R^{13})(R^{14})]_z$—$(C_6$ aryl) or —$[C(R^{13})(R^{14})]_z$-(5-6 membered heteroaryl) and $R^{10b}$ is —$[C(R^{13})(R^{14})]_z$—$(C_6$ aryl), or —$[C(R^{13})(R^{14})]_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (IV), or a pharmaceutically acceptable salt thereof, wherein $R^{10a}$ is —$[C(R^{13})(R^{14})]_z$-(5-6 membered heteroaryl) and $R^{10b}$ is —$[C(R^{13})(R^{14})]_z$-(5-6 membered heteroaryl), wherein the aryl and the heteroaryl in $R^{10a}$ and $R^{10b}$ are each independently optionally substituted by one or two $C_1$-$C_4$ alkyl groups.

Embodiments described herein relate to a compound of formula (IV), or a pharmaceutically acceptable salt thereof, wherein each $R^{13}$ and $R^{14}$ is hydrogen and each z is 1.

Embodiments described herein relate to a compound of formula (IV), or a pharmaceutically acceptable salt thereof, wherein $R^{10a}$ is —$CH_2$-pyridinyl and $R^{10b}$ is —$CH_2$-pyridinyl, wherein each pyridinyl is optionally substituted by one or two $C_1$-$C_4$ alkyl groups.

Embodiments described herein relate to a compound of formula (IV), or a pharmaceutically acceptable salt thereof, wherein $R^{10a}$ is —$CH_2$-pyridinyl optionally substituted by one or two $C_1$-$C_4$ alkyl groups and $R^{10b}$ is —$CH_2$-pyrazolyl optionally substituted by one or two $C_1$-$C_4$ alkyl groups.

Embodiments described herein relate to a compound of formula (IV), or a pharmaceutically acceptable salt thereof, wherein $R^{10a}$ is —$[C(R^{13})(R^{14})]_z$—$(C_4$-$C_{10}$ cycloalkyl), —$[C(R^{13})(R^{14})]_z$-(4-6 membered heterocycloalkyl), —$[C(R^{13})(R^{14})]_z$—$(C_6$-$C_{10}$ aryl), or —$[C(R^{13})(R^{14})]_z$-(5-10 membered heteroaryl) and $R^{10b}$ is —$[C(R^{13})(R^{14})]_z$—$(C_4$-$C_{10}$ cycloalkyl), —$[C(R^{13})(R^{14})]Z$-(4-6 membered heterocycloalkyl), —$[C(R^{13})(R^{14})]_z$—$(C_6$-$C_{10}$ aryl), or —$[C(R^{13})(R^{14})]_z$-(5-10 membered heteroaryl), and $R^{10b}$ is $C_1$-$C_4$ alkyl, wherein the $C_1$-$C_4$ alkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —$(CH_2)_w$—$N(R^{11})(R^{12})$, —$(CH_2)_w$—$C(O)N(R^{11})(R^{12})$, —$C(O)OR^{11}$, —$N(R^{11})C(O)R^{12}$, —$S(O)_2R^{11}$, or —$S(O)N(R^{11})(R^{12})$ groups.

Embodiments described herein relate to a compound of formula (IV), or a pharmaceutically acceptable salt thereof, wherein $R^{10a}$ is —$[C(R^{13})(R^{14})]_z$—$(C_6$ aryl) or —$[C(R^{13})(R^{14})]_z$-(5-6 membered heteroaryl), wherein the $C_6$ aryl and the 5-6 membered heteroaryl in $R^{10a}$ are each independently optionally substituted by one or two halogen or $C_1$-$C_4$ alkyl groups, and $R^{10b}$ is $C_1$-$C_4$ alkyl optionally substituted by $C_1$-$C_6$ alkoxy.

Embodiments described herein relate to a compound of formula (IV), or a pharmaceutically acceptable salt thereof, wherein each $R^{13}$ and $R^{14}$ is hydrogen and each z is 1.

Embodiments described herein relate to a compound of formula (IV), or a pharmaceutically acceptable salt thereof, wherein $R^{10a}$ is —$(CH_2)$-(5-6 membered heteroaryl) optionally substituted by one or two $C_1$-$C_4$ alkyl groups and $R^{10b}$ is $C_1$-$C_4$ alkyl optionally substituted by $C_1$-$C_2$ alkoxy.

Embodiments described herein relate to a compound of formula (IV), or a pharmaceutically acceptable salt thereof, wherein $R^{10a}$ is —$CH_2$-pyridinyl and $R^{10b}$ is —$CH_2CH_2$—O—$CH_3$.

Embodiments described herein relate to a compound of formula (IV), or a pharmaceutically acceptable salt thereof, wherein $R^1$ is —$C(O)R^{10a}$ and $R^2$ is $C_3$-$C_6$ cycloalkyl optionally substituted by one or two $R^{15}$ groups.

Embodiments described herein relate to a compound of formula (IV), or a pharmaceutically acceptable salt thereof, wherein $R^{10a}$ is —$[C(R^{13})(R^{14})]_z$—$(C_4$-$C_{10}$ cycloalkyl), —$[C(R^{13})(R^{14})]Z$-(4-6 membered heterocycloalkyl), —$[C(R^{13})(R^{14})]_z$—$(C_6$-$C_{10}$ aryl), or —$[C(R^{13})(R^{14})]_z$-(5-10 membered heteroaryl) and $R^{10b}$ is —$[C(R^{13})(R^{14})]_z$—$(C_4$-$C_{10}$ cycloalkyl), —$[C(R^{13})(R^{14})]Z$-(4-6 membered heterocycloalkyl), —$[C(R^{13})(R^{14})]_z$—$(C_6$-$C_{10}$ aryl), or —$[C(R^{13})(R^{14})]_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ are each independently optionally substituted by one, two or three halogen, cyano, $C_1$-$C_6$ alkyl, hydroxy, $C_1$-$C_6$ alkoxy, —$(CH_2)_w$—$N(R^{11})(R^{12})$, —$(CH_2)_w$—$C(O)N(R^{11})(R^{12})$, —$C(O)OR^{11}$, —$N(R^{11})C(O)R^{12}$, —$S(O)_2R^{11}$, or —$S(O)N(R^{11})(R^{12})$ groups.

Embodiments described herein relate to a compound of formula (IV), or a pharmaceutically acceptable salt thereof, wherein each $R^{13}$ and $R^{14}$ is hydrogen and each z is 1.

Embodiments described herein relate to a compound of formula (IV), or a pharmaceutically acceptable salt thereof, wherein $R^{10a}$ is —$CH_2$-(5-6 membered heteroaryl) optionally substituted by one or two halogen or $C_1$-$C_4$ alkyl groups.

Embodiments described herein relate to a compound of formula (IV), or a pharmaceutically acceptable salt thereof, wherein $R^{10a}$ is —$CH_2$-pyridinyl optionally substituted by one or two $C_1$-$C_4$ alkyl groups and $R^2$ is cyclopropyl.

Embodiments described herein relate to a compound of formula (IV), or a pharmaceutically acceptable salt thereof, wherein L is

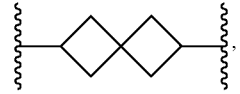 [SMILES: *C1CC2(C1)CC(*)C2]

x is 0 and y is 0.

Embodiments described herein relate to a compound of formula (IV), or a pharmaceutically acceptable salt thereof, wherein $R^1$ is —$C(O)R^{10a}$ and $R^2$ is hydrogen, $C_1$-$C_4$ alkyl, $C_3$-$C_6$ cycloalkyl, —$C(O)R^{10b}$, or 5-6 membered heteroaryl, wherein the $C_3$-$C_6$ cycloalkyl and the 5-6 membered heteroaryl are independently optionally substituted by one or two $R^{15}$ groups; or $R^2$ is —$C(O)R^{10b}$ and $R^1$ is hydrogen, $C_1$-$C_4$ alkyl, $C_3$-$C_6$ cycloalkyl, —$C(O)R^{10b}$, or 5-6 membered heteroaryl, wherein the $C_3$-$C_6$ cycloalkyl and the 5-6 membered heteroaryl are independently optionally substituted by one or two $R^{15}$ groups; or $R^1$ is —$C(O)R^{10a}$ and $R^2$ is —$C(O)R^{10b}$.

Embodiments described herein relate to a compound of formula (IV), or a pharmaceutically acceptable salt thereof, wherein $R^1$ is —C(O)$R^{10a}$ and $R^2$ is —C(O)$R^{10b}$.

Embodiments described herein relate to a compound of formula (IV), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —(CH$_2$)$_w$—N($R^{11}$)($R^{12}$), —(CH$_2$)$_w$—C(O)N($R^{11}$)($R^{12}$), —C(O)O$R^{11}$, —N($R^{11}$)C(O)$R^{12}$, —S(O)$_2R^{11}$, or —S(O)N($R^{11}$)($R^{12}$) groups.

Embodiments described herein relate to a compound of formula (IV), or a pharmaceutically acceptable salt thereof, wherein $R^{10a}$ is —[C($R^{13}$)($R^{14}$)]$_z$—($C_6$ aryl) or —[C($R^{13}$)($R^{14}$)]$_z$-(5-6 membered heteroaryl) and $R^{10b}$ is —[C($R^{13}$)($R^{14}$)]$_z$—($C_6$ aryl) or —[C($R^{13}$)($R^{14}$)]$_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (IV), or a pharmaceutically acceptable salt thereof, wherein $R^{10a}$ is —[C($R^{13}$)($R^{14}$)]$_z$-(5-6 membered heteroaryl) optionally substituted by one or two $C_1$-$C_4$ alkyl groups and $R^{10b}$ is —[C($R^{13}$)($R^{14}$)]$_z$-(5-6 membered heteroaryl) optionally substituted by one or two $C_1$-$C_4$ alkyl groups.

Embodiments described herein relate to a compound of formula (IV), or a pharmaceutically acceptable salt thereof, wherein $R^{10a}$ is —[C($R^{13}$)($R^{14}$)]$_z$-(5-6 membered heteroaryl) and $R^{10b}$ is —[C($R^{13}$)($R^{14}$)]$_z$-(5-6 membered heteroaryl), wherein the 5-6 membered heteroaryl in $R^{10a}$ and $R^{10b}$ are each independently optionally substituted by one or two $C_1$-$C_4$ alkyl groups.

Embodiments described herein relate to a compound of formula (IV), or a pharmaceutically acceptable salt thereof, wherein each $R^{13}$ and $R^{14}$ is hydrogen and each z is 1.

Embodiments described herein relate to a compound of formula (IV), or a pharmaceutically acceptable salt thereof, wherein $R^{10a}$ is —CH$_2$-pyridinyl optionally substituted by one or two $C_1$-$C_4$ alkyl groups and $R^{10b}$ is —CH$_2$-pyridinyl optionally substituted by one or two $C_1$-$C_4$ alkyl groups.

Embodiments described herein relate to a compound of formula (IV), or a pharmaceutically acceptable salt thereof, wherein $R^{10a}$ is —CH$_2$-pyrazolyl optionally substituted by one or two $C_1$-$C_4$ alkyl groups and $R^{10b}$ is —CH$_2$-pyrazolyl optionally substituted by one or two $C_1$-$C_4$ alkyl groups.

Embodiments described herein relate to a compound of formula (IV), or a pharmaceutically acceptable salt thereof, wherein L is

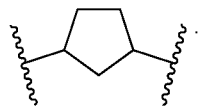 [SMILES: *C1CCC(*)C1]

Embodiments described herein relate to a compound of formula (IV), or a pharmaceutically acceptable salt thereof, wherein L is

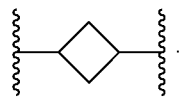 [SMILES: *C1CC(*)C1]

Embodiments described herein relate to a compound of formula (IV), or a pharmaceutically acceptable salt thereof, wherein
$R^1$ is —C(O)$R^{10a}$ and $R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^2$ is —C(O)$R^{10b}$ and $R^1$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or
$R^1$ is —C(O)$R^{10a}$ and $R^2$ is —C(O)$R^{10b}$.

Embodiments described herein relate to a compound of formula (IV), or a pharmaceutically acceptable salt thereof, wherein $R^1$ is —C(O)$R^{10a}$ and $R^2$ is —C(O)$R^{10b}$.

Embodiments described herein relate to a compound of formula (IV), or a pharmaceutically acceptable salt thereof, wherein
$R^1$ is —C(O)$R^{10a}$ and $R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or
$R^2$ is —C(O)$R^{10b}$ and $R^1$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or
$R^1$ is —C(O)$R^{10a}$ and $R^2$ is —C(O)$R^{10b}$.

Embodiments described herein relate to a compound of formula (IV), or a pharmaceutically acceptable salt thereof, wherein $R^1$ is —C(O)$R^{10a}$ and $R^2$ is —C(O)$R^{10b}$.

Embodiments described herein relate to a compound of formula (IV), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]—($C_6$-$C_{10}$ aryl), or —[C($R^{13}$)($R^{14}$)]$_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —($CH_2$)$_w$—N($R^{11}$)($R^{12}$), —($CH_2$)$_w$—C(O)N($R^{11}$)($R^{12}$), —C(O)O$R^{11}$, —N($R^{11}$)C(O)$R^{12}$, —S(O)$_2$$R^{11}$, or —S(O)N($R^{11}$)($R^{12}$) groups.

Embodiments described herein relate to a compound of formula (IV), or a pharmaceutically acceptable salt thereof, wherein $R^{10a}$ is —[C($R^{13}$)($R^{14}$)]$_z$—($C_6$ aryl) or —[C($R^{13}$)($R^{14}$)]$_z$-(5-6 membered heteroaryl) and $R^{10b}$ is —[C($R^{13}$)($R^{14}$)]$_z$—($C_6$ aryl), or —[C($R^{13}$)($R^{14}$)]$_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (IV), or a pharmaceutically acceptable salt thereof, wherein $R^{10a}$ is —[C($R^{13}$)($R^{14}$)]$_z$-(5-6 membered heteroaryl) and $R^{10b}$ is —[C($R^{13}$)($R^{14}$)]$_z$-(5-6 membered heteroaryl), wherein the 5-6 membered heteroaryl in $R^{10a}$ and $R^{10b}$ are each independently optionally substituted by one or two $C_1$-$C_4$ alkyl groups.

Embodiments described herein relate to a compound of formula (IV), or a pharmaceutically acceptable salt thereof, wherein each $R^{13}$ and $R^{14}$ is hydrogen and each z is 1.

Embodiments described herein relate to a compound of formula (IV), or a pharmaceutically acceptable salt thereof, wherein $R^{10a}$ is —$CH_2$-pyridinyl optionally substituted by one or two $C_1$-$C_4$ alkyl groups and $R^{10b}$ is —$CH_2$-pyridinyl optionally substituted by one or two $C_1$-$C_4$ alkyl groups.

Embodiments described herein relate to a compound of formula (IVa)

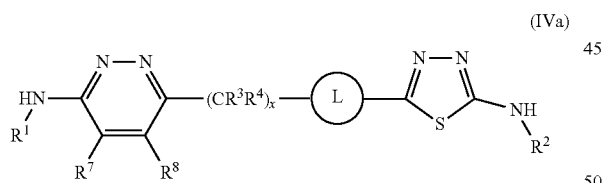

(IVa)

wherein

L is —($C_4$-$C_{10}$ cycloalkyl)- optionally substituted by one to three substituents selected from the group consisting of halogen, cyano, $C_1$-$C_4$ alkyl, hydroxy, and $C_1$-$C_4$ alkoxy;

$R^1$ is hydrogen, $C_1$-$C_4$ alkyl, $C_3$-$C_6$ cycloalkyl, —C(O)$R^{10a}$, or 5-6 membered heteroaryl, wherein the $C_3$-$C_6$ cycloalkyl and the 5-6 membered heteroaryl are independently optionally substituted by one or two $R^{15}$ groups;

$R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups;

$R^3$ and $R^4$ are each independently hydrogen, halogen, $C_1$-$C_4$ alkyl, $C_1$-$C_4$ alkoxy, or $C_3$-$C_6$ cycloalkyl;

$R^7$ and $R^8$ are each independently hydrogen, halogen, cyano, $C_1$-$C_2$ alkyl, hydroxy, $C_1$-$C_2$ alkoxy, or —N($R^{11}$)($R^{12}$), wherein the $C_1$-$C_2$ alkyl and the $C_1$-$C_2$ alkoxy are each independently optionally substituted by halogen or hydroxy;

$R^{10a}$ and $R^{11b}$ are each independently hydrogen, $C_1$-$C_4$ alkyl, —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl), wherein the $C_1$-$C_4$ alkyl, the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —($CH_2$)$_w$—N($R^{11}$)($R^{12}$), —($CH_2$)$_w$—C(O)N($R^{11}$)($R^{12}$), —C(O)O$R^{11}$, —N($R^{11}$)C(O)$R^{12}$, —S(O)$_2$$R^{11}$, or —S(O)N($R^{11}$)($R^{12}$) groups;

each $R^{11}$, $R^{12}$, $R^{13}$, $R^{14}$ and $R^{15}$ is independently hydrogen, $C_1$-$C_4$ alkyl, $C_1$-$C_4$ alkoxy, $C_3$-$C_6$ cycloalkyl, or 3-6 membered heterocycloalkyl, wherein the $C_1$-$C_4$ alkyl, the $C_3$-$C_6$ cycloalkyl, and the 3-6 membered heterocycloalkyl are each independently optionally substituted by one, two or three substituents selected from the group consisting of halogen, cyano, hydroxy, and methoxy;

w is 0, 1, 2 or 3;

x is 0 or 1; and z is 0, 1, 2 or 3;

or a pharmaceutically acceptable salt thereof.

Embodiments described herein relate to a compound of formula (IVa), or a pharmaceutically acceptable salt thereof, wherein x is 0.

Embodiments described herein relate to a compound of formula (IVa), or a pharmaceutically acceptable salt thereof, wherein x is 1.

Embodiments described herein relate to a compound of formula (IVa), or a pharmaceutically acceptable salt thereof, wherein L is

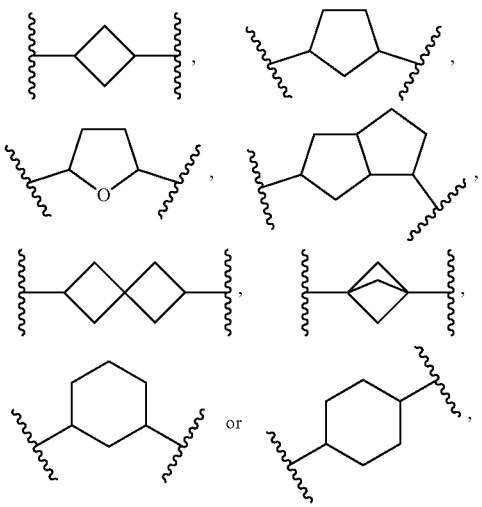

optionally substituted by one to three substituents selected from the group consisting of halogen, cyano, $C_1$-$C_4$ alkyl, hydroxy, and $C_1$-$C_4$ alkoxy.

Embodiments described herein relate to a compound of formula (IVa), or a pharmaceutically acceptable salt thereof, wherein L is

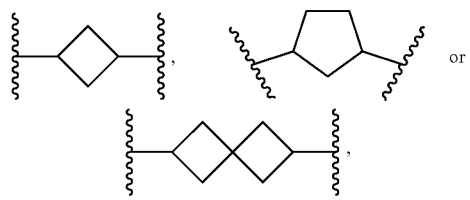

optionally substituted by one to three substituents selected from the group consisting of halogen, cyano, $C_1$-$C_4$ alkyl, hydroxy, and $C_1$-$C_4$ alkoxy.

Embodiments described herein relate to a compound of formula (IVa), or a pharmaceutically acceptable salt thereof, wherein $R^1$ is —C(O)$R^{10a}$ and $R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^2$ is —C(O)$R^{10b}$ and $R^1$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^1$ is —C(O)$R^{10a}$ and $R^2$ is —C(O)$R^{10b}$.

Embodiments described herein relate to a compound of formula (IVa), or a pharmaceutically acceptable salt thereof, wherein $R^{10a}$ is $C_1$-$C_4$ alkyl and $R^{10b}$ is $C_1$-$C_4$ alkyl.

Embodiments described herein relate to a compound of formula (IVa), or a pharmaceutically acceptable salt thereof, wherein $R^1$ is —C(O)$R^{10a}$ and $R^2$ is —C(O)$R^{10b}$.

Embodiments described herein relate to a compound of formula (IVa), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]—($C_6$-$C_{10}$ aryl), or —[C($R^{13}$)($R^{14}$)]$_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —($CH_2$)$_w$—N($R^{11}$)($R^{12}$), —($CH_2$)$_w$—C(O)N($R^{11}$)($R^{12}$), —C(O)O$R^{11}$, —N($R^{11}$)C(O)$R^{12}$, —S(O)$_2$$R^{11}$, or —S(O)N($R^{11}$)($R^{12}$) groups.

Embodiments described herein relate to a compound of formula (IVa), or a pharmaceutically acceptable salt thereof, wherein $R^{10a}$ is —[C($R^{13}$)($R^{14}$)]$_z$—($C_6$ aryl) or —[C($R^{13}$)($R^{14}$)]$_z$-(5-6 membered heteroaryl) and $R^{10b}$ is —[C($R^{13}$)($R^{14}$)]$_z$—($C_6$ aryl) or —[C($R^{13}$)($R^{14}$)]$_z$-(5-6 membered heteroaryl), wherein the 06 aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (IVa), or a pharmaceutically acceptable salt thereof, wherein at least one of $R^1$ and $R^2$ is $C_1$-$C_4$ alkyl.

Embodiments described herein relate to a compound of formula (IVa), or a pharmaceutically acceptable salt thereof, wherein $R^1$ and $R^2$ each independently $C_1$-$C_4$ alkyl.

Embodiments described herein relate to a compound of formula (IVa), or a pharmaceutically acceptable salt thereof, wherein at least one of $R^1$ and $R^2$ is hydrogen.

Embodiments described herein relate to a compound of formula (IVa), or a pharmaceutically acceptable salt thereof, wherein at least one of $R^1$ and $R^2$ is $C_3$-$C_6$ cycloalkyl optionally substituted by one or two $R^{15}$ groups.

Embodiments described herein relate to a compound of formula (IVa), or a pharmaceutically acceptable salt thereof, wherein at least one of $R^1$ and $R^2$ is 5-6 membered heteroaryl optionally substituted by one or two $R^{15}$ groups.

Embodiments described herein relate to a compound of formula (IVa), or a pharmaceutically acceptable salt thereof, wherein L is

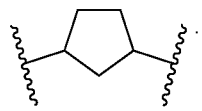 [SMILES: *C1CCC(*)C1]

Embodiments described herein relate to a compound of formula (IVa), or a pharmaceutically acceptable salt thereof, wherein $R^1$ is —C(O)$R^{10a}$ and $R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^2$ is —C(O)$R^{10b}$ and $R^1$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^1$ is —C(O)$R^{10a}$ and $R^2$ is —C(O)$R^{10b}$.

Embodiments described herein relate to a compound of formula (IVa), or a pharmaceutically acceptable salt thereof, wherein $R^1$ is —C(O)$R^{10a}$ and $R^2$ is —C(O)$R^{10b}$.

Embodiments described herein relate to a compound of formula (IVa), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —($CH_2$)$_w$—N($R^{11}$)($R^{12}$), —($CH_2$)$_w$—C(O)N($R^{11}$)($R^{12}$), —C(O)O$R^{11}$, —N($R^{11}$)C(O)$R^{12}$, —S(O)$_2$$R^{11}$, or —S(O)N($R^{11}$)($R^{12}$) groups.

Embodiments described herein relate to a compound of formula (IVa), or a pharmaceutically acceptable salt thereof, wherein $R^{10a}$ is —[C($R^{13}$)($R^{14}$)]$_z$—($C_6$ aryl) or —[C($R^{13}$)($R^{14}$)]$_z$-(5-6 membered heteroaryl) and $R^{10b}$ is —[C($R^{13}$)($R^{14}$)]$_z$—($C_6$ aryl), or —[C($R^{13}$)($R^{14}$)]$_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (IVa), or a pharmaceutically acceptable salt thereof, wherein $R^{10a}$ is —[C($R^{13}$)($R^{14}$)]$_z$-(5-6 membered heteroaryl) and $R^{10b}$ is —[C($R^{13}$)($R^{14}$)]$_z$-(5-6 membered heteroaryl), wherein the aryl and the heteroaryl in $R^{10a}$ and $R^{10b}$ are each independently optionally substituted by one or two $C_1$-$C_4$ alkyl groups.

Embodiments described herein relate to a compound of formula (IVa), or a pharmaceutically acceptable salt thereof, wherein each $R^{13}$ and $R^{14}$ is hydrogen and each z is 1.

Embodiments described herein relate to a compound of formula (IVa), or a pharmaceutically acceptable salt thereof, wherein $R^{10a}$ is —$CH_2$-pyridinyl and $R^{10b}$ is —$CH_2$-pyridinyl, wherein each pyridinyl is optionally substituted by one or two $C_1$-$C_4$ alkyl groups.

Embodiments described herein relate to a compound of formula (IVa), or a pharmaceutically acceptable salt thereof, wherein $R^{10a}$ is —$CH_2$-pyridinyl optionally substituted by one or two $C_1$-$C_4$ alkyl groups and $R^{10b}$ is —$CH_2$-pyrazolyl optionally substituted by one or two $C_1$-$C_4$ alkyl groups.

Embodiments described herein relate to a compound of formula (IVa), or a pharmaceutically acceptable salt thereof, wherein $R^{10a}$ is —$[C(R^{13})(R^{14})]_z$—($C_4$-$C_{10}$ cycloalkyl), —$[C(R^{13})(R^{14})]_z$-(4-6 membered heterocycloalkyl), —$[C(R^{13})(R^{14})]_z$—($C_6$-$C_{10}$ aryl), or —$[C(R^{13})(R^{14})]_z$-(5-10 membered heteroaryl) and $R^{10b}$ is —$[C(R^{13})(R^{14})]_z$—($C_4$-$C_{10}$ cycloalkyl), —$[C(R^{13})(R^{14})]Z$-(4-6 membered heterocycloalkyl), —$[C(R^{13})(R^{14})]_z$—($C_6$-$C_{10}$ aryl), or —$[C(R^{13})(R^{14})]_z$-(5-10 membered heteroaryl), and $R^{10b}$ is $C_1$-$C_4$ alkyl, wherein the $C_1$-$C_4$ alkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —$(CH_2)_w$—$N(R^{11})(R^{12})$, —$(CH_2)_w$—$C(O)N(R^{11})(R^{12})$, —$C(O)OR^{11}$, —$N(R^{11})C(O)R^{12}$, —$S(O)_2R^{11}$, or —$S(O)N(R^{11})(R^{12})$ groups.

Embodiments described herein relate to a compound of formula (IVa), or a pharmaceutically acceptable salt thereof, wherein $R^{10a}$ is —$[C(R^{13})(R^{14})]_z$—($C_6$ aryl) or —$[C(R^{13})(R^{14})]_z$-(5-6 membered heteroaryl), wherein the $C_6$ aryl and the 5-6 membered heteroaryl in $R^{10a}$ are each independently optionally substituted by one or two halogen or $C_1$-$C_4$ alkyl groups, and $R^{10b}$ is $C_1$-$C_4$ alkyl optionally substituted by $C_1$-$C_6$ alkoxy.

Embodiments described herein relate to a compound of formula (IVa), or a pharmaceutically acceptable salt thereof, wherein each $R^{13}$ and $R^{14}$ is hydrogen and each z is 1.

Embodiments described herein relate to a compound of formula (IVa), or a pharmaceutically acceptable salt thereof, wherein $R^{10a}$ is —$(CH_2)$-(5-6 membered heteroaryl) optionally substituted by one or two $C_1$-$C_4$ alkyl groups and $R^{10b}$ is $C_1$-$C_4$ alkyl optionally substituted by $C_1$-$C_2$ alkoxy.

Embodiments described herein relate to a compound of formula (IVa), or a pharmaceutically acceptable salt thereof, wherein $R^{10a}$ is —$CH_2$-pyridinyl and $R^{10b}$ is —$CH_2CH_2$—O—$CH_3$.

Embodiments described herein relate to a compound of formula (IVa), or a pharmaceutically acceptable salt thereof, wherein $R^1$ is —$C(O)R^{10a}$ and $R^2$ is $C_3$-$C_6$ cycloalkyl optionally substituted by one or two $R^{15}$ groups.

Embodiments described herein relate to a compound of formula (IVa), or a pharmaceutically acceptable salt thereof, wherein $R^{10a}$ is —$[C(R^{13})(R^{14})]_z$—($C_4$-$C_{10}$ cycloalkyl), —$[C(R^{13})(R^{14})]Z$-(4-6 membered heterocycloalkyl), —$[C(R^{13})(R^{14})]_z$—($C_6$-$C_{10}$ aryl), or —$[C(R^{13})(R^{14})]_z$-(5-10 membered heteroaryl) and $R^{10b}$ is —$[C(R^{13})(R^{14})]_z$—($C_4$-$C_{10}$ cycloalkyl), —$[C(R^{13})(R^{14})]Z$-(4-6 membered heterocycloalkyl), —$[C(R^{13})(R^{14})]_z$—($C_6$-$C_{10}$ aryl), or —$[C(R^{13})(R^{14})]_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ are each independently optionally substituted by one, two or three halogen, cyano, $C_1$-$C_6$ alkyl, hydroxy, $C_1$-$C_6$ alkoxy, —$(CH_2)_w$—$N(R^{11})(R^{12})$, —$(CH_2)_w$—$C(O)N(R^{11})(R^{12})$, —$C(O)OR^{11}$, —$N(R^{11})C(O)R^{12}$, —$S(O)_2R^{11}$, or —$S(O)N(R^{11})(R^{12})$ groups.

Embodiments described herein relate to a compound of formula (IVa), or a pharmaceutically acceptable salt thereof, wherein each $R^{13}$ and $R^{14}$ is hydrogen and each z is 1.

Embodiments described herein relate to a compound of formula (IVa), or a pharmaceutically acceptable salt thereof, wherein $R^{10a}$ is —$CH_2$-(5-6 membered heteroaryl) optionally substituted by one or two halogen or $C_1$-$C_4$ alkyl groups.

Embodiments described herein relate to a compound of formula (IVa), or a pharmaceutically acceptable salt thereof, wherein $R^{10a}$ is —$CH_2$-pyridinyl optionally substituted by one or two $C_1$-$C_4$ alkyl groups and $R^2$ is cyclopropyl.

Embodiments described herein relate to a compound of formula (IVa), or a pharmaceutically acceptable salt thereof, wherein L is

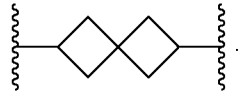

Embodiments described herein relate to a compound of formula (IVa), or a pharmaceutically acceptable salt thereof, wherein $R^1$ is —$C(O)R^{10a}$ and $R^2$ is hydrogen, $C_1$-$C_4$ alkyl, $C_3$-$C_6$ cycloalkyl, —$C(O)R^{10b}$, or 5-6 membered heteroaryl, wherein the $C_3$-$C_6$ cycloalkyl and the 5-6 membered heteroaryl are independently optionally substituted by one or two $R^{15}$ groups; or $R^2$ is —$C(O)R^{10b}$ and $R^1$ is hydrogen, $C_1$-$C_4$ alkyl, $C_3$-$C_6$ cycloalkyl, —$C(O)R^{10b}$, or 5-6 membered heteroaryl, wherein the $C_3$-$C_6$ cycloalkyl and the 5-6 membered heteroaryl are independently optionally substituted by one or two $R^{15}$ groups; or $R^1$ is —$C(O)R^{10a}$ and $R^2$ is —$C(O)R^{10b}$.

Embodiments described herein relate to a compound of formula (IVa), or a pharmaceutically acceptable salt thereof, wherein $R^1$ is —$C(O)R^{10a}$ and $R^2$ is —$C(O)R^{10b}$.

Embodiments described herein relate to a compound of formula (IVa), or a pharmaceutically acceptable salt thereof, wherein $R^{10a}$ is —$[C(R^{13})(R^{14})]_z$—($C_4$-$C_{10}$ cycloalkyl), —$[C(R^{13})(R^{14})]_z$-(4-6 membered heterocycloalkyl), —$[C(R^{13})(R^{14})]$—($C_6$-$C_{10}$ aryl), or —$[C(R^{13})(R^{14})]_z$-(5-10 membered heteroaryl) and $R^{10b}$ is —$[C(R^{13})(R^{14})]_z$—($C_4$-$C_{10}$ cycloalkyl), —$[C(R^{13})(R^{14})]_z$-(4-6 membered heterocycloalkyl), —$[C(R^{13})(R^{14})]$—($C_6$-$C_{10}$ aryl), or —$[C(R^{13})(R^{14})]_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —$(CH_2)_w$—$N(R^{11})(R^{12})$, —$(CH_2)_w$—$C(O)N(R^{11})(R^{12})$, —$C(O)OR^{11}$, —$N(R^{11})C(O)R^{12}$, —$S(O)_2R^{11}$, or —$S(O)N(R^{11})(R^{12})$ groups.

Embodiments described herein relate to a compound of formula (IVa), or a pharmaceutically acceptable salt thereof, wherein $R^{10a}$ is —$[C(R^{13})(R^{14})]_z$—($C_6$ aryl) or —$[C(R^{13})(R^{14})]_z$-(5-6 membered heteroaryl) and $R^{10b}$ is —$[C(R^{13})(R^{14})]_z$—($C_6$ aryl) or —$[C(R^{13})(R^{14})]_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (IVa), or a pharmaceutically acceptable salt thereof, wherein $R^{10a}$ is —[C($R^{13}$)($R^{14}$)]$_z$-(5-6 membered heteroaryl) optionally substituted by one or two $C_1$-$C_4$ alkyl groups and $R^{10b}$ is —[C($R^{13}$)($R^{14}$)]$_z$-(5-6 membered heteroaryl) optionally substituted by one or two $C_1$-$C_4$ alkyl groups.

Embodiments described herein relate to a compound of formula (IVa), or a pharmaceutically acceptable salt thereof, wherein $R^{10a}$ is —$CH_2$-pyrazolyl optionally substituted by one or two $C_1$-$C_4$ alkyl groups and $R^{10b}$ is —$CH_2$-pyrazolyl optionally substituted by one or two $C_1$-$C_4$ alkyl groups.

Embodiments described herein relate to a compound of formula (IVa), or a pharmaceutically acceptable salt thereof, wherein L is

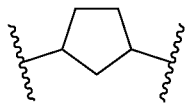

Embodiments described herein relate to a compound of formula (IVa), or a pharmaceutically acceptable salt thereof, wherein $R^1$ is —C(O)$R^{10a}$ and $R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^2$ is —C(O)$R^{10b}$ and $R^1$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^1$ is —C(O)$R^{10a}$ and $R^2$ is —C(O)$R^{10b}$.

Embodiments described herein relate to a compound of formula (IVa), or a pharmaceutically acceptable salt thereof, wherein $R^1$ is —C(O)$R^{10a}$ and $R^2$ is —C(O)$R^{10b}$.

Embodiments described herein relate to a compound of formula (IVa), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —($CH_2$)$_w$—N($R^{11}$)($R^{12}$), —($CH_2$)$_w$—C(O)N($R^{11}$)($R^{12}$), —C(O)O$R^{11}$, —N($R^{11}$)C(O)$R^{12}$, —S(O)$_2R^{11}$, or —S(O)N($R^{11}$)($R^{12}$) groups.

Embodiments described herein relate to a compound of formula (IVa), or a pharmaceutically acceptable salt thereof, wherein $R^{10a}$ is —[C($R^{13}$)($R^{14}$)]$_z$—($C_6$ aryl) or —[C($R^{13}$)($R^{14}$)]$_z$-(5-6 membered heteroaryl) and $R^{10b}$ is —[C($R^{13}$)($R^{14}$)]$_z$—($C_6$ aryl) or —[C($R^{13}$)($R^{14}$)]$_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (IVa), or a pharmaceutically acceptable salt thereof, wherein $R^{10a}$ is —[C($R^{13}$)($R^{14}$)]$_z$-(5-6 membered heteroaryl) and $R^{10b}$ is —[C($R^{13}$)($R^{14}$)]$_z$-(5-6 membered heteroaryl), wherein the 5-6 membered heteroaryl in $R^{10a}$ and $R^{10b}$ are each independently optionally substituted by one or two $C_1$-$C_4$ alkyl groups.

Embodiments described herein relate to a compound of formula (IVa), or a pharmaceutically acceptable salt thereof, wherein each $R^{13}$ and $R^{14}$ is hydrogen and each z is 1.

Embodiments described herein relate to a compound of formula (IVa), or a pharmaceutically acceptable salt thereof, wherein $R^{10a}$ is —$CH_2$-pyridinyl optionally substituted by one or two $C_1$-$C_4$ alkyl groups and $R^{10b}$ is —$CH_2$-pyridinyl optionally substituted by one or two $C_1$-$C_4$ alkyl groups.

Embodiments described herein relate to a compound of formula (IVa), or a pharmaceutically acceptable salt thereof, wherein L is

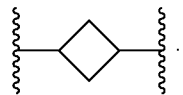

Embodiments described herein relate to a compound of formula (IVa), or a pharmaceutically acceptable salt thereof, wherein $R^1$ is —C(O)$R^{10a}$ and $R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^2$ is —C(O)$R^{10b}$ and $R^1$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^1$ is —C(O)$R^{10a}$ and $R^2$ is —C(O)$R^{10b}$.

Embodiments described herein relate to a compound of formula (IVa), or a pharmaceutically acceptable salt thereof, wherein $R^1$ is —C(O)$R^{10a}$ and $R^2$ is —C(O)$R^{10b}$.

Embodiments described herein relate to a compound of formula (IVa), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —($CH_2$)$_w$—N($R^{11}$)($R^{12}$), —($CH_2$)$_w$—C(O)N($R^{11}$)($R^{12}$), —C(O)O$R^{11}$, —N($R^{11}$)C(O)$R^{12}$, —S(O)$_2R^{11}$, or —S(O)N($R^{11}$)($R^{12}$) groups.

Embodiments described herein relate to a compound of formula (IVa), or a pharmaceutically acceptable salt thereof, wherein $R^{10a}$ is —[C($R^{13}$)($R^{14}$)]$_z$—($C_6$ aryl) or —[C($R^{13}$)($R^{14}$)]$_z$-(5-6 membered heteroaryl) and $R^{10b}$ is —[C($R^{13}$)($R^{14}$)]$_z$—($C_6$ aryl), or —[C($R^{13}$)($R^{14}$)]$_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (IVa), or a pharmaceutically acceptable salt thereof, wherein $R^{10a}$ is —[C($R^{13}$)($R^{14}$)]$_z$-(5-6 membered heteroaryl) and $R^{10b}$ is —[C($R^{13}$)($R^{14}$)]$_z$-(5-6 membered heteroaryl), wherein the 5-6 membered heteroaryl in $R^{10a}$ and $R^{10b}$ are each independently optionally substituted by one or two $C_1$-$C_4$ alkyl groups.

Embodiments described herein relate to a compound of formula (IVa), or a pharmaceutically acceptable salt thereof, wherein each $R^{13}$ and $R^{14}$ is hydrogen and each z is 1.

Embodiments described herein relate to a compound of formula (IVa), or a pharmaceutically acceptable salt thereof, wherein $R^{10a}$ is —$CH_2$-pyridinyl optionally substituted by one or two $C_1$-$C_4$ alkyl groups and $R^{10b}$ is —$CH_2$-pyridinyl optionally substituted by one or two $C_1$-$C_4$ alkyl groups.

Embodiments described herein relate to a compound of formula (IVb)

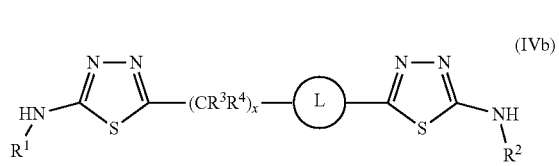

(IVb)

wherein

L is —($C_4$-$C_{10}$ cycloalkyl)- optionally substituted by one to three substituents selected from the group consisting of halogen, cyano, $C_1$-$C_4$ alkyl, hydroxy, and $C_1$-$C_4$ alkoxy;

$R^1$ is hydrogen, $C_1$-$C_4$ alkyl, $C_3$-$C_6$ cycloalkyl, —C(O)$R^{10a}$, or 5-6 membered heteroaryl, wherein the $C_3$-$C_6$ cycloalkyl and the 5-6 membered heteroaryl are independently optionally substituted by one or two $R^{15}$ groups;

$R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups;

$R^3$ and $R^4$ are each independently hydrogen, halogen, $C_1$-$C_4$ alkyl, $C_1$-$C_4$ alkoxy, or $C_3$-$C_6$ cycloalkyl;

$R^{10a}$ and $R^{11b}$ are each independently hydrogen, $C_1$-$C_4$ alkyl, —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]—($C_6$-$C_{10}$ aryl), or —[C($R^{13}$)($R^{14}$)]$_z$-(5-10 membered heteroaryl), wherein the $C_1$-$C_4$ alkyl, the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —($CH_2$)$_w$—N($R^{11}$)($R^{12}$), —($CH_2$)$_w$—C(O)N($R^{11}$)($R^{12}$), —C(O)O$R^{11}$, —N($R^{11}$)C(O)$R^{12}$, —S(O)$_2R^{11}$, or —S(O)N($R^{11}$)($R^{12}$) groups;

each $R^{11}$, $R^{12}$, $R^{13}$, $R^{14}$ and $R^{15}$ is independently hydrogen, $C_1$-$C_4$ alkyl, $C_1$-$C_4$ alkoxy, $C_3$-$C_6$ cycloalkyl, or 3-6 membered heterocycloalkyl, wherein the $C_1$-$C_4$ alkyl, the $C_3$-$C_6$ cycloalkyl, and the 3-6 membered heterocycloalkyl are each independently optionally substituted by one, two or three substituents selected from the group consisting of halogen, cyano, hydroxy, and methoxy;

w is 0, 1, 2 or 3;

x is 0 or 1; and z is 0, 1, 2 or 3;

or a pharmaceutically acceptable salt thereof.

Embodiments described herein relate to a compound of formula (IVb), or a pharmaceutically acceptable salt thereof, wherein x is 0.

Embodiments described herein relate to a compound of formula (IVb), or a pharmaceutically acceptable salt thereof, wherein x is 1.

Embodiments described herein relate to a compound of formula (IVb), or a pharmaceutically acceptable salt thereof, wherein L is

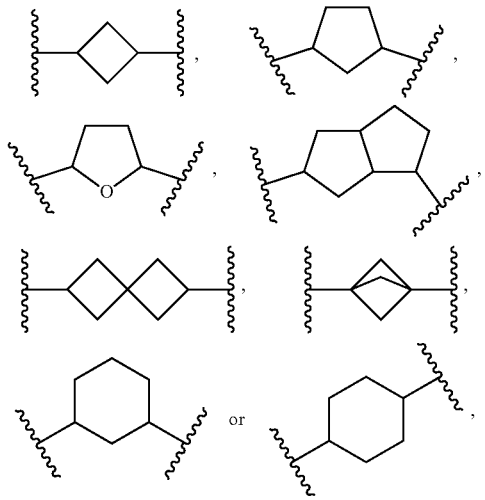

optionally substituted by one to three substituents selected from the group consisting of halogen, cyano, $C_1$-$C_4$ alkyl, hydroxy, and $C_1$-$C_4$ alkoxy.

Embodiments described herein relate to a compound of formula (IVb), or a pharmaceutically acceptable salt thereof, wherein L is

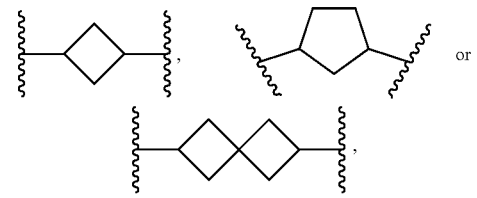

optionally substituted by one to three substituents selected from the group consisting of halogen, cyano, $C_1$-$C_4$ alkyl, hydroxy, and $C_1$-$C_4$ alkoxy.

Embodiments described herein relate to a compound of formula (IVb), or a pharmaceutically acceptable salt thereof, wherein $R^1$ is —C(O)$R^{10a}$ and $R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^2$ is —C(O)$R^{10b}$ and $R^1$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^1$ is —C(O)$R^{10a}$ and $R^2$ is —C(O)$R^{10b}$.

Embodiments described herein relate to a compound of formula (IVb), or a pharmaceutically acceptable salt thereof, wherein $R^{10a}$ is $C_1$-$C_4$ alkyl and $R^{10b}$ is $C_1$-$C_4$ alkyl.

Embodiments described herein relate to a compound of formula (IVb), or a pharmaceutically acceptable salt thereof, wherein $R^1$ is —C(O)$R^{10a}$ and $R^2$ is —C(O)$R^{10b}$.

Embodiments described herein relate to a compound of formula (IVb), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]Z-(4-6 membered heterocycloalkyl), —[C($R^{13}$)($R^{14}$)]—($C_6$-$C_{10}$ aryl), or —[C($R^{13}$)($R^{14}$)]$_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —($CH_2$)$_w$—N($R^{11}$)($R^{12}$), —($CH_2$)$_w$—C(O)N($R^{11}$)($R^{12}$), —C(O)O$R^{11}$, —N($R^{11}$)C(O)$R^{12}$, —S(O)$_2R^{11}$, or —S(O)N($R^{11}$)($R^{12}$) groups.

Embodiments described herein relate to a compound of formula (IVb), or a pharmaceutically acceptable salt thereof, wherein $R^{10a}$ is —[C($R^{13}$)($R^{14}$)]$_z$—($C_6$ aryl) or —[C($R^{13}$)($R^{14}$)]$_z$-(5-6 membered heteroaryl) and $R^{10b}$ is —[C($R^{13}$)($R^{14}$)]$_z$—($C_6$ aryl) or —[C($R^{13}$)($R^{14}$)]$_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (IVb), or a pharmaceutically acceptable salt thereof, wherein at least one of $R^1$ and $R^2$ is $C_1$-$C_4$ alkyl.

Embodiments described herein relate to a compound of formula (IVb), or a pharmaceutically acceptable salt thereof, wherein $R^1$ and $R^2$ each independently $C_1$-$C_4$ alkyl.

Embodiments described herein relate to a compound of formula (IVb), or a pharmaceutically acceptable salt thereof, wherein at least one of $R^1$ and $R^2$ is hydrogen.

Embodiments described herein relate to a compound of formula (IVb), or a pharmaceutically acceptable salt thereof, wherein at least one of $R^1$ and $R^2$ is $C_3$-$C_6$ cycloalkyl optionally substituted by one or two $R^{15}$ groups.

Embodiments described herein relate to a compound of formula (IVb), or a pharmaceutically acceptable salt thereof, wherein at least one of $R^1$ and $R^2$ is 5-6 membered heteroaryl optionally substituted by one or two $R^{15}$ groups.

Embodiments described herein relate to a compound of formula (IVb), or a pharmaceutically acceptable salt thereof, wherein L is

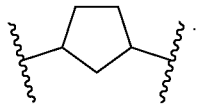 [SMILES: *C1CCC(*)C1]

Embodiments described herein relate to a compound of formula (IVb), or a pharmaceutically acceptable salt thereof, wherein $R^1$ is —C(O)$R^{10a}$ and $R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^2$ is —C(O)$R^{10b}$ and $R^1$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^1$ is —C(O)$R^{10a}$ and $R^2$ is —C(O)$R^{10b}$.

Embodiments described herein relate to a compound of formula (IVb), or a pharmaceutically acceptable salt thereof, wherein $R^1$ is —C(O)$R^{10a}$ and $R^2$ is —C(O)$R^{10b}$.

Embodiments described herein relate to a compound of formula (IVb), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —($CH_2$)$_w$—N($R^{11}$)($R^{12}$), —($CH_2$)$_w$—C(O)N($R^{11}$)($R^{12}$), —C(O)O$R^{11}$, —N($R^{11}$)C(O)$R^{12}$, —S(O)$_2R^{11}$, or —S(O)N($R^{11}$)($R^{12}$) groups.

Embodiments described herein relate to a compound of formula (IVb), or a pharmaceutically acceptable salt thereof, wherein $R^{10a}$ is —[C($R^{13}$)($R^{14}$)]$_z$—($C_6$ aryl) or —[C($R^{13}$)($R^{14}$)]$_z$-(5-6 membered heteroaryl) and $R^{10b}$ is —[C($R^{13}$)($R^{14}$)]$_z$—($C_6$ aryl), or —[C($R^{13}$)($R^{14}$)]$_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (IVb), or a pharmaceutically acceptable salt thereof, wherein $R^{10a}$ is —[C($R^{13}$)($R^{14}$)]$_z$-(5-6 membered heteroaryl) and $R^{10b}$ is —[C($R^{13}$)($R^{14}$)]$_z$-(5-6 membered heteroaryl), wherein the aryl and the heteroaryl in $R^{10a}$ and $R^{10b}$ are each independently optionally substituted by one or two $C_1$-$C_4$ alkyl groups.

Embodiments described herein relate to a compound of formula (IVb), or a pharmaceutically acceptable salt thereof, wherein each $R^{13}$ and $R^{14}$ is hydrogen and each z is 1.

Embodiments described herein relate to a compound of formula (IVb), or a pharmaceutically acceptable salt thereof, wherein $R^{10a}$ is —$CH_2$-pyridinyl and $R^{10b}$ is —$CH_2$-pyridinyl, wherein each pyridinyl is optionally substituted by one or two $C_1$-$C_4$ alkyl groups.

Embodiments described herein relate to a compound of formula (IVb), or a pharmaceutically acceptable salt thereof, wherein $R^{10a}$ is —$CH_2$-pyridinyl optionally substituted by one or two $C_1$-$C_4$ alkyl groups and $R^{10b}$ is —$CH_2$-pyrazolyl optionally substituted by one or two $C_1$-$C_4$ alkyl groups.

Embodiments described herein relate to a compound of formula (IVb), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl), and $R^{10b}$ is $C_1$-$C_4$ alkyl, wherein the $C_1$-$C_4$ alkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —($CH_2$)$_w$—N($R^{11}$)($R^{12}$), —($CH_2$)$_w$—C(O)N($R^{11}$)($R^{12}$), —C(O)O$R^{11}$, —N($R^{11}$)C(O)$R^{12}$, —S(O)$_2R^{11}$, or —S(O)N($R^{11}$)($R^{12}$) groups.

Embodiments described herein relate to a compound of formula (IVb), or a pharmaceutically acceptable salt thereof, wherein $R^{10a}$ is —[C($R^{13}$)($R^{14}$)]$_z$—($C_6$ aryl) or —[C($R^{13}$)($R^{14}$)]$_z$-(5-6 membered heteroaryl), wherein the $C_6$ aryl and the 5-6 membered heteroaryl in $R^{10a}$ are each independently optionally substituted by one or two halogen or $C_1$-$C_4$ alkyl groups, and $R^{10b}$ is $C_1$-$C_4$ alkyl optionally substituted by $C_1$-$C_6$ alkoxy.

Embodiments described herein relate to a compound of formula (IVb), or a pharmaceutically acceptable salt thereof, wherein each $R^{13}$ and $R^{14}$ is hydrogen and each z is 1.

Embodiments described herein relate to a compound of formula (IVb), or a pharmaceutically acceptable salt thereof, wherein $R^{10a}$ is —($CH_2$)-(5-6 membered heteroaryl) optionally substituted by one or two $C_1$-$C_4$ alkyl groups and $R^{10b}$ is $C_1$-$C_4$ alkyl optionally substituted by $C_1$-$C_2$ alkoxy.

Embodiments described herein relate to a compound of formula (IVb), or a pharmaceutically acceptable salt thereof, wherein $R^{10a}$ is —$CH_2$-pyridinyl and $R^{10b}$ is —$CH_2CH_2$—O—$CH_3$.

Embodiments described herein relate to a compound of formula (IVb), or a pharmaceutically acceptable salt thereof, wherein $R^1$ is —C(O)$R^{10a}$ and $R^2$ is $C_3$-$C_6$ cycloalkyl optionally substituted by one or two $R^{15}$ groups.

Embodiments described herein relate to a compound of formula (IVb), or a pharmaceutically acceptable salt thereof, wherein $R^{10a}$ is —[C($R^{13}$)($R^{14}$)]—($C_4$-$C_{10}$ cycloalkyl), —[C($R^{13}$)($R^{14}$)]Z-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]Z-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ are each independently optionally substituted by one, two or three halogen, cyano, $C_1$-$C_6$ alkyl, hydroxy, $C_1$-$C_6$ alkoxy, —($CH_2$)$_w$—N($R^{11}$)($R^{12}$), —($CH_2$)$_w$—C(O)N($R^{11}$)($R^{12}$), —C(O)O$R^{11}$, —N($R^{11}$)C(O)$R^{12}$, —S(O)$_2R^{11}$, or —S(O)N($R^{11}$)($R^{12}$) groups.

Embodiments described herein relate to a compound of formula (IVb), or a pharmaceutically acceptable salt thereof, wherein each $R^{13}$ and $R^{14}$ is hydrogen and each z is 1.

Embodiments described herein relate to a compound of formula (IVb), or a pharmaceutically acceptable salt thereof, wherein $R^{10a}$ is —$CH_2$-(5-6 membered heteroaryl) optionally substituted by one or two halogen or $C_1$-$C_4$ alkyl groups.

Embodiments described herein relate to a compound of formula (IVb), or a pharmaceutically acceptable salt thereof, wherein $R^{10a}$ is —$CH_2$-pyridinyl optionally substituted by one or two $C_1$-$C_4$ alkyl groups and $R^2$ is cyclopropyl.

Embodiments described herein relate to a compound of formula (IVb), or a pharmaceutically acceptable salt thereof, wherein L is

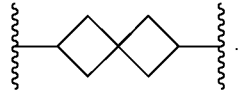

Embodiments described herein relate to a compound of formula (IVb), or a pharmaceutically acceptable salt thereof, wherein $R^1$ is —C(O)$R^{10a}$ and $R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^2$ is —C(O)$R^{10b}$ and $R^1$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^1$ is —C(O)$R^{10a}$ and $R^2$ is —C(O)$R^{10b}$.

Embodiments described herein relate to a compound of formula (IVb), or a pharmaceutically acceptable salt thereof, wherein $R^1$ is —C(O)$R^{10a}$ and $R^2$ is —C(O)$R^{10b}$.

Embodiments described herein relate to a compound of formula (IVb), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —($CH_2$)$_w$—N($R^{11}$)($R^{12}$), —($CH_2$)$_w$—C(O)N($R^{11}$)($R^{12}$), —C(O)O$R^{11}$, —N($R^{11}$)C(O)$R^{12}$, —S(O)$_2R^{11}$, or —S(O)N($R^{11}$)($R^{12}$) groups.

Embodiments described herein relate to a compound of formula (IVb), or a pharmaceutically acceptable salt thereof, wherein $R^{10a}$ is —[C($R^{13}$)($R^{14}$)]$_z$—($C_6$ aryl) or —[C($R^{13}$)($R^{14}$)]$_z$-(5-6 membered heteroaryl) and $R^{10b}$ is —[C($R^{13}$)($R^{14}$)]$_z$—($C_6$ aryl) or —[C($R^{13}$)($R^{14}$)]$_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (IVb), or a pharmaceutically acceptable salt thereof, wherein $R^{10a}$ is —[C($R^{13}$)($R^{14}$)]$_z$-(5-6 membered heteroaryl) optionally substituted by one or two $C_1$-$C_4$ alkyl groups and $R^{10b}$ is —[C($R^{13}$)($R^{14}$)]$_z$-(5-6 membered heteroaryl) optionally substituted by one or two $C_1$-$C_4$ alkyl groups.

Embodiments described herein relate to a compound of formula (IVb), or a pharmaceutically acceptable salt thereof, wherein $R^{10a}$ is —$CH_2$-pyrazolyl optionally substituted by one or two $C_1$-$C_4$ alkyl groups and $R^{10b}$ is —$CH_2$-pyrazolyl optionally substituted by one or two $C_1$-$C_4$ alkyl groups.

Embodiments described herein relate to a compound of formula (IVb), or a pharmaceutically acceptable salt thereof, wherein L is

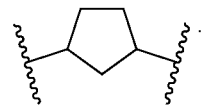 [SMILES: *C1CCC(*)C1]

Embodiments described herein relate to a compound of formula (IVb), or a pharmaceutically acceptable salt thereof, wherein $R^1$ is —C(O)$R^{10a}$ and $R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^2$ is —C(O)$R^{10b}$ and $R^1$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or $R^1$ is —C(O)$R^{10a}$ and $R^2$ is —C(O)$R^{10b}$.

Embodiments described herein relate to a compound of formula (IVb), or a pharmaceutically acceptable salt thereof, wherein $R^1$ is —C(O)$R^{10a}$ and $R^2$ is —C(O)$R^{10b}$.

Embodiments described herein relate to a compound of formula (IVb), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —(CH$_2$)$_w$—N($R^{11}$)($R^{12}$), —(CH$_2$)$_w$—C(O)N($R^{11}$)($R^{12}$), —C(O)O$R^{11}$, —N($R^{11}$)C(O)$R^{12}$, —S(O)$_2R^{11}$, or —S(O)N($R^{11}$)($R^{12}$) groups.

Embodiments described herein relate to a compound of formula (IVb), or a pharmaceutically acceptable salt thereof, wherein $R^{10a}$ is —[C($R^{13}$)($R^{14}$)]$_z$—($C_6$ aryl) or —[C($R^{13}$)($R^{14}$)]$_z$-(5-6 membered heteroaryl) and $R^{10b}$ is —[C($R^{13}$)($R^{14}$)]$_z$—($C_6$ aryl) or —[C($R^{13}$)($R^{14}$)]$_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (IVb), or a pharmaceutically acceptable salt thereof, wherein $R^{10a}$ is —[C($R^{13}$)($R^{14}$)]$_z$-(5-6 membered heteroaryl) and $R^{10b}$ is —[C($R^{13}$)($R^{14}$)]$_z$-(5-6 membered heteroaryl), wherein the 5-6 membered heteroaryl in $R^{10a}$ and $R^{10b}$ are each independently optionally substituted by one or two $C_1$-$C_4$ alkyl groups.

Embodiments described herein relate to a compound of formula (IVb), or a pharmaceutically acceptable salt thereof, wherein each $R^{13}$ and $R^{14}$ is hydrogen and each z is 1.

Embodiments described herein relate to a compound of formula (IVb), or a pharmaceutically acceptable salt thereof, wherein $R^{10a}$ is —CH$_2$-pyridinyl optionally substituted by one or two $C_1$-$C_4$ alkyl groups and $R^{10b}$ is —CH$_2$-pyridinyl optionally substituted by one or two $C_1$-$C_4$ alkyl groups.

Embodiments described herein relate to a compound of formula (IVb), or a pharmaceutically acceptable salt thereof, wherein L is

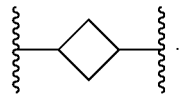

Embodiments described herein relate to a compound of formula (IVb), or a pharmaceutically acceptable salt thereof, wherein
$R^1$ is —C(O)$R^{10a}$ and $R^2$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or
$R^2$ is —C(O)$R^{10b}$ and $R^1$ is hydrogen, $C_1$-$C_4$ alkyl, $C_3$-$C_6$ cycloalkyl, —C(O)$R^{10b}$, or 5-6 membered heteroaryl, wherein the $C_3$-$C_6$ cycloalkyl and the 5-6 membered heteroaryl are independently optionally substituted by one or two $R^{15}$ groups; or
$R^1$ is —C(O)$R^{10a}$ and $R^2$ is —C(O)$R^{10b}$.

Embodiments described herein relate to a compound of formula (IVb), or a pharmaceutically acceptable salt thereof, wherein $R^1$ is —C(O)$R^{10a}$ and $R^2$ is —C(O)$R^{10b}$.

Embodiments described herein relate to a compound of formula (IVb), or a pharmaceutically acceptable salt thereof, wherein $R^{10a}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl) and $R^{10b}$ is —[C($R^{13}$)($R^{14}$)]$_z$—($C_4$-$C_{10}$ cycloalkyl), —[C($R^{13}$)($R^{14}$)]$_z$-(4-6 membered heterocycloalkyl), —[C($R^{13}$)($R^{14}$)]$_z$—($C_6$-$C_{10}$ aryl), or —[C($R^{13}$)($R^{14}$)]$_z$-(5-10 membered heteroaryl), wherein the $C_4$-$C_{10}$ cycloalkyl, the 4-6 membered heterocycloalkyl, the $C_6$-$C_{10}$ aryl, and the 5-10 membered heteroaryl in $R^{10a}$ and $R^{10b}$ are each independently optionally substituted by one, two or three halogen, cyano, $C_1$-$C_6$ alkyl, hydroxy, $C_1$-$C_6$ alkoxy, —(CH$_2$)$_w$—N($R^{11}$)($R^{12}$), —(CH$_2$)$_w$—C(O)N($R^{11}$)($R^{12}$), —C(O)O$R^{11}$, —N($R^{11}$)C(O)$R^{12}$, —S(O)$_2R^{11}$, or —S(O)N($R^{11}$)($R^{12}$) groups.

Embodiments described herein relate to a compound of formula (IVb), or a pharmaceutically acceptable salt thereof, wherein $R^{10a}$ is —[C($R^{13}$)($R^{14}$)]$_z$—($C_6$ aryl) or —[C($R^{13}$)($R^{14}$)]$_z$-(5-6 membered heteroaryl) and $R^{10b}$ is —[C($R^{13}$)($R^{14}$)]$_z$—($C_6$ aryl), or —[C($R^{13}$)($R^{14}$)]$_z$-(5-6 membered heteroaryl), wherein the $C_6$ aryl and the 5-6 membered heteroaryl in $R^{10a}$ and $R^{10b}$ are each independently optionally substituted by one or two halogen or $C_1$-$C_4$ alkyl groups.

Embodiments described herein relate to a compound of formula (IVb), or a pharmaceutically acceptable salt thereof, wherein $R^{10a}$ is —[C($R^{13}$)($R^{14}$)]$_z$-(5-6 membered heteroaryl) and $R^{10b}$ is —[C($R^{13}$)($R^{14}$)]$_z$-(5-6 membered heteroaryl), wherein the 5-6 membered heteroaryl in $R^{10a}$ and $R^{10b}$ are each independently optionally substituted by one or two $C_1$-$C_4$ alkyl groups.

Embodiments described herein relate to a compound of formula (IVb), or a pharmaceutically acceptable salt thereof, wherein each $R^{13}$ and $R^{14}$ is hydrogen and each z is 1.

Embodiments described herein relate to a compound of formula (IVb), or a pharmaceutically acceptable salt thereof, wherein $R^{10a}$ is —CH$_2$-pyridinyl optionally substituted by one or two $C_1$-$C_4$ alkyl groups and $R^{10b}$ is —CH$_2$-pyridinyl optionally substituted by one or two $C_1$-$C_4$ alkyl groups.

In some embodiments, the compound is selected from:
(rac)-2-phenyl-N-{6-[(cis)-3-{5-[(pyridin-2-ylacetyl)amino]-1,3,4-thiadiazol-2-yl}cyclopentyl)methyl]pyridazin-3-yl}acetamide;
2-(pyridin-2-yl)-N-(5-{[(1R,3S)-3-{5-[(pyridin-2-ylacetyl)amino]-1,3,4-thiadiazol-2-yl}cyclopentyl]methyl}-1,3,4-thiadiazol-2-yl)acetamide;
(rac)-2-(pyridin-2-yl)-N-(5-{[(cis)-3-{5-[(pyridin-2-ylacetyl)amino]-1,3,4-thiadiazol-2-yl}cyclopentyl]methyl}-1,3,4-thiadiazol-2-yl)acetamide;
2-(pyridin-2-yl)-N-(5-{[(1 S,3R)-3-{5-[(pyridin-2-ylacetyl)amino]-1,3,4-thiadiazol-2-yl}cyclopentyl]methyl}-1,3,4-thiadiazol-2-yl)acetamide;
N-[5-({(1R,3S)-3-[5-(acetylamino)-1,3,4-thiadiazol-2-yl]cyclopentyl}methyl)-1,3,4-thiadiazol-2-yl]acetamide;
(rac)-N-[5-({(cis)-3-[5-(acetylamino)-1,3,4-thiadiazol-2-yl]cyclopentyl}methyl)-1,3,4-thiadiazol-2-yl]acetamide;
N-[5-({(1 S,3R)-3-[5-(acetylamino)-1,3,4-thiadiazol-2-yl]cyclopentyl}methyl)-1,3,4-thiadiazol-2-yl]acetamide;
2-phenyl-N-(5-{[(1R,3S)-3-{5-[(phenylacetyl)amino]-1,3,4-thiadiazol-2-yl}cyclopentyl]methyl}-1,3,4-thiadiazol-2-yl)acetamide;
(rac)-2-phenyl-N-(5-{[(cis)-3-{5-[(phenylacetyl)amino]-1,3,4-thiadiazol-2-yl}cyclopentyl]methyl}-1,3,4-thiadiazol-2-yl)acetamide;

2-phenyl-N-(5-{[(1S,3R)-3-{5-[(phenylacetyl)amino]-1,3,4-thiadiazol-2-yl}cyclopentyl]methyl}-1,3,4-thiadiazol-2-yl)acetamide;

(rac)-N-[5-({(cis)-3-[5-(acetylamino)-1,3,4-thiadiazol-2-yl]cyclopentyl}methyl)-1,3,4-thiadiazol-2-yl]benzamide;

(+)-N-[5-({(cis)-3-[5-(acetylamino)-1,3,4-thiadiazol-2-yl]cyclopentyl}methyl)-1,3,4-thiadiazol-2-yl]benzamide;

(−)-N-[5-({(cis)-3-[5-(acetylamino)-1,3,4-thiadiazol-2-yl]cyclopentyl}methyl)-1,3,4-thiadiazol-2-yl]benzamide;

(+)-N-[5-({(cis)-3-[5-(acetylamino)-1,3,4-thiadiazol-2-yl]cyclopentyl}methyl)-1,3,4-thiadiazol-2-yl]-2-phenylacetamide;

(rac)-N-[5-({(cis)-3-[5-(acetylamino)-1,3,4-thiadiazol-2-yl]cyclopentyl}methyl)-1,3,4-thiadiazol-2-yl]-2-phenylacetamide;

(−)-N-[5-({(cis)-3-[5-(acetylamino)-1,3,4-thiadiazol-2-yl]cyclopentyl}methyl)-1,3,4-thiadiazol-2-yl]-2-phenylacetamide;

(+)-N-[5-({(cis)-3-[5-(acetylamino)-1,3,4-thiadiazol-2-yl]cyclopentyl}methyl)-1,3,4-thiadiazol-2-yl]-2-(pyridin-2-yl)acetamide;

(−)-N-[5-({(cis)-3-[5-(acetylamino)-1,3,4-thiadiazol-2-yl]cyclopentyl}methyl)-1,3,4-thiadiazol-2-yl]-2-(pyridin-2-yl)acetamide;

(rac)-N-[5-({(cis)-3-[5-(acetylamino)-1,3,4-thiadiazol-2-yl]cyclopentyl}methyl)-1,3,4-thiadiazol-2-yl]-2-(pyridin-2-yl)acetamide;

(+)-N-{5-[(cis)-3-{[5-(acetylamino)-1,3,4-thiadiazol-2-yl]methyl}cyclopentyl]-1,3,4-thiadiazol-2-yl}-2-(pyrimidin-4-yl)acetamide;

(−)-N-{5-[(cis)-3-{[5-(acetylamino)-1,3,4-thiadiazol-2-yl]methyl}cyclopentyl]-1,3,4-thiadiazol-2-yl}-2-(pyrimidin-4-yl)acetamide;

2-(pyridin-2-yl)-N-{5-[(cis-3-{5-[(pyridin-2-ylacetyl)amino]-1,3,4-thiadiazol-2-yl}cyclobutyl)methyl]-1,3,4-thiadiazol-2-yl}acetamide;

2-(pyridin-2-yl)-N-{5-[(trans-3-{5-[(pyridin-2-ylacetyl)amino]-1,3,4-thiadiazol-2-yl}cyclobutyl)methyl]-1,3,4-thiadiazol-2-yl}acetamide;

(rac)-N-[5-({(cis)-3-[5-(ethylamino)-1,3,4-thiadiazol-2-yl]cyclopentyl}methyl)-1,3,4-thiadiazol-2-yl]-2-(pyridin-2-yl)acetamide;

N,N'-(spiro[3.3]heptane-2,6-diyldipyridazine-6,3-diyl)bis[2-(pyridin-2-yl)acetamide];

2-(pyridin-2-yl)-N-{5-[(3-{6-[(pyridin-2-ylacetyl)amino]pyridazin-3-yl}cyclopentyl)methyl]-1,3,4-thiadiazol-2-yl}acetamide;

(rac)-N-(5-{[(cis)-3-{5-[(2,2-dimethylpropanoyl)amino]-1,3,4-thiadiazol-2-yl}cyclopentyl]methyl}-1,3,4-thiadiazol-2-yl)-2,2-dimethylpropanamide;

(+)-N-(5-{[(cis)-3-{5-[(2,2-dimethylpropanoyl)amino]-1,3,4-thiadiazol-2-yl}cyclopentyl]methyl}-1,3,4-thiadiazol-2-yl)-2,2-dimethylpropanamide;

(−)-N-(5-{[(cis)-3-{5-[(2,2-dimethylpropanoyl)amino]-1,3,4-thiadiazol-2-yl}cyclopentyl]methyl}-1,3,4-thiadiazol-2-yl)-2,2-dimethylpropanamide;

(rac)-2-(pyridin-3-yl)-N-(5-{[(cis)-3-(5-{[2-(pyridin-3-yl)propanoyl]amino}-1,3,4-thiadiazol-2-yl)cyclopentyl]methyl}-1,3,4-thiadiazol-2-yl)propanamide;

(+)-2-(pyridin-3-yl)-N-(5-{[(cis)-3-(5-{[2-(pyridin-3-yl)propanoyl]amino}-1,3,4-thiadiazol-2-yl)cyclopentyl]methyl}-1,3,4-thiadiazol-2-yl)propanamide;

(−)-2-(pyridin-3-yl)-N-(5-{[(cis)-3-(5-{[2-(pyridin-3-yl)propanoyl]amino}-1,3,4-thiadiazol-2-yl)cyclopentyl]methyl}-1,3,4-thiadiazol-2-yl)propanamide;

(rac)-5-{[(cis)-3-(5-amino-1,3,4-thiadiazol-2-yl)cyclopentyl]methyl}-1,3,4-thiadiazol-2-amine;

5-{[(1R,3S)-3-(5-amino-1,3,4-thiadiazol-2-yl)cyclopentyl]methyl}-1,3,4-thiadiazol-2-amine;

5-{[(1S,3R)-3-(5-amino-1,3,4-thiadiazol-2-yl)cyclopentyl]methyl}-1,3,4-thiadiazol-2-amine;

(rac)-N-(5-{(cis)-3-[(5-amino-1,3,4-thiadiazol-2-yl)methyl]cyclopentyl}-1,3,4-thiadiazol-2-yl)acetamide;

(rac)-N-{5-[(cis)-3-{[5-(acetylamino)-1,3,4-thiadiazol-2-yl]methyl}cyclopentyl]-1,3,4-thiadiazol-2-yl}-2-phenylacetamide;

(+)-N-{5-[(cis)-3-{[5-(acetylamino)-1,3,4-thiadiazol-2-yl]methyl}cyclopentyl]-1,3,4-thiadiazol-2-yl}-2-phenylacetamide;

(−)-N-{5-[(cis)-3-{[5-(acetylamino)-1,3,4-thiadiazol-2-yl]methyl}cyclopentyl]-1,3,4-thiadiazol-2-yl}-2-phenylacetamide;

(rac)-N-[5-({(cis)-3-[5-(acetylamino)-1,3,4-thiadiazol-2-yl]cyclopentyl}methyl)-1,3,4-thiadiazol-2-yl]-2-(pyrimidin-2-yl)acetamide;

(rac)-N-[5-({(cis)-3-[5-(acetylamino)-1,3,4-thiadiazol-2-yl]cyclopentyl}methyl)-1,3,4-thiadiazol-2-yl]-2-(pyrazin-2-yl)acetamide;

(rac)-N-{5-[(cis)-3-{[5-(acetylamino)-1,3,4-thiadiazol-2-yl]methyl}cyclopentyl]-1,3,4-thiadiazol-2-yl}benzamide;

(rac)-N-[(cis)-5-({3-[5-(acetylamino)-1,3,4-thiadiazol-2-yl]cyclopentyl}methyl)-1,3,4-thiadiazol-2-yl]-2-(pyrimidin-5-yl)acetamide;

(+)-N-[5-({(cis)-3-[5-(acetylamino)-1,3,4-thiadiazol-2-yl]cyclopentyl}methyl)-1,3,4-thiadiazol-2-yl]-2-(pyrimidin-5-yl)acetamide;

(−)-N-[5-({(cis)-3-[5-(acetylamino)-1,3,4-thiadiazol-2-yl]cyclopentyl}methyl)-1,3,4-thiadiazol-2-yl]-2-(pyrimidin-5-yl)acetamide;

(rac)-N-[5-({(cis)-3-[5-(acetylamino)-1,3,4-thiadiazol-2-yl]cyclopentyl}methyl)-1,3,4-thiadiazol-2-yl]-2-(6-methylpyridin-3-yl)acetamide;

(+)-N-[5-({(cis)-3-[5-(acetylamino)-1,3,4-thiadiazol-2-yl]cyclopentyl}methyl)-1,3,4-thiadiazol-2-yl]-2-(6-methylpyridin-3-yl)acetamide;

(−)-N-[5-({(cis)-3-[5-(acetylamino)-1,3,4-thiadiazol-2-yl]cyclopentyl}methyl)-1,3,4-thiadiazol-2-yl]-2-(6-methylpyridin-3-yl)acetamide;

(rac)-N-{5-[(cis)-3-{[5-(acetylamino)-1,3,4-thiadiazol-2-yl]methyl}cyclopentyl]-1,3,4-thiadiazol-2-yl}-2-(pyridin-2-yl)acetamide;

(+)-N-{5-[(cis)-3-{[5-(acetylamino)-1,3,4-thiadiazol-2-yl]methyl}cyclopentyl]-1,3,4-thiadiazol-2-yl}-2-(pyridin-2-yl)acetamide;

(−)-N-{5-[(cis)-3-{[5-(acetylamino)-1,3,4-thiadiazol-2-yl]methyl}cyclopentyl]-1,3,4-thiadiazol-2-yl}-2-(pyridin-2-yl)acetamide;

(+)-N-{5-[(cis)-3-{[5-(acetylamino)-1,3,4-thiadiazol-2-yl]methyl}cyclopentyl]-1,3,4-thiadiazol-2-yl}-2-(pyrimidin-5-yl)acetamide;

(−)-N-{5-[(cis)-3-{[5-(acetylamino)-1,3,4-thiadiazol-2-yl]methyl}cyclopentyl]-1,3,4-thiadiazol-2-yl}-2-(pyrimidin-5-yl)acetamide;

N,N'-{[-1,2,2-trimethylcyclopentane-1,3-diyl]di-1,3,4-thiadiazole-5,2-diyl}diacetamide;

N,N'-(spiro[3.3]heptane-2,6-diyldi-1,3,4-thiadiazole-5,2-diyl)bis[2-(pyridin-2-yl)acetamide];

N-[5-({cis-3-[5-(acetylamino)-1,3,4-thiadiazol-2-yl]cyclobutyl}methyl)-1,3,4-thiadiazol-2-yl]acetamide;

N-[5-({trans-3-[5-(acetylamino)-1,3,4-thiadiazol-2-yl]cyclobutyl}methyl)-1,3,4-thiadiazol-2-yl]acetamide;

(+)-N-(5-{(cis)-3-[(5-amino-1,3,4-thiadiazol-2-yl)methyl]cyclopentyl}-1,3,4-thiadiazol-2-yl)-2-phenylacetamide;

(−)-N-(5-{(cis)-3-[(5-amino-1,3,4-thiadiazol-2-yl)methyl]cyclopentyl}-1,3,4-thiadiazol-2-yl)-2-phenylacetamide;
(rac)-N-[5-({(cis)-3-[5-(ethylamino)-1,3,4-thiadiazol-2-yl]cyclopentyl}methyl)-1,3,4-thiadiazol-2-yl]acetamide;
(rac)-N-(5-{(cis)-3-[(5-amino-1,3,4-thiadiazol-2-yl)methyl]cyclopentyl}-1,3,4-thiadiazol-2-yl)-2-(pyridin-2-yl)acetamide;
(+)-N-{5-[(cis)-3-{[6-(acetylamino)pyridazin-3-yl]methyl}cyclopentyl]-1,3,4-thiadiazol-2-yl}-2-(pyridin-2-yl)acetamide;
(−)-N-{5-[(cis)-3-{[6-(acetylamino)pyridazin-3-yl]methyl}cyclopentyl]-1,3,4-thiadiazol-2-yl}-2-(pyridin-2-yl)acetamide;
(rac)-2-(pyridin-2-yl)-N-{5-[(cis)-3-({6-[(pyridin-2-ylacetyl)amino]pyridazin-3-yl}methyl)cyclopentyl]-1,3,4-thiadiazol-2-yl}acetamide;
(+)-2-(pyridin-2-yl)-N-{5-[(cis)-3-({6-[(pyridin-2-ylacetyl)amino]pyridazin-3-yl}methyl)cyclopentyl]-1,3,4-thiadiazol-2-yl}acetamide;
(−)-2-(pyridin-2-yl)-N-{5-[(cis)-3-({6-[(pyridin-2-ylacetyl)amino]pyridazin-3-yl}methyl)cyclopentyl]-1,3,4-thiadiazol-2-yl}acetamide;
N-{6-[(cis-3-{5-[(pyridin-2-ylacetyl)amino]-1,3,4-thiadiazol-2-yl}cyclobutyl)methyl]pyridazin-3-yl}propanamide;
(+)-2-(pyridin-2-yl)-N-[6-({(cis)-3-[5-(pyridin-2-ylamino)-1,3,4-thiadiazol-2-yl]cyclopentyl}methyl)pyridazin-3-yl]acetamide;
(−)-2-(pyridin-2-yl)-N-[6-({(cis)-3-[5-(pyridin-2-ylamino)-1,3,4-thiadiazol-2-yl]cyclopentyl}methyl)pyridazin-3-yl]acetamide;
(rac)-2-methyl-N-(6-{[(cis)-3-{5-[(pyridin-2-ylacetyl)amino]-1,3,4-thiadiazol-2-yl}cyclopentyl]methyl}pyridazin-3-yl)propanamide;
(+)-2-methyl-N-(6-{[(cis)-3-{5-[(pyridin-2-ylacetyl)amino]-1,3,4-thiadiazol-2-yl}cyclopentyl]methyl}pyridazin-3-yl)propanamide;
(−)-2-methyl-N-(6-{[(cis)-3-{5-[(pyridin-2-ylacetyl)amino]-1,3,4-thiadiazol-2-yl}cyclopentyl]methyl}pyridazin-3-yl)propanamide;
N-(6-{[(cis)-3-{5-[(pyridin-2-ylacetyl)amino]-1,3,4-thiadiazol-2-yl}cyclopentyl]methyl}pyridazin-3-yl)propanamide;
(+)-2-phenyl-N-(6-{[(cis)-3-{5-[(pyridin-2-ylacetyl)amino]-1,3,4-thiadiazol-2-yl}cyclopentyl]methyl}pyridazin-3-yl)acetamide;
(−)-2-phenyl-N-(6-{[(cis)-3-{5-[(pyridin-2-ylacetyl)amino]-1,3,4-thiadiazol-2-yl}cyclopentyl]methyl}pyridazin-3-yl)acetamide;
(rac)-2-(pyridin-2-yl)-N-[5-({(cis)-3-[5-(pyrimidin-2-ylamino)-1,3,4-thiadiazol-2-yl]cyclopentyl}methyl)-1,3,4-thiadiazol-2-yl]acetamide;
2-(pyridin-2-yl)-N-[5-({(cis)-3-[5-(pyrimidin-2-ylamino)-1,3,4-thiadiazol-2-yl]cyclopentyl}methyl)-1,3,4-thiadiazol-2-yl]acetamide;
2-(pyridin-2-yl)-N-[5-({3-[5-(trans)(pyridin-2-ylamino)-1,3,4-thiadiazol-2-yl]cyclopentyl}methyl)-1,3,4-thiadiazol-2-yl]acetamide;
2-(pyridin-2-yl)-N-[5-({(cis)-3-[5-(pyridin-2-ylamino)-1,3,4-thiadiazol-2-yl]cyclopentyl}methyl)-1,3,4-thiadiazol-2-yl]acetamide;
(rac)-N-[5-({(cis)-3-[5-(pyrazin-2-ylamino)-1,3,4-thiadiazol-2-yl]cyclopentyl}methyl)-1,3,4-thiadiazol-2-yl]-2-(pyridin-2-yl)acetamide;
(rac)-N-(5-{[(cis)-3-{5-[(1-methyl-1H-pyrazol-3-yl)amino]-1,3,4-thiadiazol-2-yl}cyclopentyl]methyl}-1,3,4-thiadiazol-2-yl)-2-(pyridin-2-yl)acetamide;
N-(5-{[(cis)-3-{5-[(1-methyl-1H-pyrazol-3-yl)amino]-1,3,4-thiadiazol-2-yl}cyclopentyl]methyl}-1,3,4-thiadiazol-2-yl)-2-(pyridin-2-yl)acetamide;
3-methoxy-N-{5-[(cis)-3-{[6-(propanoylamino)pyridazin-3-yl]methyl}cyclopentyl]-1,3,4-thiadiazol-2-yl}propanamide;
(+)-N-(6-{[(cis)-3-(5-{[(1-methyl-1H-pyrazol-3-yl)acetyl]amino}-1,3,4-thiadiazol-2-yl)cyclopentyl]methyl}pyridazin-3-yl)propanamide;
(−)-N-(6-{[(cis)-3-(5-{[(1-methyl-1H-pyrazol-3-yl)acetyl]amino}-1,3,4-thiadiazol-2-yl)cyclopentyl]methyl}pyridazin-3-yl)propanamide;
N,N'-(spiro[3.3]heptane-2,6-diyldi-1,3,4-thiadiazole-5,2-diyl)diacetamide;
(rac)-N,N'-(spiro[3.3]heptane-2,6-diyldi-1,3,4-thiadiazole-5,2-diyl)bis(2-methylpropanamide);
(S)—N,N'-(spiro[3.3]heptane-2,6-diyldi-1,3,4-thiadiazole-5,2-diyl)bis(2-methylpropanamide);
(rac)-N,N'-(spiro[3.3]heptane-2,6-diyldi-1,3,4-thiadiazole-5,2-diyl)bis[2-(1-methyl-1H-pyrazol-3-yl)acetamide];
(R)—N,N'-(spiro[3.3]heptane-2,6-diyldi-1,3,4-thiadiazole-5,2-diyl)bis[2-(1-methyl-1H-pyrazol-3-yl)acetamide];
(S)—N,N'-(spiro[3.3]heptane-2,6-diyldi-1,3,4-thiadiazole-5,2-diyl)bis[2-(1-methyl-1H-pyrazol-3-yl)acetamide];
N,N'-(spiro[3.3]heptane-2,6-diyldi-1,3,4-thiadiazole-5,2-diyl)bis[2-(pyridin-2-yl)acetamide];
N-[6-({cis-3-[5-(ethylamino)-1,3,4-thiadiazol-2-yl]cyclobutyl}methyl)pyridazin-3-yl]-2-phenylacetamide;
N-[6-({(cis)-3-[5-(ethylamino)-1,3,4-thiadiazol-2-yl]cyclopentyl}methyl)pyridazin-3-yl]-2-(pyridin-2-yl)acetamide;
(+)-2-(pyridin-2-yl)-N-{5-[(1-(cis)-3-{5-[(pyridin-2-ylacetyl)amino]-1,3,4-thiadiazol-2-yl}cyclobutyl)ethyl]-1,3,4-thiadiazol-2-yl}acetamide;
(−)-2-(pyridin-2-yl)-N-{5-[(1-(cis)-3-{5-[(pyridin-2-ylacetyl)amino]-1,3,4-thiadiazol-2-yl}cyclobutyl)ethyl]-1,3,4-thiadiazol-2-yl}acetamide;
2-methyl-N-{5-[(cis-3-{5-[(pyridin-2-ylacetyl)amino]-1,3,4-thiadiazol-2-yl}cyclobutyl)methyl]-1,3,4-thiadiazol-2-yl}propanamide;
N-{5-[cis-3-({5-[(pyridin-2-ylacetyl)amino]-1,3,4-thiadiazol-2-yl}methyl)cyclobutyl]-1,3,4-thiadiazol-2-yl}propanamide;
N-{5-[trans-3-({5-[(pyridin-2-ylacetyl)amino]-1,3,4-thiadiazol-2-yl}methyl)cyclobutyl]-1,3,4-thiadiazol-2-yl}propanamide;
N-[5-(cis-3-{[5-(acetylamino)-1,3,4-thiadiazol-2-yl]methyl}cyclobutyl)-1,3,4-thiadiazol-2-yl]-2-(5-methylpyridin-2-yl)acetamide;
2-(5-methylpyridin-2-yl)-N-(5-{[cis-3-(5-{[(5-methylpyridin-2-yl)acetyl]amino}-1,3,4-thiadiazol-2-yl)cyclobutyl]methyl}-1,3,4-thiadiazol-2-yl)acetamide;
2-(5-methylpyridin-2-yl)-N-(5-{[trans-3-(5-{[(5-methylpyridin-2-yl)acetyl]amino}-1,3,4-thiadiazol-2-yl)cyclobutyl]methyl}-1,3,4-thiadiazol-2-yl)acetamide;
N-[6-({(cis)-3-[5-(cyclopropylamino)-1,3,4-thiadiazol-2-yl]cyclopentyl}methyl)pyridazin-3-yl]-2-(pyridin-2-yl)acetamide;
2-(5-methylpyridin-2-yl)-N-{5-[(cis-3-{5-[(pyridin-2-ylacetyl)amino]-1,3,4-thiadiazol-2-yl}cyclobutyl)methyl]-1,3,4-thiadiazol-2-yl}acetamide;
2-(5-methylpyridin-2-yl)-N-{5-[cis-3-({5-[(pyridin-2-ylacetyl)amino]-1,3,4-thiadiazol-2-yl}methyl)cyclobutyl]-1,3,4-thiadiazol-2-yl}acetamide;
N-[6-({trans-3-[5-(ethylamino)-1,3,4-thiadiazol-2-yl]cyclobutyl}methyl)pyridazin-3-yl]-2-(pyridin-2-yl)acetamide;

N-[5-(cis-3-{[6-(acetylamino)pyridazin-3-yl]
methyl}cyclobutyl)-1,3,4-thiadiazol-2-yl]-2-(pyridin-2-
yl)acetamide;
N-[6-({trans-3-[5-(acetylamino)-1,3,4-thiadiazol-2-yl]
cyclobutyl}methyl)pyridazin-3-yl]-2-(pyridin-2-yl)acet-
amide;
(+)-N-{5-[(cis)-3-({6-[(pyridin-2-ylacetyl)amino]pyridazin-
3-yl}methyl)cyclopentyl]-1,3,4-thiadiazol-2-yl}pyridine-
2-carboxamide;
(−)-N-{5-[(cis)-3-({6-[(pyridin-2-ylacetyl)amino]pyridazin-
3-yl}methyl)cyclopentyl]-1,3,4-thiadiazol-2-yl}pyridine-
2-carboxamide;
2-phenyl-N-{6-[(cis-3-{5-[(pyridin-2-ylacetyl)amino]-1,3,
4-thiadiazol-2-yl}cyclobutyl)methyl]pyridazin-3-
yl}acetamide;
N-{5-[(1 S,3R)-3-({6-[(pyridin-2-ylacetyl)amino]
pyridazin-3-yl}methyl)cyclopentyl]-1,3,4-thiadiazol-2-
yl}propanamide;
2-methyl-N-{5-[(1 S,3R)-3-({6-[(pyridin-2-ylacetyl)amino]
pyridazin-3-yl}methyl)cyclopentyl]-1,3,4-thiadiazol-2-
yl}propanamide;
(+)-3-methoxy-N-{5-[(cis)-3-({6-[(pyridin-2-ylacetyl)
amino]pyridazin-3-yl}methyl)cyclopentyl]-1,3,4-thiadi-
azol-2-yl}propanamide;
(−)-3-methoxy-N-{5-[(cis)-3-({6-[(pyridin-2-ylacetyl)
amino]pyridazin-3-yl}methyl)cyclopentyl]-1,3,4-thiadi-
azol-2-yl}propanamide;
2-(pyridin-2-yl)-N-{5-[(trans-3-{6-[(pyridin-2-ylacetyl)
amino]pyridazin-3-yl}cyclobutyl)methyl]-1,3,4-thiadi-
azol-2-yl}acetamide;
2-(pyridin-2-yl)-N-{5-[(cis-3-{6-[(pyridin-2-ylacetyl)
amino]pyridazin-3-yl}cyclobutyl)methyl]-1,3,4-thiadi-
azol-2-yl}acetamide;
2-methyl-N-{6-[cis-3-({5-[(pyridin-2-ylacetyl)amino]-1,3,
4-thiadiazol-2-yl}methyl)cyclobutyl]pyridazin-3-
yl}propanamide;
(+)-2-(1-methyl-1H-pyrazol-3-yl)-N-{5-[(cis)-3-({6-[(pyri-
din-2-ylacetyl)amino]pyridazin-3-yl}methyl)cyclopen-
tyl]-1,3,4-thiadiazol-2-yl}acetamide;
(−)-2-(1-methyl-1H-pyrazol-3-yl)-N-{5-[(cis)-3-({6-[(pyri-
din-2-ylacetyl)amino]pyridazin-3-yl}methyl)cyclopen-
tyl]-1,3,4-thiadiazol-2-yl}acetamide;
2-(1-methyl-1H-imidazol-4-yl)-N-{5-[(cis)-3-({6-[(pyridin-
2-ylacetyl)amino]pyridazin-3-yl}methyl)cyclopentyl]-1,
3,4-thiadiazol-2-yl}acetamide;
(rac)-2-(pyridin-2-yl)-N-(6-{[(cis)-3-(5-{[(2R)-tetrahydro-
furan-2-ylacetyl]amino}-1,3,4-thiadiazol-2-yl)cyclopen-
tyl]methyl}pyridazin-3-yl)acetamide;
(+)-2-(pyridin-2-yl)-N-(6-{[(cis)-3-(5-{[(2R)-tetrahydro-
furan-2-ylacetyl]amino}-1,3,4-thiadiazol-2-yl)cyclopen-
tyl]methyl}pyridazin-3-yl)acetamide;
(−)-2-(pyridin-2-yl)-N-(6-{[(cis)-3-(5-{[(2R)-tetrahydro-
furan-2-ylacetyl]amino}-1,3,4-thiadiazol-2-yl)cyclopen-
tyl]methyl}pyridazin-3-yl)acetamide;
N-[6-({cis-3-[5-(acetylamino)-1,3,4-thiadiazol-2-yl]
cyclobutyl}methyl)pyridazin-3-yl]-2-phenylacetamide;
2-(pyridin-2-yl)-N-[5-({(cis)-3-[5-(pyridin-2-ylamino)-1,3,
4-thiadiazol-2-yl]cyclopentyl}methyl)-1,3,4-thiadiazol-
2-yl]acetamide;
(S)—N,N'-(spiro[3.3]heptane-2,6-diyldi-1,3,4-thiadiazole-
5,2-diyl)dipropanamide;
2-methyl-N-[5-(6-{5-[(pyridin-2-ylacetyl)amino]-1,3,4-
thiadiazol-2-yl}spiro[3.3]hept-2-yl)-1,3,4-thiadiazol-2-
yl]propanamide;
2-methyl-N-{5-[6-(5-{[(1-methyl-1H-pyrazol-3-yl)acetyl]
amino}-1,3,4-thiadiazol-2-yl)spiro[3.3]hept-2-yl]-1,3,4-
thiadiazol-2-yl}propanamide;
(rac)-1-methyl-N-(5-{[(cis)-3-{5-[(pyridin-2-ylacetyl)
amino]-1,3,4-thiadiazol-2-yl}cyclopentyl]methyl}-1,3,4-
thiadiazol-2-yl)-1H-pyrazole-3-carboxamide;
N,N'-[cyclopentane-1,3-diyldi-1,3,4-thiadiazole-5,2-diyl]
bis[2-(pyridin-2-yl)acetamide];
N,N'-[cyclohexane-1,3-diyldi-1,3,4-thiadiazole-5,2-diyl]bis
[2-(pyridin-2-yl)acetamide];
N,N'-(cyclohexane-1,4-diyldi-1,3,4-thiadiazole-5,2-diyl)bis
[2-(pyridin-2-yl)acetamide];
N,N'-(spiro[3.3]heptane-2,6-diyldi-1,3,4-thiadiazole-5,2-
diyl)diacetamide;
(rac)-2-(1H-pyrazol-1-yl)-N-(5-{[(cis)-3-{5-[(pyridin-2-
ylacetyl)amino]-1,3,4-thiadiazol-2-yl}cyclopentyl]
methyl}-1,3,4-thiadiazol-2-yl)acetamide;
(rac)-3-(1H-pyrazol-1-yl)-N-(5-{[(cis)-3-{5-[(pyridin-2-
ylacetyl)amino]-1,3,4-thiadiazol-2-yl}cyclopentyl]
methyl}-1,3,4-thiadiazol-2-yl)propanamide;
(rac)-2-fluoro-N-(5-{[(cis)-3-{5-[(pyridin-2-ylacetyl)
amino]-1,3,4-thiadiazol-2-yl}cyclopentyl]methyl}-1,3,4-
thiadiazol-2-yl)benzamide;
(rac)-N-[5-({(cis)-3-[5-(acetylamino)-1,3,4-thiadiazol-2-yl]
cyclopentyl}methyl)-1,3,4-thiadiazol-2-yl]-2-(1,3-thi-
azol-4-yl)acetamide;
(rac)-2-fluoro-N-(5-{[(cis)-3-{5-[(pyridin-2-ylacetyl)
amino]-1,3,4-thiadiazol-2-yl}cyclopentyl]methyl}-1,3,4-
thiadiazol-2-yl)benzamide;
(rac)-N-[5-({(cis)-3-[5-(acetylamino)-1,3,4-thiadiazol-2-yl]
cyclopentyl}methyl)-1,3,4-thiadiazol-2-yl]-2-(1,3-thi-
azol-4-yl)acetamide;
(rac)-N-[5-({(cis)-3-[5-(acetylamino)-1,3,4-thiadiazol-2-yl]
cyclopentyl}methyl)-1,3,4-thiadiazol-2-yl]-2-(1-methyl-
1H-pyrazol-3-yl)acetamide;
(rac)-N-[5-({(cis)-3-[5-(acetylamino)-1,3,4-thiadiazol-2-yl]
cyclopentyl}methyl)-1,3,4-thiadiazol-2-yl]-2-(1-methyl-
1H-pyrazol-3-yl)acetamide;
(rac)-N-[5-({(cis)-3-[5-(acetylamino)-1,3,4-thiadiazol-2-yl]
cyclopentyl}methyl)-1,3,4-thiadiazol-2-yl]-2-fluorobenz-
amide;
(rac)-N-[5-({(cis)-3-[5-(acetylamino)-1,3,4-thiadiazol-2-yl]
cyclopentyl}methyl)-1,3,4-thiadiazol-2-yl]-2-(imidazo[1,
2-a]pyridin-2-yl)acetamide; and
(rac)-1-methyl-N-(5-{[(cis)-3-{5-[(pyridin-2-ylacetyl)
amino]-1,3,4-thiadiazol-2-yl}cyclopentyl]methyl}-1,3,4-
thiadiazol-2-yl)-1H-imidazole-4-carboxamide,
or a pharmaceutically acceptable salt thereof.

Embodiments relate to a pharmaceutical composition comprising a compound of any of the embodiments of the compounds of formula (I), formula (II), formula (III), formula (IV), formula (IVa), or formula (IVb), or a pharmaceutically acceptable salt thereof, and a pharmaceutically acceptable carrier or diluent.

Embodiments relate to a pharmaceutical composition comprising a compound of any of the embodiments of the compounds of formula (I), formula (II), formula (III), formula (IV), formula (IVa), or formula (IVb), or a pharmaceutically acceptable salt thereof, with an anti-tumor agent or with radiation therapy, for the treatment of cancer.

Embodiments relate to a pharmaceutical composition comprising a compound of any of the embodiments of the compounds of formula (I), formula (II), formula (III), formula (IV), formula (IVa), or formula (IVb), or a pharmaceutically acceptable salt thereof, with an anti-tumor agent, for the treatment of cancer.

Embodiments relate to a method of treating abnormal cell growth in a mammal comprising administering to the mammal an amount of a composition of any of the embodiments of the compounds of formula (I), formula (II), formula (III), formula (IV), formula (IVa), or formula (IVb), or a pharmaceutically acceptable salt thereof, that is effective in treating abnormal cell growth.

Embodiments relate to a method of treating abnormal cell growth in a mammal comprising administering to the mammal an amount of a compound of any of the embodiments of the compounds of formula (I), formula (II), formula (III), formula (IV), formula (IVa), or formula (IVb), or a pharmaceutically acceptable salt thereof, that is effective in treating abnormal cell growth.

Embodiments relate to the method of treating abnormal cell growth, wherein the abnormal cell growth is cancer.

Embodiments relate to the method of treating cancer, wherein the cancer is selected from the group consisting of basal cell cancer, medulloblastoma cancer, liver cancer, rhabdomyosarcoma, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system, primary central nervous system lymphoma, spinal axis tumors, brain stem glioma and pituitary adenoma, or a combination of one or more of the foregoing cancers.

Embodiments relate to the method of treating lung cancer, wherein the cancer is selected from the group consisting of lung cancer, cancer of the head or neck, colon cancer, breast cancer, and ovarian cancer, or a combination of one or more of the foregoing cancers.

DETAILED DESCRIPTION OF THE INVENTION

The following abbreviations may be used herein: Ac (acetyl); AcOH (acetic acid); Ac2O (acetic anhydride); aq. (aqueous); ca. (about or approximately); DCM (dichloromethane); DEA (diethylamine); DIPEA (N,N-diisopropylethylamine); DMA (dimethylacetamide); DMF (dimethylformamide); DMSO (dimethylsulphoxide); Et (ethyl); Et$_3$N (triethylamine); EtOH (ethanol); EtOAc (ethyl acetate); Et$_2$O (diethyl ether); Hal (halogen); HATU (2-(7-aza-1H-benzotriazole-1-yl)-1,1,3,3-tetramethyluronium hexafluorophosphate); H BTU (o-(benzotriazole-1-yl)-1,1,3,3-tetramethyluronium hexafluorophosphate); HPLC (high-performance liquid chromatography); hr (hour or hours, as appropriate); IPA (isopropyl alcohol); LCMS (liquid chromatography-mass spectrometry); L-Selectride (lithium tri-sec-butylborohydride); Me (methyl); MeOH (methanol); MeCN (acetonitrile); min (minute or minutes, as appropriate); N (normal); N/D (not determined) NMR (nuclear magnetic resonance); Pd/C (palladium on carbon); Pd$_2$(dba)$_3$ (tris(dibenzylideneacetone)dipalladium(0)); Pd(dppf)C$_2$ ([1,1'-bis(diphenylphosphino)ferrocene]dichloropalladium(II)); Ph (phenyl); Rt (retention time); sec (second or seconds, as appropriate); SFC (supercritical fluid chromatography); Si-Thiol (silica 1-propanethiol); T3P (propylphosphonic anhydride); TBME (tert-butyl methyl ether); t-BuOH (2-methyl-2-propanol, tert-butanol or tert-butyl alcohol); THF (tetrahydrofuran); TLC (thin layer chromatography); TMSCl (trimethylsilyl chloride); Tris (tris(hydroxymethyl)aminomethane or 2-Amino-2-hydroxymethyl-propane-1,3-diol); U (units); and v/v (volume/volume).

The term "halogen", as used herein, refers to a fluorine, chlorine, bromine, or iodine atom or fluoro, chloro, bromo, or iodo. Additionally, the term "halogen" refers to F, Cl, Br, or I. The terms fluorine, fluoro and F, for example, are understood to be equivalent herein.

The term "alkyl", as used herein, refers to saturated monovalent hydrocarbon radicals containing, in certain embodiments, from one to six, from one to four or from one to three carbon atoms, having straight or branched moieties. The term "$C_1$-$C_6$ alkyl" refers to an alkyl radical containing from one to six carbon atoms, having straight or branched moieties. The term "$C_1$-$C_6$ alkyl" includes within its definition the terms "$C_1$-$C_2$ alkyl", "$C_1$-$C_3$ alkyl", and "$C_1$-$C_4$ alkyl". Examples of alkyl groups include, but are not limited to, methyl, ethyl, propyl, isopropyl, butyl, isobutyl, sec-butyl, tert-butyl, pentyl, 2-pentyl, 3-pentyl, isopentyl, neopentyl, (R)-2-methylbutyl, (S)-2-methylbutyl, 3-methylbutyl, 2,3-dimethylpropyl, 2,3-dimethylbutyl, hexyl, and the like.

The term "alkoxy", as used herein, refers to an alkyl radical that is single bonded to an oxygen atom. The attachment point of an alkoxy radical to a molecule is through the oxygen atom. An alkoxy radical may be depicted as alkyl-O—. The term "$C_1$-$C_6$ alkoxy", refers to an alkoxy radical containing from one to six carbon atoms, having straight or branched moieties. The terms "$C_1$-$C_2$ alkoxy" and "$C_1$-$C_4$ alkoxy", refer to an alkoxy radical containing from one to two carbon atoms and from one to four carbon atoms, respectively, having straight or branched moieties. Alkoxy groups, include, but are not limited to, methoxy, ethoxy, propoxy, isopropoxy, butoxy, hexyloxy, and the like.

The term "cycloalkyl", as used herein, refers to a monocyclic, fused or bridged bicyclic or tricyclic carbocyclic ring group containing, in certain embodiments, from three to ten carbon atoms. As used herein, a cycloalkyl group rings may optionally contain one or two double bonds. The term "cycloalkyl" also includes spirocyclic cycloalkyl groups, including multi-ring systems joined by a single atom. The terms "$C_3$-$C_{10}$ cycloalkyl", "$C_3$-$C_7$ cycloalkyl", "$C_3$-$C_4$ cycloalkyl", "$C_3$-$C_6$ cycloalkyl", "$C_4$-$C_{10}$ cycloalkyl", and "$C_5$-$C_7$ cycloalkyl" contain from three to ten, from three to seven, from three to four, from three to six, from four to ten, and from five to seven carbon atoms, respectively. Cycloalkyl groups include, but are not limited to, cyclopropyl, cyclobutyl, cyclopentyl, cyclohexyl, cycloheptyl, cyclopentenyl, cyclohexenyl, bicyclo[2.2.1]heptanyl, bicyclo[3.2.1]octanyl, bicyclo[5.2.0]nonanyl, adamantanyl, spiro[3.3]heptanyl, and the like.

The term "heterocycloalkyl", as used herein, refers to a non-aromatic, monocyclic, fused or bridged bicyclic or tricyclic or spirocyclic ring group containing, in certain embodiments, a total of three to ten ring atoms, in which one to four ring atoms are heteroatoms independently selected from nitrogen, oxygen, and sulfur, and wherein the sulfur atom may be optionally oxidized with one or two oxygen atoms, the remaining ring atoms being carbon, with the proviso that such ring systems may not contain two adjacent oxygen atoms or two adjacent sulfur atoms. The heterocycloalkyl ring may also be substituted by an oxo (=O) group at any available carbon atom. The rings may also have one or more double bonds. Furthermore, such groups may be bonded to the remainder of the compounds of embodiments disclosed herein through either a carbon atom or a heteroatom, if possible. The terms "3-10 membered heterocycloalkyl", "4-10 membered heterocycloalkyl", "3-7 membered heterocycloalkyl", "3-6 membered heterocycloalkyl", and "4-6 membered heterocycloalkyl" contain from three to ten, from four to ten, from three to seven, from three to six carbon atoms, and from four to six carbon atoms, respectively. Examples of saturated heterocycloalkyl groups include, but are not limited to:

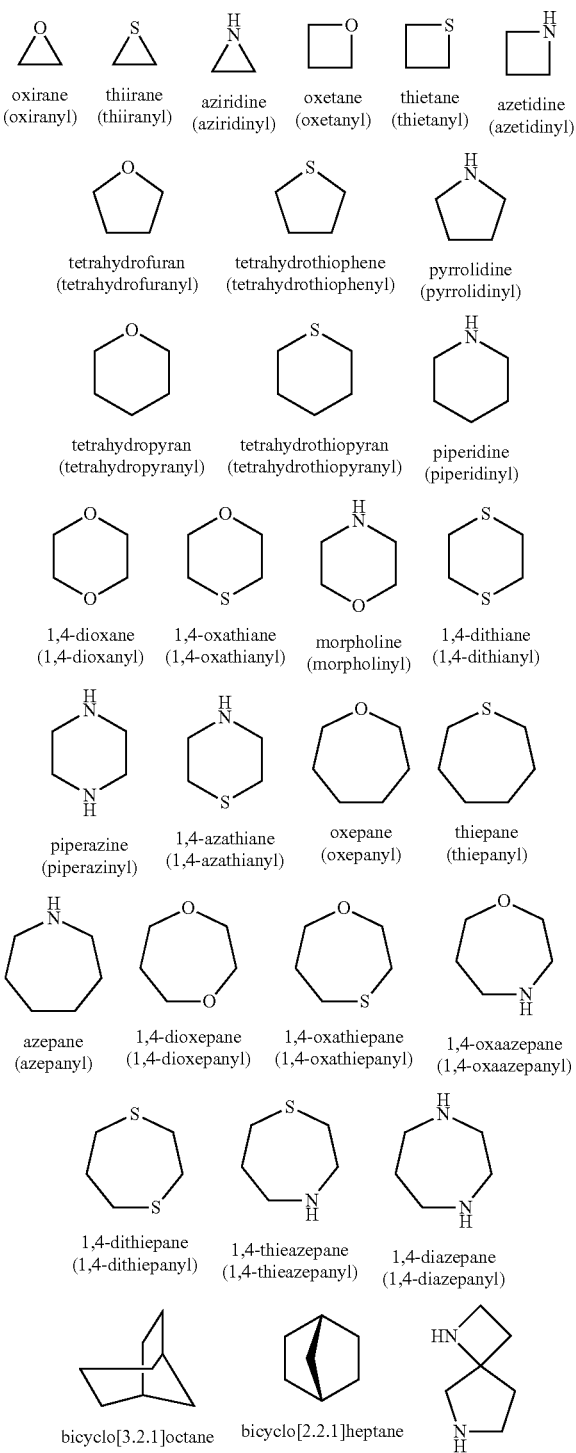

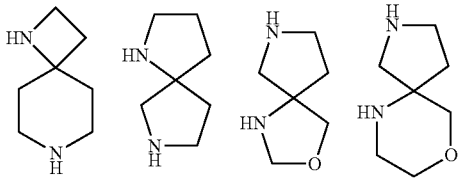

Examples of suitable partially unsaturated heterocycloalkyl groups include, but are not limited to:

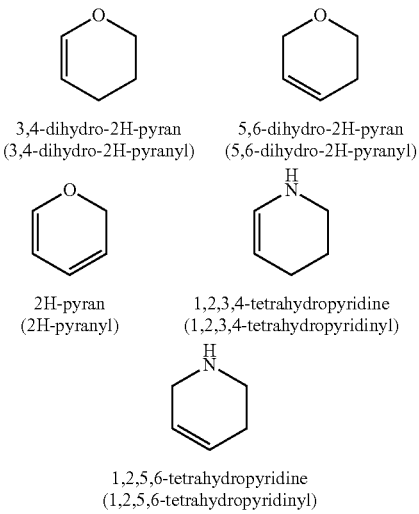

The term "aryl", as used herein, refers to a group derived from an aromatic hydrocarbon containing in certain embodiments, from six to ten carbon atoms. The term "$C_6$-$C_{10}$ aryl" contains from five to ten carbon atoms. Examples of such groups include, but are not limited to, phenyl and naphthyl. The term "aryl" also includes fused polycyclic aromatic ring systems in which an aromatic ring is fused to one or more rings. Examples include, but are not limited to, 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl, or tetrahydronaphthyl, where the radical or point of attachment is on the aromatic ring.

The term "heteroaryl, as used herein, refers to an aromatic monocyclic or bicyclic heterocyclic group having a total of from 5 to 12 atoms in its ring, and containing from 2 to 9 carbon atoms and from one to four heteroatoms each independently selected from nitrogen, oxygen, and sulfur, with the proviso that the ring of said group does not contain two adjacent oxygen atoms or two adjacent sulfur atoms. The terms "5-membered heteroaryl", "6-membered heteroaryl", "5-10 membered heteroaryl", "5-12 membered heteroaryl", "5-6 membered heteroaryl", "4-6 membered heteroaryl", and "3-5 membered heteroaryl" contain five, six, from five to ten, from five to twelve, contain from five to six, from four to six ring atoms, and from three to five ring atoms, respectively. The heteroaryl groups include benzo-fused ring systems. Examples of heteroaryl groups include, but are not limited to, pyrrolyl, furyl, thienyl, imidazolyl, pyrazolyl, oxazolyl, isoxazolyl, isothiazolyl, triazolyl, oxadiazolyl, furazanyl, thiadiazolyl, thiazolyl, tetrazolyl, pyridinyl, pyrazinyl, pyrimidinyl, pyridazinyl, triazinyl, indolyl, isoindolyl, indolizinyl, benzofuranyl, benzothiophenyl, indazolyl, benzimidazolyl, benzoxazolyl, furo[3,2-b]pyridinyl, benzothiazolyl, benzofurazanyl, purinyl, quinolinyl, isoquinolinyl, quinazolinyl, quinoxalinyl, naphthyridinyl, cinnolinyl, phthalazinyl, pyrido[3,4-d]pyrimidinyl, pteridinyl, and the like.

Also included within the scope of the term "5-12 membered heteroaryl", as used herein, are benzo-fused unsaturated nitrogen heterocycles, which refer to a heterocyclic group in which a heteroatomic ring is fused to one or more aromatic rings. Examples include, but are not limited to, indolinyl, isoindolinyl, tetrahydroquinolinyl, tetrahydroisoquinolinyl, and the like.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

As used herein, an "effective" amount refers to an amount of a substance, agent, compound, or composition that is of sufficient quantity to result in a decrease in severity of disease symptoms, an increase in frequency and duration of disease symptom-free periods, or a prevention of impairment or disability due to the disease affliction—either as a single dose or according to a multiple dose regimen, alone or in combination with other agents or substances. One of ordinary skill in the art would be able to determine such amounts based on such factors as the subject's size, the severity of the subject's symptoms, and the particular composition or route of administration selected. The subject may be a human or non-human mammal (e.g., rabbit, rat, mouse, monkey or other lower-order primate).

Embodiments disclosed herein include isotopically-labeled compounds, which are identical to those recited in formula (I), formula (II), formula (III), formula (IV), formula (IVa), or formula (IVb), but for the fact that one or more atoms are replaced by an atom having an atomic mass or mass number different from the atomic mass or mass number usually found in nature. Examples of isotopes that can be incorporated into compounds of the embodiments disclosed herein include isotopes of hydrogen, carbon, nitrogen, oxygen, phosphorous, sulfur, fluorine and chlorine, such as, but not limited to, $^2$H, $^3$H, $^{13}$C, $^{14}$, $^{15}$N, $^{18}$O, $^{17}$O, $^{31}$P, $^{32}$P, $^{35}$S, $^{18}$F, and $^{36}$Cl, respectively. Compounds described herein and pharmaceutically acceptable salts of said compounds which contain the aforementioned isotopes and/or other isotopes of other atoms are within the scope of the present embodiments. Certain isotopically-labeled compounds of the embodiments disclosed herein, for example, those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example, increased in vivo half-life or reduced dosage requirements and, hence, may be preferred in some circumstances. Isotopically-labeled compounds of embodiments disclosed herein can generally be prepared by carrying out the procedures disclosed in the Schemes and/or in the Examples and Preparations below, by substituting a readily available isotopically-labeled reagent for a non-isotopically-labeled reagent.

Some embodiments relate to the pharmaceutically acceptable salts of the compounds described herein. Pharmaceutically acceptable salts of the compounds described herein include the acid addition and base addition salts thereof.

Some embodiments also relate to the pharmaceutically acceptable acid addition salts of the compounds described herein. Suitable acid addition salts are formed from acids which form non-toxic salts. Non-limiting examples of suitable acid addition salts, i.e., salts containing pharmacologically acceptable anions, include, but are not limited to, the acetate, acid citrate, adipate, aspartate, benzoate, besylate, bicarbonate/carbonate, bisulphate/sulphate, bitartrate, borate, camsylate, citrate, cyclamate, edisylate, esylate, ethanesulfonate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methanesulfonate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, p-toluenesulfonate, tosylate, trifluoroacetate and xinofoate salts.

Additional embodiments relate to base addition salts of the compounds described herein. Suitable base addition salts are formed from bases which form non-toxic salts. Non-limiting examples of suitable base salts include the aluminium, arginine, benzathine, calcium, choline, diethylamine, diolamine, glycine, lysine, magnesium, meglumine, olamine, potassium, sodium, tromethamine and zinc salts.

The compounds described herein that are basic in nature are capable of forming a wide variety of salts with various inorganic and organic acids. The acids that may be used to prepare pharmaceutically acceptable acid addition salts of such basic compounds described herein are those that form non-toxic acid addition salts, e.g., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds described herein that include a basic moiety, such as an amino group, may form pharmaceutically acceptable salts with various amino acids, in addition to the acids mentioned above.

The chemical bases that may be used as reagents to prepare pharmaceutically acceptable base salts of those compounds of the compounds described herein that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds of the embodiments described herein include all stereoisomers (e.g., cis and trans isomers) and all optical isomers of compounds described herein (e.g., R and S enantiomers), as well as racemic, diastereomeric and other mixtures of such isomers. While all stereoisomers are encompassed within the scope of our claims, one skilled in the art will recognize that particular stereoisomers may be preferred.

In some embodiments, the compounds described herein can exist in several tautomeric forms, including the enol and imine form, and the keto and enamine form and geometric isomers and mixtures thereof. All such tautomeric forms are included within the scope of the present embodiments. Tautomers exist as mixtures of a tautomeric set in solution. In solid form, usually one tautomer predominates. Even though one tautomer may be described, the present embodiments includes all tautomers of the present compounds.

The present embodiments also include atropisomers of the compounds described herein. Atropisomers refer to compounds that can be separated into rotationally restricted isomers.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002). Methods for making pharmaceutically acceptable salts of compounds described herein are known to one of skill in the art.

The term "solvate" is used herein to describe a molecular complex comprising a compound described herein and one or more pharmaceutically acceptable solvent molecules, for example, ethanol.

The compounds described herein may also exist in unsolvated and solvated forms. Accordingly, some embodiments relate to the hydrates and solvates of the compounds described herein.

Compounds described herein containing one or more asymmetric carbon atoms can exist as two or more stereoisomers. Where a compound described herein contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds described herein containing, for example, an imino, keto, or oxime group, or so-called valence tautomerism in compounds which contain an aromatic moiety. A single compound may exhibit more than one type of isomerism.

Included within the scope of the present embodiments are all stereoisomers, geometric isomers and tautomeric forms of the compounds described herein, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC) or SFC.

Alternatively, the racemate (or a racemic precursor) may be reacted with a suitable optically active compound, for example, an alcohol, or, in the case where a compound described herein contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; (5) benign and malignant cells of other proliferative diseases in which aberrant serine/threonine kinase activation occurs; (6) any tumors that proliferate by aberrant signaling, metabolic, epigenetic and transcriptional mechanism; and (7) benign and malignant cells of other proliferative diseases in which aberrant signaling, metabolic, epigenetic and transcriptional mechanism.

Further embodiments relate to methods of treating abnormal cell growth in a mammal. Additional embodiments relate to a method of treating abnormal cell growth in a mammal comprising administering to the mammal an amount of a compound described herein that is effective in treating abnormal cell growth.

In other embodiments, the abnormal cell growth is cancer.

In some embodiments, the cancer is selected from the group consisting of lung cancer, mesothelioma, bone cancer, pancreatic cancer, skin cancer, cancer of the head or neck, cutaneous or intraocular melanoma, uterine cancer, ovarian cancer, rectal cancer, cancer of the anal region, stomach cancer, hepatic carcinoma, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, hematology malignancy, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, glioblastoma, brain stem glioma, pituitary adenoma, or a combination of two or more of the foregoing cancers.

Additional embodiments relate to methods of treating cancer solid tumors in a mammal. Some embodiments relate to the treatment of cancer solid tumor in a mammal comprising administering to the mammal an amount of a compound described herein that is effective in treating said cancer solid tumor.

In other embodiments, the cancer solid tumor is breast, lung, colon, brain, prostate, stomach, pancreatic, ovarian, skin (melanoma), endocrine, uterine, testicular, or bladder.

Further embodiments relate to methods of treating abnormal cell growth in a mammal which comprises administering to said mammal an amount of a compound described herein that is effective in treating abnormal cell growth in combination with an anti-tumor agent selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

More embodiments relate to pharmaceutical compositions for treating abnormal cell growth in a mammal comprising an amount of a compound described herein that is effective in treating abnormal cell growth, and a pharmaceutically acceptable carrier.

Additional embodiments relate to a method of treating abnormal cell growth in a mammal, including a human, comprising administering to the mammal an amount of a compound described herein, or a pharmaceutically acceptable salt, solvate, hydrate or prodrug thereof, that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In one embodiment the method comprises comprising administering to a mammal an amount of a compound described herein that is effective in treating said cancer solid tumor. In one preferred embodiment the solid tumor is breast, lung, colon, brain, prostate, stomach, pancreatic, ovarian, skin (melanoma), endocrine, uterine, testicular, and bladder cancer.

In another embodiment of said method, said abnormal cell growth is a benign proliferative disease, including, but not limited to, psoriasis, benign prostatic hypertrophy or restinosis.

Some embodiments relate to a method of treating abnormal cell growth in a mammal which comprises administering to said mammal an amount of a compound described herein, or a pharmaceutically acceptable salt, solvate, hydrate or prodrug thereof, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

Additional embodiments relate to a pharmaceutical composition for treating abnormal cell growth in a mammal, including a human, comprising an amount of a compound described herein, or a pharmaceutically acceptable salt, solvate, hydrate or prodrug thereof, that is effective in treating abnormal cell growth, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

Further embodiments relate to a method of treating abnormal cell growth in a mammal which comprises administering to said mammal an amount of a compound described herein, or a pharmaceutically acceptable salt, solvate, or hydrate thereof, that is effective in treating abnormal cell growth in combination with another anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens. Some embodiments contemplate a pharmaceutical composition for treating abnormal cell growth wherein the composition includes a compound described herein, or a pharmaceutically acceptable salt, solvate, or hydrate thereof, that is effective in treating abnormal cell growth, and another anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

Yet more embodiments relate to a method of treating a disorder associated with angiogenesis in a mammal, including a human, comprising administering to said mammal an amount of a compound described herein, as defined above, or a pharmaceutically acceptable salt, solvate, hydrate or prodrug thereof, that is effective in treating said disorder in combination with one or more anti-tumor agents listed above. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi*, *Yersinia* spp., *Bordetella pertussis*, and group A *Streptococcus*.

Some embodiments relate to a method of (and to a pharmaceutical composition for) treating abnormal cell growth in a mammal which comprise an amount of a compound described herein, or a pharmaceutically acceptable salt, solvate, or hydrate thereof, in combination with an amount of one or more substances selected from anti-angiogenesis agents, signal transduction inhibitors inhibitor (e.g., inhibiting the means by which regulatory molecules that govern the fundamental processes of cell growth, differentiation, and survival communicated within the cell), and antiproliferative agents, which amounts are together effective in treating said abnormal cell growth.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound described herein in the methods and pharmaceutical compositions described herein. Examples of useful COX-II inhibitors include CELEBREX™ (celecoxib), Bextra (valdecoxib), paracoxib, Vioxx (rofecoxib), and Arcoxia (etoricoxib). Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in combination with the compounds described herein are AG-3340, RO 32-3555, RS 13-0830, and the following compounds:

3-[[4-(4-fluoro-phenoxy)-benzenesulfonyl]-(1-hydroxycarbamoyl-cyclopentyl)-amino]-propionic acid;
3-exo-3-[4-(4-fluoro-phenoxy)-benzenesulfonylamino]-8-oxa-bicyclo[3.2.1]octane-3-carboxylic acid hydroxyamide;
(2R, 3R) 1-[4-(2-chloro-4-fluoro-benzyloxy)-benzenesulfonyl]-3-hydroxy-3-methyl-piperidine-2-carboxylic acid hydroxyamide;
4-[4-(4-fluoro-phenoxy)-benzenesulfonylamino]-tetrahydro-pyran-4-carboxylic acid hydroxyamide;
3-[[4-(4-fluoro-phenoxy)-benzenesulfonyl]-(1-hydroxycarbamoyl-cyclobutyl)-amino]-propionic acid;
4-[4-(4-chloro-phenoxy)-benzenesulfonylamino]-tetrahydro-pyran-4-carboxylic acid hydroxyamide;
3-[4-(4-chloro-phenoxy)-benzenesulfonylamino]-tetrahydro-pyran-3-carboxylic acid hydroxyamide;
(2R, 3R) 1-[4-(4-fluoro-2-methyl-benzyloxy)-benzenesulfonyl]-3-hydroxy-3-methyl-piperidine-2-carboxylic acid hydroxyamide;
3-[[4-(4-fluoro-phenoxy)-benzenesulfonyl]-(1-hydroxycarbamoyl-1-methyl-ethyl)-amino]-propionic acid;
3-[[4-(4-fluoro-phenoxy)-benzenesulfonyl]-(4-hydroxycarbamoyl-tetrahydro-pyran-4-yl)-amino]-propionic acid;
3-exo-3-[4-(4-chloro-phenoxy)-benzenesulfonylamino]-8-oxa-bicyclo[3.2.1]octane-3-carboxylic acid hydroxyamide;
3-endo-3-[4-(4-fluoro-phenoxy)-benzenesulfonylamino]-8-oxa-bicyclo[3.2.1]octane-3-carboxylic acid hydroxyamide; and
3-[4-(4-fluoro-phenoxy)-benzenesulfonylamino]-tetrahydro-furan-3-carboxylic acid hydroxyamide;
and pharmaceutically acceptable salts and solvates of said compounds.

VEGF inhibitors, for example, sutent and axitinib, can also be combined with a compound described herein. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), U.S. Pat. No. 6,653,308 (issued Nov. 25, 2003), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); Avastin, an anti-VEGF monoclonal antibody of Genentech, Inc. of South San Francisco, Calif.; and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with a compound described herein. Such erbB2 inhibitors include Herceptin, $2C_4$, and pertuzumab. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the embodiments described herein are also described in U.S. Provisional Application No. 60/117,341, filed Jan. 27, 1999, and in U.S. Provisional Application No. 60/117,346, filed Jan. 27, 1999, both of which are herein incorporated by reference in their entirety. Other erbb2 receptor inhibitors include TAK-165 (Takeda) and GW-572016 (Glaxo-Wellcome).

Various other compounds, such as styrene derivatives, have also been shown to possess tyrosine kinase inhibitory properties, and some of tyrosine kinase inhibitors have been identified as erbB2 receptor inhibitors. More recently, five European patent publications, namely EP 0 566 226 A1 (published Oct. 20, 1993), EP 0 602 851 A1 (published Jun. 22, 1994), EP 0 635 507 A1 (published Jan. 25, 1995), EP 0 635 498 A1 (published Jan. 25, 1995), and EP 0 520 722 A1 (published Dec. 30, 1992), refer to certain bicyclic derivatives, in particular quinazoline derivatives, as possessing anti-cancer properties that result from their tyrosine kinase inhibitory properties. Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/

16960 (published Jun. 6, 1996), WO 96/09294 (published Mar. 6, 1996), WO 97/30034 (published Aug. 21, 1997), WO 98/02434 (published Jan. 22, 1998), WO 98/02437 (published Jan. 22, 1998), and WO 98/02438 (published Jan. 22, 1998), also refer to substituted bicyclic heteroaromatic derivatives as tyrosine kinase inhibitors that are useful for the same purpose. Other patent applications that refer to anti-cancer compounds are World Patent Application WO00/44728 (published Aug. 3, 2000), EP 1029853A1 (published Aug. 23, 2000), and WO01/98277 (published Dec. 12, 2001) all of which are incorporated herein by reference in their entirety.

Epidermal growth factor receptor (EGFR) inhibitors may be administered in combination with a compound of the presentation invention. Such EGFR inhibitors include gefinitib, erlotinib, icotinib, afatinib and dacomitinib. Monoclonal antibody inhibitors of EGFR, such as cetuximab, may also be combined with a compound of the present invention.

PI3K inhibitors, such as PI3K beta inhibitors, may be administered in combination with a compound of the presentation invention.

Mammalian target of rapamycin (mTOR) inhibitors may be administered in combination with a compound of the presentation invention. Such mTOR inhibitors include rapamycin analogs and ATP competitive inhibitors.

c-Met inhibitors may be administered in combination with a compound of the presentation invention. Such c-Met inhibitors include crizotinib and ARQ-197. Monoclonal antibody inhibitors of c-Met, such as METMab, may also be combined with a compound of the present invention.

CDK inhibitors may be administered in combination with a compound of the presentation invention. Such CDK inhibitors include palbociclib.

MEK inhibitors may be administered in combination with a compound of the presentation invention. Such MEK inhibitors include PD-325901.

PARP inhibitors may be administered in combination with a compound of the presentation invention.

JAK inhibitors may be administered in combination with a compound of the presentation invention.

An antagonist of a Programmed Death 1 protein (PD-1) may be administered in combination with a compound of the presentation invention.

Other antiproliferative agents that may be used with the compounds described herein include inhibitors of the enzyme farnesyl protein transferase and inhibitors of the receptor tyrosine kinase PDGFr, including the compounds disclosed and claimed in the following U.S. patent application Ser. No. 09/221,946 (filed Dec. 28, 1998); Ser. No. 09/454,058 (filed Dec. 2, 1999); Ser. No. 09/501,163 (filed Feb. 9, 2000); Ser. No. 09/539,930 (filed Mar. 31, 2000); Ser. No. 09/202,796 (filed May 22, 1997); Ser. No. 09/384,339 (filed Aug. 26, 1999); and Ser. No. 09/383,755 (filed Aug. 26, 1999); and the compounds disclosed and claimed in the following U.S. provisional patent applications: 60/168,207 (filed Nov. 30, 1999); 60/170,119 (filed Dec. 10, 1999); 60/177,718 (filed Jan. 21, 2000); 60/168,217 (filed Nov. 30, 1999), and 60/200,834 (filed May 1, 2000). Each of the foregoing patent applications and provisional patent applications is herein incorporated by reference in their entirety.

A compound described herein may also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, supra. Specific CTLA4 antibodies that can be used in the present embodiments include those described in U.S. Provisional Application 60/113,647 (filed Dec. 23, 1998) which is herein incorporated by reference in its entirety.

A compound described herein may be applied as a sole therapy or may involve one or more other anti-tumor substances, for example those selected from, for example, mitotic inhibitors, for example vinblastine; alkylating agents, for example cis-platin, oxaliplatin, carboplatin and cyclophosphamide; anti-metabolites, for example 5-fluorouracil, capecitabine, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex (tamoxifen) or, for example anti-androgens such as Casodex (4'-cyano-3-(4-fluorophenylsulphonyl)-2-hydroxy-2-methyl-3'-(trifluoromethyl)propionanilide).

The compounds described herein may be used alone or in combination with one or more of a variety of anti-cancer agents or supportive care agents. For example, the compounds described herein may be used with cytotoxic agents, e.g., one or more selected from the group consisting of a camptothecin, irinotecan HCl (Camptosar), edotecarin, SU-11248, epirubicin (Ellence), docetaxel (Taxotere), paclitaxel, rituximab (Rituxan) bevacizumab (Avastin), imatinib mesylate (Gleevac), Erbitux, gefitinib (Iressa), and combinations thereof. Some embodiments also contemplate the use of the compounds described herein together with hormonal therapy, e.g., exemestane (Aromasin), Lupron, anastrozole (Arimidex), tamoxifen citrate (Nolvadex), Trelstar, and combinations thereof. Further, some embodiments provide a compound described herein alone or in combination with one or more supportive care products, e.g., a product selected from the group consisting of Filgrastim (Neupogen), ondansetron (Zofran), Fragmin, Procrit, Aloxi, Emend, or combinations thereof. Such conjoint treatment may be achieved by way of the simultaneous, sequential or separate dosing of the individual components of the treatment.

The compounds described herein may be used with anti-tumor agents, alkylating agents, antimetabolites, antibiotics, plant-derived antitumor agents, camptothecin derivatives, tyrosine kinase inhibitors, antibodies, interferons, and/or biological response modifiers. In this regard, the following is a non-limiting list of examples of secondary agents that may be used with the compounds described herein.

Alkylating agents include, but are not limited to, nitrogen mustard N-oxide, cyclophosphamide, ifosfamide, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, ifosfamide, KW-2170, mafosfamide, and mitolactol; platinum-coordinated alkylating compounds include but are not limited to, cisplatin, carboplatin, eptaplatin, lobaplatin, nedaplatin, oxaliplatin or satrplatin.

Antimetabolites include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, gemcitabine, fludarabin, 5-azacitidine, capecitabine, cladribine, clofarabine, decitabine, eflornithine, ethynylcytidine, cytosine arabinoside, hydroxyurea, TS-1, melphalan, nelarabine, nolatrexed, ocfosfate, disodium premetrexed, pentostatin, pelitrexol, raltitrexed, triapine, trimetrexate, vidarabine, vincristine, vinorelbine; or for example, one of the preferred antimetabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid.

Antibiotics include but are not limited to: aclarubicin, actinomycin D, amrubicin, annamycin, bleomycin, daunorubicin, doxorubicin, elsamitrucin, epirubicin, galarubicin, idarubicin, mitomycin C, nemorubicin, neocarzinostatin, peplomycin, pirarubicin, rebeccamycin, stimalamer, streptozocin, valrubicin or zinostatin.

Hormonal therapy agents, e.g., exemestane (Aromasin), Lupron, anastrozole (Arimidex), doxercalciferol, fadrozole, formestane, anti-estrogens such as tamoxifen citrate (Nolvadex) and fulvestrant, Trelstar, toremifene, raloxifene, lasofoxifene, letrozole (Femara), or anti-androgens such as bicalutamide, flutamide, mifepristone, nilutamide, Casodex® (4'-cyano-3-(4-fluorophenylsulphonyl)-2-hydroxy-2-methyl-3'-(trifluoromethyl)propionanilide) and combinations thereof.

Plant derived anti-tumor substances include for example those selected from mitotic inhibitors, for example vinblastine, docetaxel (Taxotere) and paclitaxel.

Cytotoxic topoisomerase inhibiting agents include one or more agents selected from the group consisting of aclarubicn, amonafide, belotecan, camptothecin, 10-hydroxycamptothecin, 9-aminocamptothecin, diflomotecan, irinotecan HCl (Camptosar), edotecarin, epirubicin (Ellence), etoposide, exatecan, gimatecan, lurtotecan, mitoxantrone, pirarubicin, pixantrone, rubitecan, sobuzoxane, SN-38, taflupo-side, and topotecan, and combinations thereof.

Immunologicals include interferons and numerous other immune enhancing agents. Interferons include interferon alpha, interferon alpha-2a, interferon, alpha-2b, interferon beta, interferon gamma-1a or interferon gamma-n1. Other agents include PF3512676, filgrastim, lentinan, sizofilan, TheraCys, ubenimex, WF-10, aldesleukin, alemtuzumab, BAM-002, dacarbazine, daclizumab, denileukin, gemtuzumab ozogamicin, ibritumomab, imiquimod, lenograstim, lentinan, melanoma vaccine (Corixa), molgramostim, Onco-VAX-CL, sargramostim, tasonermin, tecleukin, thymalasin, tositumomab, Virulizin, Z-100, epratuzumab, mitumomab, oregovomab, pemtumomab, Provenge.

Biological response modifiers are agents that modify defense mechanisms of living organisms or biological responses, such as survival, growth, or differentiation of tissue cells to direct them to have anti-tumor activity. Such agents include krestin, lentinan, sizofiran, picibanil, or ubenimex.

Other anticancer agents include alitretinoin, ampligen, atrasentan bexarotene, bortezomib. Bosentan, calcitriol, exisulind, finasteride, fotemustine, ibandronic acid, miltefosine, mitoxantrone, l-asparaginase, procarbazine, dacarbazine, hydroxycarbamide, pegaspargase, pentostatin, tazarotne, TLK-286, Velcade, Tarceva, or tretinoin.

Other anti-angiogenic compounds include acitretin, fenretinide, thalidomide, zoledronic acid, angiostatin, aplidine, cilengtide, combretastatin A-4, endostatin, halofuginone, rebimastat, removab, Revlimid, squalamine, ukrain and Vitaxin.

Platinum-coordinated compounds include but are not limited to, cisplatin, carboplatin, nedaplatin, or oxaliplatin.

Camptothecin derivatives include but are not limited to camptothecin, 10-hydroxycamptothecin, 9-aminocamptothecin, irinotecan, SN-38, edotecarin, and topotecan.

Tyrosine kinase inhibitors include, for example, Iressa and SU5416.

Antibodies include, for example, Herceptin, Erbitux, Avastin, and Rituximab.

Interferons include, for example, interferon alpha, interferon alpha-2a, interferon, alpha-2b, interferon beta, interferon gamma-1a and interferon gamma-n1.

Biological response modifiers include agents that modify defense mechanisms of living organisms or biological responses, such as survival, growth, or differentiation of tissue cells to direct them to have anti-tumor activity. Such agents include, for example, krestin, lentinan, sizofiran, picibanil, and ubenimex.

Other antitumor agents include, for example, mitoxantrone, I-asparaginase, procarbazine, dacarbazine, hydroxycarbamide, pentostatin, and tretinoin. Additionally, PI3K inhibitors and RAS-targeted cancer treatments may be combined with the compounds described herein.

Some embodiments also relate to a pharmaceutical composition comprising a compound of formula (I), formula (II), formula (III), formula (IV), formula (IVa), or formula (IVb), or a pharmaceutically acceptable salt or solvate thereof, as hereinbefore defined in association with a pharmaceutically acceptable adjuvant, diluent or carrier.

Further embodiments relate to a pharmaceutical composition which comprises mixing a compound of formula (I), formula (II), formula (III), formula (IV), formula (IVa), or formula (IVb), or a pharmaceutically acceptable salt or solvate thereof, as hereinbefore defined with a pharmaceutically acceptable adjuvant, diluent or carrier.

For the above-mentioned therapeutic uses the dosage administered will, of course, vary with the compound employed, the mode of administration, the treatment desired and the disorder indicated. The daily dosage of the compound formula (I), formula (II), formula (III), formula (IV), formula (IVa), or formula (IVb), or pharmaceutically acceptable salt thereof, may be in the range from 1 mg to 1 gram, preferably 1 mg to 250 mg, more preferably 10 mg to 100 mg.

The present embodiments also encompass sustained release compositions.

Administration of the compounds described herein (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The active compound may be applied as a sole therapy or may involve one or more other anti-tumor substances, for example those selected from, for example, mitotic inhibitors, for example vinblastine; alkylating agents, for example cis-platin, carboplatin and cyclophosphamide; anti-metabolites, for example 5-fluorouracil, cytosine arabinoside and hydroxyurea, or, for example, one of the preferred antimetabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex® (tamoxifen) or, for example anti-androgens such as Casodex® (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound described herein as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The examples and preparations provided below further illustrate and exemplify the compounds described herein and methods of preparing such compounds. The scope of the embodiments described herein is not limited in any way by the following examples and preparations. In the following examples, molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

In the examples shown, salt forms were occasionally isolated as a consequence of the mobile phase additives during HPLC based chromatographic purification. In these cases, salts such as formate, trifluorooacetate and acetate were isolated and tested without further processing. It will be recognized that one of ordinary skill in the art will be able to realize the free base form by standard methodology (such as using ion exchange columns, or performing simple basic extractions using a mild aqueous base).

In general, the compounds described herein may be prepared by processes known in the chemical arts, particularly in light of the description contained herein. Certain processes for the manufacture of the compounds described herein are provided as further features of the embodiments and are illustrated in the reaction schemes provided below and in the experimental section.

Unless stated otherwise, the variables in Schemes A-H have the same meanings as defined herein.

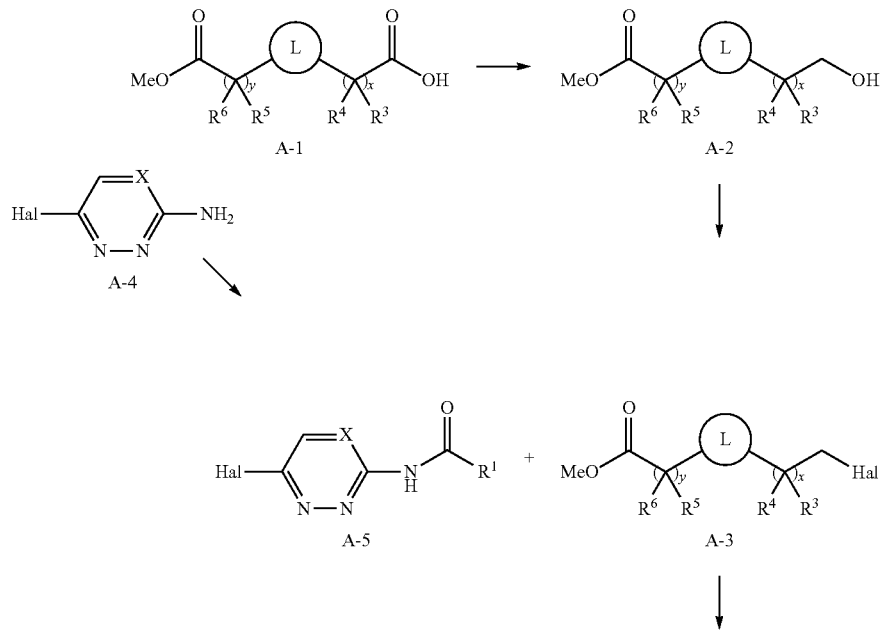

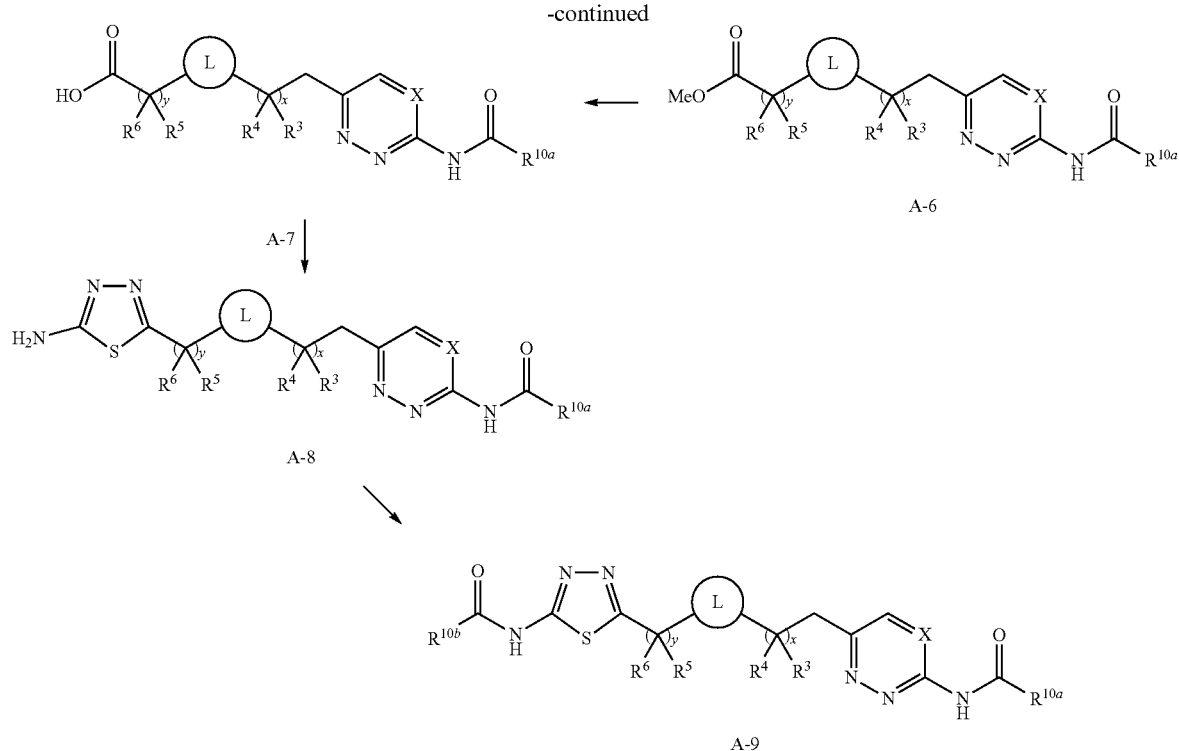

X = N or CH

As exemplified in Scheme A, the mono-ester mono-acid A-1, which may be obtained either from commercial sources, or from selective ester hydrolysis or desymmetrization of symmetrical anhydrides under standard literature conditions (see for example, *J. Am. Chem. Soc.,* 2000, 122, 9542 and *Helv. Chim. Acta.,* 1983, 66, 2501), is subjected to selective reduction of the carboxylic acid moiety using a reducing agent such as borane.dimethylsulfide to afford A-2. The alcohol in A-2 may be halogenated to form an alkyl halide such as an iodide or a bromide using reagents such as iodine/triphenylphosphine in the presence of a base such as imidazole or carbon tetrabromide to afford A-3. The coupling partner A-5 is obtained from the acylation of a commercially available 2-amino-6-halogenated heterocycle, A-4, using an acid in the presence of a standard coupling reagent such as HATU or HBTU in the presence of a base such as Hunig's base or triethylamine. The reaction between A-5 and A-3 takes place through a palladium-mediated process such as a Negishi reaction. For example, the halogenated compound A-3 may be activated as an organometallic species such as an organozincate by treatment with species such as zinc dust in the presence of an activating agent such a 1,2-dibromoethane and TMSCl in a solvent such as DMF, or without activation by using diethyl zinc for the metallation process. The zincate obtained may be coupled with the halogenated heterocycle A-5 through a Negishi reaction using a palladium catalyst such as Pd$_2$(dba)$_3$ in the presence of a suitable ligand such as tri(o-tolylphoshine) in a solvent such as DMF to afford A-6. The ester in A-6 is hydrolyzed by an inorganic base such as lithium hydroxide or sodium hydroxide in a solvent such as methanol and water to afford the carboxylic acid A-7. Condensation of A-7 with thiosemicarbazide in the presence of phosphorus oxychloride as both an activating and dehydrating agent provides the aminothiadiazole A-8. Acylation of A-8 either using by reaction with an acid chloride or by using a suitable amide coupling agent (such as T3P, HATU or HBTU) and an appropriate carboxylic acid in the presence of a base such as pyridine, TEA or Hunig's base in a solvent such as DMF or DMA affords A-9. Separation of the enantiomers may be carried out under standard methods known in the art such as chiral SFC or HPLC to afford the single enantiomer A-9.

Scheme B

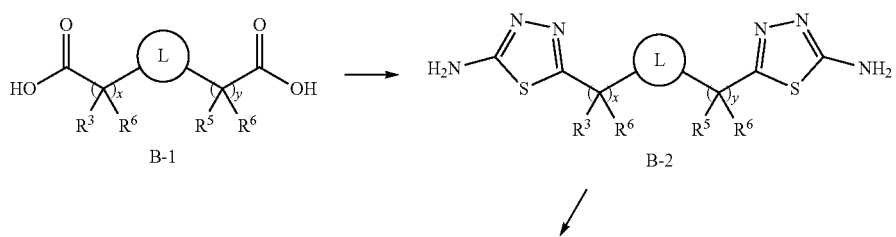

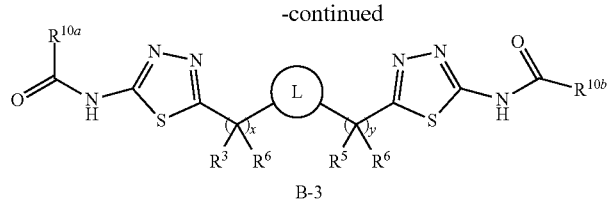

B-3

As exemplified in Scheme B, the di-acid B-1 may be either obtained from commercial sources, or prepared by methods, which are established in the literature or reported herein. Condensation of B-1 with thiosemicarbazide in the presence of phosphorus oxychloride as both an activating and dehydrating agent provides the bis-aminothiadiazole B-2. Acylation of B-2 either by reaction with an acid chloride or by using a suitable amide coupling agent (such as T3P, HATU or HBTU) and an appropriate carboxylic acid in the presence of a base such as pyridine, TEA or Hunig's base in a solvent such as DMF or DMA affords the symmetrically substituted bis-aminothidiazole, B-3. Separation of the enantiomers may be carried out under standard methods known in the art such as chiral SFC or HPLC to afford single enantiomers of B-3.

Scheme C

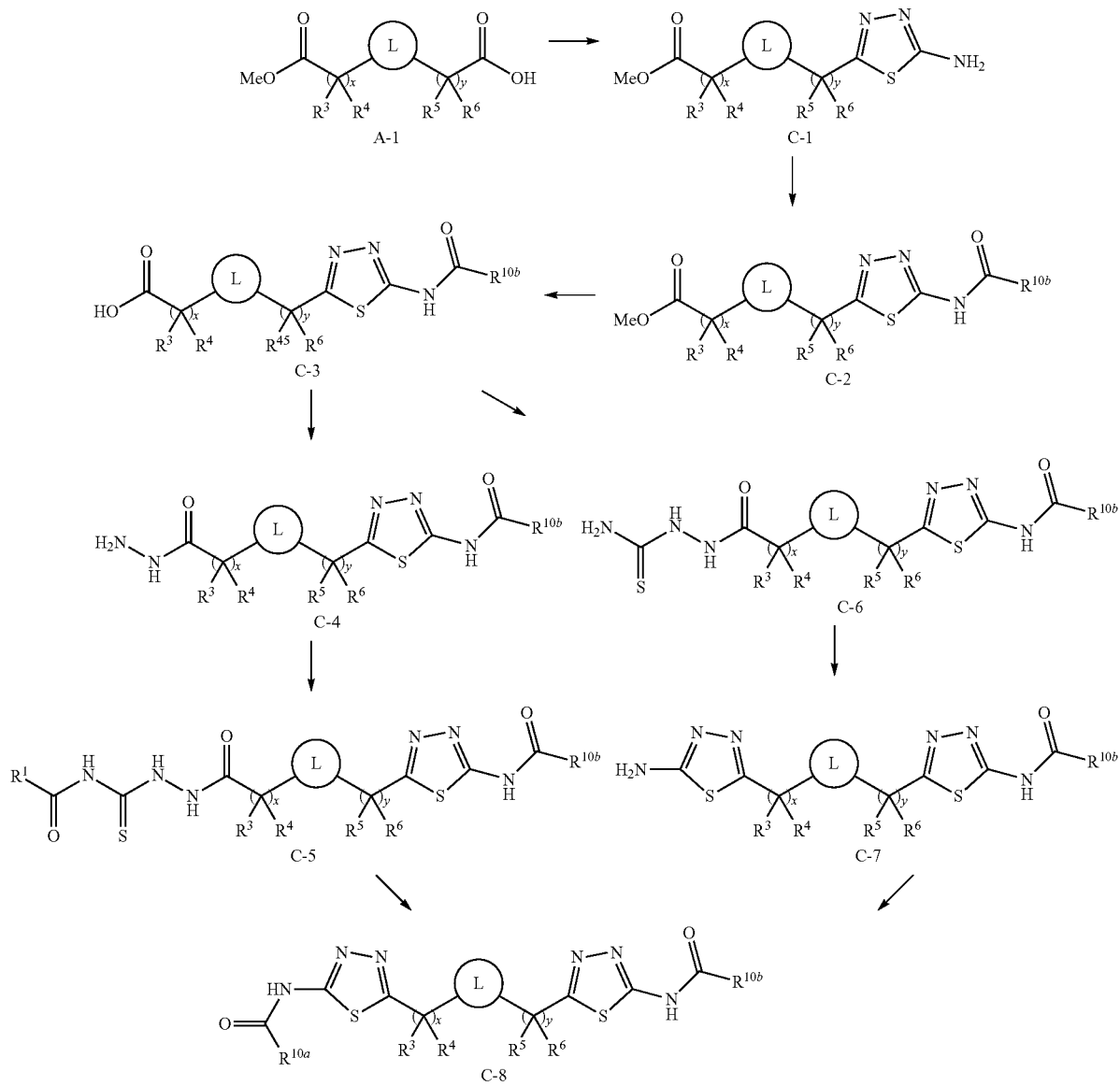

As exemplified in Scheme C, the mono-ester mono-acid (A-1 in scheme A) is converted into the mono-thiadiazole under standard conditions known in the art such as condensation with thiosemicarbazide in the presence of an activating/dehydrating agent such as phosphorus oxychloride to provide C-1. Acylation of C-1 is carried out under standard conditions such as condensation with acetyl chloride or acetic anhydride in the presence of a base such as triethylamine in a solvent such as DMF to afford C-2. Ester hydrolysis of C-2 is carried out under basic conditions using a base such as NaOH or LiOH in a solvent such as methanol to afford C-3. Condensation of C-3 with hydrazine in the presence of a suitable coupling agent (such as T3P, HBTU or HATU) and a base (such as pyridine, TEA or DIPEA) in a suitable solvent such as DMF affords C-4. Reaction with C-4 with an isothiocyanate in a suitable solvent such as ethyl acetate, THF or methylene chloride affords C-5. Isothiocyanates are either commercially available or may be prepared by direct reaction of an acid chloride with sodium isothiocyanate under conditions, which are well established in the literature. C-5 is cyclized by dehydration under acidic conditions in the presence of a suitable acid such as sulfuric acid to afford C-8. Alternatively, C-3 is condensed with thiosemicarbazide in the presence of a suitable coupling agent (such as HBTU or HATU) and a base (such as TEA or DIPEA) in a suitable solvent such as DMF to afford C-6. C-6 is cyclized by dehydration under acidic conditions in the presence of a suitable acid such as sulfuric acid to afford C-7. Acylation of C-7 either using by reaction with an acid chloride or by using a suitable amide coupling agent (such as T3P, HATU or HBTU) and an appropriate carboxylic acid in the presence of a base such as pyridine, TEA or Hunig's base in a solvent such as DMF or DMA affords C-8. Separation of the enantiomers may be carried out under standard methods known in the art such as chiral SFC or HPLC to afford single enantiomer C-8.

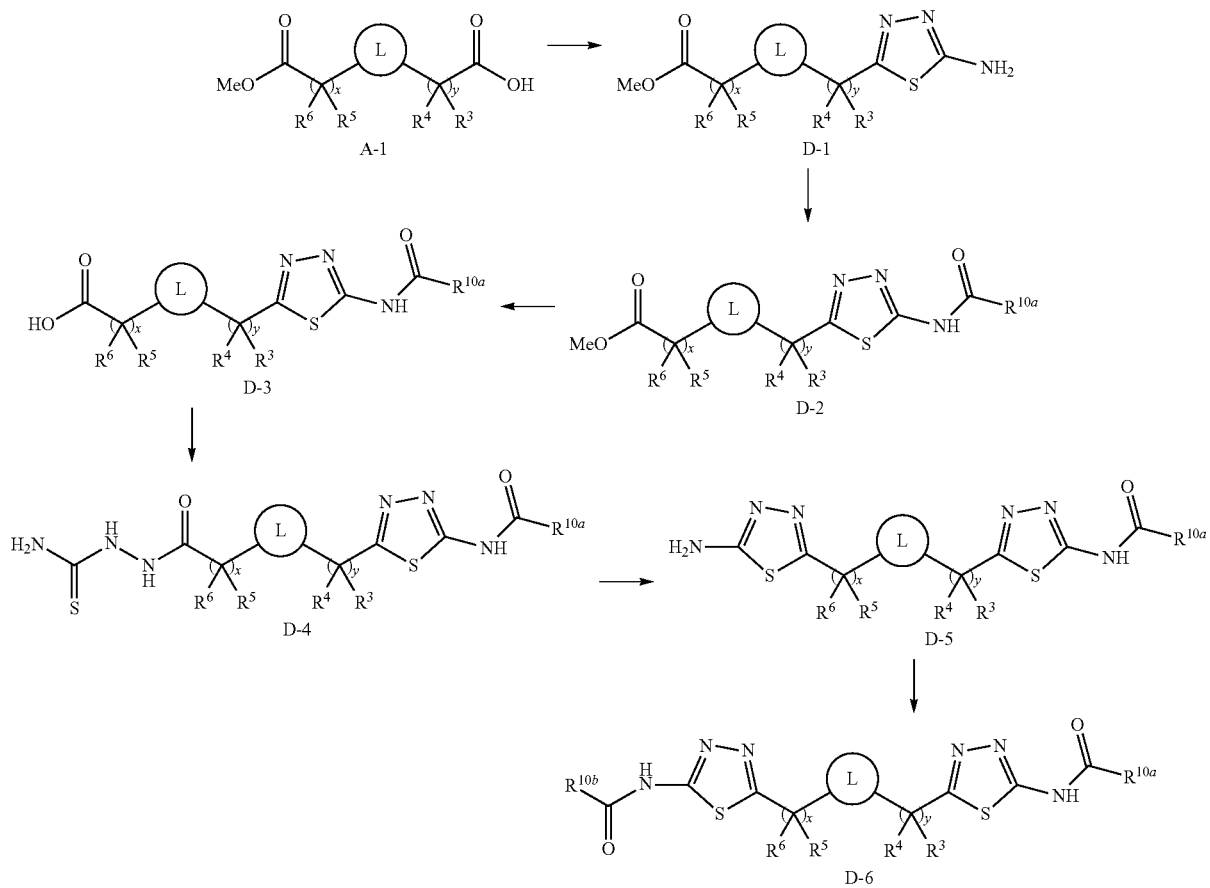

Scheme D

As exemplified in Scheme D, the mono-ester mono-acid (A-s in Scheme A) is converted into the mono-thiadiazole under standard conditions known in the art such as condensation with thiosemicarbazide in the presence of an activating/dehydrating agent such as phosphorus oxychloride to provide D-1. Acylation of D-1 either by reaction with an acid chloride or by using a suitable amide coupling agent (such as T3P, HATU or HBTU) and an appropriate carboxylic acid in the presence of a base such as pyridine, TEA or Hunig's base in a solvent such as DMF or DMA affords D-2. Ester hydrolysis of D-2 is carried out under basic conditions using a base such as NaOH or LiOH in a solvent such as methanol to afford D-3. D-3 is condensed with thiosemicarbazide in the presence of a suitable coupling agent (such as T3P, HBTU or HATU) and a base (such as pyridine, TEA or Hunig's base) in a suitable solvent such as DMF to afford D-4. D-4 is cyclized by dehydration under acidic conditions in the presence of a suitable acid such as sulfuric acid to afford D-5. Acylation of D-5 is carried out under standard conditions using an acylation agent such as acetic anhydride in a solvent such as acetic acid to afford D-6. Separation of the enantiomers may be carried out under standard methods known in the art such as chiral SFC or HPLC to afford single enantiomer D-6.

hindered face will be preferred. Condensation of E-3 with thiosemicarbazide in the presence of phosphorus oxychloride as both an activating and dehydrating agent provides the

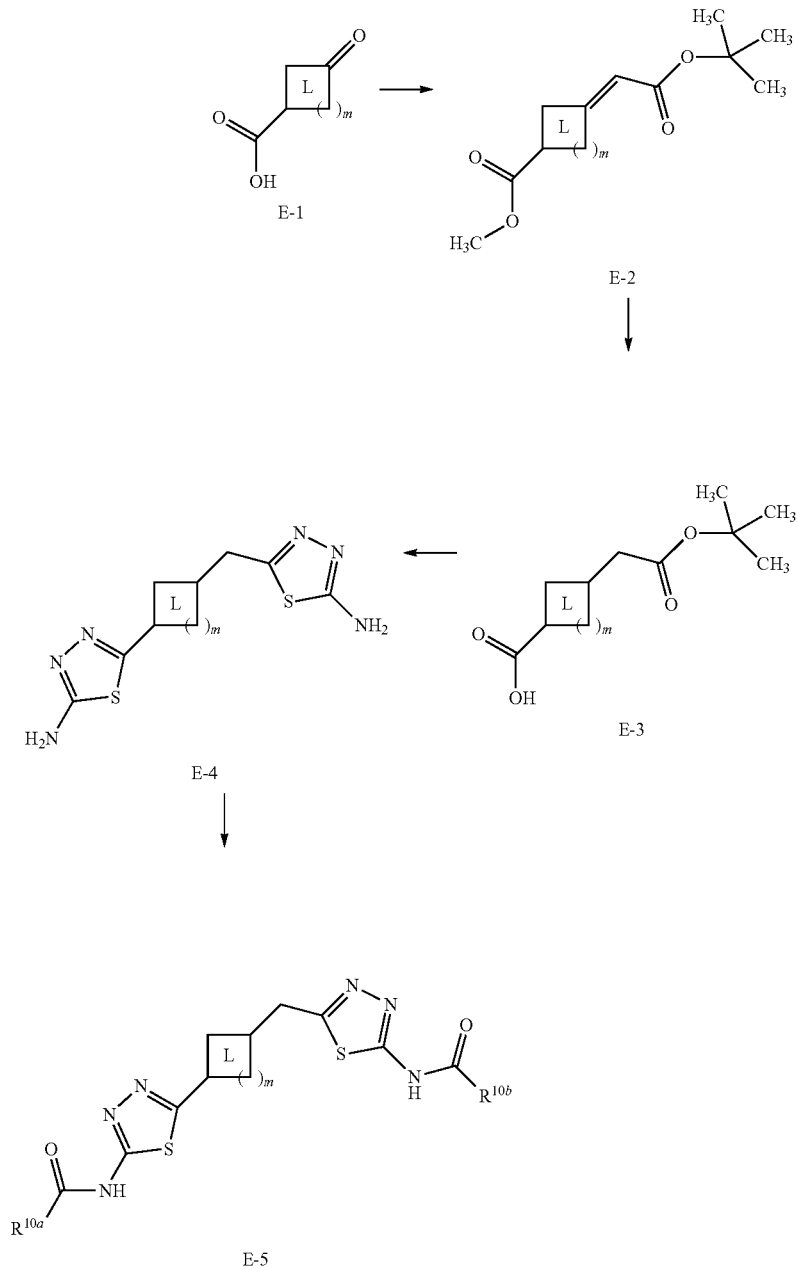

Scheme E

As exemplified in Scheme E, the cyclic keto-acid E-1 may be either obtained from commercial sources, or prepared by methods, which are established in the literature or reported herein. Reaction of the ketone function with an organophosphorane in the presence of a base such as sodium hydride in a solvent such as THF in a Horner-Wittig-Emmons reaction gives the unsaturated ester, E-2. Reduction of the olefin under hydrogen pressure in the presence of a heterogeneous catalyst such as palladium on carbon or platinum oxide in a solvent such as methanol or dichloromethane gives E-3 as a mixture of diastereomers in which reduction from the less bis-aminothiadiazole E-4. Acylation of E-4 either using by reaction with an acid chloride or by using a suitable amide coupling agent (such as T3P, HATU or HBTU) and an appropriate carboxylic acid in the presence of a base such as pyridine, TEA or Hunig's base in a solvent such as DMF or DMA affords the symmetrically substituted bis-aminothidiazole, E-5. Separation of the diastereomers and enantiomers may be carried out under standard methods known in the art such as flash chromatography, chiral SFC or HPLC to afford a single diastereomer or enantiomer E-5.

Scheme F

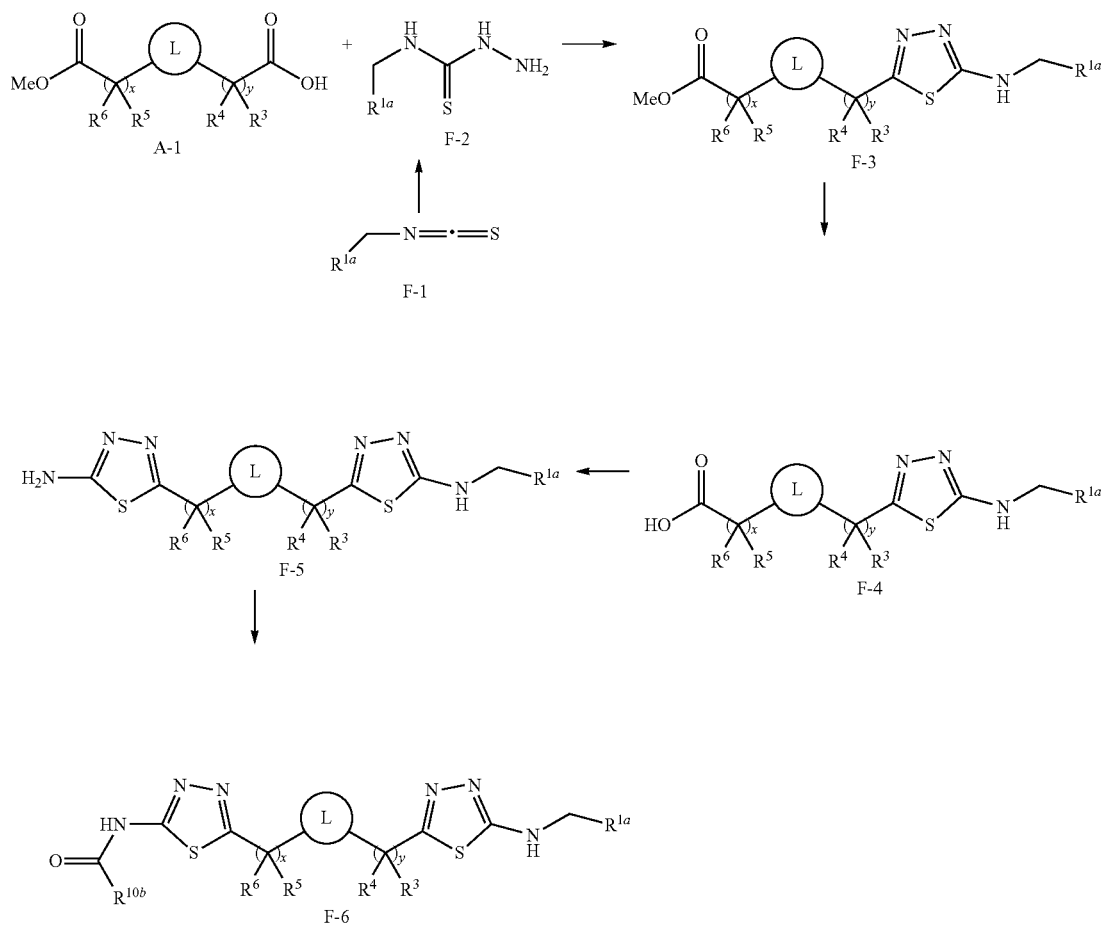

$R^{1a}$ = $C_1$-$C_3$ alkyl, $C_3$-$C_6$ cycloalkyl, or 5-6 membered heteroaryl As exemplified in Scheme F, the mono-ester mono-acid A-1 is condensed with the alkyl or aryl-substituted thiosemicarbazide, F-2, in the presence of phosphorus oxychloride as both an activating and dehydrating agent to provide the alkyl or aryl-substituted aminothiadiazole F-3. The alkyl-substituted thiosemicarbazide F-2 is obtained either from commercial sources or by the action of hydrazine on a commercial alkyl or aryl isothiocyanide, F-1 or by using alternative methods which are well established in the literature (*Phosphorus, Sulfur, and Silicon and the Related Elements*, 1991, 60 (1-2), 15-19). Hydrolysis of the ester F-3 using an inorganic base such as lithium hydroxide or sodium hydroxide in a solvent such as methanol and water gives the carboxylic acid, F-4. Condensation of F-4 with thiosemicarbazide in the presence of phosphorus oxychloride as both an activating and dehydrating agent provides the bis-aminothiadiazole E-5. Acylation of F-5 either using by reaction with an acid chloride or by using a suitable amide coupling agent (such as T3P, HATU or HBTU) and an appropriate carboxylic acid in the presence of a base such as pyridine, TEA or Hunig's base in a solvent such as DMF or DMA affords the symmetrically substituted bis-aminothidiazole, F-6. Separation of the enantiomers may be carried out under standard methods known in the art such as chiral SFC or HPLC to afford single enantiomers of F-6.

Scheme G

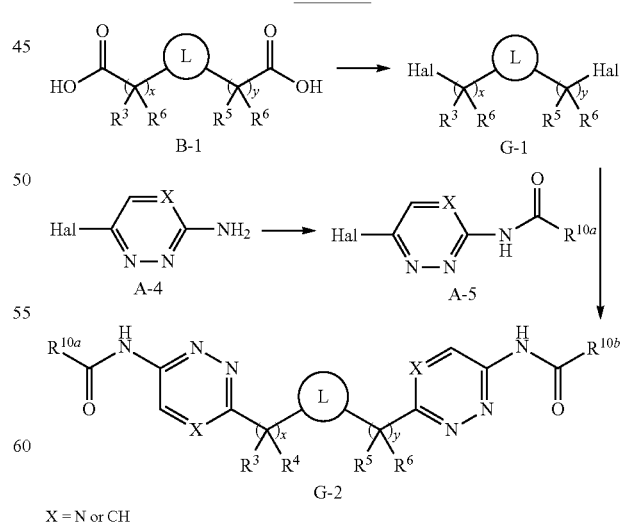

X = N or CH

As exemplified in Scheme G, the di-acid B-1 may be either obtained from commercial sources, or prepared by methods, which are established in the literature or reported herein. B-1 may be converted to the dihalide G-1 through a decarboxylation-halogenation type sequence typically referred to as a Hunsdiecker reaction, which may take place under photochemical conditions in the presence of a suitable halogen source, such as diiodohydantoin in a solvent such as 1,2-dichloroethane. The coupling partner A-5 is obtained from the acylation of a commercially available 2-amino-6-halogenated heterocycle, A-4, using an acid in the presence of a standard coupling reagent such as T3P, HATU or HBTU in the presence of a base such as pyridine, Hunig's base or TEA. The reaction between A-5 and B-1 takes place through a palladium-mediated process such as a Negishi reaction. For example, the di-halogenated compound B-1 may be activated as an organometallic species such as an organozincate by treatment with species such as zinc dust in the presence of an activating agent such a 1,2-dibromoethane and TMS-Cl in a solvent such as DMF, or without activation by using diethyl zinc for the metallation process. The zincate obtained may be coupled with the halogenated heterocycle A-5 through a Negishi reaction using a palladium catalyst such as $Pd_2(dba)_3$ in the presence of a suitable ligand such as tri(o-tolylphoshine) in a solvent such as DMF to afford G-2. If necessary, separation of the enantiomers of G-2 may be carried out under standard methods known in the art such as chiral SFC or HPLC to afford the single enantiomers of G-2.

Scheme H

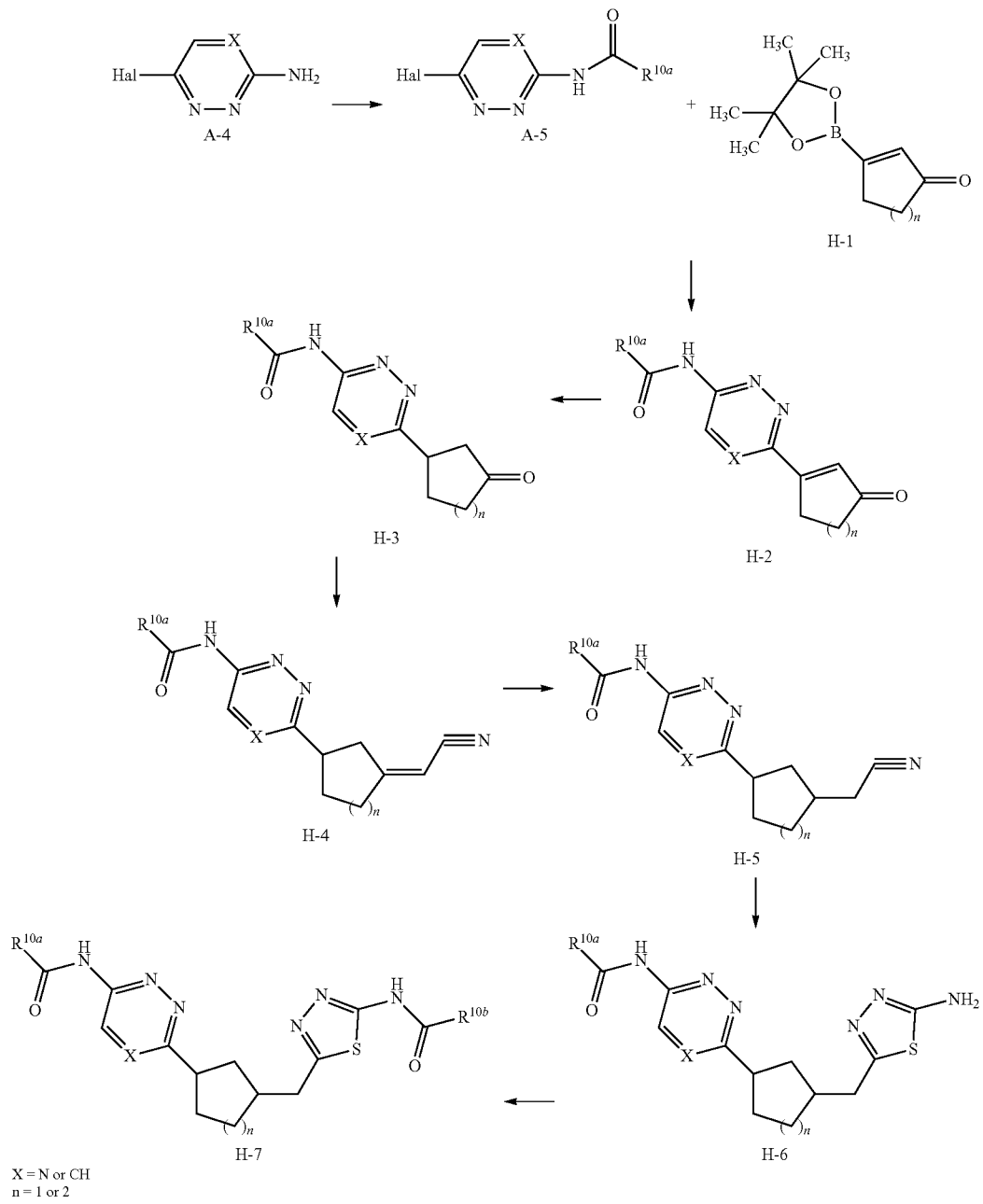

X = N or CH
n = 1 or 2

As exemplified in Scheme H, coupling partner A-5 is obtained from the acylation of a commercially available 2-amino-6-halogenated heterocycle, A-4, using an acid in the presence of a standard coupling reagent such as T3P, HATU or HBTU in the presence of a base such as pyridine, Hunig's base or TEA. Vinyl boronate H-1 may be obtained from an established literature procedure involving borylation of the corresponding halogenated α,β-unsaturated cyclic ketone (US 2012/0077814). The reaction between A-5 and H-1 takes place through a palladium-mediated process such as a Suzuki reaction to give H-2. For example, A-5 and H-1 may be reacted together at elevated temperature in the presence of a palladium catalyst, such as Pd(dppf)Cl$_2$ in the presence of suitable base (such as K$_3$PO$_4$ or CsF) in a mixed solvent system comprising of an organic solvent (for example, THF, DME or toluene) and water. Reduction of the endocyclic olefin of H-2 under hydrogen pressure in the presence of a heterogeneous catalyst such as palladium on carbon or platinum oxide in a solvent such as methanol or dichloromethane gives H-3. H-3 may be elaborated to H-4 through a Horner-Wittig-Emmons type olefination involving treatment of with a phosphonate reagent such as diethyl (cyanomethyl)phosphonate in the presence of a strong base such as NaH in a suitable solvent (for example, THF). Reduction of the exocyclic olefin of H-4 to give H-5 may be achieved through utilization of a hydride-based reagent. For example, L-Selectride may be employed as the reductant in a solvent such as THF at depressed temperature to provide H-5 as a mixture of diastereomers. Condensation of H-5 with thiosemicarbazide in the presence of an acid such as TFA at elevated temperature provides the aminothiadiazole H-6. Acylation of H-6 either using by reaction with an acid chloride or by using a suitable amide coupling agent (such as T3P, HATU or HBTU) and an appropriate carboxylic acid in the presence of a base such as pyridine, TEA or Hunig's base in a solvent such as DMF or DMA affords H-7. Separation of the diastereomers and enantiomers may be carried out under standard methods known in the art such as chiral SFC or HPLC to afford the single enantiomers of H-7.

For some of the steps of the here above described process of preparation of the compounds of the invention, it may be necessary to protect potential reactive functions that are not wished to react, and to cleave said protecting groups in consequence. In such a case, any compatible protecting radical may be used. In particular methods of protection and deprotection such as those described by T. W. Greene (*Protective Groups in Organic Synthesis*, A. Wiley-Interscience Publication, 1981) or by P. J. Kocienski (*Protecting groups*, Georg Thieme Verlag, 1994), may be used.

All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Example 1 (Scheme A): Preparation of 2-phenyl-N-(6-{[(cis)-3-{5-[(pyridine-2-ylacetyl)amino]-1,3,4-thiadiazol-2-yl}cyclopentyl]methyl}pyridazin-3-yl)acetamide

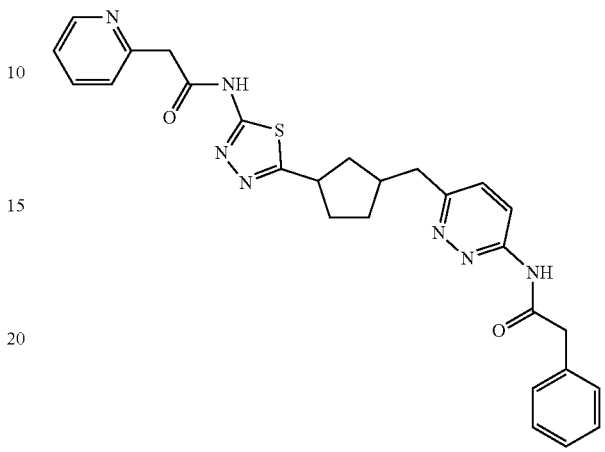

Step 1: Preparation of methyl-(cis)-3-(hydroxymethyl)cyclopentanecarboxylate

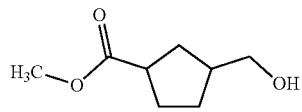

To a solution of (cis)-3-(methoxycarbonyl)cyclopentanecarboxylic acid (2.7 g, 15.7 mmol) in THF (42 mL) was added borane dimethylsulfide complex (2.5 mL, 26 mmol) dropwise at −78° C. The reaction mixture was warmed to 0° C. and stirred for 1 hr at this temperature. The reaction was stirred at room temperature for 3 hr, cooled back to −20° C. and quenched with 1 M KH$_2$PO$_4$. The resulting reaction mixture was warmed to room temperature, stirred for 20 min and extracted with Et$_2$O (3×100 mL). Then, the combined organics were washed with brine, dried over Na$_2$SO$_4$ and concentrated down to give the title compound (2.3 g, 55%) as a clear oil. $^1$H NMR (400 MHz, CDCl$_3$) δ ppm 3.68 (s, 3H), 3.59 (dd, J=6.5, 2.1 Hz, 2H), 2.81 (quin, J=8.2 Hz, 1H), 2.13-2.26 (m, 1H), 2.02-2.13 (m, 1H), 1.84-1.96 (m, 2H), 1.72-1.84 (m, 1H), 1.44-1.58 (m, 2H). m/z (APCl+) for C$_8$H$_{14}$O$_3$ 159.2 (M+H)$^+$.

Step 2: Preparation of methyl-(cis)-3-(iodomethyl)cyclopentanecarboxylate

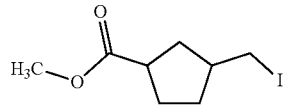

To a mixture of PPh$_3$ (1.0 g, 3.74 mmol) and imidazole (255 mg, 3.74 mmol) in CH$_2$Cl$_2$ (14 mL) was added I$_2$ (954 mg, 3.74 mmol) portionwise at room temperature. The resulting orange suspension was treated slowly with a solution of methyl-(cis)-3-(hydroxymethyl)cyclopentanecarboxylate (538 mg, 3.4 mmol) in CH$_2$Cl$_2$ (4 mL) and then stirred at room temperature for 14 hr. Then, the reaction mixture was washed with aq. Na$_2$S$_2$O$_3$ and extracted with CH$_2$Cl$_2$. The combined organics were dried over Na$_2$SO$_4$ and evaporated to give the crude title compound. The crude residue was diluted with heptanes and the solids filtered to remove triphenylphosphine oxide. The filtrate was evaporated to give a clear oil which was then purified by flash chromatography with a gradient of 0%-15% CH$_2$Cl$_2$ in heptanes to give methyl-(cis)-3-(iodomethyl)cyclopentanecarboxylate (718 mg, 79%) as a clear oil. $^1$H NMR (400 MHz, CDCl$_3$) δ ppm 3.69 (s, 3H), 3.23 (d, J=6.80 Hz, 2H), 2.81-2.92 (m, 1H), 2.16-2.33 (m, 2H), 1.86-2.02 (m, 3H), 1.51-1.55 (m, 1H), 1.38-1.49 (m, 1H).

Step 3: Preparation of N-(6-iodopyridazin-3-yl)-2-phenylacetamide

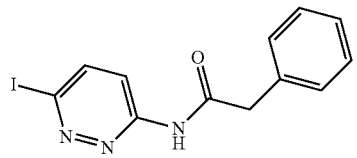 [SMILES: O=C(Cc1ccccc1)Nc1ccc(I)nn1]

To a solution of 5-iodopyridazin-3-amine (1.3 g, 5.7 mmol) in DMF (6.7 mL) was added dropwise diisopropylethylamine (1.14 mL, 6.83 mmol) followed by phenylacetyl chloride (0.9 mL, 6.83 mmol) at 0° C. Then, the reaction mixture was slowly warmed to room temperature overnight. The resulting solution was diluted with water, filtered off and rinsed with water to give the title compound (1.18 g, 61%) as a tan powder. $^1$H NMR (400 MHz, CDCl$_3$) δ ppm 3.84 (s, 2H), 7.34-7.44 (m, 5H), 7.82 (d, J=9.32 Hz, 1H), 8.25 (d, J=9.32 Hz, 1H). m/z (APCl+) for C$_{12}$H$_{10}$IN$_3$O 340.1 (M+H)$^+$.

Step 4: Preparation of (cis)-3-({6-[(phenlyacetyl) amino]pyridazin-3-yl}methyl) cyclopentanecarboxylate

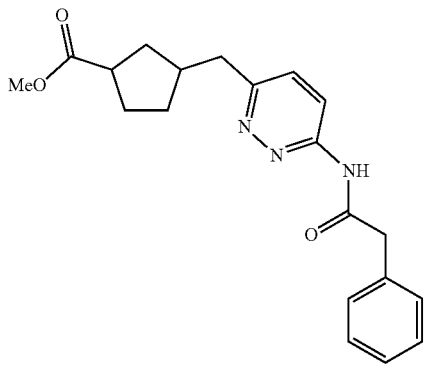 [SMILES: COC(=O)C1CCC(Cc2ccc(NC(=O)Cc3ccccc3)nn2)C1]

To a suspension of Zn dust (226 mg, 3.45 mmol) in dry degassed DMF (0.5 mL) was added 1,2-dibromoethane (11 µL, 0.12 mmol) under N$_2$. Then, the mixture was heated with a heat gun for about 30 sec until gas evolution was observed from the solution, indicating the activation of Zn. The mixture was allowed to cool to room temperature, followed by the addition of TMSCl (16 µL, 0.13 mmol) and allowed to stir at room temperature for 30 min. A solution of methyl-(cis)-3-(iodomethyl)cyclopentanecarboxylate (308 mg, 1.15 mmol) in DMF (1 mL) was added to the Zn solution, and then the resulting mixture was stirred at room temperature for 1 hr. After allowing the Zn to settle, the reaction mixture was filtered through a syringe filter into a mixture of N-(6-iodopyridazin-3-yl)-2-phenylacetamide (195 mg, 0.58 mmol), Pd$_2$(dba)$_3$ (105 mg, 0.12 mmol), and tri(o-tolyl)phosphine (70 mg, 0.23 mmol) in DMF (2.3 mL). The reaction mixture was flushed with N$_2$, and stirred at 40° C. for 50 min. Then, Si-Thiol was added to the warm reaction mixture to remove Pd residues. After 20 min at 40° C., the mixture ws diluted with EtOAc and filtered off to remove the Si-Thiol. The filtrate was washed with water twice followed by brine and dried over Na$_2$SO$_4$. Purification via flash chromatography with a gradient of 0%-55% EtOAc in heptanes afforded (cis)-3-({6-[(phenylacetyl)amino] pyridazin-3-yl}methyl)cyclopentanecarboxylate (69 mg, 34% yield) as a white solid. $^1$H NMR (400 MHz, CDCl$_3$) δ ppm 8.63 (d, J=9.3 Hz, 1H), 7.52 (d, J=9.3 Hz, 1H), 7.36-7.45 (m, 5H), 3.92 (s, 2H), 3.68 (s, 3H), 2.99 (d, J=7.30 Hz, 2H), 2.74-2.87 (m, 1H), 2.31-2.44 (m, 1H), 2.02-2.12 (m, 1H), 1.86-1.99 (m, 2H), 1.73-1.85 (m, 1H), 1.49-1.60 (m, 1H), 1.37-1.49 (m, 1H). m/z (APCl+) for C$_{20}$H$_{23}$N$_3$O$_3$ 354.3 (M+H)$^+$.

Step 5: Preparation of (cis)-3-({6-[(phenylacetyl) amino]pyridazin-3-yl}methyl)cyclopentanecarboxylic acid

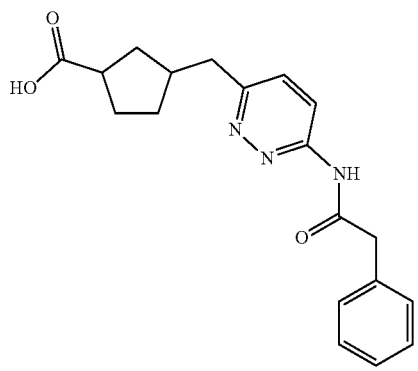 [SMILES: O=C(Cc1ccccc1)Nc1ccc(CC2CCC(C(=O)O)C2)nn1]

To a solution of (cis)-3-({6-[(phenylacetyl)amino] pyridazin-3-yl}methyl)cyclopentanecarboxylate (205 mg, 0.58 mmol) in a mixture of MeOH (5 mL), water (1.5 mL) and THF (3 mL) was added LiOH (111 mg, 4.64 mmol) at room temperature. After 1 hr, the reaction mixture was evaporated to remove solvent, and washed with Et$_2$O. Then, the aq. layer was acidified with 1 N HCl to pH 2. The resulting solid was filtered off, washed with water and dried under vacuum to give the title compound (96 mg, 49%) as a white solid. m/z (APCl+) for C$_{19}$H$_{21}$N$_3$O$_3$ 340.3 (M+H)$^+$.

Step 6: Preparation of N-[6-({(cis)-3-[(2-carbamo-thioylhydrazinyl)carbonyl]cyclopentyl}methyl)pyridazin-3-yl]-2-phenylacetamide

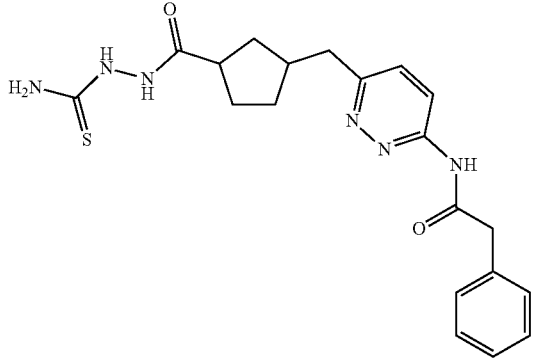 [SMILES: NC(=S)NNC(=O)C1CCC(Cc2ccc(NC(=O)Cc3ccccc3)nn2)C1]

To a mixture of (cis)-3-({6-[(phenylacetyl)amino]pyridazin-3-yl}methyl)cyclopentanecarboxylic acid (96 mg, 0.28 mmol) and HATU (170 mg, 0.42 mmol) in DMF (1.4 mL) was added Et$_3$N (79 µL, 0.57 mmol) at room temperature. After 10 min, the resulting mixture was treated with thiosemicarbazide (39 mg, 0.42 mmol) and stirred for 40 min at room temperature. Then, the reaction mixture was evaporated under vacuum to remove DMF. The crude compound was used directly for the next step without further purification. m/z (APCl+) for $C_{20}H_{24}N_6O_2S$ 413.3 (M+H)$^+$.

Step 7: Preparation of N-[6-{[(cis)-3-(5-amino-1,3,4-thiadiazol-2-yl)cyclopentyl]methyl}pyridazin-3-yl)-2-phenylacetamide

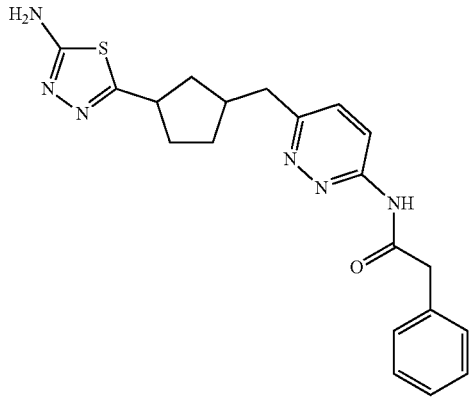 [SMILES: Nc1nnc(C2CCC(Cc3ccc(NC(=O)Cc4ccccc4)nn3)C2)s1]

N-[6-({(cis)-3-[(2-carbamothioylhydrazinyl)carbonyl]cyclopentyl}methyl)pyridazin-3-yl]-2-phenylacetamide (120 mg, 0.29 mmol) was treated with neat sulfuric acid (0.58 mL) at 0° C. After 30 min at 0° C., the reaction mixture was added dropwise to a solution of ice-cold aq. NaHCO$_3$. The resulting mixture was extracted with CH$_2$Cl$_2$ four times, and dried over Na$_2$SO$_4$. Purification via flash chromatography with a gradient of 0%-10% MeOH in CH$_2$Cl$_2$ afforded N-[6-{[(cis)-3-(5-amino-1,3,4-thiadiazol-2-yl)cyclopentyl]methyl}pyridazin-3-yl)-2-phenylacetamide (44 mg, 38% yield) as a yellow solid. m/z (APCl+) for $C_{20}H_{22}N_6OS$ 395.3 (M+H)$^+$.

Step 8: Preparation of 2-phenyl-N-(6-{[(cis)-3-{5-[(pyridine-2-ylacetyl)amino]-1,3,4-thiadiazol-2-yl}cyclopentyl]methyl}pyridazin-3-yl)acetamide

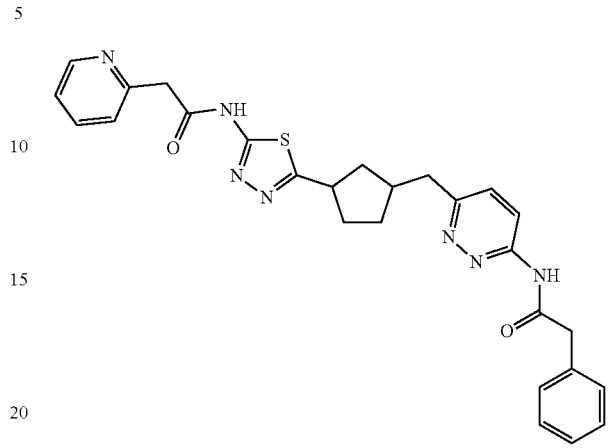

To a mixture of N-[6-{[(cis)-3-(5-amino-1,3,4-thiadiazol-2-yl)cyclopentyl]methyl}pyridazin-3-yl)-2-phenylacetamide (44 mg, 0.11 mmol) and HATU (54 mg, 0.13 mmol) in DMF (2.2 mL) was added Et$_3$N (63 µL, 0.45 mmol) at room temperature. Then, the resulting mixture was treated with 2-pyridyl acetic acid hydrochloride (22 mg, 0.12 mmol), and it was stirred for 2 hr at room temperature. The crude was purified by reverse phase chromatography eluting with MeCN:water (5:95 to 95:5) to give 2-phenyl-N-(6-{[(cis)-3-{5-[(pyridine-2-ylacetyl)amino]-1,3,4-thiadiazol-2-yl}cyclopentyl]methyl}pyridazin-3-yl)acetamide (18 mg, 30%) as a white solid. $^1$H NMR (400 MHz, DMSO-d$_6$) δ ppm 12.63 (br s, 1H), 11.22 (s, 1H), 8.49 (d, J=4.78 Hz, 1H), 8.19 (d, J=9.06 Hz, 1H), 7.76 (td, J=7.68, 1.76 Hz, 1H), 7.56 (d, J=9.32 Hz, 1H), 7.19-7.43 (m, 7H), 3.99 (s, 2H), 3.76 (s, 2H), 3.44-3.55 (m, 1H), 2.94 (d, J=7.30 Hz, 2H), 2.03-2.28 (m, 3H), 1.74-1.91 (m, 2H), 1.42-1.60 (m, 2H). m/z (APCl+) for $C_{27}H_{27}N_7O_2S$ 514.1 (M+H)$^+$.

Example 2A (Scheme B): Preparation of 2-(pyridin-2-yl)-N-(5-{[(1R,3S)-3-{5-[(pyridin-2-ylacetyl)amino]-1,3,4-thiadiazol-2-yl}cyclopentyl]methyl}-1,3,4-thiadiazol-2-yl)acetamide

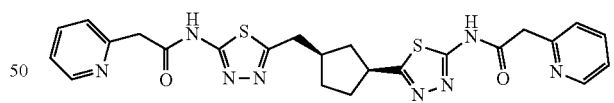

Step 1: Preparation of 5-(((1R,3S)-3-(5-amino-1,3,4-thiadiazol-2-yl)cyclopentyl)methyl)-1,3,4-thiadiazol-2-amine

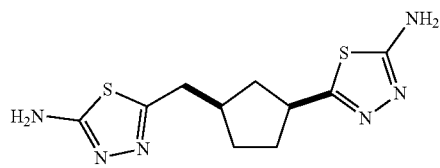 [SMILES: Nc1nnc(C[C@@H]2CC[C@H](c3nnc(N)s3)C2)s1]

To a flask containing (1S,3R)-3-(carboxymethyl)cyclopentane carboxylic acid (11.4 g, 66.2 mmol) and ground thiosemicarbazide (13.9 g, 152 mmol) was added slowly in a drop-wise manner POCl₃ until a slurry was formed, then the remainder of POCl₃ (60.8 mL total, 652 mmol) was added. The mixture was then stirred for 30 min at 80° C. with a strong exotherm being observed upon initial heating. The reaction was then allowed to cool to room temperature and then added dropwise to cold 3 M NaOH (1.32 L). The solids formed were filtered off, rinsed with water and dried overnight under vacuum. Trituration with EtOH followed by filtration afforded 5-(((1R,3S)-3-(5-amino-1,3,4-thiadiazol-2-yl)cyclopentyl)methyl)-1,3,4-thiadiazol-2-amine (12.25 g, 66%) as a tan solid. (400 MHz, DMSO-d₆) δ ppm 6.97 (s, 4H), 3.27-3.34 (m, 1H), 2.85 (d, J=7.2 Hz, 2H), 2.13-2.38 (m, 2H), 1.94-2.10 (m, 1H), 1.72-1.89 (m, 2H), 1.32-1.52 (m, 2H) ppm. m/z (ESI+) for $C_{10}H_{14}N_6S_2$ 283.17 (M+H)⁺.

Step 2: Preparation of 2-(pyridin-2-yl)-N-(5-{[(1R,3S)-3-{5-[(pyridin-2-ylacetyl)amino]-1,3,4-thiadiazol-2-yl}cyclopentyl]methyl}-1,3,4-thiadiazol-2-yl)acetamide

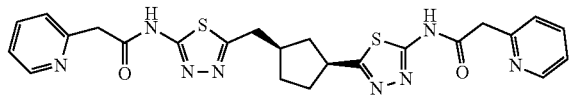 [SMILES: O=C(Cc1ccccn1)Nc1nnc(C[C@@H]2CC[C@H](c3nnc(NC(=O)Cc4ccccn4)s3)C2)s1]

Pyridine (60 mL, 730 mmol) was added to a mixture of 5-(((1R,3S)-3-(5-amino-1,3,4-thiadiazol-2-yl)cyclopentyl)methyl)-1,3,4-thiadiazol-2-amine (12.25 g, 43.4 mmol) and 2-pyridylacetic acid hydrochloride (18.8 g, 108 mmol). After stirring for 5 min, T3P (72.3 mL, 50% in DMF, 121 mmol) was added. Upon addition, a minor exotherm was observed, accompanied by effervesence. The reaction was stirred for 15 min and then checked by LCMS. The mono-acylated product was still observed, and as such additional 2-pyridylacetic acid hydrochloride (5 g, 28.7 mmol), T3P (10 mL, 50% in DMF, 16.7 mmol) and pyridine (20 mL, 243 mmol) were added and the reaction stirred overnight. The reaction was concentrated to remove excess pyridine, and then the residue was added dropwise to water with stirring. After addition was complete, the mixture was brought to pH ~7.5 and the solids filtered off, and rinsed with water. The solids were triturated with acetone and filtered to give 2-(pyridin-2-yl)-N-(5-{[(1R,3S)-3-{5-[(pyridin-2-ylacetyl)amino]-1,3,4-thiadiazol-2-yl}cyclopentyl]methyl}-1,3,4-thiadiazol-2-yl)acetamide (14.6 g, 65%) as a yellow solid. ¹H NMR (400 MHz, DMSO-d₆) δ ppm 12.65 (br s, 2H), 8.49 (d, J=4.77 Hz, 2H), 7.77 (td, J=7.6, 1.9 Hz, 2H), 7.39 (d, J=7.8 Hz, 2H), 7.28 (ddd, J=7.6, 4.9, 1.2 Hz, 2H), 4.00 (s, 4H), 3.50 (dt, J=10.3, 7.7 Hz, 1H), 3.07 (d, J=7.3 Hz, 2H), 2.35-2.47 (m, 1H), 2.29 (dt, J=13.5, 7.1 Hz, 1H), 2.12 (dtd, J=15.9, 8.9, 7.7, 3.8 Hz, 1H), 1.76-1.96 (m, 2H), 1.44-1.61 (m, 2H). m/z (ESI+) for $C_{24}H_{24}N_8O_2S_2$ 521.1 (M+H)⁺.

Example 2B: Preparation of 2-(pyridin-2-yl)-N-(5-{[(1R,3S)-3-{5-[{pyridin-2-ylacetyl)amino]-1,3,4-thiadiazol-2-yl}cyclopentyl]methyl}-1,3,4-thiadiazol-2-yl)acetamide Dihydrochloride

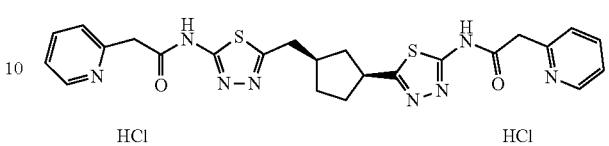

2-(pyridin-2-yl)-N-(5-{[(1R,3S)-3-{5-[(pyridin-2-ylacetyl)amino]-1,3,4-thiadiazol-2-yl}cyclo pentylmethyl}-1,3,4-thiadiazol-2-yl)acetamide (10 g, 19.2 mmol) was stirred in MeOH (100 mL) at room temperature before HCl (3.47 mL, 42.3 mmol) was added in a drop-wise fashion. The solution was heated to 65° C. for 1 hr. The slurry was allowed to cool to room temperature, and the colorless solids were filtered, rinsed with MeOH and dried to give 2-(pyridin-2-yl)-N-(5-{[(1R,3S)-3-{5-[(pyridin-2-ylacetyl)amino]-1,3,4-thiadiazol-2-yl}cyclo pentyl]methyl}-1,3,4-thiadiazol-2-yl)acetamide (11.25 g, 98%) as the bis-HCl salt, which was shown to be a mono-hydrate by CHN analysis. ¹H NMR (400 MHz, DMSO-d₆) δ ppm 13.00 (br s, 2H), 8.70-8.80 (m, 2H), 8.21-8.30 (m, 2H), 7.68-7.81 (m, 4H), 4.28 (s, 4H), 3.43-3.52 (m, 1H), 3.11-3.43 (m, 2H), 2.28-2.49 (m, 2H), 2.12-2.17 (m, 1H), 1.81-1.90 (m, 2H), 1.41-1.61 (m, 2H). m/z (ESI+) for $C_{24}H_{24}N_8O_2S_2$ 521.1 (M+H)⁺.

The absolute stereochemistry of the final compounds was determined by processing the racemic (cis)-di-acid through the identical chemical sequence as described below.

Step 1: Preparation of 5-(((cis)-3-(5-amino-1,3,4-thiadiazol-2-yl)cyclopentyl)methyl)-1,3,4-thiadiazol-2-amine

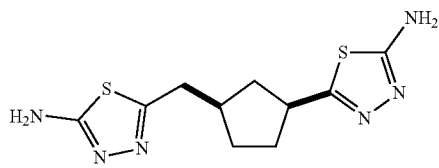 [SMILES: Nc1nnc(C[C@@H]2CC[C@H](c3nnc(N)s3)C2)s1]

Cis-3-(carboxymethyl)cyclopentane carboxylic acid (12.0 g, 63.89 mmol) and thiosemicarbazide (11.64 g, 127.77 mmol) were combined and POCl₃ (80 mL) was added. The reaction mixture was heated at 100° C. for 3 hr to give a yellow solution, which was then cooled to room temperature. The crude was quenched in warm water and basified to pH 7 with NaOH 50%. The resulting solid was filtered off, washed well with water and dried at 60° C. under vacuum to give 5-(((cis)-3-(5-amino-1,3,4-thiadiazol-2-yl)cyclopentyl)methyl)-1,3,4-thiadiazol-2-amine as a white solid (17.0 g, 86%). ¹H NMR (400 MHz, DMSO-d₆) δ ppm 7.00 (s, 4H), 3.27-3.34 (m, 1H), 2.85 (d, J=7.2 Hz, 2H), 2.13-2.38 (m, 2H), 1.94-2.10 (m, 1H), 1.72-1.89 (m, 2H), 1.32-1.52 (m, 2H) ppm. m/z (ESI+) for $C_{10}H_{14}N_6S_2$ 283.17 (M+H)⁺.

Step 2: Preparation of 2-(pyridin-2-yl)-N-(5-{[(1R,3S)-3-{5-[(pyridin-2-ylacetyl)amino]-1,3,4-thiadiazol-2-yl}cyclopentyl]methyl}-1,3,4-thiadiazol-2-yl)acetamide Example 2

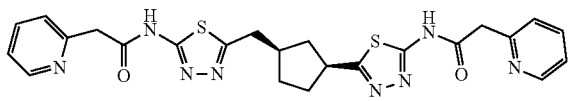 [SMILES: O=C(Cc1ccccn1)Nc1nnc(C[C@@H]2CC[C@H](c3nnc(NC(=O)Cc4ccccn4)s3)C2)s1]

5-(((cis)-3-(5-amino-1,3,4-thiadiazol-2-yl)cyclopentyl)methyl)-1,3,4-thiadiazol-2-amine (273 mg, 0.97 mmol) and 2-pyridine acetic acid hydrochloric acid salt (369 mg, 2.13 mmol) were slurried in DMF (3 mL) with HATU (882 mg, 2.32 mmol). DIPEA (0.74 mL, 4.2 mmol) was added and the resultant yellow solution stirred at room temperature under nitrogen overnight. Once reaction completion was confirmed, water (20 mL) was added and the reaction was extracted three times with $CH_2Cl_2$:MeOH (20 mL, 90:10). The combined organics were washed with saturated brine and stripped to afford an oil. This was purified first with flash chromatography eluting with $CH_2CO_2$:MeOH (97:3 to 90:10) to give 140 mg of an oily solid. This was then purified by reverse phase chromatography eluting with MeCN:water with 0.1% $NH_3$ (5:95 to 95:5) to give racemic Example 3 as an off white solid (47 mg, 9%). $^1$H NMR (400 MHz, DMSO-$d_6$) δ ppm 12.68 (s, 2H), 8.45-8.52 (m, 2H), 7.77 (td, J=7.6, 1.9 Hz, 2H), 7.39 (d, J=7.8 Hz, 2 H), 7.28 (ddd, J=7.6, 4.9, 1.2 Hz, 2H), 4.00 (s, 4H), 3.50 (dt, J=10.3, 7.7 Hz, 1H), 3.07 (d, J=7.3 Hz, 2H), 2.35-2.47 (m, 1H), 2.29 (dt, J=13.5, 7.1 Hz, 1H), 2.12 (dtd, J=15.9, 8.9, 7.7, 3.8 Hz, 1H), 1.76-1.96 (m, 2H), 1.40-1.63 (m, 2H). m/z (ESI+) for $C_{24}H_{24}N_8O_2S_2$ 521.1 (M+H)$^+$.

19 mg was subjected to chiral separation by SFC to afford both enantiomers. The analytical chiral separation by SFC was performed using a Chiralcel OJ-H column (4.6 mm×100 mm column, 3 micron particle size), which was eluted with 30% MeOH (with 0.1% DEA) in $CO_2$ held at 120 bar. A flow rate of 4 mL/min gave Rt$_{(Peak\ 1)}$=1.60 minutes and Rt$_{(Peak2)}$=1.98 minutes.

Example 4 (Peak 1): 2 mg, 99% ee (−). $^1$H NMR (400 MHz, DMSO-$d_6$) δ ppm 12.68 (s, 2H), 8.45-8.52 (m, 2H), 7.77 (td, J=7.6, 1.9 Hz, 2H), 7.39 (d, J=7.8 Hz, 2H), 7.28 (ddd, J=7.6, 4.9, 1.2 Hz, 2H), 4.00 (s, 4H), 3.50 (dt, J=10.3, 7.7 Hz, 1H), 3.07 (d, J=7.3 Hz, 2H), 2.35-2.47 (m, 1H), 2.29 (dt, J=13.5, 7.1 Hz, 1H), 2.12 (dtd, J=15.9, 8.9, 7.7, 3.8 Hz, 1H), 1.76-1.96 (m, 2H), 1.40-1.63 (m, 2H). m/z (ESI+) for $C_{24}H_{24}N_8O_2S_2$ 521.1 (M+H)$^+$.

Example 2 (Peak 2): 2 mg, 98% ee (+). $^1$H NMR (400 MHz, DMSO-$d_6$) δ ppm 12.68 (s, 2H), 8.45-8.52 (m, 2H), 7.77 (td, J=7.6, 1.9 Hz, 2H), 7.39 (d, J=7.8 Hz, 2H), 7.28 (ddd, J=7.6, 4.9, 1.2 Hz, 2H), 4.00 (s, 4H), 3.50 (dt, J=10.3, 7.7 Hz, 1H), 3.07 (d, J=7.3 Hz, 2H), 2.35-2.47 (m, 1H), 2.29 (dt, J=13.5, 7.1 Hz, 1H), 2.12 (dtd, J=15.9, 8.9, 7.7, 3.8 Hz, 1H), 1.76-1.96 (m, 2H), 1.40-1.63 (m, 2H). m/z (ESI+) for $C_{24}H_{24}N_8O_2S_2$ 521.1 (M+H)$^+$.

Crystals of Example 4 were grown by vapor diffusion of ether into an 80/20 dichloromethane/methanol solution, and were subjected to single crystal X-ray diffraction studies to obtain the absolute stereochemistry of the cyclopentane ring junction. Example 4 was shown to be 2-(pyridin-2-yl)-N-(5-{[(1 S,3R)-3-{5-[(pyridin-2-ylacetyl)amino]-1,3,4-thiadiazol-2-yl}cyclopentyl]methyl}-1,3,4-thiadiazol-2-yl)acetamide, thus enabling the assignment of Example 2 as 2-(pyridin-2-yl)-N-(5-{[(1R,3S)-3-{5-[(pyridin-2-ylacetyl)amino]-1,3,4-thiadiazol-2-yl}cyclopentyl]methyl}-1,3,4-thiadiazol-2-yl)acetamide. In addition, chiral SFC separation of 5-(((cis)-3-(5-amino-1,3,4-thiadiazol-2-yl)cyclopentyl)methyl)-1,3,4-thiadiazol-2-amine, and subsequent derivatization to Example 4 and Example 2 enabled assignment of the stereochemistry of this intermediate for the preparation of enantiopure analogues.

Example 5 (Scheme B): Preparation of N-[5-({(1R,3S)-3-[5-(acetylamino)-1,3,4-thiadiazol-2-yl]cyclopentyl}methyl)-1,3,4-thiadiazol-2-yl]acetamide

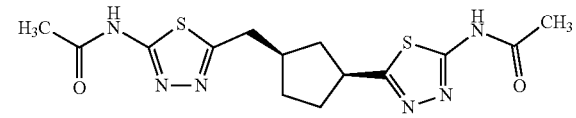 [SMILES: CC(=O)Nc1nnc(C[C@@H]2CC[C@H](c3nnc(NC(C)=O)s3)C2)s1]

5-(((cis)-3-(5-amino-1,3,4-thiadiazol-2-yl)cyclopentyl)methyl)-1,3,4-thiadiazol-2-amine (200 mg, 0.708 mmol) suspended in DMA (2 mL) was added dimethylaminopyridine (173 mg, 1.416 mmol), followed by acetyl chloride (151 μL, 2.124 mmol). The reaction was stirred at room temperature for 16 hr to give a suspension, which was then diluted with water (7 mL). The resultant solid was filtered off, washed well with water, and dried at 60° C. under vacuum to give 194 mg of a fawn solid. After being dissolved in hot DMSO (2 mL), the compound was purified via reverse-phase chromatography, eluting with 5-100% MeCN in 0.1% aq. formic acid to provide racemic Example 6 as a colorless solid (38 mg, 15% yield). $^1$H NMR (400 MHz, DMSO-$d_6$) δ ppm 12.38 (s, 2H), 3.57 (m, 1H), 3.07 (d, J=7.4 Hz, 2H), 2.42 (dq, J=9.8, 7.6 Hz, 1H), 2.29 (dt, J=13.4, 7.0 Hz, 1H), 2.16 (d, J=1.2 Hz, 6H), 2.09-2.14 (m, 1H), 1.78-1.95 (m, 2H), 1.43-1.62 (m, 2H). m/z (ESI+) for $C_{14}H_{18}N_6O_2S_2$ 367.12 (M+H)$^+$. 11 mg was subjected to chiral separation by SFC to afford both enantiomers. The analytical chiral separation by SFC was performed using a Chiralpak AS-H column (4.6 mm×250 mm column, 5 micron particle size), which was eluted with 30% MeOH (with 0.1% DEA) in $CO_2$ held at 140 bar. A flow rate of 3 mL/min gave Rt$_{(Peak\ 1)}$=3.00 minutes and Rt$_{(Peak\ 2)}$=4.62 minutes.

Example 5 (Peak 1): 3.89 mg, >98% ee. $^1$H NMR (400 MHz, DMSO-$d_6$) δ ppm 12.38 (s, 2H), 3.57 (m, 1H), 3.07 (d, J=7.4 Hz, 2H), 2.42 (dq, J=9.8, 7.6 Hz, 1H), 2.29 (dt, J=13.4, 7.0 Hz, 1H), 2.16 (d, J=1.2 Hz, 6H), 2.09-2.14 (m, 1H), 1.78-1.95 (m, 2H), 1.43-1.62 (m, 2H). m/z (ESI+) for $C_{14}H_{18}N_6O_2S_2$ 367.12 (M+H)$^+$.

Example 7 (Peak 2): 3.72 mg, >98% ee. $^1$H NMR (400 MHz, DMSO-$d_6$) δ ppm 12.38 (s, 2H), 3.57 (m, 1H), 3.07 (d, J=7.4 Hz, 2H), 2.42 (dq, J=9.8, 7.6 Hz, 1H), 2.29 (dt, J=13.4, 7.0 Hz, 1H), 2.16 (d, J=1.2 Hz, 6H), 2.09-2.14 (m, 1H), 1.78-1.95 (m, 2H), 1.43-1.62 (m, 2H). m/z (ESI+) for $C_{14}H_{18}N_6O_2S_2$ 367.12 (M+H)$^+$.

Example 8 (Scheme B): Preparation of 2-phenyl-N-(5-{[(1R, 3S)-3-{5-[(phenylacetyl)amino]-1,3,4-thiadiazol-2-yl}cyclopentyl]methyl}-1,3,4-thiadiazol-2-yl)acetamide

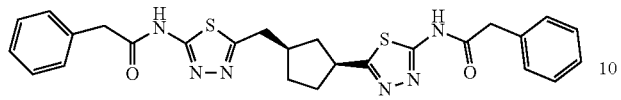

To 5-(((cis)-3-(5-amino-1,3,4-thiadiazol-2-yl)cyclopentyl)methyl)-1,3,4-thiadiazol-2-amine (200 mg, 0.708 mmol) suspended in DMA (2 mL) was added dimethylaminopyridine (87 mg, 0.708 mmol), followed by phenylacetyl chloride (281 μL, 2.124 mmol). The reaction was stirred at room temperature for 64 hr to give a clear solution. Water (3 mL) was added, and the mixture stirred for 30 min to give a fawn solid, which was filtered, washed with water and dried. This solid was dissolved in DMSO (2 mL) and water (4 mL) added to re-precipitate the product, which was filtered off, washed well with water and dried at 60° C. under vacuum to give racemic Example 9 (225 mg, 55% yield) as a fawn solid. $^1$H NMR (400 MHz, DMSO-d$_6$) δ ppm 12.66 (s, 2H), 6.72-7.88 (m, 10H), 3.78 (d, J=1.5 Hz, 4H), 3.49 (dd, J=10.0, 7.5 Hz, 1H), 3.05 (d, J=7.3 Hz, 2H), 2.34-2.47 (m, 1H), 2.26 (dt, J=13.0, 6.9 Hz, 1H), 2.03-2.17 (m, 1H), 1.76-1.93 (m, 2H), 1.41-1.60 (m, 2H). m/z (ESI+) for $C_{26}H_{26}N_6O_2S_2$ 519.24 (M+H)$^+$.

190 mg was subjected to chiral separation by SFC to afford both enantiomers. The analytical chiral separation by SFC was performed using a Chiralpak AS-H column (4.6 mm×250 mm column, 5 micron particle size), which was eluted with 40% MeOH (with 0.1% DEA) in CO$_2$ held at 140 bar. A flow rate of 3 mL/min gave Rt$_{(Peak\ 1)}$=8.51 minutes and Rt$_{(Peak\ 2)}$=10.20 minutes.

Example 8 (Peak 1): 60.83 mg, >99% ee (+). $^1$H NMR (400 MHz, DMSO-d$_6$) δ ppm 12.66 (s, 2H), 6.72-7.88 (m, 10H), 3.78 (d, J=1.5 Hz, 4H), 3.49 (dd, J=10.0, 7.5 Hz, 1H), 3.05 (d, J=7.3 Hz, 2H), 2.34-2.47 (m, 1H), 2.26 (dt, J=13.0, 6.9 Hz, 1H), 2.03-2.17 (m, 1H), 1.76-1.93 (m, 2H), 1.41-1.60 (m, 2H). m/z (ESI+) for $C_{26}H_{26}N_6O_2S_2$ 519.24 (M+H)$^+$.

Example 10 (Peak 2): 61.32 mg, 99% ee (−). $^1$H NMR (400 MHz, DMSO-d$_6$) δ ppm 12.66 (s, 2H), 6.72-7.88 (m, 10H), 3.78 (d, J=1.5 Hz, 4H), 3.49 (dd, J=10.0, 7.5 Hz, 1H), 3.05 (d, J=7.3 Hz, 2H), 2.34-2.47 (m, 1H), 2.26 (dt, J=13.0, 6.9 Hz, 1H), 2.03-2.17 (m, 1H), 1.76-1.93 (m, 2H), 1.41-1.60 (m, 2H). m/z (ESI+) for $C_{26}H_{26}N_6O_2S_2$ 519.24 (M+H)$^+$.

Example 11 (Scheme C): Preparation of N-{5-[3-{[5-(acetylamino)-1,3,4-thiadiazol-2-yl]methyl}cyclopentyl]-1,3,4-thiadiazol-2-yl}-2-(pyrimidin-4-yl)acetamide

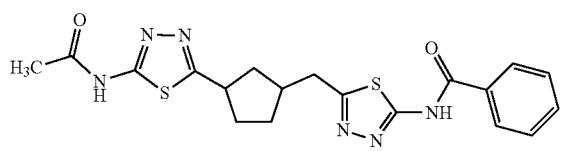 [SMILES: CC(=O)Nc1nnc(C2CCC(Cc3nnc(NC(=O)c4ccccc4)s3)C2)s1]

Step 1: Preparation of methyl [(cis)-3-(5-amino-1,3,4-thiadiazol-2-yl)cyclopentyl]acetate

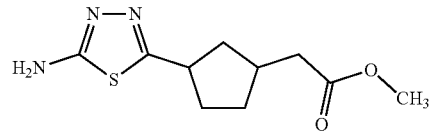 [SMILES: COC(=O)CC1CCC(c2nnc(N)s2)C1]

(Cis)-3-(2-methoxy-2-oxoethyl)cyclopentanecarboxylic acid (10 g, 53.7 mmol) and thiosemicarbazide (5.45 g, 59.0 mmol) were suspended in POCl$_3$ (50 mL) and heated to reflux for 40 min, during which the suspension became a clear yellow solution. The mixture was allowed to cool, evaporated in vacuo, and then azeotoped three times with toluene to remove POCl$_3$ residues. The resulting amber oil was carefully quenched with saturated NaHCO$_3$ solution (350 mL), and then extracted into EtOAc (2×300 mL). The combined organic extracts were dried over MgSO$_4$, and evaporated to afford a yellow solid (10.3 g). This was purified by flash chromatography (eluting 0-10% methanol in EtOAc) to afford methyl [(cis)-3-(5-amino-1,3,4-thiadiazol-2-yl)cyclopentyl]acetate as an off white solid (6.3 g, 49% yield). $^1$H NMR (400 MHz, DMSO-d$_6$) δ ppm 7.00 (s, 2H), 3.58 (s, 3H), 3.25-3.33 (m, 1H), 2.40 (d, J=2.3 Hz, 1H), 2.39 (d, J=1.1 Hz, 1H), 2.16-2.35 (m, 2H), 1.97-2.05 (m, 1H), 1.81-1.91 (m, 1H), 1.68-1.80 (m, 1H), 1.28-1.41 (m, 2H). m/z (APCl+) for $C_{10}H_{15}N_3O_2S$ 242.1 (M+H)$^+$.

Step 2: Preparation of methyl {(cis)-3-[5-(acetylamino)-1,3,4-thiadiazol-2-yl]cyclopentyl}acetate

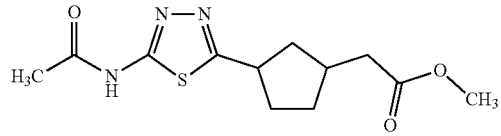 [SMILES: COC(=O)CC1CCC(c2nnc(NC(C)=O)s2)C1]

To a solution of methyl [(cis)-3-(5-amino-1,3,4-thiadiazol-2-yl)cyclopentyl]acetate (1.8 g, 7.46 mmol) in CH$_2$Cl$_2$ (20 mL) under nitrogen at room temperature was added Et$_3$N (2.08 mL, 14.9 mmol) followed by acetyl chloride (0.58 mL, 8.20 mmol). The resulting yellow suspension was stirred for 4 hr then washed with water. The organic layer was separated, washed with brine, dried over Na$_2$SO$_4$ and evaporated to give a methyl {(cis)-3-[5-(acetylamino)-1,3,4-thiadiazol-2-yl]cyclopentyl}acetate (2.15 g, 100%) as a cream solid. $^1$H NMR (400 MHz, MeOH-d$_4$) δ ppm 3.70 (s, 3H), 3.47-3.63 (m, 1 H), 2.40-2.58 (m, 4H), 2.26 (s, 3H), 1.90-2.14 (m, 3H), 1.48-1.63 (m, 2H). m/z (APCl+) for $C_{12}H_{17}N_3O_3S$ 284.1 (M+H)$^+$.

Step 3: Preparation of {(cis)-3-[5-(acetylamino)-1,3,4-thiadiazol-2-yl]cyclopentyl}acetic acid

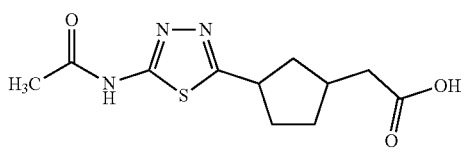 [SMILES: CC(=O)Nc1nnc(C2CCC(CC(=O)O)C2)s1]

To a solution of methyl {(cis)-3-[5-(acetylamino)-1,3,4-thiadiazol-2-yl]cyclopentyl}acetate (2.11 g, 7.447 mmol) in MeOH (30 mL) was added aq. 3 M lithium hydroxide solution (5.0 mL, 14.9 mmol). The solution was stirred at 45° C. for 4 hr, and then concentrated to remove the MeOH followed by acidification to pH 4 with 1 M AcOH. The resulting solution was extracted with EtOAc (3×30 mL), and the combined organic layers washed with brine. The organics were dried over $Na_2SO_4$, filtered, and evaporated under vacuum to yield {(cis)-3-[5-(acetylamino)-1,3,4-thiadiazol-2-yl]cyclopentyl}acetic acid (1.7 g, 85%) as a cream solid. m/z (APCl+) for $C_{11}H_{15}N_3O_3S$ 270.5 $(M+H)^+$.

Step 4: Preparation of N-{5-[(cis)-3-(2-hydrazinyl-2-oxoethyl)cyclopentyl]-1,3,4-thiadiazol-2-yl}acetamide

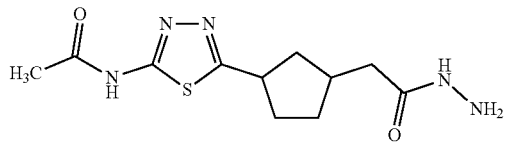 [SMILES: CC(=O)Nc1nnc(C2CCC(CC(=O)NN)C2)s1]

To a solution of {(cis)-3-[5-(acetylamino)-1,3,4-thiadiazol-2-yl]cyclopentyl}acetic acid (450 mg, 1.67 mmol) in dry DMF (10 mL) was added HBTU (711 mg, 1.84 mmol) and $Et_3N$ (0.35 mL, 2.51 mmol). The resulting clear yellow solution was stirred for 1 hr, then hydrazine (0.09 mL, 2.51 mmol) was added and the solution stirred for a further 3 hr. The mixture was concentrated to give a cream solid, which was slurried in $CH_2Cl_2$ (40 mL) and filtered under vacuum. The solid was washed with more $CH_2Cl_2$ and dried under vacuum to give N-{5-[(cis)-3-(2-hydrazinyl-2-oxoethyl)cyclopentyl]-1,3,4-thiadiazol-2-yl}acetamide (447 mg 94%) as a white powder. $^1H$ NMR (400 MHz, DMSO-$d_6$) δ ppm 8.93 (brs, 1H), 4.17 (brs, 2H), 3.40-3.53 (m, 1H), 2.20-2.38 (m, 2H), 2.16 (s, 3H), 2.03-2.14 (m, 3H), 1.74-1.90 (m, 2H), 1.31-1.50 (m, 2H). m/z (APCl+) for $C_{11}H_{17}N_5O_2S$ 284.1 $(M+H)^+$.

Step 5: Preparation of N-{[2-({(cis)-3-[5-(acetylamino)-1,3,4-thiadiazol-2-yl]cyclopentyl}acetyl)hydrazinyl]carbonothioyl}benzamide

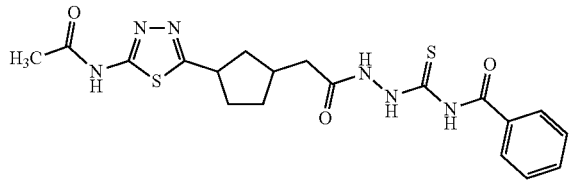 [SMILES: CC(=O)Nc1nnc(C2CCC(CC(=O)NNC(=S)NC(=O)c3ccccc3)C2)s1]

To a solution of N-{5-[(cis)-3-(2-hydrazinyl-2-oxoethyl)cyclopentyl]-1,3,4-thiadiazol-2-yl}acetamide (50 mg, 0.18 mmol) in (2 mL) was added benzoylisothiocyanate (0.028 mL, 0.211 mmol) and the suspension stirred at 40° C. for 3 hr. The mixture was cooled and filtered under vacuum. The solid was washed with EtOAc followed by $CH_2Cl_2$ to give N-{[2-({(cis)-3-[5-(acetylamino)-1,3,4-thiadiazol-2-yl]cyclopentyl}acetyl)hydrazinyl]carbonothioyl}benzamide (58 mg, 74%) as a cream solid. $^1H$ NMR (400 MHz, DMSO-$d_6$) δ ppm 12.60 (d, J=4.40 Hz, 1H), 12.37 (s, 1H), 11.67 (s, 1H), 10.83 (d, J=4.40 Hz, 1H), 7.95 (d, J=7.34 Hz, 2H), 7.64 (m, J=7.30 Hz, 1H), 7.52 (t, J=1.00 Hz, 2H), 3.44-3.58 (m, 1H), 2.28-2.45 (m, 4H), 2.06-2.21 (m, 4H), 1.88 (m, J=7.30 Hz, 2H), 1.43-1.60 (m, 2H). m/z (APCl+) for $C_{20}H_{24}N_6O_3S_2$ 447.1 $(M+H)^+$.

Step 6: Preparation of N-[5-({(cis)-3-[5-(acetylamino)-1,3,4-thiadiazol-2-yl]cyclopentyl}methyl)-1,3,4-thiadiazol-2-yl]benzamide (Example 11)

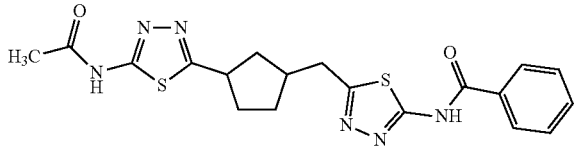 [SMILES: CC(=O)Nc1nnc(C2CCC(Cc3nnc(NC(=O)c4ccccc4)s3)C2)s1]

N-{[2-({(cis)-3-[5-(acetylamino)-1,3,4-thiadiazol-2-yl]cyclopentyl}acetyl)hydrazinyl]carbonothioyl}benzamide (58 mg, 0.13 mmol) was stirred in ice cold sulfuric acid (3 mL) for 3 hr. The clear solution was slowly added to ice cold water (10 mL) giving an oily suspension. EtOAc (10 mL) was added and the mixture stirred giving a cream solid. The mixture was filtered under vacuum and the solid washed with water followed by heptanes to give N-[5-({(cis)-3-[5-(acetylamino)-1,3,4-thiadiazol-2-yl]cyclopentyl}methyl)-1,3,4-thiadiazol-2-yl]benzamide (25 mg, 45%, Example 11) as a cream solid. $^1H$ NMR (400 MHz, DMSO-$d_6$) δ ppm 12.89 (br s, 1H), 12.35 (br s, 1H), 8.10 (d, J=7.46 Hz, 2H), 7.62-7.71 (m, 1H), 7.50-7.60 (m, 2H), 3.45-3.61 (m, 1H), 3.12 (d, J=7.09 Hz, 2H), 2.27-2.40 (m, 1H), 2.07-2.24 (m, 4H), 1.81-2.02 (m, 2H), 1.48-1.69 (m, 2H). m/z (APCl+) for $C_{19}H_{20}N_6O_2S_2$ 429.1 $(M+H)^+$.

16 mg was subjected to chiral separation by SFC to afford both enantiomers. The analytical chiral separation by SFC was performed using a Chiralpak OJ-H column (4.6 mm×250 mm column, 5 micron particle size), which was eluted with 30% MeOH in $CO_2$ held at 140 bar. A flow rate of 3 mL/min gave $Rt_{(Peak\ 1)}$=4.63 minutes and $Rt_{(Peak\ 2)}$=5.57 minutes.

Example 12 (Peak 1): 5.15 mg, >99% ee. $^1H$ NMR (400 MHz, DMSO-$d_6$) δ ppm 12.89 (brs, 1H), 12.35 (brs, 1H), 8.10 (d, J=7.46 Hz, 2H), 7.62-7.71 (m, 1H), 7.50-7.60 (m, 2H), 3.45-3.61 (m, 1H), 3.12 (d, J=7.09 Hz, 2H), 2.27-2.40 (m, 1H), 2.07-2.24 (m, 4H), 1.81-2.02 (m, 2H), 1.48-1.69 (m, 2H). m/z (APCl+) for $C_{19}H_{20}N_6O_2S_2$ 429.1 $(M+H)^+$.

Example 13 (Peak 2): 5.65 mg, 99% ee. $^1H$ NMR (400 MHz, DMSO-$d_6$) δ ppm 12.89 (brs, 1H), 12.35 (brs, 1H), 8.10 (d, J=7.46 Hz, 2H), 7.62-7.71 (m, 1H), 7.50-7.60 (m, 2H), 3.45-3.61 (m, 1H), 3.12 (d, J=7.09 Hz, 2H), 2.27-2.40 (m, 1H), 2.07-2.24 (m, 4H), 1.81-2.02 (m, 2H), 1.48-1.69 (m, 2H). m/z (APCl+) for $C_{19}H_{20}N_6O_2S_2$ 429.1 $(M+H)^+$.

Example 14 (Scheme C): Preparation of N-[5-({(1R,3S)-3-[5-(acetylamino)-1,3,4-thiadiazol-2-yl]cyclopentyl}methyl)-1,3,4-thiadiazol-2-yl]-2-phenylacetamide

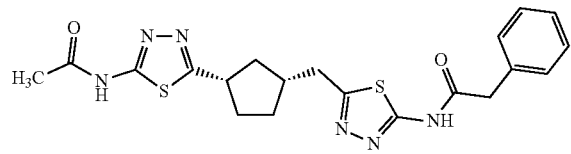 [SMILES: CC(=O)Nc1nnc([C@H]2CC[C@@H](Cc3nnc(NC(=O)Cc4ccccc4)s3)C2)s1]

Step 1: Preparation of N-{[2-({(cis)-3-[5-(acetylamino)-1,3,4-thiadiazol-2-yl]cyclopentyl}acetyl)hydrazinyl]carbonothioyl}-2-phenylacetamide

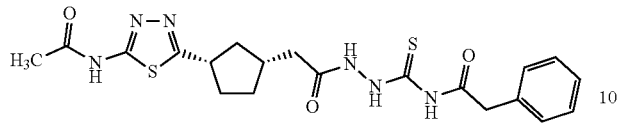

To a solution of the product of Example 5, step 4, N-{5-[(cis)-3-(2-hydrazinyl-2-oxoethyl)cyclopentyl]-1,3,4-thiadiazol-2-yl}acetamide (100 mg, 0.353 mmol) in EtOAc (2 mL) was added phenylacetyl isothiocyanate (75 mg, 0.424 mmol) and the suspension stirred at 40° C. for 3 hr. The mixture was cooled and filtered under vacuum. The solid was washed with EtOAc to give a 50% pure sample of N-{[2-({(cis)-3-[5-(acetylamino)-1,3,4-thiadiazol-2-yl]cyclopentyl}acetyl)hydrazinyl]carbonothioyl}-2-phenylacetamide (147 mg, 91%) as a brown solid. m/z (APCl+) for $C_{20}H_{24}N_6O_3S_2$ 460.9 (M+H)+, 483 (M+Na)+.

Step 2: Preparation of N-[5-({(cis)-3-[5-(acetylamino)-1,3,4-thiadiazol-2-yl]cyclopentyl}methyl)-1,3,4-thiadiazol-2-yl]-2-phenylacetamide (Example 14)

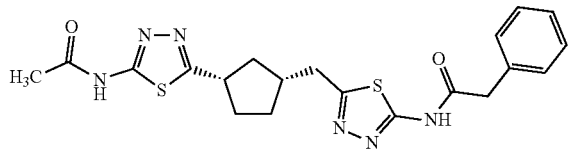 [SMILES: CC(=O)Nc1nnc([C@H]2CC[C@@H](Cc3nnc(NC(=O)Cc4ccccc4)s3)C2)s1]

The 50% pure sample of N-{[2-({(cis)-3-[5-(acetylamino)-1,3,4-thiadiazol-2-yl]cyclopentyl}acetyl)hydrazinyl]carbonothioyl}-2-phenylacetamide (147 mg, 0.16 mmol) was stirred in ice cold sulfuric acid (3 mL) for 3 hr. The clear solution was slowly added to ice cold water (10 mL) giving a brown solid, which was filtered under vacuum and washed with water followed by heptane. The brown solid was purified by preparative HPLC to afford racemic N-[5-({(cis)-3-[5-(acetylamino)-1,3,4-thiadiazol-2-yl]cyclopentyl}methyl)-1,3,4-thiadiazol-2-yl]-2-phenylacetamide (33 mg, 44%, Example 15 as a cream solid. $^1$H NMR (400 MHz, DMSO-$d_6$) δ ppm 12.46 (br s, 2H), 7.16-7.42 (m, 5H), 3.79 (s, 2H), 3.43-3.58 (m, 1H), 3.06 (d, J=7.34 Hz, 2H), 2.36-2.47 (m, 1H), 2.28 (d, J=12.35 Hz, 1H), 2.16 (s, 4H), 1.78-1.99 (m, 2H), 1.41-1.64 (m, 2H). m/z (APCl+) for $C_{20}H_{22}N_6O_2S_2$ 443.0 (M+H)+.

20 mg was subjected to chiral separation by SFC to afford both enantiomers. The analytical chiral separation by SFC was performed using a Chiralpak OJ-H column (4.6 mm×250 mm column, 5 micron particle size), which was eluted with 40% MeOH in $CO_2$ held at 120 bar. A flow rate of 3 mL/min gave $Rt_{(Peak\ 1)}$=4.54 minutes and $Rt_{(Peak\ 2)}$=7.67 minutes.

Example 16 (Peak 1): 6.89 mg, >99% ee (−). $^1$H NMR (400 MHz, DMSO-$d_6$) δ ppm 12.46 (br s, 2H), 7.16-7.42 (m, 5H), 3.79 (s, 2H), 3.43-3.58 (m, 1H), 3.06 (d, J=7.34 Hz, 2H), 2.36-2.47 (m, 1H), 2.28 (d, J=12.35 Hz, 1H), 2.16 (s, 4H), 1.78-1.99 (m, 2H), 1.41-1.64 (m, 2H). m/z (APCl+) for $C_{20}H_{22}N_6O_2S_2$ 443.0 (M+H)+.

Example 14) (Peak 2): 6.98 mg, >99% ee (+). $^1$H NMR (400 MHz, DMSO-$d_6$) δ ppm 12.46 (br s, 2H), 7.16-7.42 (m, 5H), 3.79 (s, 2H), 3.43-3.58 (m, 1H), 3.06 (d, J=7.34 Hz, 2H), 2.36-2.47 (m, 1H), 2.28 (d, J=12.35 Hz, 1H), 2.16 (s, 4H), 1.78-1.99 (m, 2H), 1.41-1.64 (m, 2H). m/z (APCl+) for $C_{20}H_{22}N_6O_2S_2$ 443.0 (M+H)+.

Example 17 (Scheme C): Preparation of N-[5-({(cis)-3-[5-(acetylamino)-1,3,4-thiadiazol-2-yl]cyclopentyl}methyl)-1,3,4-thiadiazol-2-yl]-2-(pyridin-2-yl)acetamide

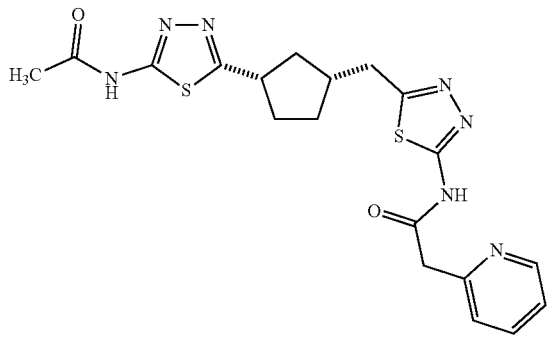 [SMILES: CC(=O)Nc1nnc([C@H]2CC[C@@H](Cc3nnc(NC(=O)Cc4ccccn4)s3)C2)s1]

Step 1: Preparation of N-(5-{(cis)-3-[2-(2-carbamothioylhydrazinyl)-2-oxoethyl]cyclopentyl}-1,3,4-thiadiazol-2-yl)acetamide

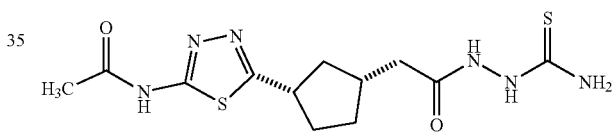

To a solution of {(cis)-3-[5-(acetylamino)-1,3,4-thiadiazol-2-yl]cyclopentyl}acetic acid (700 mg, 2.60 mmol) in dry DMF (10 mL) was added HBTU (1.51 g, 3.90 mmol) and Et$_3$N (0.73 mL, 5.20 mmol). The resulting clear yellow solution was stirred for 1 hr before thiosemicarbazide (359 mg, 3.90 mmol) was added, and the solution then stirred overnight. The reaction was concentrated to give a yellow slurry to which CH$_2$Cl$_2$ (40 mL) was added to afford a cream solid. The solid was filtered under vacuum and washed with CH$_2$Cl$_2$ and dried to give N-(5-{(cis)-3-[2-(2-carbamothioylhydrazinyl)-2-oxoethyl]cyclopentyl}-1,3,4-thiadiazol-2-yl)acetamide (671 mg, 75%) as a white powder. m/z (APCl+) for $C_{12}H_{18}N_6O_2S_2$ 343.05 (M+H)+.

Step 2: Preparation of N-(5-{(cis)-3-[(5-amino-1,3,4-thiadiazol-2-yl)methyl]cyclopentyl}-1,3,4-thiadiazol-2-yl)acetamide

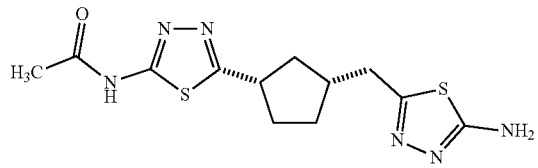 [SMILES: CC(=O)Nc1nnc([C@H]2CC[C@@H](Cc3nnc(N)s3)C2)s1]

N-(5-{(cis)-3-[2-(2-carbamothioylhydrazinyl)-2-oxo-ethyl]cyclopentyl}-1,3,4-thiadiazol-2-yl)acetamide (671 mg, 1.96 mmol) was stirred in ice cold sulfuric acid (3 mL) for 3 hr. The clear solution was slowly added to an ice cold aqueous solution of NaHCO$_3$ to adjust to pH 8 (Caution—vigorous gas evolution). The resulting solid was filtered under vacuum and washed well with water to give N-(5-{(cis)-3-[(5-amino-1,3,4-thiadiazol-2-yl)methyl]cyclopentyl}-1,3,4-thiadiazol-2-yl)acetamide (449 mg, 71%) as a cream powder. $^1$H NMR (400 MHz, DMSO-d$_6$) δ ppm 6.96 (s, 2H), 3.47-3.53 (m, 1H), 2.88 (d, J=7.30 Hz, 2H), 2.23-2.39 (m, 2H), 2.06-2.16 (m, 4H), 1.79-1.94 (m, 2H), 1.42-1.58 (m, 2H). m/z (APCl+) for C$_{12}$H$_{16}$N$_6$OS$_2$ 325.05 (M+H)$^+$.

Step 3: Preparation of N-[5-({(1R,3S)-3-[5-(acetylamino)-1,3,4-thiadiazol-2-yl]cyclopentyl}methyl)-1,3,4-thiadiazol-2-yl]-2-(pyridin-2-yl)acetamide (Example 17)

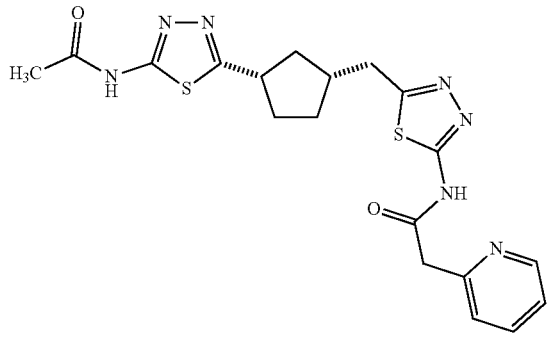 [SMILES: CC(=O)Nc1nnc([C@H]2CC[C@@H](Cc3nnc(NC(=O)Cc4ccccn4)s3)C2)s1]

To a solution of N-(5-{(cis)-3-[(5-amino-1,3,4-thiadiazol-2-yl)methyl]cyclopentyl}-1,3,4-thiadiazol-2-yl)acetamide (95 mg, 0.29 mmol) in dry DMF (2 mL) was added HBTU (136 mg, 0.352 mmol) and Et$_3$N (0.1 mL, 0.732 mmol) and 2-pyridyl acetic acid hydrochloride (61 mg, 0.352 mmol). The resulting clear brown solution was stirred for 2 hr at 50° C. Purification by preparative HPLC afforded racemic N-[5-({(1R,3S)-3-[5-(acetylamino)-1,3,4-thiadiazol-2-yl]cyclopentyl}methyl)-1,3,4-thiadiazol-2-yl]-2-(pyridin-2-yl)acetamide (52 mg, 40%, Example 18 as a yellow powder. $^1$H NMR (400 MHz, DMSO-d$_6$) δ ppm 12.50 (br s, 2H), 8.49 (d, J=4.03 Hz, 1H), 7.77 (td, J=7.70, 1.83 Hz, 1H), 7.39 (d, J=7.82 Hz, 1H), 7.28 (dd, J=7.03, 5.32 Hz, 1H), 4.00 (s, 2H) 3.43-3.58 (m, 1H), 3.06 (d, J=1.00 Hz, 2H), 2.37-2.48 (m, 1H), 2.25-2.35 (m, 1H), 2.05-2.21 (m, 4H), 1.80-1.96 (m, 2H), 1.44-1.62 (m, 2H). m/z (APCl+) for C$_{19}$H$_{21}$N$_7$O$_2$S$_2$ 444.1 (M+H)$^+$.

40 mg was subjected to chiral separation by SFC to afford both enantiomers. The analytical chiral separation by SFC was performed using a Chiralpak OJ-H column (4.6 mm×250 mm column, 5 micron particle size), which was eluted with 30% MeOH in CO$_2$ held at 120 bar. A flow rate of 3 mL/min gave Rt$_{(Peak\ 1)}$=3.47 minutes and Rt$_{(Peak\ 2)}$=4.72 minutes.

Example 17 (Peak 1): 16.78 mg, >99% ee (−). $^1$H NMR (400 MHz, DMSO-d$_6$) δ ppm 12.50 (br s, 2H), 8.49 (d, J=4.03 Hz, 1H), 7.77 (td, J=7.70, 1.83 Hz, 1H), 7.39 (d, J=7.82 Hz, 1H), 7.28 (dd, J=7.03, 5.32 Hz, 1H), 4.00 (s, 2H) 3.43-3.58 (m, 1H), 3.06 (d, J=1.00 Hz, 2H), 2.37-2.48 (m, 1H), 2.25-2.35 (m, 1H), 2.05-2.21 (m, 4H), 1.80-1.96 (m, 2H), 1.44-1.62 (m, 2H). m/z (APCl+) for C$_{19}$H$_{21}$N$_7$O$_2$S$_2$ 444.1 (M+H)$^+$.

Example 19 (Peak 2): 16.86 mg, 99% ee (+). $^1$H NMR (400 MHz, DMSO-d$_6$) δ ppm 12.50 (br s, 2H), 8.49 (d, J=4.03 Hz, 1H), 7.77 (td, J=7.70, 1.83 Hz, 1H), 7.39 (d, J=7.82 Hz, 1H), 7.28 (dd, J=7.03, 5.32 Hz, 1H), 4.00 (s, 2H), 3.43-3.58 (m, 1H), 3.06 (d, J=1.00 Hz, 2H), 2.37-2.48 (m, 1H), 2.25-2.35 (m, 1H), 2.05-2.21 (m, 4H), 1.80-1.96 (m, 2H), 1.44-1.62 (m, 2H). m/z (APCl+) for C$_{19}$H$_{21}$N$_7$O$_2$S$_2$ 444.1 (M+H)$^+$.

Example 20 (Scheme D): Preparation of N-{5-[(1R,3S)-3-{[5-(acetylamino)-1,3,4-thiadiazol-2-yl]methyl}cyclopentyl]-1,3,4-thiadiazol-2-yl}-2-(pyrimidin-4-yl)acetamide

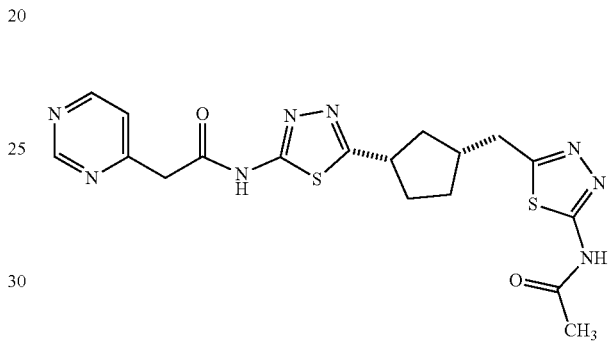

Step 1: Preparation of methyl 2-((cis)-3-(5-(2-pyrimidin-4-yl)acetamino)-1,3,4-thiadiazol-2-yl)cyclopentyl)acetate

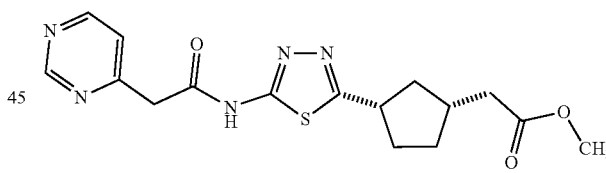

To a mixture of methyl-[(cis)-3-(5-amino-1,3,4-thiadiazol-2-yl)cyclopentyl]acetate (241 mg, 1.0 mmol) and HATU (480 mg, 1.2 mmol) in CH$_2$Cl$_2$ (20 mL) was added Et$_3$N (0.28 mL, 2.0 mmol) at room temperature. Then, the resulting mixture was treated with 2-(pyrimidine-4-yl) acetic acid (152 mg, 1.1 mmol), and it was stirred for 2 hr at room temperature. The resulting orange solution was diluted with water and CH$_2$Cl$_2$. The organic layer was separated, washed with brine, dried over Na$_2$SO$_4$ and evaporated to give a yellow solid. Purification via flash chromatography with a gradient of 0%-30% MeOH in CH$_2$Cl$_2$ afforded the title compound (185 mg, 51% yield) as a yellow solid. $^1$H NMR (400 MHz, CDCl$_3$) δ ppm 9.16 (s, 1H), 8.69 (d, J=5.29 Hz, 1H), 7.47 (d, J=5.04 Hz, 1H), 4.22 (s, 2H), 3.62 (s, 3H), 3.47-3.56 (m, 1H), 2.34-2.48 (m, 4H), 2.11-2.26 (m, 1H), 1.79-2.05 (m, 2H), 1.38-1.58 (m, 2H). m/z (APCl+) for C$_{16}$H$_{19}$N$_5$O$_3$S 362.2 (M+H)$^+$.

Step 2: Preparation of 2-((cis)-3-(5-(2-pyrimidin-4-yl)acetamino)-1,3,4-thiadiazol-2yl)cyclopentyl)acetic Acid

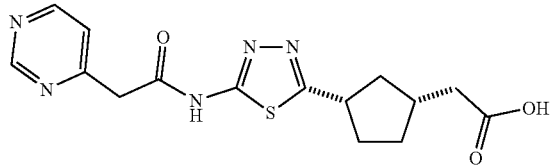 [SMILES: O=C(O)C[C@@H]1CC[C@H](c2nnc(NC(=O)Cc3ccncn3)s2)C1]

Methyl-2-((cis)-3-(5-(2-pyrimidin-4-yl)acetamino)-1,3,4-thiadiazol-2-yl)-cyclopentyl)acetate (1.27 g, 3.52 mmol) was dissolved in a mixture of MeOH (20 mL) and water (10 mL). Then, LiOH (674 mg, 28.2 mmol) was added to the methyl ester at room temperature, and stirred for 2 hr. The reaction mixture was evaporated to remove MeOH and the resulting mixture was diluted with water. Then, the crude was washed with EtOAc and the aq. layer was acidified with 1 N HCl to pH 3. The resulting solid was filtered off, washed with water and dried under vacuum to yield 2-((cis)-3-(5-(2-pyrimidin-4-yl)acetamino)-1,3,4-thiadiazol-2yl)cyclopentyl)acetic acid as a yellow solid (238 mg, 19.5%). m/z (APCl+) for $C_{15}H_{17}N_5O_3S$ 348.2 $(M+H)^+$.

Step 3: Preparation of N-(5-((cis)-3-(2-(2-carbamothioylhydrazinyl)-2-oxoethyl)cyclopentyl)-1,3,4-thiadiazol-2-yl)-2-(pyrimidin-4-yl)acetamide

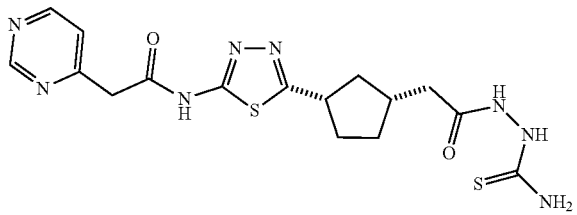 [SMILES: NC(=S)NNC(=O)C[C@@H]1CC[C@H](c2nnc(NC(=O)Cc3ccncn3)s2)C1]

To a mixture of 2-((cis)-3-(5-(2-pyrimidin-4-yl)acetamino)-1,3,4-thiadiazol-2yl)cyclopentyl)acetic acid (238 mg, 0.69 mmol) and HATU (412 mg, 1.03 mmol) in DMF (3 mL) was added $Et_3N$ (0.19 mL, 1.37 mmol) at room temperature. After 30 min, the resulting mixture was treated with thiosemicarbazide (96 mg, 1.03 mmol) and stirred for 3 hr at room temperature. Then, the reaction mixture was evaporated under vacuum to remove DMF. The crude was diluted with $CH_2Cl_2$ and the resulting solid was filtered off. The title compound was immediately transferred to a flask to be utilized in the dehydration step (step 4). m/z (APCl+) for $C_{16}H_{20}N_8O_2S_2$ 421.05 $(M+H)^+$.

Step 4: Preparation of N-(5-((cis)-3-((5-amino-1,3,4-thiadiazol-2-yl)-methyl)cyclopentyl)-1,3,4-thiadiazol-2-yl)-2-(pyrimidin-4-yl)acetamide

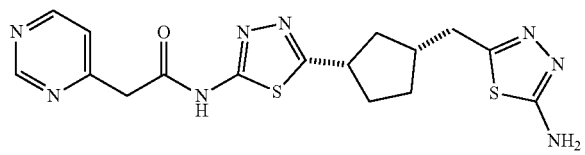

N-(5-((cis)-3-(2-(2-carbamothioylhydrazinyl)-2-oxoethyl)cyclopentyl)-1,3,4-thiadiazol-2-yl)-2-(pyrimidin-4-yl)acetamide was treated with neat sulfuric acid at 0° C. After 3 hr at 0° C., the reaction mixture was added dropwise to an ice-cold aq. $NaHCO_3$ solution. The resulting solid was filtered off, washed with water and dried under vacuum to give N-(5-((cis)-3-((5-amino-1,3,4-thiadiazol-2-yl)methyl)cyclopentyl)-1,3,4-thiadiazol-2-yl)-2-(pyrimidin-4-yl)acetamide (118 mg, 38%) as a yellow solid. m/z (APCl+) for $C_{16}H_{18}N_8OS_2$ 403.2 $(M+H)^+$.

Step 5: Preparation of N-{5-[(cis)-3-{[5-(acetylamino)-1,3,4-thiadiazol-2-yl]methyl}cyclopentyl]-1,3,4-thiadiazol-2-yl}-2-(pyrimidin-4-yl)acetamide (Example 20)

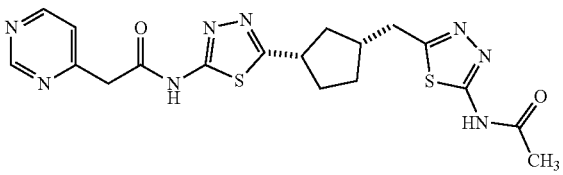

N-(5-((cis)-3-((5-amino-1,3,4-thiadiazol-2-yl)methyl)cyclopentyl)-1,3,4-thiadiazol-2-yl)-2-(pyrimidin-4-yl)acetamide (118 mg, 0.293 mmol) was dissolved in AcOH (1 mL) and treated with $Ac_2O$ (56 µL, 0.586 mmol) at room temperature. After 30 min, the reaction mixture was purified by reverse phase chromatography eluting with MeCN:water (5:95 to 95:5) to give racemic N-{5-[(cis)-3-{[5-(acetylamino)-1,3,4-thiadiazol-2-yl]methyl} cyclopentyl]-1,3,4-thiadiazol-2-yl}-2-(pyrimidin-4-yl)acetamide as an orange solid (26 mg, 20%).

26 mg was subjected to chiral separation by SFC to afford both enantiomers. The analytical chiral separation by SFC was performed using a Chiralpak OJ-H column (4.6 mm×100 mm column, 5 micron particle size), which was eluted with 20% MeOH in $CO_2$ held at 120 bar. A flow rate of 4 mL/min gave $Rt_{(Peak\ 1)}$=1.68 minutes and $Rt_{(Peak\ 2)}$=1.95 minutes.

Example 21 (Peak 1): 7.56 mg, >99% ee (−). $^1$H NMR (600 MHz, DMSO-$d_6$) δ ppm 9.10 (d, J=2.9 Hz, 1H), 8.76 (dd, J=5.3, 2.2 Hz, 1H), 7.55 (t, J=3.8 Hz, 1H), 4.03 (d, J=2.0 Hz, 2H), 3.50 (dq, J=10.4, 8.1 Hz, 1H), 3.06 (dd, J=7.3, 2.5 Hz, 2H), 2.35-2.47 (m, 1H), 2.21-2.34 (m, 1H), 2.07-2.20 (m, 4H), 1.77-1.95 (m, 2H), 1.43-1.60 (m, 2H). m/z (APCl+) for $C_{18}H_{20}N_8O_2S_2$ 445.2 $(M+H)^+$.

Example 20 (Peak 2): 7.96 mg, 92% ee (+). $^1$H NMR (600 MHz, DMSO-$d_6$) δ ppm 9.10 (d, J=2.9 Hz, 1H), 8.76 (dd, J=5.3, 2.2 Hz, 1H), 7.55 (t, J=3.8 Hz, 1H), 4.03 (d, J=2.0 Hz, 2H), 3.50 (dq, J=10.4, 8.1 Hz, 1H), 3.06 (dd, J=7.3, 2.5 Hz, 2H), 2.35-2.47 (m, 1H), 2.21-2.34 (m, 1H), 2.07-2.20 (m, 4H), 1.77-1.95 (m, 2H), 1.43-1.60 (m, 2H). m/z (APCl+) for $C_{18}H_{20}N_8O_2S_2$ 445.2 $(M+H)^+$.

Example 22 and Example 23 (Scheme E): Preparation of 2-(pyridin-2-yl)-N-{5-[(cis)-3-{5-[(pyridin-2-ylacetyl)amino]-1,3,4-thiadiazol-2-yl}cyclobutyl)methyl]-1,3,4-thiadiazol-2-yl}acetamide (Example 22) and 2-(pyridin-2-yl)-N-{5-[(trans)-3-{5-[(pyridin-2-ylacetyl)amino]-1,3,4-thiadiazol-2-yl}cyclobutyl)methyl]-1,3,4-thiadiazol-2-yl}acetamide (Example 23)

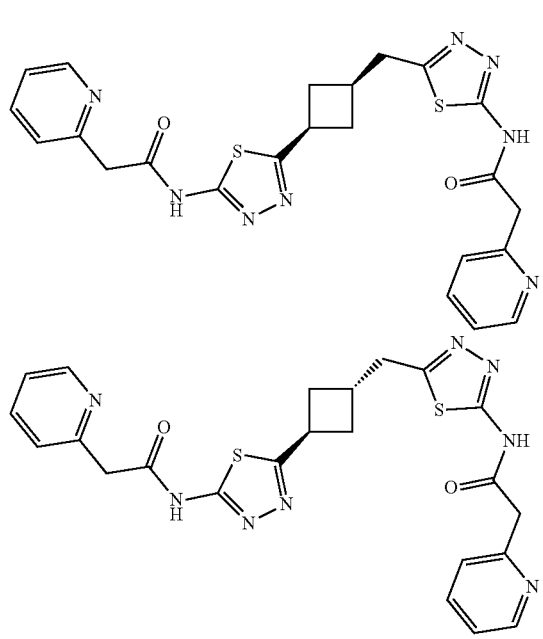

Step 1: Preparation of 5-{[3-(5-amino-1,3,4-thiadiazol-2-yl)cyclobutyl]methyl}-1,3,4-thiadiazol-2-amine

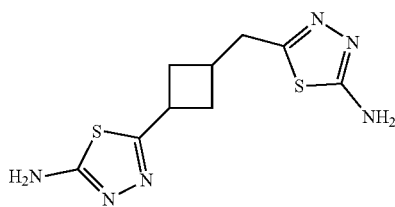 [SMILES: Nc1nnc(CC2CC(c3nnc(N)s3)C2)s1]

3-(2-tert-butoxy-2-oxoethyl)cyclobutanecarboxylic acid (prepared as in WO2005019221 as mixture of cis to trans isomers 4:1) (2.3 g, 10.74 mmol) and thiosemicarbazide (2.17 g, 23.60 mmol) were suspended in POCl₃ (10 mL) and heated to reflux for 1 hr, during which time, the suspension became a clear yellow solution. The mixture was allowed to cool, evaporated in vacuo, and azeotoped three times with toluene to remove POCl₃ residues. The resulting amber oil was carefully quenched with saturated NaHCO₃ solution (100 mL). The resulting suspension was filtered off and washed well with water and heptanes to give 5-{[3-(5-amino-1,3,4-thiadiazol-2-yl)cyclobutyl]methyl}-1,3,4-thiadiazol-2-amine (1.34 g, 46%) as a tan powder as a 4:1 mixture of cis to trans isomers. m/z (APCl+) for $C_9H_{12}N_6S_2$ 269.05 (M+H)⁺.

Step 2: Preparation of 2-(pyridin-2-yl)-N-{5-[(cis-3-{5-[(pyridin-2-ylacetyl)amino]-1,3,4-thiadiazol-2-yl}cyclobutyl)methyl]-1,3,4-thiadiazol-2-yl}acetamide (Example 22) and 2-(pyridin-2-yl)-N-{5-[(cis-3-{5-[(pyridin-2-ylacetyl)amino]-1,3,4-thiadiazol-2-yl}cyclobutyl)methyl]-1,3,4-thiadiazol-2-yl}acetamide (Example 23)

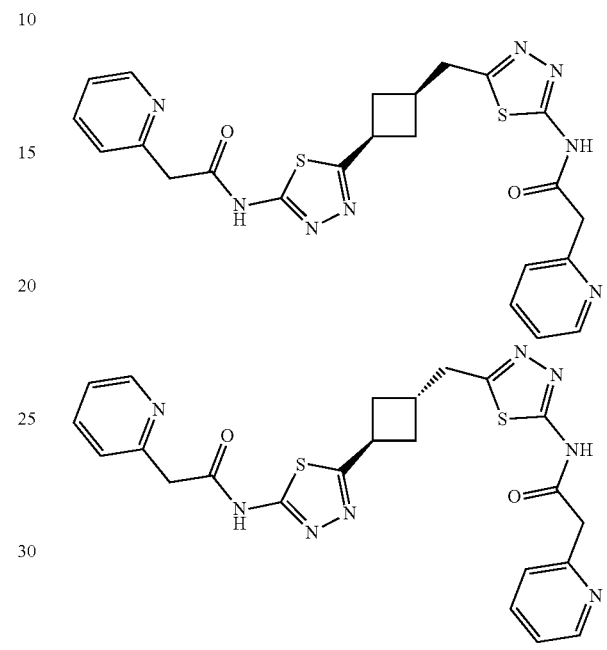

To a solution of 5-{[3-(5-amino-1,3,4-thiadiazol-2-yl)cyclobutyl]methyl}-1,3,4-thiadiazol-2-amine (200 mg, 7.45 mmol) in dry DMF (2 mL) was added HBTU (865 mg, 2.24 mmol), Et₃N (0.42 mL, 2.98 mmol) and 2-pyridyl acetic acid hydrochloride (284 mg, 1.64 mmol). The resulting clear yellow solution was stirred for 2 hr at 50° C. then purified by preparative HPLC to give a mixture of cis- and trans-2-(pyridin-2-yl)-N-{5-[3-{5-[(pyridin-2-ylacetyl)amino]-1,3,4-thiadiazol-2-yl}cyclobutyl)methyl]-1,3,4-thiadiazol-2-yl}acetamide (113 mg, 30%) as a brown solid.

The cis and trans isomers were separated by SFC to afford both diastereomers. The analytical separation by SFC was performed using a Chiralpak OJ-H column (4.6 mm×150 mm column, 5 micron particle size), which was eluted with 40% MeOH in CO₂ held at 120 bar. A flow rate of 4 mL/min gave $Rt_{(Peak\ 1,\ Cis)}$=1.34 minutes and $Rt_{(Peak\ 2,\ Trans)}$=1.72 minutes.

2-(pyridin-2-yl)-N-{5-[(cis)-3-{5-[(pyridin-2-ylacetyl)amino]-1,3,4-thiadiazol-2-yl}cyclobutyl)methyl]-1,3,4-thiadiazol-2-yl}acetamide (Example 22) >99% de (61.5 mg, 54%) as a cream powder. ¹H NMR (400 MHz, DMSO-d₆) δ ppm 12.65 (br s, 2H), 8.49 (d, J=4.28 Hz, 2H), 7.77 (t, J=7.52 Hz, 2H), 7.39 (d, J=7.70 Hz, 2H), 7.24-7.32 (m, 2H), 4.00 (s, 4H), 3.74 (s, 1H), 3.12 (d, J=7.34 Hz, 2H), 2.69 (br s, 1H), 2.52-2.61 (m, 2H), 2.06 (d, J=10.88 Hz, 2H). m/z (APCl+) for $C_{23}H_{22}N_8O_2S_2$ 507.1 (M+H)⁺

2-(pyridin-2-yl)-N-{5-[(trans)-3-{5-[(pyridin-2-ylacetyl)amino]-1,3,4-thiadiazol-2-yl}cyclobutyl)methyl]-1,3,4-thiadiazol-2-yl}acetamide (Example 23) 98% de (12.3 mg, 11%) as a cream powder. ¹H NMR (400 MHz, DMSO-d₆) δ ppm 12.66 (br s, 2H), 8.49 (d, J=4.03 Hz, 2H), 7.76 (t, J=7.03 Hz, 2H), 7.39 (d, J=7.70 Hz, 2H), 7.20-7.34 (m, 2H), 3.87-4.08 (m, 5H), 3.23 (d, J=7.58 Hz, 2H), 2.73-2.88 (m, 1H), 2.37-2.45 (m, 2H), 2.21-2.34 (m, 2H). m/z (APCl+) for $C_{23}H_{22}N_8O_2S_2$ 507.1 (M+H)$^+$ Example 24 (Scheme F): Preparation of N-[5-({(cis)-3-[5-(ethylamino)-1,3,4-thiadiazol-2-yl]cyclopentyl}methyl)-1,3,4-thiadiazol-2-yl]-2-(pyridin-2-yl)acetamide

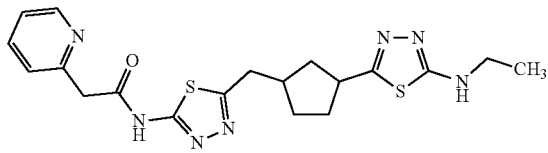 [SMILES: CCNc1nnc(C2CCC(Cc3nnc(NC(=O)Cc4ccccn4)s3)C2)s1]

Step 1: Preparation of methyl {3-[(cis)-5-(ethylamino)-1,3,4-thiadiazol-2-yl]cyclopentyl}acetate

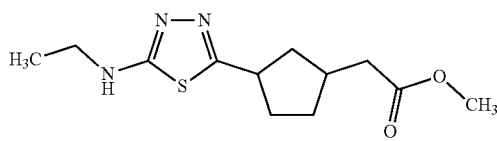 [SMILES: CCNc1nnc(C2CCC(CC(=O)OC)C2)s1]

3-(2-methoxy-2-oxoethyl)-cyclopentanecarboxylic acid (500 mg, 2.68 mmol) and 4-ethyl-3-thiosemicarbazide (320 mg, 2.68 mmol) were suspended in POCl$_3$ (8 mL) and heated to reflux for 40 min, after which time the suspension became a clear yellow solution. The mixture was allowed to cool, evaporated in vacuo, and then azeotoped three times with toluene to remove POCl$_3$ residues. The resulting amber oil was carefully quenched with saturated NaHCO$_3$ solution (100 mL), and then extracted into EtOAc (3×50 mL). The combined organic extracts were dried over magnesium sulfate, and evaporated to a give methyl {3-[(cis)-5-(ethylamino)-1,3,4-thiadiazol-2-yl]cyclopentyl}acetate. (325 mg, 45%) as a pale yellow solid. $^1$H NMR (400 MHz, CDCl$_3$) δ ppm 3.68 (s, 3H) 3.29-3.47 (m, 3H) 2.33-2.48 (m, 4H) 2.10-2.24 (m, 1H) 1.81-2.07 (m, 2H) 1.40-1.56 (m, 2H) 1.32 (t, J=7.21 Hz, 3H). m/z (APCl+) for $C_{12}H_{19}N_3O_2S$ 270.1 (M+H)$^+$.

Step 2: Preparation of {(cis)-3-[5-(ethylamino)-1,3,4-thiadiazol-2-yl]cyclopentyl}acetic Acid

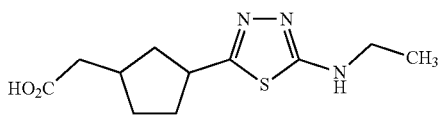 [SMILES: CCNc1nnc(C2CCC(CC(=O)O)C2)s1]

To a solution of methyl {3-[(cis)-5-(ethylamino)-1,3,4-thiadiazol-2-yl]cyclopentyl}acetate (325 mg, 1.21 mmol) in MeOH (10 mL) was added 3 M LiOH solution (0.81 mL, 2.41 mmol). The solution was stirred at room temperature overnight, concentrated to remove the MeOH then acidified to pH 4 with 1 M AcOH. The resulting solution was extracted with EtOAc (3×10 mL) followed by CH$_2$Cl$_2$:MeOH (95:5, 10 mL). The combined organic layers were dried over Na$_2$SO$_4$, filtered, and evaporated under vacuum to yield {(cis)-3-[5-(ethylamino)-1,3,4-thiadiazol-2-yl]cyclopentyl}acetic acid (289 mg, 94%) as a yellow oil. $^1$H NMR (400 MHz, CDCl$_3$) δ ppm 3.33-3.51 (m, 3H), 2.40-2.61 (m, 3H), 2.15-2.29 (m, 1H), 1.98-2.11 (m, 1H), 1.93 (dd, J=8.74, 4.83 Hz, 1H), 1.47-1.63 (m, 2H), 1.41 (t, 3H). m/z (APCl+) for $C_{11}H_{17}N_3O_2S$ 256.1 (M+H)$^+$.

Step 3: Preparation of 5-{(cis)-3-[(5-amino-1,3,4-thiadiazol-2-yl)methyl]cyclopentyl}-N-ethyl-1,3,4-thiadiazol-2-amine

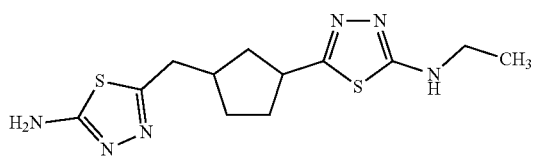 [SMILES: CCNc1nnc(C2CCC(Cc3nnc(N)s3)C2)s1]

{(Cis)-3-[5-(ethylamino)-1,3,4-thiadiazol-2-yl]cyclopentyl}acetic acid (289 mg, 1.13 mmol) and thiosemicarbazide (104 mg, 1.13 mmol) were suspended in POCl$_3$ (10 mL) and heated to reflux for 1 hr, after which time the suspension became a clear yellow solution. The mixture was allowed to cool, evaporated in vacuo, and then azeotoped three times with toluene to remove POCl$_3$ residues. The resulting amber oil was slowly added to ice cold water (100 mL) and basified with 0.88 N ammonia. The resulting oil was extracted with EtOAc (3×40 mL) then CH$_2$Cl$_2$:MeOH (95:5, 3×30 mL). The combined organics were dried over Na$_2$SO$_4$ and concentrated to give 5-{(cis)-3-[(5-amino-1,3,4-thiadiazol-2-yl)methyl]cyclopentyl}-N-ethyl-1,3,4-thiadiazol-2-amine (175 mg, 50%) as a cream solid. $^1$H NMR (400 MHz, DMSO-d$_6$) δ ppm 7.51 (t, J=5.07 Hz, 1H), 6.97 (s, 2H), 3.34 (m, J=9.80 Hz, 1H), 3.16-3.29 (m, 2H), 2.81-2.93 (m, 2H), 2.15-2.47 (m, 2H), 2.03 (m, J=11.90, 7.20 Hz, 1H), 1.70-1.90 (m, 2H), 1.34-1.52 (m, 2H), 1.14 (t, J=1.00 Hz, 3H). m/z (APCl+) for $C_{12}H_{18}N_6S_2$ 311.10 (M+H)$^+$.

Step 4: Preparation N-[5-({(cis)-3-[5-(ethylamino)-1,3,4-thiadiazol-2-yl]cyclopentyl}methyl)-1,3,4-thiadiazol-2-yl]-2-(pyridin-2-yl)acetamide

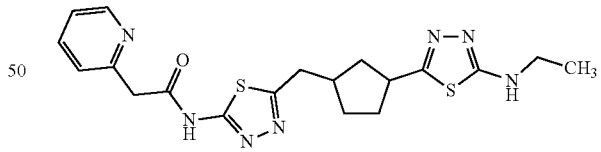

To a solution of 5-{(cis)-3-[(5-amino-1,3,4-thiadiazol-2-yl)methyl]cyclopentyl}-N-ethyl-1,3,4-thiadiazol-2-amine (88 mg, 0.28 mmol) in dry DMF (2 mL) was added HBTU (164 mg, 0.424 mmol), Et$_3$N (0.08 mL, 0.566 mmol) and 2-pyridyl acetic acid hydrochloride (54 mg, 0.311 mmol). The resulting clear yellow solution was stirred for 2 hr at 50° C. then purified by preparative HPLC to give a solid which was slurried in heptanes, filtered and dried to give N-[5-({(cis)-3-[5-(ethylamino)-1,3,4-thiadiazol-2-yl]cyclopentyl}methyl)-1,3,4-thiadiazol-2-yl]-2-(pyridin-2-yl)acetamide (36 mg, 30%) as a pale yellow solid. $^1$H NMR (400 MHz, DMSO-d$_6$) δ ppm 12.65 (br s, 1H), 8.47-8.52 (m, 1H), 7.77 (td, J=7.70, 1.83 Hz, 1H), 7.50 (t, J=5.20 Hz, 1H), 7.39 (d, J=7.70 Hz, 1H), 7.28 (dd, J=6.60, 5.01 Hz, 1H), 4.00 (s, 2H), 3.29 (m, 1H), 3.18-3.27 (m, 2H), 3.05 (d, J=7.34 Hz, 2H), 2.31-2.45 (m, 1H), 2.15-2.27 (m, 1H), 1.98-2.11 (m, 1H), 1.71-1.93 (m, 2H), 1.39-1.53 (m, 2H), 1.14 (t, J=7.15 Hz, 3H). m/z (APCl+) for $C_{19}H_{23}N_7OS_2$ 430.10 (M+H)$^+$.

Example 25 (Scheme G): Preparation of N,N'-(spiro[3.3]heptane-2,6-diyldipyridazine-6,3-diyl)bis[2-(pyridin-2-yl)acetamide]

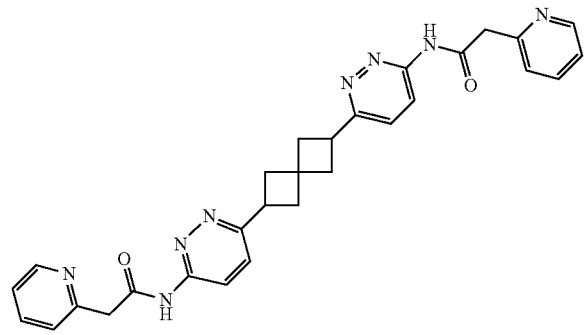 [SMILES: O=C(Cc1ccccn1)Nc1ccc(C2CC3(C2)CC(c2ccc(NC(=O)Cc4ccccn4)nn2)C3)nn1]

Step 1: Preparation of 2,6-diiodospiro[3.3]heptanes

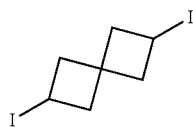

A solution of spiro[3.3]heptane-2,6-dicarboxylic acid (2.5 g, 11.0 mmol), diiodohydantoin (11.4 g, 29.9 mmol) in 1,2-dichloroethane (136 mL) under nitrogen was irradiated with a 500 W halogen lamp for 30 hr. The reaction was poured into saturated $Na_2SO_3$ (100 mL), and extracted with $CH_2Cl_2$ (2×100 mL). The organic extracts were washed with saturated $Na_2SO_3$ (100 mL), dried over $Na_2SO_4$, and concentrated. The residue was purified by column chromatography over silica gel eluting with 0%-25% EtOAc in heptanes to provide 2,6-diiodospiro[3.3]heptanes (1.7 g, 36%) as a colorless solid. $^1$H NMR (400 MHz, CDCl$_3$) δ ppm 4.32 (quin, J=8 Hz, 2H), 2.81-2.88 (m, 4H), 2.59-2.70 (m, 4H).

Step 2: Preparation of N,N'-(spiro[3.3]heptane-2,6-diyldipyridazine-6,3-diyl)bis[2-(pyridin-2-yl)acetamide]

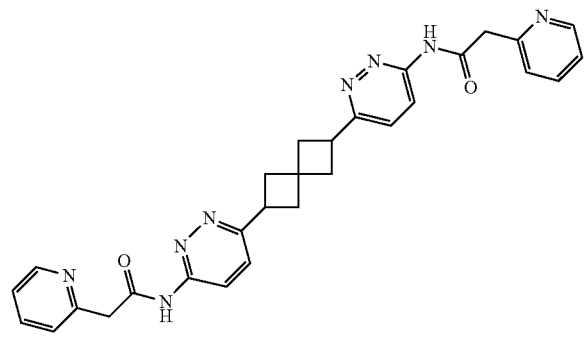 [SMILES: O=C(Cc1ccccn1)Nc1ccc(C2CC3(C2)CC(c2ccc(NC(=O)Cc4ccccn4)nn2)C3)nn1]

To a suspension of Zn dust (386 mg, 5.75 mmol) in dry degassed THF (0.58 mL) was added 1,2-dibromoethane (26 µL, 0.21 mmol) under nitrogen. Then, the mixture was heated with a heat gun for about 30 sec until gas evolution was observed from the solution, indicating the activation of Zn. This process was repeated twice, before the mixture was allowed to cool to room temperature, followed by the addition of TMSCl (22 µL, 0.17 mmol) and allowed to stir at room temperature for 5 min. A solution of 2,6-diiodospiro[3.3]heptanes (500 mg, 1.44 mmol) in THF (1.4 mL) was added to the Zn solution, and then the resulting mixture was stirred at 40° C. for 6 hr. After allowing the Zn to settle, the reaction mixture was filtered through a syringe filter into a mixture of N-(6-iodopyridazin-3-yl)-2-(pyridin-2-yl)-acetamide (489 mg, 1.44 mmol), Pd$_2$(dba)$_3$ (266 mg, 0.29 mmol), and tri(o-tolyl)phosphine (175 mg, 0.58 mmol) in THF (5.2 mL). The reaction mixture was flushed with nitrogen, and stirred at 40° C. for 18 hr. The reaction mixture was cooled to room temperature, and quenched by addition of aq. NH$_4$Cl solution (containing 10% NH$_4$OH). The mixture was stirred for 1 hr, extracted with CH$_2$Cl$_2$, and the organic extracts dried over Na$_2$SO$_4$, filtered and concentrated. Crude LCMS showed ca. 10% product formation. The material was purified by reverse phase HPLC to afford N'-(spiro[3.3]heptane-2,6-diyldipyridazine-6,3-diyl)bis[2-(pyridin-2-yl)acetamide] (6.8 mg, 1%) as a colorless solid. $^1$H NMR (400 MHz, MeOD-d$_4$) δ ppm 8.52 (d, J=4 Hz, 2H), 8.37 (d, J=8 Hz, 2H), 7.81-7.84 (m, 2H), 7.61 (d, J=12 Hz, 2H), 7.47 (d, J=8 Hz, 2H), 7.34-7.36 (m, 2H), 4.04 (s, 4H), 3.74 (quin, J=8 Hz, 2H), 2.45-2.72 (m, 2H), 2.48-2.54 (m, 2H), 2.39-2.44 (m, 2H), 2.33-2.39 (m, 2H). m/z (APCl+) for $C_{29}H_{28}N_8O_2$ 521.1 (M+H)$^+$.

Example 26 (Scheme H): Preparation of 2-(pyridin-2-yl)-N-{5-[(3-{6-[(pyridin-2-ylacetyl)amino]pyridazin-3-yl}cyclopentyl)methyl]-1,3,4-thiadiazol-2-yl}acetamide

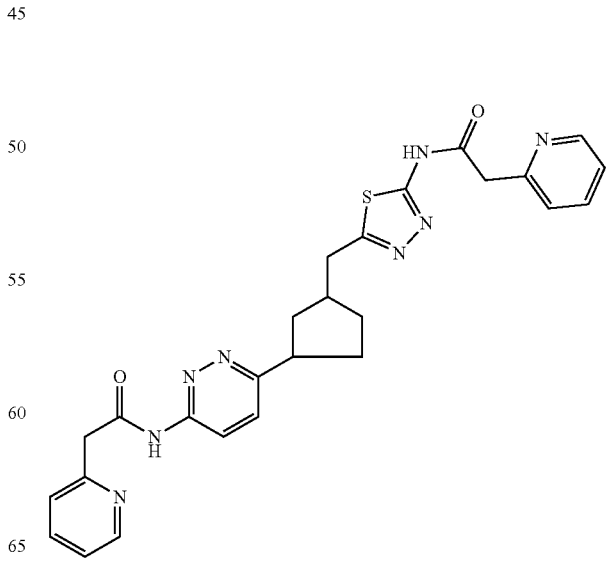

Step 1: Preparation of N-[6-(3-oxocyclopent-1-en-1-yl)pyridazin-3-yl]-2-(pyridin-2-yl)acetamide

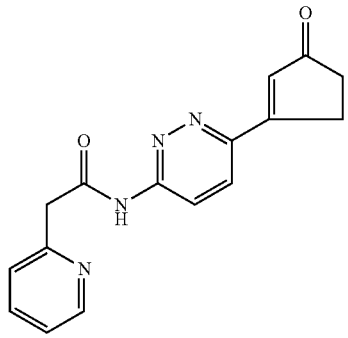 [SMILES: O=C1C=C(c2ccc(NC(=O)Cc3ccccn3)nn2)CC1]

To a 100 mL pressure flask charged with N-(6-bromopyridazin-3-yl)-2-(pyridin-2-yl)-acetamide (5 g, 17.1 mmol), 3-(4,4,5,5-tetramethyl-1,3,2-dioxaborolan-2-yl)cyclopent-2-en-1-one (10.7 g, 51.2 mmol), Pd(dppf)Cl$_2$ (1.39 g, 1.71 mmol), and CsF 13.0 g, 85.4 mmol) was added THF (142 mL) and water (22.9 mL) under nitrogen. After 5 min at room temperature with stirring and nitrogen bubbling, the reaction vessel was placed in a pre-heated 100° C. sand bath behind a blast shield. After 18 hr, the mixture was cooled to room temperature, concentrated, diluted with 750 mL CH$_2$Cl$_2$ and allowed to stir for 15 min. The suspension was filtered through a plug of Celite® and concentrated. The residue was purified by silica gel chromatography eluting with 0-5% EtOH in EtOAc to provide N-[6-(3-oxocyclopent-1-en-1-yl)pyridazin-3-yl]-2-(pyridin-2-yl)acetamide (3.75 g, 75%) as a solid. $^1$H NMR (400 MHz, CDCl$_3$) δ ppm 8.69-8.72 (m, 1H), 8.56 (d, J=8 Hz, 2H), 7.78-7.82 (m, 2H), 7.35-7.39 (m, 2H), 6.76 (s, 1H), 4.08 (s, 2H), 3.27-3.29 (m, 2H), 2.62-2.65 (m, 2H). m/z (APCl+) for C$_{16}$H$_{14}$N$_4$O$_2$ 295.1 (M+H)$^+$.

Step 2: Preparation of N-[6-(3-oxocyclopentyl)pyridazin-3-yl]-2-(pyridin-2-yl)acetamide

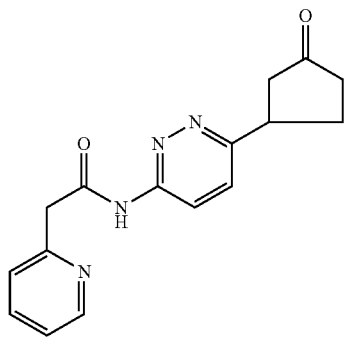 [SMILES: O=C1CCC(c2ccc(NC(=O)Cc3ccccn3)nn2)C1]

N-[6-(3-oxocyclopent-1-en-1-yl)pyridazin-3-yl]-2-(pyridin-2-yl)acetamide (1.5 g, 5.1 mmol) was placed in a 500 mL stainless steel Parr bomb and MeOH (255 mL) was added followed by Pd/C (E101, 10%, wet, 150 mg). The reaction was stirred for 7 hr under 4 bar H$_2$ pressure. LCMS indicated about 50% conversion. A further portion of Pd/C (150 mg) was added, and the reaction stirred for a further 18 hr at 50° C. under 6 bar H$_2$ pressure. LCMS indicated complete conversion to the desired product with about 10% over-reduction. The reaction was filtered through a plug of Celite® and concentrated. The residue was purified by silica gel chromatography eluting with 0%-5% EtOH in EtOAc to provide N-[6-(3-oxocyclopentyl)pyridazin-3-yl]-2-(pyridin-2-yl)acetamide (877 mg, 58%) as a solid. $^1$H NMR (400 MHz, MeOD-d$_4$) δ ppm 8.68-8.70 (m, 1H), 8.44 (d, J=8 Hz, 1H), 7.75-7.79 (m, 1H), 7.27-7.39 (m, 3H), 4.06 (s, 2H), 3.66-3.71 (m, 1H), 2.66-2.76 (m, 2H), 2.46-2.53 (m, 2H), 2.18-2.40 (m, 2H). m/z (APCl+) for C$_{16}$H$_{16}$N$_4$O$_2$ 297.1 (M+H)$^+$.

Step 3: Preparation of N-{6-[(3E)-3-(cyanomethylidene)cyclopentyl]pyridazin-3-yl}-2-(pyridin-2-yl)acetamide

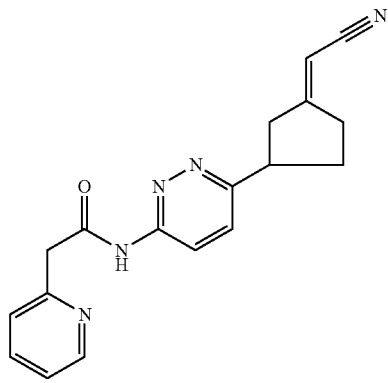 [SMILES: N#C/C=C1\CCC(c2ccc(NC(=O)Cc3ccccn3)nn2)C1]

To a suspension of NaH (65.8 mg, 60% suspension, 1.65 mmol) in THF (4.2 mL) was added diethyl(cyanomethyl)phosphonate (292 mg, 1.65 mmol) in a drop-wise manner at 0° C. After being stirred for 10 min at room temperature, the solution was diluted with THF (5 mL), and then N-[6-(3-oxocyclopentyl)pyridazin-3-yl]-2-(pyridin-2-yl)acetamide (250 mg, 0.84 mmol) was added in one portion. After 3 hr, the reaction was clean and complete by LCMS and TLC. The reaction was quenched with saturated aq. NH$_4$Cl and extracted with CH$_2$Cl$_2$. The organic layers were washed with brine, dried over Na$_2$SO$_4$, and concentrated. The residue was purified by silica gel chromatography eluting with 0%-5% EtOH in EtOAc to provide N-{6-[(3E)-3-(cyanomethylidene)cyclopentyl]pyridazin-3-yl}-2-(pyridin-2-yl)acetamide (245 mg, 91%) as a solid. $^1$H NMR (400 MHz, DMSO-d$_6$) δ ppm 11.30 (br s, 1H), 8.48-8.50 (m, 1H), 8.22-8.24 (m, 1H), 7.74-7.76 (m, 1H), 7.63-7.76 (m, 1H), 7.40-7.42 (m, 1H), 7.27-7.28 (m, 1H), 5.23-5.25 (m, 1H), 4.00 (s, 2H), 3.52-3.56 (m, 1H), 2.65-2.91 (m, 4H), 2.23-2.27 (m, 1H), 1.92-2.01 (m, 1H). m/z (APCl+) for C$_{18}$H$_{17}$N$_5$O 320.1 (M+H)$^+$.

Step 4: Preparation of N-{6-[3-(cyanomethyl)cyclopentyl]pyridazin-3-yl}-2-(pyridin-2-yl)acetamide

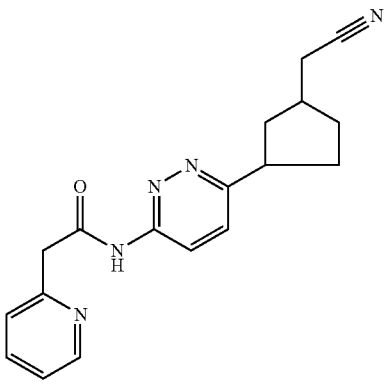 [SMILES: N#CCC1CCC(c2ccc(NC(=O)Cc3ccccn3)nn2)C1]

To a stirred solution of N-{6-[(3E)-3-(cyanomethylidene)cyclopentyl]pyridazin-3-yl}-2-(pyridin-2-yl)acetamide (100 mg, 0.31 mmol) in THF (6.26 mL) at −78° C. was added L-Selectride (1.56 mL, 1 M in THF, 1.56 mmol), and the reaction was stirred at −78° C. for a further 4 hr. The reaction was quenched with saturated aq. NH$_4$Cl and allowed to warm to room temperature. The reaction was extracted with CH$_2$Cl$_2$, washed with brine, dried over Na$_2$SO$_4$, and concentrated. The residue was purified by silica gel chromatography eluting with 0%-5% EtOH in EtOAc to provide N-{6-[3-(cyanomethyl)cyclopentyl]pyridazin-3-yl}-2-(pyridin-2-yl)acetamide (85 mg, 91%) as a 1:1 mixture of cis and trans diastereomers, which was used directly in the next step without further purification. $^1$H NMR (400 MHz, CDCl$_3$) δ ppm 8.61-8.63 (m, 1H), 8.29-8.32 (m, 1H), 7.55-7.65 (m, 1H), 7.13-7.24 (m, 3H), 3.98 (s, 2H), 3.32-3.45 (m, 2H), 2.20-2.41 (m, 4H), 1.64-2.01 (m, 5H). m/z (APCI+) for C$_{18}$H$_{19}$N$_5$O 322.1 (M+H)$^+$.

Step 5: Preparation of 2-(pyridin-2-yl)-N-{5-[(3-{6-[(pyridin-2-ylacetyl)amino]pyridazin-3-yl}cyclopentyl)methyl]-1,3,4-thiadiazol-2-yl}acetamide

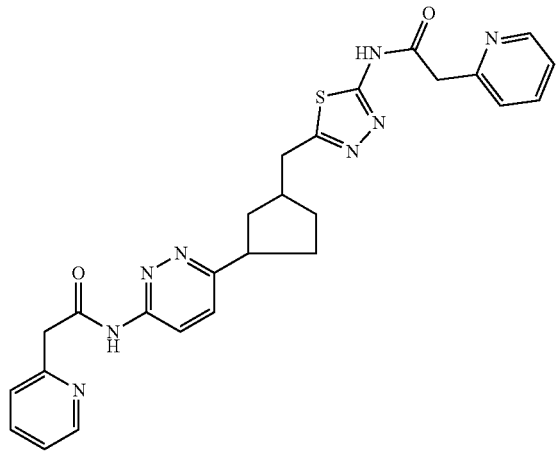 [SMILES: O=C(Cc1ccccn1)Nc1ccc(C2CCC(Cc3nnc(NC(=O)Cc4ccccn4)s3)C2)nn1]

To a vial containing N-{6-[3-(cyanomethyl)cyclopentyl]pyridazin-3-yl}-2-(pyridin-2-yl)acetamide (80 mg, 0.25 mmol) and thiosemicarbazide (25 mg, 0.27 mmol) was added trifluoroacetic acid (250 μL). The resultant suspension was placed in a pre-heated 70° C. sand bath at which time it became homogeneous. After 2 hr, the reaction was about 80% complete. The reaction was allowed to stir for an additional 2 hr at 70° C., cooled to room temperature, and concentrated. The residue was quenched with saturated aq. NaHCO$_3$, and extracted with CH$_2$Cl$_2$ to provide the crude material, which was purified by silica gel chromatography eluting with 0%-25% EtOH in EtOAc to provide 27 mg of the intermediate aminothiadiazole, and 10 mg of recovered starting material. The aminothiadiazole was taken up in DMF (70 μL) and the 2-pyridylacetic acid hydrochloride (23 mg, 0.13 mmol) and pyridine (32.3 μL, 0.40 mmol) were added. To this mixture was added T3P (86.3 μL, 50% in DMF, 0.15 mmol), and the reaction allowed to stir for 2 hr at room temperature. LCMS indicated complete consumption of the starting material. The pyridine was removed in vacuo, and the residue quenched with saturated aq. NaHCO$_3$. The mixture was extracted with CH$_2$Cl$_2$, and the extracts dried over Na$_2$SO$_4$, and concentrated. The residue was purified by silica gel chromatography eluting with 0%-5% EtOH in EtOAc to provide 2-(pyridin-2-yl)-N-{5-[(3-{6-[(pyridin-2-ylacetyl)amino]pyridazin-3-yl}cyclopentyl)methyl]-1,3,4-thiadiazol-2-yl}acetamide (60 mg) as a 1:1 mixture of cis and trans diastereomers. The compound was evaluated by a variety of purification methods, though no conditions could be identified to separate any of the four isomers. Further purification was carried out by reverse-phase HPLC to afford 2-(pyridin-2-yl)-N-{5-[(3-{6-[(pyridin-2-ylacetyl)amino]pyridazin-3-yl}cyclopentyl)methyl]-1,3,4-thiadiazol-2-yl}acetamide (3 mg, 2%) as a solid. $^1$H NMR (400 MHz, DMSO-d$_6$) δ ppm 12.63 (br s, 1H), 11.24 (d, J=4 Hz, 1H), 8.49 (t, J=8 Hz, 2H), 8.18 (d, J=4 Hz, 1H), 7.76 (t, J=8 Hz, 2H), 7.57-7.61 (m, 1H), 7.39 (d, J=8 Hz, 2H), 7.26-7.29 (m, 2H), 3.99 (s, 4H), 3.46-3.50 (m, 1H), 3.29-3.39 (m, 1H), 3.05-3.10 (m, 2H), 1.75-2.24 (m, 4H), 1.51-1.59 (m, 1H), 1.40-1.46 (m, 1H). m/z (APCI+) for C$_{28}$H$_{26}$N$_8$O$_2$S 515.1 (M+H)$^+$.

Preparation 1. Preparation of (cis)-3-(methoxycarbonyl)cyclopentane Carboxylic Acid

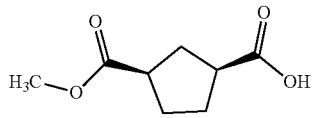

To a suspension of cis-1,3-cyclopentanedicarboxylic anhydride (3.0 g, 21 mmol) in MeOH (35 mL) was added sodium methoxide (1.2 g, 21 mmol) portionwise at room temperature. After 1 hr, the resulting clear solution was evaporated, basified with 1 M NaOH and washed with EtOAc twice. Then, the aq. layer was acidified with 1 N HCl to pH 2 and extracted with CH$_2$Cl$_2$ (3×25 mL). The combined organics were dried over Na$_2$SO$_4$ and evaporated to give (cis)-3-(methoxycarbonyl) cyclopentanecarboxylic acid (2.7 g, 75%) as a clear oil. $^1$H NMR (400 MHz, CDCl$_3$) δ ppm 3.70 (s, 3H), 2.76-2.94 (m, 2H), 2.28 (dt, J=13.3, 8.0 Hz, 1H), 2.15 (dt, J=13.3, 9.1 Hz, 1H), 1.89-2.07 (m, 4H). m/z (APCI+) for C$_8$H$_{12}$O$_4$ 173.2 (M+H)$^+$.

Preparation 2. Preparation of methyl 3-bromopropiolate

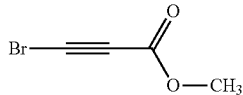

To methyl propiolate (60 g, 713.6 mmol) dissolved in acetone (2 L) was added N-bromosuccinimide (147.22 g, 827.13 mmol), followed by silver nitrate (12.12 g, 71.37 mmol). A slight exotherm was observed with the reaction temperature increasing from 21-32° C. before the reaction mixture was left to stir at room temperature overnight. The resulting grey suspension was evaporated to dryness in vacuo, pentane added (100 mL) and filtered through Celite®, washing through with more pentane. This procedure was carried out twice more and then the combined filtrates evaporated in vacuo to give 113 g of methyl 3-bromopropiolate (98% yield) containing approximately 10% of starting material. $^1$H NMR (400 MHz, CDCl$_3$) δ ppm 3.78 (s, 3H).

Preparation 3. Preparation of Methyl 3-bromobicyclo[2.2.1]hepta-2,5-diene-2-carboxylate

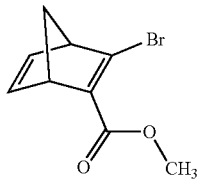

Methyl 3-bromopropiolate (113 g, 698 mmol) and freshly cracked cyclopentadiene (92 g, 1.39 mol) were dissolved in toluene (570 mL) and heated to 90° C., under nitrogen for 2 hr. The reaction was cooled to room temperature, and the toluene evaporated in vacuo to give a dark brown oil. This was azeotroped three times with acetonitrile to remove excess dicyclopentadiene, giving the title compound (119 g, 74% yield) as a brown oil. $^1$H NMR (400 MHz, CDCl$_3$) δ ppm 6.88-6.94 (m, 1H), 6.85 (ddd, J=5.2, 3.1, 1.0 Hz, 1H), 4.00 (dqd, J=2.8, 1.7, 0.8 Hz, 1H), 3.76 (s, 3H), 3.69 (ddtd, J=3.2, 2.4, 1.5, 0.7 Hz, 1H), 2.32 (dt, J=6.7, 1.7 Hz, 1H), 2.13 (dt, J=6.7, 1.7 Hz, 1H).

Preparation 4. Preparation of Methyl 3,3-dimethoxybicyclo[2.2.1]hept-5-ene-2-carboxylate

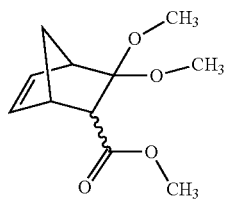

Methyl 3-bromobicyclo[2.2.1]hepta-2,5-diene-2-carboxylate (119.0 g, 519.5 mmol) was dissolved in MeOH (1 L) and sodium methoxide (289 mL of a 30% solution in MeOH) added and the reaction was heated at reflux for 45 min, and then saturated aq. NaHCO$_3$ (500 mL) was added, followed by water (500 mL) and TBME (1 L). The TBME layer was separated and the aqueous layer extracted once more with TBME (1 L). The combined organic extracts were dried over MgSO$_4$ and evaporated in vacuo to give methyl 3,3-dimethoxybicyclo[2.2.1]hept-5-ene-2-carboxylate as a yellow oil (75.0 g, 68%). $^1$H NMR (400 MHz, CDCl$_3$) δ ppm 6.60 (dd, J=5.7, 2.8 Hz, 0.5H), 6.25 (dd, J=5.6, 3.0 Hz, 0.5H), 6.13-6.18 (m, 0.5H), 6.07 (dd, J=5.6, 3.1 Hz, 0.5H), 3.67 (d, J=18.5 Hz, 3H), 3.40 (s, 1.5H), 3.31 (s, 1.5H), 3.24 (s, 1.5H), 3.17 (s, 1.5H), 3.06 (d, J=3.4 Hz, 0.5H), 2.92-3.04 (m, 2H), 2.50 (d, J=2.7 Hz, 0.5H), 2.18 (ddt, J=9.0, 1.6, 0.9 Hz, 0.5H), 1.67-1.73 (m, 0.5H), 1.63 (dq, J=9.1, 2.2 Hz, 1H).

Preparation 5. Preparation of Methyl 3-oxobicyclo[2.2.1]hept-5-ene-2-carboxylate

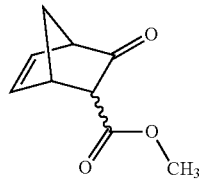

Methyl 3,3-dimethoxybicyclo[2.2.1]hept-5-ene-2-carboxylate (75.0 g, 353.37 mmol) was dissolved in THF (400 mL) and 2 M HCl (400 mL) added. The mixture was stirred at room temperature for 1 hr, then diluted with TBME (1000 mL) and the layers separated. The aq. layer was extracted once more with TBME (1000 mL) and the combined organic extracts dried over MgSO$_4$ and evaporated in vacuo to give methyl 3-oxobicyclo[2.2.1]hept-5-ene-2-carboxylate as a yellow oil (55.0 g, 93%), as a mixture of diastereoisomers. $^1$H NMR (400 MHz, CDCl$_3$) δ ppm 6.77 (dd, J=5.4, 2.7 Hz, 1H), 6.03-6.09 (m, 1H), 3.72 (d, J=13.0 Hz, 3H), 3.34 (dq, J=2.8, 1.4 Hz, 1H), 3.18-3.23 (m, 1H), 3.16 (dt, J=3.1, 0.7 Hz, 1H), 2.14 (dddd, J=9.6, 2.4, 1.4, 0.6 Hz, 1H), 1.92 (dtd, J=9.1, 1.5, 0.8 Hz, 1H).

Preparation 6. Preparation of (cis)-4-(2-methoxy-2-oxoethyl)cyclopent-2-enecarboxylic Acid

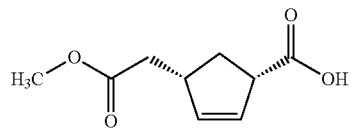

Methyl 3-oxobicyclo[2.2.1]hept-5-ene-2-carboxylate (55.21 g, 332.24 mmol) was dissolved in dioxane (600 mL) and cooled to 0° C. After drop wise addition of NaOH (2 M, 149.51 mL, 299.02 mmol) over 30 min, the reaction was stirred for a further 30 min, before quenching with HCl (3 M, 100 mL). The resulting mixture was extracted with EtOAc (2×500 mL). After drying of the organic layers over MgSO$_4$, the solvent was removed under reduced pressure to give a brown oil purified by dry flash, eluting with neat CH$_2$Cl$_2$, followed by 10%, then 15% and 20% EtOAc in CH$_2$Cl$_2$. Evaporation of the appropriate fractions gave (cis)-

4-(2-methoxy-2-oxoethyl)cyclopent-2-enecarboxylic acid (40.4 g, 66%). ¹H NMR (400 MHz, CDCl₃) δ ppm 5.85 (dt, J=5.7, 2.3 Hz, 1H), 5.79 (dt, J=5.6, 2.2 Hz, 1H), 3.68 (s, 3H), 3.60 (ddq, J=9.0, 6.9, 2.4 Hz, 1H), 3.09-3.23 (m, 1H), 2.36-2.55 (m, 3H), 1.79 (dt, J=13.3, 6.5 Hz, 1H).

Preparation 7. Preparation of (cis)-3-(2-methoxy-2 oxoethyl)cyclopentane carboxylic Acid

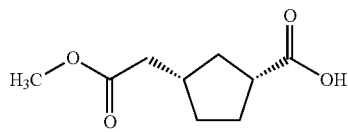

(Cis)-methyl 3-oxobicyclo[2.2.1]heptane-2-carboxylate (40.4 g, 219.3 mmol) was dissolved in EtOAc (400 mL), and 10% wt. Pd/C (2 g, 5% w/w relative to substrate) was added. The mixture was then stirred at room temperature for 2 hrs, under an atmosphere of 50 psi hydrogen. The catalyst was then removed via filtration through a pad of Celite®, and the filtrate evaporated, affording a pale yellow oil (41 g). ¹H NMR indicated trace impurities; heptane was added, and the suspension filtered and evaporated to give (cis)-3-(2-methoxy-2 oxoethyl)cyclopentane carboxylic acid (31 g, 76% yield). ¹H NMR (400 MHz, CDCl₃) δ ppm 3.67 (s, 3H), 2.85 (ddd, J=8.8, 7.5, 1.5 Hz, 1H), 2.37-2.43 (m, 2H), 2.15-2.37 (m, 2H), 1.84-2.01 (m, 3H), 1.49 (dt, J=12.6, 9.4 Hz, 1H), 1.29-1.42 (m, 1H).

Preparation 8. Preparation of (cis)-3-(carboxymethyl)cyclopentane Carboxylic Acid

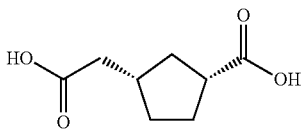 [SMILES: O=C(O)C[C@H]1CC[C@@H](C(=O)O)C1]

(Cis)-3-(2-methoxy-2-oxoethyl)cyclopentanecarboxylic acid (10.6 g, 56.93 mmol) was dissolved in 2 M NaOH (56.9 mL) and stirred at room temperature for 2 hr. The reaction was acidified with concentrated HCl with ice cooling to pH 4 and stirred at room temperature overnight to allow crystallization. The resulting solid was filtered off, washed well with water and dried at 60° C. under vacuum to give (cis)-3-(carboxymethyl)cyclopentanecarboxylic acid (6.70 g, 68%) as a white solid. ¹H NMR (400 MHz, DMSO-d₆) δ ppm 12.00 (s, 2H), 2.61-2.78 (m, 1H), 2.21-2.28 (m, 2H), 2.10-2.21 (m, 1H), 2.02 (dt, J=12.4, 7.4 Hz, 1H), 1.70-1.84 (m, 3H), 1.14-1.38 (m, 2H).

Alternate Preparation 8. Preparation of (cis)-3-(carboxymethyl)cyclopentane Carboxylic Acid

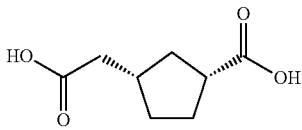

(Cis)-3-(2-methoxy-2-oxoethyl)cyclopentane carboxylic acid (10.6 g, 56.93 mmol) was dissolved in 2 M NaOH (56.9 mL) and stirred at room temperature for 2 hr. The reaction was acidified with concentrated HCl with ice cooling to ca. pH 4 and stirred at room temperature overnight to allow crystallization. The resulting solid was filtered off, washed well with water and dried at 60° C. under vacuum to give (cis)-3-(carboxymethyl)cyclopentanecarboxylic acid (6.70 g, 68%) as a white solid. ¹H NMR (400 MHz, DMSO-d₆) δ ppm 12.00 (s, 2H), 2.61-2.78 (m, 1H), 2.21-2.28 (m, 2H), 2.10-2.21 (m, 1H), 2.02 (dt, J=12.4, 7.4 Hz, 1H), 1.70-1.84 (m, 3H), 1.14-1.38 (m, 2H).

Preparation 9. Preparation of bicyclo[3.2.1]oct-2-ene

To a stirred solution of norbornene (120 g, 1.27 mol) and triethylbenzyl ammonium chloride (900 mg, 3.95 mmol) in CHCl₃ (129 mL) was added 50% aq. NaOH (130 mL). The resulting solution was stirred at room temperature for 3 days. Water (130 mL) was added and the reaction filtered. The precipitate was washed with CH₂Cl₂ (ca. 500 mL), and the combined organic layers washed with brine (2×300 mL), dried over Na₂SO₄, and concentrated to give crude product, which was purified by distillization to give 3,4-dichlorobicyclo[3.2.1]oct-2-ene (123 g, 54%) as a yellow oil.

To a well-stirred solvent of liquid NH₃ (ca. 500 mL) was added Na (24 g, 1.04 mol) in portions over a period of 40 min at ca. −65° C. After being stirred for ca. 20 min, a solution of 3,4-dichlorobicyclo[3.2.1]oct-2-ene (20 g, 0.11 mol) in t-BuOH (20 mL) and THF (20 mL) was added in a drop-wise manner. During addition, a large amount of precipitate was formed. The reaction mixture was stirred at ca. −65° C. for a further ca. 3 hr. TLC (petroleum ether, detected by I₂) showed the reaction was complete. The reaction mixture was warmed to ca. 35° C., solid NH₄Cl (30 g) was added slowly, and the reaction stirred for 20 min. The resulting mixture was poured into a 5 L beaker, water (300 mL) was added slowly, and the mixture stirred for 20 min. The reaction flask was carefully washed with EtOH to quench residual sodium. The mixture was extracted with CH₂Cl₂ (2×500 mL), the organic layer was washed with water (200 mL), dried over Na₂SO₄, and concentrated in vacuo at ca. 25° C. to give bicyclo[3.2.1]oct-2-ene (8 g, 80% pure, bpt ~138 C, 66%), as a pale yellow oil, which was used without further purification (for references on the synthesis of the olefin, and an alternative route that has been employed from 4-vinylcyclohex-1-ene, see *Tetrahedron Lett.*, 2004, 45, 9447 and *Tetrahedron Lett.*, 1976, 16, 1257).

Preparation 10. Preparation of (1 S,3R)-3-(carboxymethyl)cyclopentane Carboxylic Acid

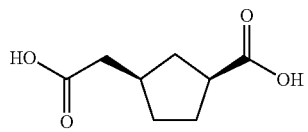 [SMILES: O=C(O)C[C@@H]1CC[C@H](C(=O)O)C1]

To a well-stirred mixture of bicyclo[3.2.1]oct-2-ene (25 g, 231 mmol) and $RuCl_3 \cdot H_2O$ (1.04 g, 4.62 mmol) in MeCN (250 mL), EtOAc (250 mL) and water (350 mL) was added $NaIO_4$ (295 g, 231 mmol) at room temperature in portions over a period of ca. 60 min. The resulting mixture was stirred at room temperature for ca. 16 hr. TLC (petroleum ether) indicated the reaction was complete. The reaction mixture was filtered and the cake was washed with EtOAc (ca. 700 mL) and water (300 mL). The organic layer was washed with brine (500 mL), dried over $Na_2SO_4$, filtered through Celite® and concentrated in vacuo to afford a gummy residue (30 g). The residue was dissolved in water (ca. 200 mL) and basified to pH ~10 with 2 M aq. NaOH. The aqueous solution was washed with EtOAc (400 mL), acidified to pH ~4 and then extracted with EtOAc (2×500 mL). The combined organic layers were dried over $Na_2SO_4$ and concentrated under high vacuum to give racemic (cis)-3-(carboxymethyl)cyclopentane carboxylic acid (26 g, >90% purity, 65%) as a pale brown solid, which was subjected to chiral SFC separation.

A 105 g batch of racemic diacid was subjected to chiral separation by SFC using an Chiralcel AD-3 3 μm column (4.6×100 mm) eluting with 10% MeOH @ 120 bar with a flow rate of 4 mL/min.

(1R,3S)-3-(carboxymethyl)cyclopentanecarboxylic acid (49.2 g) was obtained as a white solid as peak 1 ($R_t$=1.45 min, >99% ee); $[\alpha]^{22}_D$=−7.1° (c=1.0, MeOH). $^1$H NMR (400 MHz, DMSO-$d_6$) δ ppm 12.00 (s, 2H), 2.61-2.78 (m, 1H), 2.21-2.28 (m, 2H), 2.10-2.21 (m, 1H), 2.02 (dt, J=12.4, 7.4 Hz, 1H), 1.70-1.84 (m, 3H), 1.14-1.38 (m, 2H).

(1S,3R)-3-(carboxymethyl)cyclopentane carboxylic acid (49 g) was obtained as a white solid as peak 2 ($R_t$=2.33 min, >99% ee); $[\alpha]^{22}_D$=+7.1° (c=1.0, MeOH). $^1$H NMR (400 MHz, DMSO-$d_6$) δ ppm 12.00 (s, 2H), 2.61-2.78 (m, 1H), 2.21-2.28 (m, 2 H), 2.10-2.21 (m, 1H), 2.02 (dt, J=12.4, 7.4 Hz, 1H), 1.70-1.84 (m, 3H), 1.14-1.38 (m, 2H).

The following examples were made with non-critical changes or substitutions to the exemplified procedures that would be understood to one skilled in the art.

TABLE 1

| Example No. (Scheme) Structure and Compound Name | LRMS m/z [M + H]+ | $^1$H NMR | Chiral Separation Conditions (SFC) |
|---|---|---|---|
| 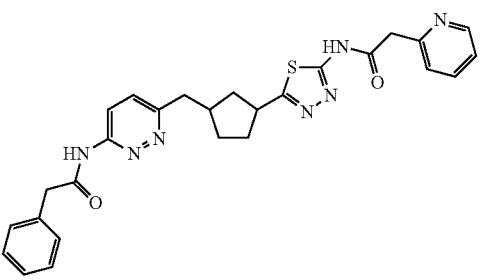 [SMILES: O=C(Cc1ccccc1)Nc1ccc(CC2CCC(c3nnc(NC(=O)Cc4ccccn4)s3)C2)nn1]<br>(Scheme A)<br>(rac)-2-phenyl-N-{6-[(cis)-3-{5-[(pyridin-2-ylacetyl)amino]-1,3,4-thiadiazol-2-yl}cyclopentyl)methyl]pyridazin-3-yl}acetamide | 1   514.1 | (400 MHz, DMSO-$d_6$) δ ppm 12.63 (br s, 1 H), 11.22 (s, 1 H), 8.49 (d, J = 4.78 Hz, 1 H), 8.19 (d, J = 9.06 Hz, 1 H), 7.76 (td, J = 7.68, 1.76 Hz, 1 H), 7.56 (d, J = 9.32 Hz, 1 H), 7.19-7.43 (m, 7 H), 3.99 (s, 2 H), 3.76 (s, 2 H), 3.44-3.55 (m, 1 H), 2.94 (d, J = 7.30 Hz, 2 H), 2.03-2.28 (m, 3 H), 1.74-1.91 (m, 2 H), 1.42-1.60 (m, 2 H). | Racemic Cis |
| 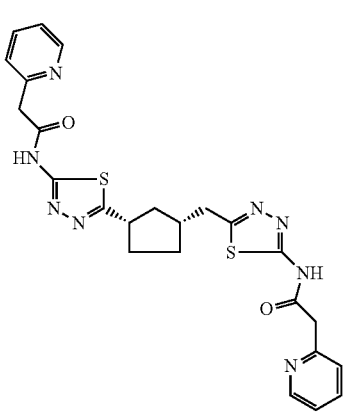 [SMILES: O=C(Cc1ccccn1)Nc1nnc(C[C@@H]2CC[C@H](c3nnc(NC(=O)Cc4ccccn4)s3)C2)s1]<br>(Scheme B)<br>2-(pyridin-2-yl)-N-(5-{[(1R,3S)-3-{5-[(pyridin-2-ylacetyl)amino]-1,3,4-thiadiazol-2-yl}cyclopentyl]methyl}-1,3,4-thiadiazol-2-yl)acetamide | 2*   521.1 | (400 MHz, DMSO-$d_6$) δ ppm 12.65 (br s, 2 H), 8.49 (d, J = 4.77 Hz, 2 H), 7.77 (td, J = 7.6, 1.9 Hz, 2 H), 7.39 (d, J = 7.8 Hz, 2 H), 7.28 (ddd, J = 7.6, 4.9, 1.2 Hz, 2 H), 4.00 (s, 4 H), 3.50 (dt, J = 10.3, 7.7 Hz, 1 H), 3.07 (d, J = 7.3 Hz, 2 H), 2.35-2.47 (m, 1 H), 2.29 (dt, J = 13.5, 7.1 Hz, 1 H), 2.12 (dtd, J = 15.9, 8.9, 7.7, 3.8 Hz, 1 H), 1.76-1.96 (m, 2 H), 1.44-1.61 (m, 2 H). | Rt (Peak 2) = 1.98 minutes Chiralpak OJ-H 4.6 x 100 mm column 30% MeOH (w 0.1% DEA) @ 120 bar $CO_2$, 4 mL/min. |

TABLE 1-continued

| Example No. (Scheme) Structure and Compound Name | | LRMS m/z [M + H]+ | 1H NMR | Chiral Separation Conditions (SFC) |
|---|---|---|---|---|
| 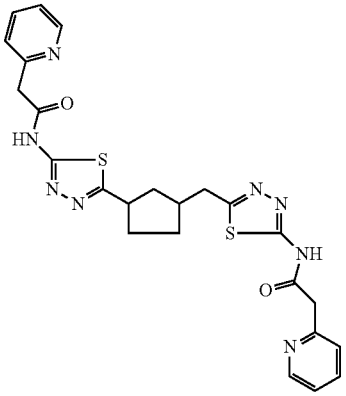 [SMILES: O=C(Cc1ccccn1)Nc1nnc(CC2CCC(c3nnc(NC(=O)Cc4ccccn4)s3)C2)s1]<br>(Scheme B)<br>(rac)-2-(pyridin-2-yl)-N-(5-{[(cis)-3-{5-[(pyridin-2-ylacetyl)amino]-1,3,4-thiadiazol-2-yl}cyclopentyl]methyl}-1,3,4-thiadiazol-2-yl)acetamide | 3 | 521.1 | (400 MHz, DMSO-d6) δ ppm 12.68 (s, 2 H), 8.45-8.52 (m, 2 H), 7.77 (td, J = 7.6, 1.9 Hz, 2 H), 7.39 (d, J = 7.8 Hz, 2 H), 7.28 (ddd, J = 7.6, 4.9, 1.2 Hz, 2 H), 4.00 (s, 4 H), 3.50 (dt, J = 10.3, 7.7 Hz, 1 H), 3.07 (d, J = 7.3 Hz, 2 H), 2.35-2.47 (m, 1 H), 2.29 (dt, J = 13.5, 7.1 Hz, 1 H), 2.12 (dtd, J = 15.9, 8.9, 7.7, 3.8 Hz, 1 H), 1.76-1.96 (m, 2 H), 1.40-1.63 (m, 2 H). | Racemic Cis |
| 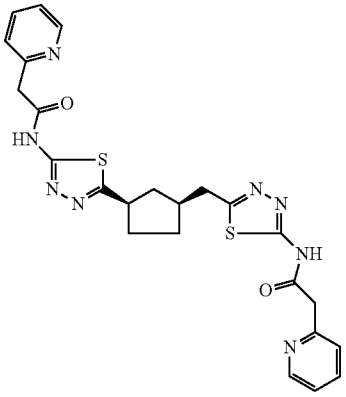 [SMILES: O=C(Cc1ccccn1)Nc1nnc(C[C@H]2CC[C@@H](c3nnc(NC(=O)Cc4ccccn4)s3)C2)s1]<br>(Scheme B)<br>2-(pyridin-2-yl)-N-(5-{[(1S,3R)-3-{5-[(pyridin-2-ylacetyl)amino]-1,3,4-thiadiazol-2-yl}cyclopentyl]methyl}-1,3,4-thiadiazol-2-yl)acetamide | 4* | 521.1 | (400 MHz, DMSO-d6) δ ppm 12.68 (s, 2 H), 8.45-8.52 (m, 2 H), 7.77 (td, J = 7.6, 1.9 Hz, 2 H), 7.39 (d, J = 7.8 Hz, 2 H), 7.28 (ddd, J = 7.6, 4.9, 1.2 Hz, 2 H), 4.00 (s, 4 H), 3.50 (dt, J = 10.3, 7.7 Hz, 1 H), 3.07 (d, J = 7.3 Hz, 2 H), 2.35-2.47 (m, 1 H), 2.29 (dt, J = 13.5, 7.1 Hz, 1 H), 2.12 (dtd, J = 15.9, 8.9, 7.7, 3.8 Hz, 1 H), 1.76-1.96 (m, 2 H), 1.40-1.63 (m, 2 H). | Rt (Peak 1) = 1.60 minutes Chiralpak OJ-H 4.6 x 100 mm column 30% MeOH (w 0.1% DEA) @ 120 bar CO2, 4 mL/min. |
| 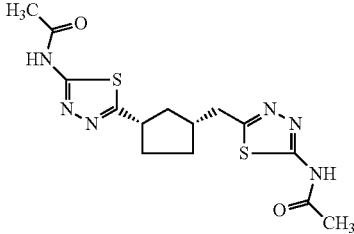 [SMILES: CC(=O)Nc1nnc(C[C@@H]2CC[C@H](c3nnc(NC(C)=O)s3)C2)s1]<br>(Scheme B)<br>N-[5-({(1R,3S)-3-[5-(acetylamino)-1,3,4-thiadiazol-2-yl]cyclopentyl}methyl)-1,3,4-thiadiazol-2-yl]acetamide | 5 | 367.1 | (400 MHz, DMSO-d6) δ ppm 12.38 (s, 2 H), 3.57 (m, 1 H), 3.07 (d, J = 7.4 Hz, 2 H), 2.42 (dq, J = 9.8, 7.6 Hz, 1 H), 2.29 (dt, J = 13.4, 7.0 Hz, 1 H), 2.16 (d, J = 1.2 Hz, 6 H), 2.09-2.14 (m, 1 H), 1.78-1.95 (m, 2 H), 1.43-1.62 (m, 2 H). | Rt (Peak 1) = 3.30 minutes Chiralpak AS-H 4.6 x 250 mm column 30% MeOH (w. 0.1% DEA) @ 140 bar CO2, 3 mL/min. |

TABLE 1-continued

| Example No. (Scheme) Structure and Compound Name | LRMS m/z [M + H]+ | 1H NMR | Chiral Separation Conditions (SFC) |
|---|---|---|---|
| (Scheme B)<br>(rac)-N-[5-({(cis)-3-[5-(acetylamino)-1,3,4-thiadiazol-2-yl]cyclopentyl}methyl)-1,3,4-thiadiazol-2-yl]acetamide | 6** 367.1 | (400 MHz, DMSO-$d_6$) δ ppm 12.38 (s, 2 H), 3.57 (m, 1 H), 3.07 (d, J = 7.4 Hz, 2 H), 2.42 (dq, J = 9.8, 7.6 Hz, 1 H), 2.29 (dt, J = 13.4, 7.0 Hz, 1 H), 2.16 (d, J = 1.2 Hz, 6 H), 2.09-2.14 (m, 1 H), 1.78-1.95 (m, 2 H), 1.43-1.62 (m, 2 H). | Racemic Cis |
| (Scheme B)<br>N-[5-({(1S,3R)-3-[5-(acetylamino)-1,3,4-thiadiazol-2-yl]cyclopentyl}methyl)-1,3,4-thiadiazol-2-yl]acetamide | 7 367.1 | (400 MHz, DMSO-$d_6$) δ ppm 12.38 (s, 2 H), 3.57 (m, 1 H), 3.07 (d, J = 7.4 Hz, 2 H), 2.42 (dq, J = 9.8, 7.6 Hz, 1 H), 2.29 (dt, J = 13.4, 7.0 Hz, 1 H), 2.16 (d, J = 1.2 Hz, 6 H), 2.09-2.14 (m, 1 H), 1.78-1.95 (m, 2H), 1.43-1.62 (m, 2 H). | Rt (Peak 2) = 4.62 minutes Chiralpak AS-H 4.6 x 250 mm column 30% MeOH (w. 0.1% DEA) @ 140 bar $CO_2$, 3 mL/min. |
| (Scheme B)<br>2-phenyl-N-(5-{[(1R,3S)-3-{5-[(phenylacetyl)amino]-1,3,4-thiadiazol-2-yl}cyclopentyl]methyl}-1,3,4-thiadiazol-2-yl)acetamide | 8 519.2 | (400 MHz, DMSO-$d_6$) δ ppm 12.66 (s, 2 H), 6.72-7.88 (m, 10 H), 3.78 (d, J = 1.5 Hz, 4 H), 3.49 (dd, J = 10.0, 7.5 Hz, 1 H), 3.05 (d, J = 7.3 Hz, 2 H), 2.34-2.47 (m, 1 H), 2.26 (dt, J = 13.0, 6.9 Hz, 1 H), 2.03-2.17 (m, 1 H), 1.76-1.93 (m, 2 H), 1.41-1.60 (m, 2 H). | Rt (Peak 1) = 8.51 minutes Chiralpak AS-H 4.6 x 250 mm column 40% MeOH (w. 0.1% DEA) @ 140 bar $CO_2$, 3 mL/min. |

TABLE 1-continued

| Example No. (Scheme) Structure and Compound Name | | LRMS m/z [M + H]+ | 1H NMR | Chiral Separation Conditions (SFC) |
|---|---|---|---|---|
| (Scheme B)<br>(rac)-2-phenyl-N-(5-{[(cis)-3-{5-[(phenylacetyl)amino]-1,3,4-thiadiazol-2-yl}cyclopentyl]methyl}-1,3,4-thiadiazol-2-yl)acetamide | 9 | 519.2 | (400 MHz, DMSO-$d_6$) δ ppm 12.66 (s, 2 H), 6.72-7.88 (m, 10 H), 3.78 (d, J = 1.5 Hz, 4 H), 3.49 (dd, J = 10.0, 7.5 Hz, 1 H), 3.05 (d, J = 7.3 Hz, 2 H), 2.34-2.47 (m, 1 H), 2.26 (dt, J = 13.0, 6.9 Hz, 1 H), 2.03-2.17 (m, 1 H), 1.76-1.93 (m, 2 H), 1.41-1.60 (m, 2 H). | Racemic Cis |
| (Scheme B)<br>2-phenyl-N-(5-{[(1S,3R)-3-{5-[(phenylacetyl)amino]-1,3,4-thiadiazol-2-yl}cyclopentyl]methyl}-1,3,4-thiadiazol-2-yl)acetamide | 10 | 519.2 | (400 MHz, DMSO-$d_6$) δ ppm 12.66 (s, 2 H), 6.72-7.88 (m, 10 H), 3.78 (d, J = 1.5 Hz, 4 H), 3.49 (dd, J = 10.0, 7.5 Hz, 1 H), 3.05 (d, J = 7.3 Hz, 2 H), 2.34-2.47 (m, 1 H), 2.26 (dt, J = 13.0, 6.9 Hz, 1 H), 2.03-2.17 (m, 1 H), 1.76-1.93 (m, 2 H), 1.41-1.60 (m, 2 H). | Rt (Peak 2) = 10.20 minutes Chiralpak AS-H 4.6 x 250 mm column 40% MeOH (w. 0.1% DEA) @ 140 bar $CO_2$, 3 mL/min. |
| (Scheme C)<br>(rac)-N-[5-({(cis)-3-[5-(acetylamino)-1,3,4-thiadiazol-2-yl]cyclopentyl}methyl)-1,3,4-thiadiazol-2-yl]benzamide | 11** | 429.1 | (400 MHz, DMSO-$d_6$) δ ppm 12.89 (br s, 1 H), 12.35 (br s, 1 H), 8.10 (d, J = 7.46 Hz, 2 H), 7.62-7.71 (m, 1 H), 7.50-7.60 (m, 2 H), 3.45-3.61 (m, 1 H), 3.12 (d, J = 7.09 Hz, 2 H), 2.27-2.40 (m, 1 H), 2.07-2.24 (m, 4 H), 1.81-2.02 (m, 2 H), 1.48-1.69 (m, 2 H). | Racemic Cis |

TABLE 1-continued

| Example No. (Scheme) Structure and Compound Name | LRMS m/z [M + H]+ | 1H NMR | Chiral Separation Conditions (SFC) |
|---|---|---|---|
| (Scheme C)<br>N-[5-({(cis)-3-[5-(acetylamino)-1,3,4-thiadiazol-2-yl]cyclopentyl}methyl)-1,3,4-thiadiazol-2-yl]benzamide | 12* 429.1 | (400 MHz, DMSO-$d_6$) δ ppm 12.89 (br s, 1 H), 12.35 (br s, 1 H), 8.10 (d, J = 7.46 Hz, 2 H), 7.62-7.71 (m, 1 H), 7.50-7.60 (m, 2 H), 3.45-3.61 (m, 1 H), 3.12 (d, J = 7.09 Hz, 2 H), 2.27-2.40 (m, 1 H), 2.07-2.24 (m, 4 H), 1.81-2.02 (m, 2 H), 1.48-1.69 (m, 2 H). | Rt (Peak 1) = 4.63 minutes Chiralpak OJ-H 4.6 x 250 mm column 30% MeOH @ 140 bar $CO_2$, 3 mL/min. |
| (Scheme C)<br>N-[5-({(cis)-3-[5-(acetylamino)-1,3,4-thiadiazol-2-yl]cyclopentyl}methyl)-1,3,4-thiadiazol-2-yl]benzamide | 13* 429.1 | (400 MHz, DMSO-$d_6$) δ ppm 12.89 (br s, 1 H), 12.35 (br s, 1 H), 8.10 (d, J = 7.46 Hz, 2 H), 7.62-7.71 (m, 1 H), 7.50-7.60 (m, 2 H), 3.45-3.61 (m, 1 H), 3.12 (d, J = 7.09 Hz, 2 H), 2.27-2.40 (m, 1 H), 2.07-2.24 (m, 4 H), 1.81-2.02 (m, 2 H), 1.48-1.69 (m, 2 H). | Rt (Peak 2) = 5.57 minutes Chiralpak OJ-H 4.6 x 250 mm column 30% MeOH @ 140 bar $CO_2$, 3 mL/min. |
| (Scheme C)<br>N-[5-({(cis)-3-[5-(acetylamino)-1,3,4-thiadiazol-2-yl]cyclopentyl}methyl)-1,3,4-thiadiazol-2-yl]-2-phenylacetamide | 14* 443.0 | (600 MHz, DMSO-$d_6$) δ ppm 7.22-7.38 (m, 3 H), 3.79 (s, 2 H), 3.45-3.55 (m, 1 H), 3.06 (d, J = 7.46 Hz, 2 H), 2.36-2.47 (m, 1 H), 2.28 (d, J = 12.15 Hz, 1 H). | Rt (Peak 2) = 7.67 minutes Chiralpak OJ-H 4.6 x 250 mm column 40% MeOH (w. 0.1% DEA) @ 140 bar $CO_2$, 3 mL/min. |
| (Scheme C)<br>(rac)-N-[5-({(cis)-3-[5-(acetylamino)-1,3,4-thiadiazol-2-yl]cyclopentyl}methyl)-1,3,4-thiadiazol-2-yl]-2-phenylacetamide | 15 443.0 | (600 MHz, DMSO-$d_6$) δ ppm 7.22-7.38 (m, 3 H), 3.79 (s, 2 H), 3.45-3.55 (m, 1 H), 3.06 (d, J = 7.46 Hz, 2 H), 2.36-2.47 (m, 1 H), 2.28 (d, J = 12.15 Hz, 1 H). | Racemic Cis |
| (Scheme C)<br>N-[5-({(cis)-3-[5-(acetylamino)-1,3,4-thiadiazol-2-yl]cyclopentyl}methyl)-1,3,4-thiadiazol-2-yl]-2-phenylacetamide | 16* 443.0 | (600 MHz, DMSO-$d_6$) δ ppm 7.22-7.38 (m, 3 H), 3.79 (s, 2 H), 3.45-3.55 (m, 1 H), 3.06 (d, J = 7.46 Hz, 2 H), 2.36-2.47 (m, 1 H), 2.28 (d, J = 12.15 Hz, 1 H). | Rt (Peak 1) = 4.54 minutes Chiralpak OJ-H 4.6 x 250 mm column 40% MeOH (w. 0.1% DEA) @ 140 bar $CO_2$, 3 mL/min. |

TABLE 1-continued

| Example No. (Scheme) Structure and Compound Name | LRMS m/z [M + H]+ | 1H NMR | Chiral Separation Conditions (SFC) |
|---|---|---|---|
| 17* (Scheme C) N-[5-({(cis)-3-[5-(acetylamino)-1,3,4-thiadiazol-2-yl]cyclopentyl}methyl)-1,3,4-thiadiazol-2-yl]-2-(pyridin-2-yl)acetamide | 443.1 | (600 MHz, DMSO-$d_6$) δ ppm 8.49 (d, J = 4.68 Hz, 1 H), 7.71-7.79 (m, 1 H), 7.39 (d, J = 7.76 Hz, 1 H), 7.28 (dd, J = 7.02, 5.12 Hz, 1 H), 4.00 (s, 2 H), 3.44-3.57 (m, 1 H), 3.07 (d, J = 7.32 Hz, 2 H), 2.41 (m, 1 H), 2.24-2.34 (m, 1 H), 2.06-2.19 (m, 4 H), 1.80-1.96 (m, 2 H), 1.55 (m, J = 12.15 Hz, 2 H). | Rt (Peak 2) = 4.72 minutes Chiralpak OJ-H 4.6 x 250 mm column 30% MeOH (w. 0.1% DEA) @ 140 bar $CO_2$, 3 mL/min. |
| 18 (Scheme C) (rac)-N-[5-({(cis)-3-[5-(acetylamino)-1,3,4-thiadiazol-2-yl]cyclopentyl}methyl)-1,3,4-thiadiazol-2-yl]-2-(pyridin-2-yl)acetamide | 443.1 | (600 MHz, DMSO-$d_6$) δ ppm 8.49 (d, J = 4.68 Hz, 1 H), 7.71-7.79 (m, 1 H), 7.39 (d, J = 7.76 Hz, 1 H), 7.28 (dd, J = 7.02, 5.12 Hz, 1 H), 4.00 (s, 2 H), 3.44-3.57 (m, 1 H), 3.07 (d, J = 7.32 Hz, 2 H), 2.41 (m, 1 H), 2.24-2.34 (m, 1 H), 2.06-2.19 (m, 4 H), 1.80-1.96 (m, 2 H), 1.55 (m, J = 12.15 Hz, 2 H). | Racemic Cis |
| 19* (Scheme C) N-[5-({(cis)-3-[5-(acetylamino)-1,3,4-thiadiazol-2-yl]cyclopentyl}methyl)-1,3,4-thiadiazol-2-yl]-2-(pyridin-2-yl)acetamide | 443.1 | (600 MHz, DMSO-$d_6$) δ ppm 8.49 (d, J = 4.68 Hz, 1 H), 7.71-7.79 (m, 1 H), 7.39 (d, J = 7.76 Hz, 1 H), 7.28 (dd, J = 7.02, 5.12 Hz, 1 H), 4.00 (s, 2 H), 3.44-3.57 (m, 1 H), 3.07 (d, J = 7.32 Hz, 2 H), 2.41 (m, 1 H), 2.24-2.34 (m, 1 H), 2.06-2.19 (m, 4 H), 1.80-1.96 (m, 2 H), 1.55 (m, J = 12.15 Hz, 2 H). | Rt (Peak 1) = 3.47 minutes Chiralpak OJ-H 4.6 x 250 mm column 30% MeOH (w. 0.1% DEA) @ 140 bar $CO_2$, 3 mL/min. |
| 20* (Scheme D) N-{5-[(cis)-3-{[5-(acetylamino)-1,3,4-thiadiazol-2-yl]methyl}cyclopentyl]-1,3,4-thiadiazol-2-yl}-2-(pyrimidin-4-yl)acetamide | 445.2 | (600 MHz, DMSO-$d_6$) δ ppm 9.10 (d, J = 2.9 Hz, 1 H), 8.76 (dd, J = 5.3, 2.2 Hz, 1 H), 7.55 (t, J = 3.8 Hz, 1 H), 4.03 (d, J = 2.0 Hz, 2 H), 3.50 (dq, J = 10.4, 8.1 Hz, 1 H), 3.06 (dd, J = 7.3, 2.5 Hz, 2 H), 2.47-2.35 (m, 1 H), 2.21-2.34 (m, 1 H), 2.07-2.20 (m, 4 H), 1.77-1.95 (m, 2 H), 1.43-1.60 (m, 2 H). | Rt (Peak 2) = 1.95 minutes Chiralcel OJ-H 4.6 x 100 mm column 20% MeOH @ 120 bar $CO_2$, 4 mL/min. |

TABLE 1-continued

| Example No. (Scheme) Structure and Compound Name | LRMS m/z [M + H]⁺ | ¹H NMR | Chiral Separation Conditions (SFC) |
|---|---|---|---|
| 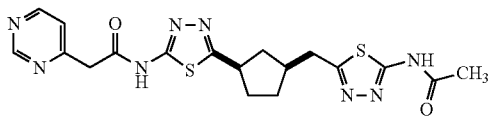<br>(Scheme D)<br>N-{5-[(cis)-3-{[5-(acetylamino)-1,3,4-thiadiazol-2-yl]methyl}cyclopentyl]-1,3,4-thiadiazol-2-yl}-2-(pyrimidin-4-yl)acetamide | 21* 445.2 | (600 MHz, DMSO-d₆) δ ppm 9.10 (d, J = 2.9 Hz, 1 H), 8.76 (dd, J = 5.3, 2.2 Hz, 1 H), 7.55 (t, J = 3.8 Hz, 1 H), 4.03 (d, J = 2.0 Hz, 2 H), 3.50 (dq, J = 10.4, 8.1 Hz, 1 H), 3.06 (dd, J = 7.3, 2.5 Hz, 2 H), 2.47-2.35 (m, 1 H), 2.21-2.34 (m, 1 H), 2.07-2.20 (m, 4 H), 1.77-1.95 (m, 2 H), 1.43-1.60 (m, 2 H). | Rt (Peak 1) = 1.68 minutes Chiralcel OJ-H 4.6 x 100 mm column 20% MeOH @ 120 bar CO₂, 4 mL/min. |
| 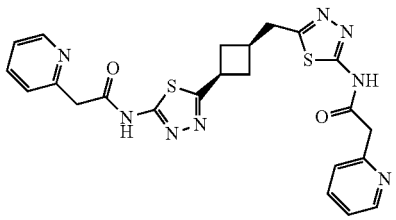 [SMILES: O=C(Cc1ccccn1)Nc1nnc(C[C@H]2C[C@@H](c3nnc(NC(=O)Cc4ccccn4)s3)C2)s1]<br>(Scheme E)<br>2-(pyridin-2-yl)-N-{5-[(cis-3-{5-[(pyridin-2-ylacetyl)amino]-1,3,4-thiadiazol-2-yl}cyclobutyl)methyl]-1,3,4-thiadiazol-2-yl}acetamide | 22 507.1 | (400 MHz, DMSO-d₆) δ ppm 12.65 (br s, 2 H), 8.49 (d, J = 4.28 Hz, 2 H), 7.77 (t, J = 7.52 Hz, 2 H), 7.39 (d, J = 7.70 Hz, 2 H), 7.24-7.32 (m, 2 H), 4.00 (s, 4 H), 3.74 (s, 1 H), 3.12 (d, J = 7.34 Hz, 2 H), 2.69 (br s, 1 H), 2.52-2.61 (m, 2 H), 2.06 (d, J = 10.88 Hz, 2 H). | Rt (Peak 1) = 1.34 minutes Chiralcel OJ-H 4.6 x 150 mm column 40% MeOH @ 120 bar CO₂, 4 mL/min (diastereomer separation). |
| 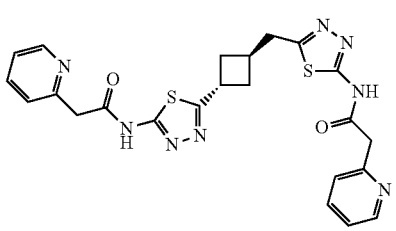 [SMILES: O=C(Cc1ccccn1)Nc1nnc(C[C@H]2C[C@H](c3nnc(NC(=O)Cc4ccccn4)s3)C2)s1]<br>(Scheme E)<br>2-(pyridin-2-yl)-N-{5-[(trans-3-{5-[(pyridin-2-ylacetyl)amino]-1,3,4-thiadiazol-2-yl}cyclobutyl)methyl]-1,3,4-thiadiazol-2-yl}acetamide | 23 507.1 | (400 MHz, DMSO-d₆) δ ppm 12.66 (br s, 2 H), 8.49 (d, J = 4.03 Hz, 2 H), 7.76 (t, J = 7.03 Hz, 2 H), 7.39 (d, J = 7.70 Hz, 2 H), 7.20-7.34 (m, 2 H), 3.87-4.08 (m, 5 H), 3.23 (d, J = 7.58 Hz, 2 H), 2.73-2.88 (m, 1 H), 2.37-2.45 (m, 2 H), 2.21-2.34 (m, 2 H). | Rt (Peak 2) = 1.72 minutes Chiralcel OJ-H 4.6 x 150 mm column 40% MeOH @ 120 bar CO₂, 4 mL/min (diastereomer separation). |
| 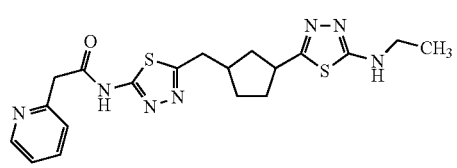 [SMILES: CCNc1nnc(C2CCC(Cc3nnc(NC(=O)Cc4ccccn4)s3)C2)s1]<br>(Scheme F)<br>(rac)-N-[5-({(cis)-3-[5-(ethylamino)-1,3,4-thiadiazol-2-yl]cyclopentyl}methyl)-1,3,4-thiadiazol-2-yl]-2-(pyridin-2-yl)acetamide | 24 430.1 | (400 MHz, DMSO-d₆) δ ppm 12.65 (br s, 1 H), 8.47-8.52 (m, 1 H), 7.77 (td, J = 7.70, 1.83 Hz, 1 H), 7.50 (t, J = 5.20 Hz, 1 H), 7.39 (d, J = 7.70 Hz, 1 H), 7.28 (dd, J = 6.60, 5.01 Hz, 1 H), 4.00 (s, 2 H), 3.29 (m, 1 H), 3.18-3.27 (m, 2 H), 3.05 (d, J = 7.34 Hz, 2 H), 2.31-2.45 (m, 1 H), 2.15-2.27 (m, 1 H), 1.98-2.11 (m, 1 H), 1.71-1.93 (m, 2 H), 1.39-1.53 (m, 2 H), 1.14 (t, J = 7.15 Hz, 3 H). | Racemic Cis |

TABLE 1-continued

| Example No. (Scheme) Structure and Compound Name | | LRMS m/z [M + H]⁺ | ¹H NMR | Chiral Separation Conditions (SFC) |
|---|---|---|---|---|
| (Scheme G) N,N'-(spiro[3.3]heptane-2,6-diyldipyridazine-6,3-diyl)bis[2-(pyridin-2-yl)acetamide] | 25 | 521.1 | (400 MHz, MeOD-d₄) δ ppm 8.52 (d, J = 4 Hz, 2 H), 8.37 (d, J = 8 Hz, 2 H), 7.81-7.84 (m, 2 H), 7.61 (d, J = 12 Hz, 2 H), 7.47 (d, J = 8 Hz, 2 H), 7.34-7.36 (m, 2 H), 4.04 (s, 4 H), 3.74 (quin, J = 8 Hz, 2 H), 2.45-2.72 (m, 2 H), 2.48-2.54 (m, 2 H), 2.39-2.44 (m, 2 H), 2.33-2.39 (m, 2 H). | Racemic |
| (Scheme G) 2-(pyridin-2-yl)-N-{5-[(3-{6-[(pyridin-2-ylacetyl)amino]pyridazin-3-yl}cyclopentyl)methyl]-1,3,4-thiadiazol-2-yl}acetamide | 26 | 515.1 | 400 MHz, DMSO-d₆) δ ppm 12.63 (br s, 1 H), 11.24 (d, J = 4 Hz, 1 H), 8.49 (t, J = 8 Hz, 2 H), 8.18 (d, J = 4 Hz, 1 H), 7.76 (t, J = 8 Hz, 2 H), 7.57-7.61 (m, 1 H), 7.39 (d, J = 8 Hz, 2 H), 7.26-7.29 (m, 2 H), 3.99 (s, 4 H), 3.46-3.50 (m, 1 H), 3.29-3.39 (m, 1 H), 3.05-3.10 (m, 2 H), 1.75-2.24 (m, 4 H), 1.51-1.59 (m, 1 H), 1.40-1.46 (m, 1 H). | 1:1 mix of racemic cis/trans diastereomers |
| (Scheme B) (rac)-N-(5-{[(cis)-3-{5-[(2,2-dimethylpropanoyl)amino]-1,3,4-thiadiazol-2-yl}cyclopentyl]methyl}-1,3,4-thiadiazol-2-yl)-2,2-dimethylpropanamide | 27 | 451.2 | (400 MHz, DMSO-d₆) δ ppm 12.06 (s, 2 H), 3.46-3.57 (m, 1 H), 3.07 (d, J = 7.3 Hz, 2 H), 2.36-2.47 (m, 1 H), 2.30 (dt, J = 13.5, 6.9 Hz, 1 H), 2.05-2.19 (m, 1 H), 1.80-1.98 (m, 2 H), 1.55 (dt, J = 19.9, 9.9 Hz, 2 H), 1.21-1.27 (m, 18 H). | Racemic Cis |

TABLE 1-continued

| Example No. (Scheme) Structure and Compound Name | | LRMS m/z [M + H]+ | 1H NMR | Chiral Separation Conditions (SFC) |
|---|---|---|---|---|
| (Scheme B) N-(5-{[(cis)-3-{5-[(2,2-dimethylpropanoyl)amino]-1,3,4-thiadiazol-2-yl}cyclopentyl]methyl}-1,3,4-thiadiazol-2-yl)-2,2-dimethylpropanamide | 28* | 451.2 | (400 MHz, DMSO-$d_6$) δ ppm 12.06 (s, 2 H), 3.46-3.57 (m, 1 H), 3.07 (d, J = 7.3 Hz, 2 H), 2.36-2.47 (m, 1 H), 2.30 (dt, J = 13.5, 6.9 Hz, 1 H), 2.05-2.19 (m, 1 H), 1.80-1.98 (m, 2 H), 1.55 (dt, J = 19.9, 9.9 Hz, 2 H), 1.21-1.27 (m, 18 H). | Rt (Peak 1) = 1.93 minutes Chiralpak AS-H 4.6 x 250 mm column 20% MeOH (w. 0.1% DEA) @ 140 bar $CO_2$, 3 mL/min. |
| (Scheme B) N-(5-{[(cis)-3-{5-[(2,2-dimethylpropanoyl)amino]-1,3,4-thiadiazol-2-yl}cyclopentyl]methyl}-1,3,4-thiadiazol-2-yl)-2,2-dimethylpropanamide | 29* | 451.2 | (400 MHz, DMSO-$d_6$) δ ppm 12.06 (s, 2 H), 3.46-3.57 (m, 1 H), 3.07 (d, J = 7.3 Hz, 2 H), 2.36-2.47 (m, 1 H), 2.30 (dt, J = 13.5, 6.9 Hz, 1 H), 2.05-2.19 (m, 1 H), 1.80-1.98 (m, 2 H), 1.55 (dt, J = 19.9, 9.9 Hz, 2 H), 1.21-1.27 (m, 18 H). | Rt (Peak 2) = 2.51 minutes Chiralpak AS-H 4.6 x 250 mm column 20% MeOH (w. 0.1% DEA) @ 140 bar $CO_2$, 3 mL/min. |
| (Scheme B) (rac)-2-(pyridin-3-yl)-N-(5-{[(cis)-3-(5-{[2-(pyridin-3-yl)propanoyl]amino}-1,3,4-thiadiazol-2-yl)cyclopentyl]methyl}-1,3,4-thiadiazol-2-yl)propanamide | 30 | 549.2 | (400 MHz, MeOH-$d_4$) δ ppm 8.56 (s, 2 H), 8.46 (dt, J = 5.0, 1.4 Hz, 2 H), 7.87-7.96 (m, 2 H), 7.44 (dd, J = 8.0, 4.9 Hz, 2 H), 4.02 (qd, J = 7.1, 3.8 Hz, 2 H), 3.49-3.63 (m, 1 H), 3.13 (d, J = 7.3 Hz, 2 H), 2.45-2.58 (m, 1 H), 2.40 (dt, J = 13.6, 6.9 Hz, 1 H), 2.22 (dt, J = 13.0, 7.6 Hz, 1 H), 1.89-2.05 (m, 2 H), 1.58 (m, 8 H). | Racemic Cis |

TABLE 1-continued

| Example No. (Scheme) Structure and Compound Name | | LRMS m/z [M + H]+ | 1H NMR | Chiral Separation Conditions (SFC) |
|---|---|---|---|---|
| 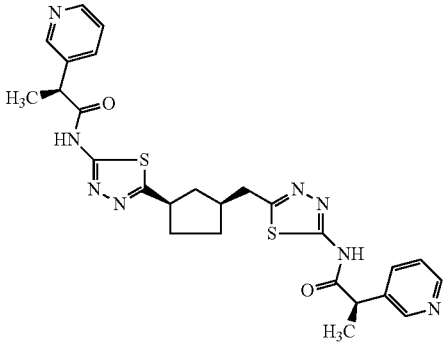<br>(Scheme B)<br>2-(pyridin-3-yl)-N-(5-{[(cis)-3-(5-{[2-(pyridin-3-yl)propanoyl]amino}-1,3,4-thiadiazol-2-yl)cyclopentyl]methyl}-1,3,4-thiadiazol-2-yl)propanamide | 31* | 549.2 | (700 MHz, DMSO-$d_6$) δ ppm 8.51 (br s, 2 H), 8.42 (dd, 2 H), 7.76 (m, 2 H), 7.38 (d, J = 2.56 Hz, 2 H), 4.02 (m, 1 H), 3.45 (m, 1 H), 3.00 (m, 2 H), 2.36 (m, 1 H), 2.23 (m, 1 H), 2.08 (br s, 1 H), 1.69-1.92 (m, 3 H), 1.45 (br s, 6 H), 1.04-1.25 (m, 2 H). | Rt (Peak 1) = 15.42 minutes Chiralpak OJ-H 4.6 x 250 mm column 10% MeOH (w. 0.1% DEA) @ 140 bar $CO_2$, 3 mL/min. |
| 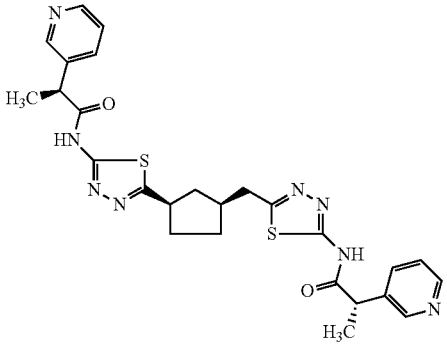 [SMILES: C[C@H](C(=O)Nc1nnc(C[C@H]2CC[C@@H](c3nnc(NC(=O)[C@@H](C)c4cccnc4)s3)C2)s1)c1cccnc1]<br>(Scheme B)<br>2-(pyridin-3-yl)-N-(5-{[(cis)-3-(5-{[2-(pyridin-3-yl)propanoyl]amino}-1,3,4-thiadiazol-2-yl)cyclopentyl]methyl}-1,3,4-thiadiazol-2-yl)propanamide | 32* | 549.2 | (700 MHz, DMSO-$d_6$) δ ppm 8.49-8.53 (m, 2 H), 8.40-8.44 (m, 2 H), 7.72-7.78 (m, 2 H), 7.36-7.41 (m, 2 H), 3.98-4.07 (m, 2 H), 3.43-3.50 (m, 1 H) 2.98-3.06 (d, 2 H), 2.33-2.42 (m, 1 H), 2.18-2.28 (m, 1 H), 2.05-2.12 (m, 1 H), 1.71-1.87 (m, 2 H), 1.45 (m, 8 H). | Rt (Peak 2) = 17.45 minutes Chiralpak OJ-H 4.6 x 250 mm column 10% MeOH (w. 0.1% DEA) @ 140 bar $CO_2$, 3 mL/min. |
| 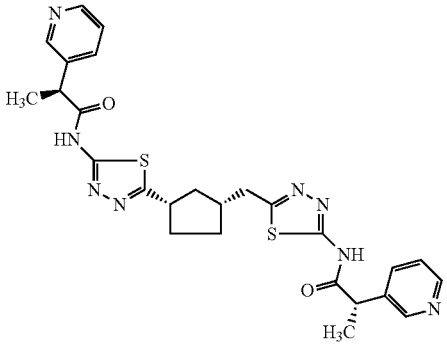 [SMILES: C[C@H](C(=O)Nc1nnc(C[C@@H]2CC[C@H](c3nnc(NC(=O)[C@@H](C)c4cccnc4)s3)C2)s1)c1cccnc1]<br>(Scheme B)<br>2-(pyridin-3-yl)-N-(5-{[(cis)-3-(5-{[2-(pyridin-3-yl)propanoyl]amino}-1,3,4-thiadiazol-2-yl)cyclopentyl]methyl}-1,3,4-thiadiazol-2-yl)propanamide | 33* | 549.2 | (400 MHz, MeOH-$d_4$) δ ppm 8.56 (s, 2 H), 8.46 (dt, J = 5.0, 1.4 Hz, 2 H), 7.87-7.96 (m, 2 H), 7.44 (dd, J = 8.0, 4.9 Hz, 2 H), 4.02 (qd, J = 7.1, 3.8 Hz, 2 H), 3.49-3.63 (m, 1 H), 3.13 (d, J = 7.3 Hz, 2 H), 2.45-2.58 (m, 1 H), 2.40 (dt, J = 13.6, 6.9 Hz, 1 H), 2.22 (dt, J = 13.0, 7.6 Hz, 1 H), 1.89-2.05 (m, 2 H), 1.58 (m, 8 H). | Rt (Peak 4) = 19.02 minutes Chiralpak OJ-H 4.6 x 250 mm column 10% MeOH (w. 0.1% DEA) @ 140 bar $CO_2$, 3 mL/min. |

TABLE 1-continued

| Example No. (Scheme) Structure and Compound Name | LRMS m/z [M + H]+ | 1H NMR | Chiral Separation Conditions (SFC) |
|---|---|---|---|
| 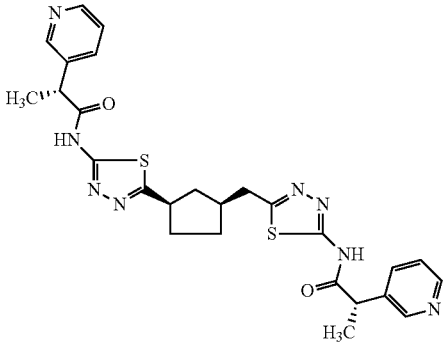 [SMILES: C[C@H](C(=O)Nc1nnc(C[C@H]2CC[C@@H](c3nnc(NC(=O)[C@H](C)c4cccnc4)s3)C2)s1)c1cccnc1]<br>(Scheme B)<br>2-(pyridin-3-yl)-N-(5-{[(cis)-3-(5-{[2-(pyridin-3-yl)propanoyl]amino}-1,3,4-thiadiazol-2-yl)cyclopentyl]methyl}-1,3,4-thiadiazol-2-yl)propanamide | 34* 549.2 | (700 MHz, DMSO-d$_6$) δ ppm 8.51-8.58 (m, 2 H), 8.44 (dd, J = 2.90 Hz, 2 H), 7.77 (m, 2 H), 7.29-7.48 (m, 2 H), 4.03 (m, 2 H), 3.46 (m, 1 H), 3.03 (d, J = 7.00 Hz, 2 H), 2.37 (m, 1 H), 2.24 (m, J = 11.61, 6.15 Hz, 1 H), 2.09 (m, J = 4.78 Hz, 1 H), 1.75-1.91 (m, 2 H), 1.41-1.58 (m, 8 H). | Rt (Peak 3) = 18.15 minutes Chiralpak OJ-H 4.6 x 250 mm column 10% MeOH (w. 0.1% DEA) @ 140 bar CO$_2$, 3 mL/min. |
| 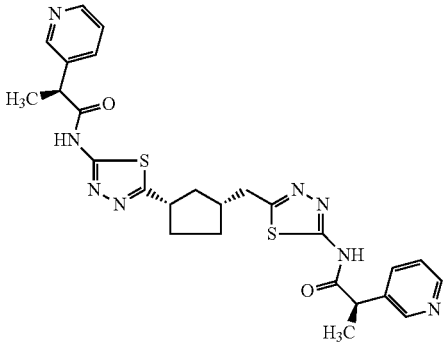<br>(Scheme B)<br>2-(pyridin-3-yl)-N-(5-{[(cis)-3-(5-{[2-(pyridin-3-yl)propanoyl]amino}-1,3,4-thiadiazol-2-yl)cyclopentyl]methyl}-1,3,4-thiadiazol-2-yl)propanamide | 35* 549.2 | (700 MHz, DMSO-d$_6$) δ ppm 8.51 (br s, 2 H), 8.42 (dd, J = 4.70, 1.28 Hz, 2 H), 7.75 (ddt, J = 7.90, 3.93, 1.94, 1.94 Hz, 2 H), 7.38 (dd, J = 7.86, 4.78 Hz, 2 H), 3.96-4.12 (m, 2 H), 3.42-3.50 (m, 1 H), 3.01 (d, J = 7.34 Hz, 2 H), 2.32-2.42 (m, 1 H), 2.19-2.27 (m, 1 H), 2.02-2.14 (m, 1 H), 1.72-1.86 (m, 2 H), 1.39-1.52 (m, 8 H). | Rt (Peak 6) = 23.19 minutes Chiralpak OJ-H 4.6 x 250 mm column 10% MeOH (w. 0.1% DEA) @ 140 bar CO$_2$, 3 mL/min. |
| 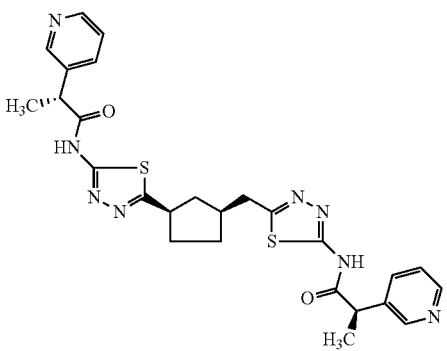<br>(Scheme B)<br>2-(pyridin-3-yl)-N-(5-{[(cis)-3-(5-{[2-(pyridin-3-yl)propanoyl]amino}-1,3,4-thiadiazol-2-yl)cyclopentyl]methyl}-1,3,4-thiadiazol-2-yl)propanamide | 36* 549.2 | (700 MHz, DMSO-d$_6$) δ ppm 8.51 (br. s., 2H), 8.42 (dd, J = 4.70, 1.28 Hz, 2H), 7.75 (dddd, J = 7.86, 4.27, 2.05, 1.88 Hz, 2H), 7.38 (dd, J = 7.86, 4.78 Hz, 2H), 3.96-4.07 (m, 2H), 3.40-3.54 (m, 1H), 3.01 (d, J = 7.34 Hz, 2H), 2.32-2.42 (m, 1H), 2.20-2.29 (m, 1H), 2.07 (dd, J = 12.73, 6.23 Hz, 1H), 1.73-1.91 (m, 2H) 1.39-1.54 (m, 8H). | Rt (Peak 7) = 24.41 minutes Chiralpak OJ-H 4.6 x 250 mm column 10% MeOH (w. 0.1% DEA) @ 140 bar CO$_2$, 3 mL/min. |

TABLE 1-continued

| Example No. (Scheme) Structure and Compound Name | LRMS m/z [M + H]+ | 1H NMR | Chiral Separation Conditions (SFC) |
|---|---|---|---|
| 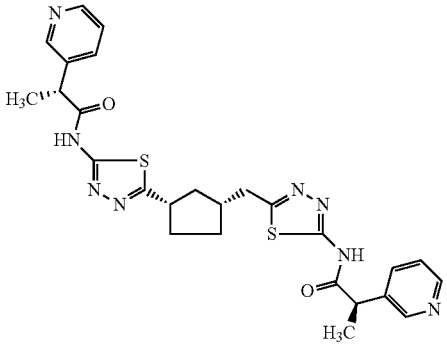<br>(Scheme B)<br>2-(pyridin-3-yl)-N-(5-{[(cis)-3-(5-{[2-(pyridin-3-yl)propanoyl]amino}-1,3,4-thiadiazol-2-yl)cyclopentyl]methyl}-1,3,4-thiadiazol-2-yl)propanamide | 37* 549.2 | (700 MHz, DMSO-d6) δ ppm 8.50 (d, J = 2.22 Hz, 2 H), 8.39-8.45 (m, 2 H), 7.75 (td, J = 3.89, 2.14 Hz, 2 H), 7.33-7.45 (m, 2 H), 3.95-4.04 (m, 2 H), 3.45 (d, J = 7.86 Hz, 1 H), 2.95-3.07 (m, 2 H), 2.32-2.42 (m, 1 H), 2.19-2.29 (m, 1 H), 2.04-2.15 (m, 1 H), 1.74-1.94 (m, 2 H), 1.38-1.54 (m, 8 H). | Rt (Peak 5) = 22.05 minutes Chiralpak OJ-H 4.6 x 250 mm column 10% MeOH (w. 0.1% DEA) @ 140 bar CO2, 3 mL/min. |
| 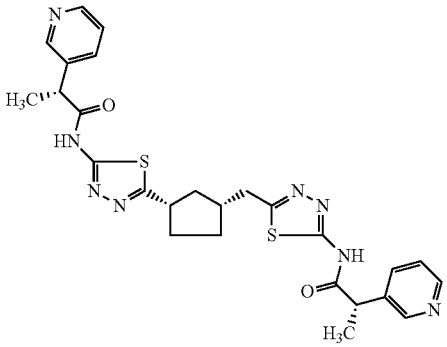 [SMILES: C[C@H](C(=O)Nc1nnc(C[C@@H]2CC[C@H](c3nnc(NC(=O)[C@H](C)c4cccnc4)s3)C2)s1)c1cccnc1]<br>(Scheme B)<br>2-(pyridin-3-yl)-N-(5-{[(cis)-3-(5-{[2-(pyridin-3-yl)propanoyl]amino}-1,3,4-thiadiazol-2-yl)cyclopentyl]methyl}-1,3,4-thiadiazol-2-yl)propanamide | 38* 549.2 | (700 MHz, DMSO-d6) δ ppm 8.51 (br s, 2 H), 8.42 (dd, J = 4.78, 1.37 Hz, 2 H), 7.75 (ddt, J = 8.01, 4.04, 1.92, 1.92 Hz, 2 H), 7.38 (dd, J = 7.86, 4.78 Hz, 2 H), 3.98-4.04 (m, 2 H), 3.45 (dd, J = 9.82, 7.60 Hz, 1 H), 3.01 (d, J = 7.34 Hz, 2 H), 2.36 (dd, J = 9.31, 7.60 Hz, 1 H), 2.22 (dd, J = 12.73, 6.75 Hz, 1 H), 2.08 (dd, J = 12.81, 6.32 Hz, 1 H), 1.72-1.89 (m, 2 H), 1.40-1.52 (m, 8 H). | Rt (Peak 8) = 30.41 minutes Chiralpak OJ-H 4.6 x 250 mm column 10% MeOH (w. 0.1% DEA) @ 140 bar CO2, 3 mL/min. |
| 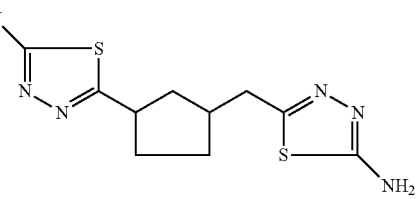<br>(Scheme B)<br>(rac)-5-{[(cis)-3-(5-amino-1,3,4-thiadiazol-2-yl)cyclopentyl]methyl}-1,3,4-thiadiazol-2-amine | 39 283.2 | (400 MHz, DMSO-d6) δ ppm 7.00 (s, 4 H), 3.34-3.27 (m, 1 H), 2.85 (d, J = 7.2 Hz, 2 H), 2.13-2.38 (m, 2 H), 2.10-1.94 (m, 1 H), 1.72-1.89 (m, 2 H), 1.32-1.52 (m, 2 H). | Racemic Cis |

TABLE 1-continued

| Example No. (Scheme) Structure and Compound Name | LRMS m/z [M + H]+ | 1H NMR | Chiral Separation Conditions (SFC) |
|---|---|---|---|
| 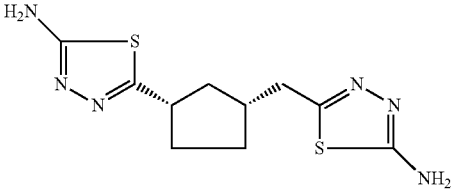<br>(Scheme B)<br>5-{[(1R,3S)-3-(5-amino-1,3,4-thiadiazol-2-yl)cyclopentyl]methyl}-1,3,4-thiadiazol-2-amine | 40  283.2 | (400 MHz, DMSO-$d_6$) δ ppm 7.00 (s, 4 H), 3.34-3.27 (m, 1 H), 2.85 (d, J = 7.2 Hz, 2 H), 2.13-2.38 (m, 2 H), 2.10-1.94 (m, 1 H), 1.72-1.89 (m, 2 H), 1.32-1.52 (m, 2 H). | Rt (Peak 1) = 2.01 minutes Chiralpak AS-H 4.6 x 100 mm column 40% MeOH @ 140 bar $CO_2$, 4 mL/min. |
| 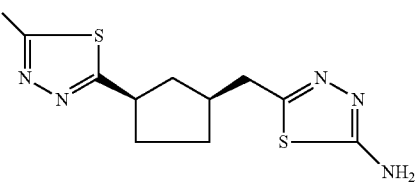<br>(Scheme B)<br>5-{[(1S,3R)-3-(5-amino-1,3,4-thiadiazol-2-yl)cyclopentyl]methyl}-1,3,4-thiadiazol-2-amine | 41  283.2 | (400 MHz, DMSO-$d_6$) δ ppm 7.00 (s, 4 H), 3.34-3.27 (m, 1 H), 2.85 (d, J = 7.2 Hz, 2 H), 2.13-2.38 (m, 2 H), 2.10-1.94 (m, 1 H), 1.72-1.89 (m, 2 H), 1.32-1.52 (m, 2 H). | Rt (Peak 2) = 5.27 minutes Chiralpak AS-H 4.6 x 100 mm column 40% MeOH @ 140 bar $CO_2$, 4 mL/min. |
| 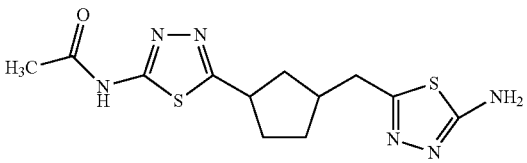 [SMILES: CC(=O)Nc1nnc(C2CCC(Cc3nnc(N)s3)C2)s1]<br>(Scheme C)<br>(rac)-N-(5-{(cis)-3-[(5-amino-1,3,4-thiadiazol-2-yl)methyl]cyclopentyl}-1,3,4-thiadiazol-2-yl)acetamide | 42  325.1 | (400 MHz, DMSO-$d_6$) δ ppm 6.96 (s, 2 H), 3.47-3.53 (m, 1 H), 2.88 (d, J = 7.30 Hz, 2 H), 2.23-2.39 (m, 2 H), 2.06-2.16 (m, 4 H), 1.79-1.94 (m, 2 H), 1.42-1.58 (m, 2 H). | Racemic Cis |
| 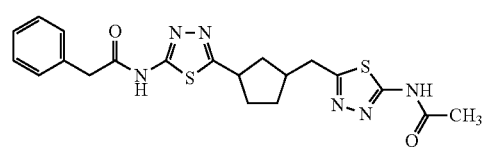<br>(Scheme D)<br>(rac)-N-{5-[(cis)-3-{[5-(acetylamino)-1,3,4-thiadiazol-2-yl]methyl}cyclopentyl]-1,3,4-thiadiazol-2-yl}-2-phenylacetamide | 43  443.0 | (600 MHz, DMSO-$d_6$) δ ppm 7.30-7.33 (m, 4 H), 7.26 (td, J = 6.11, 2.71 Hz, 1 H), 3.79 (s, 2 H), 3.50 (dd, J = 9.95, 7.46 Hz, 1 H), 3.05 (d, J = 7.46 Hz, 2 H), 2.41 (dd, J = 9.44, 7.39 Hz, 1 H), 2.24-2.31 (m, 1 H), 2.15 (s, 3 H), 2.07-2.13 (m, 1 H), 1.80-1.92 (m, 2 H), 1.45-1.58 (m, 2 H). | Racemic Cis |
| 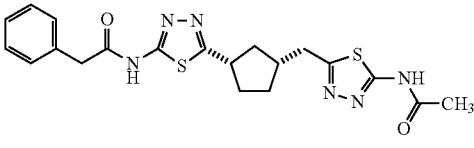 [SMILES: CC(=O)Nc1nnc(CC2CCC(c3nnc(NC(=O)Cc4ccccc4)s3)C2)s1]<br>(Scheme D)<br>N-{5-[(cis)-3-{[5-(acetylamino)-1,3,4-thiadiazol-2-yl]methyl}cyclopentyl]-1,3,4-thiadiazol-2-yl}-2-phenylacetamide | 44*  443.0 | (600 MHz, DMSO-$d_6$) δ ppm 7.30-7.33 (m, 4 H), 7.26 (td, J = 6.11, 2.71 Hz, 1 H), 3.79 (s, 2 H), 3.50 (dd, J = 9.95, 7.46 Hz, 1 H), 3.05 (d, J = 7.46 Hz, 2 H), 2.41 (dd, J = 9.44, 7.39 Hz, 1 H), 2.24-2.31 (m, 1 H), 2.15 (s, 3 H), 2.07-2.13 (m, 1 H), 1.80- | Rt (Peak 1) = 2.78 minutes Chiralpak AS-H 4.6 x 250 mm column 40% MeOH @ 140 bar $CO_2$, 3 mL/min. |

TABLE 1-continued

| Example No. (Scheme) Structure and Compound Name | LRMS m/z [M + H]+ | 1H NMR | Chiral Separation Conditions (SFC) |
|---|---|---|---|
| | | 1.92 (m, 2 H), 1.45-1.58 (m, 2 H). | |
| (Scheme D)<br>N-{5-[(cis)-3-{[5-(acetylamino)-1,3,4-thiadiazol-2-yl]methyl}cyclopentyl]-1,3,4-thiadiazol-2-yl}-2-phenylacetamide | 45* 443.0 | (600 MHz, DMSO-$d_6$) δ ppm 7.30-7.33 (m, 4 H), 7.26 (td, J = 6.11, 2.71 Hz, 1 H), 3.79 (s, 2 H), 3.50 (dd, J = 9.95, 7.46 Hz, 1 H), 3.05 (d, J = 7.46 Hz, 2 H), 2.41 (dd, J = 9.44, 7.39 Hz, 1 H), 2.24-2.31 (m, 1 H), 2.15 (s, 3 H), 2.07-2.13 (m, 1 H), 1.80-1.92 (m, 2 H), 1.45-1.58 (m, 2 H). | Rt (Peak 2) = 3.69 minutes Chiralpak AS-H 4.6 x 250 mm column 40% MeOH @ 140 bar $CO_2$, 3 mL/min. |
| (Scheme C)<br>(rac)-N-[5-({(cis)-3-[5-(acetylamino)-1,3,4-thiadiazol-2-yl]cyclopentyl}methyl)-1,3,4-thiadiazol-2-yl]-2-(pyrimidin-2-yl)acetamide | 46 444.1 | (400 MHz, DMSO-$d_6$) δ ppm 8.77 (d, J = 5.04 Hz, 2 H), 7.39-7.45 (m, 1 H), 4.14 (s, 2 H), 3.46-3.56 (m, 1 H), 3.04-3.11 (m, 2 H), 2.39-2.48 (m, 1 H), 2.24-2.36 (m, 1 H), 2.08-2.20 (m, 4 H), 1.81-1.95 (m, 2 H), 1.46-1.64 (m, 2 H). | Racemic Cis |
| (Scheme C)<br>(rac)-N-[5-({(cis)-3-[5-(acetylamino)-1,3,4-thiadiazol-2-yl]cyclopentyl}methyl)-1,3,4-thiadiazol-2-yl]-2-(pyrazin-2-yl)acetamide | 47 444.1 | (400 MHz, DMSO-$d_6$) δ ppm 12.37 (br s, 2 H), 8.67 (d, J = 1.35 Hz, 1 H), 8.58 (d, J = 1.47 Hz, 1 H), 8.53-8.57 (m, 1 H), 4.08 (s, 2 H), 3.43-3.57 (m, 1 H), 3.07 (d, J = 7.34 Hz, 2 H), 2.38-2.47 (m, 1 H), 2.24-2.35 (m, 1 H), 2.06-2.18 (m, 4 H), 1.80-1.94 (m, 2 H), 1.44-1.62 (m, 2 H). | Racemic Cis |
| (Scheme D)<br>(rac)-N-{5-[(cis)-3-{[5-(acetylamino)-1,3,4-thiadiazol-2-yl]methyl}cyclopentyl]-1,3,4-thiadiazol-2-yl}benzamide | 48 429.0 | (400 MHz, DMSO-$d_6$) δ 8.10 (dd, J = 7.1, 1.8 Hz, 2 H), 7.52 (dt, J = 28.5, 7.3 Hz, 3 H), 3.44-3.58 (m, 1 H), 3.08 (d, J = 7.3 Hz, 2 H), 2.37-2.48 (m, 1 H), 2.23-2.36 (m, 1 H), 2.16 (s, 3 H), 2.05-2.14 (m, 1 H), 1.76-1.97 (m, 2 H), 1.42-1.67 (m, 2 H). | Racemic Cis |

TABLE 1-continued

| Example No. (Scheme) Structure and Compound Name | LRMS m/z [M + H]+ | 1H NMR | Chiral Separation Conditions (SFC) |
|---|---|---|---|
| 49 (Scheme C) (rac)-N-[(cis)-5-({3-[5-(acetylamino)-1,3,4-thiadiazol-2-yl]cyclopentyl}methyl)-1,3,4-thiadiazol-2-yl]-2-(pyrimidin-5-yl)acetamide | 445.1 | (600 MHz, DMSO-$d_6$) δ ppm 9.09 (s, 1 H), 8.74 (s, 2 H), 3.92 (s, 2 H), 3.49 (m, 1 H), 3.06(d, J = 7.17 Hz, 2 H), 2.36-2.46 (m, 1 H), 2.23-2.33 (m, 1 H), 2.07-2.22 (m, 4 H), 1.79-1.93(m, 2 H), 1.42-1.62 (m, 2 H). | Racemic Cis |
| 50* (Scheme C) N-[5-({(cis)-3-[5-(acetylamino)-1,3,4-thiadiazol-2-yl]cyclopentyl}methyl)-1,3,4-thiadiazol-2-yl]-2-(pyrimidin-5-yl)acetamide | 445.1 | (600 MHz, DMSO-$d_6$) δ ppm 9.09 (s, 1 H), 8.74 (s, 2 H), 3.92 (s, 2 H), 3.49 (m, 1 H), 3.06 (d, J = 7.17 Hz, 2 H), 2.36-2.46 (m, 1 H), 2.23-2.33 (m, 1 H), 2.07-2.22 (m, 4 H), 1.79-1.93 (m, 2 H), 1.42-1.62 (m, 2 H). | Rt (Peak 1) = 2.60 minutes Chiralcel OJ-H 4.6 x 250 mm column 30% MeOH @ 140 bar $CO_2$, 3 mL/min. |
| 51* (Scheme C) N-[5-({(cis)-3-[5-(acetylamino)-1,3,4-thiadiazol-2-yl]cyclopentyl}methyl)-1,3,4-thiadiazol-2-yl]-2-(pyrimidin-5-yl)acetamide | 445.1 | (600 MHz, DMSO-$d_6$) δ ppm 9.09 (s, 1 H), 8.74 (s, 2 H), 3.92 (s, 2 H), 3.49 (m, 1 H), 3.06 (d, J = 7.17 Hz, 2 H), 2.36-2.46 (m, 1 H), 2.23-2.33 (m, 1 H), 2.07-2.22 (m, 4 H), 1.79-1.93 (m, 2 H), 1.42-1.62 (m, 2 H). | Rt (Peak 2) = 3.36 minutes Chiralcel OJ-H 4.6 x 250 mm column 30% MeOH @ 140 bar $CO_2$, 3 mL/min. |
| 52 (Scheme C) (rac)-N-[5-({(cis)-3-[5-(acetylamino)-1,3,4-thiadiazol-2-yl]cyclopentyl}methyl)-1,3,4-thiadiazol-2-yl]-2-(6-methylpyridin-3-yl)acetamide | 458.1 | (600 MHz, DMSO-$d_6$) δ ppm 8.36 (s, 1 H), 7.60 (dd, J = 7.90, 2.05 Hz, 1 H), 7.21 (d, J = 8.05 Hz, 1 H), 3.79 (s, 2 H), 3.48 (m, J = 7.90 Hz, 1 H), 3.05 (d, J = 7.32 Hz, 2 H), 2.43 (s, 3 H), 2.40 (m, 1 H), 2.24-2.31 (m, 1 H), 2.15 (s, 3 H), 2.12 (m, 1 H), 1.80-1.92 (m, 2 H), 1.45-1.59 (m, 2 H). | Racemic Cis |

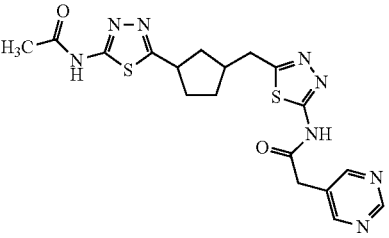 [SMILES: CC(=O)Nc1nnc(C2CCC(Cc3nnc(NC(=O)Cc4cncnc4)s3)C2)s1]

TABLE 1-continued

| Example No. (Scheme) Structure and Compound Name | | LRMS m/z [M + H]+ | 1H NMR | Chiral Separation Conditions (SFC) |
|---|---|---|---|---|
| 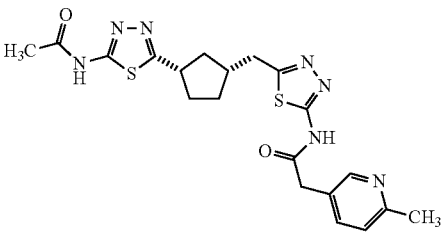 [SMILES: CC(=O)Nc1nnc([C@H]2CC[C@@H](Cc3nnc(NC(=O)Cc4ccc(C)nc4)s3)C2)s1]<br>(Scheme C)<br>N-[5-({(cis)-3-[5-(acetylamino)-1,3,4-thiadiazol-2-yl]cyclopentyl}methyl)-1,3,4-thiadiazol-2-yl]-2-(6-methylpyridin-3-yl)acetamide | 53* | 458.1 | (600 MHz, DMSO-d6) δ ppm 8.36 (s, 1 H), 7.60 (dd, J = 7.90, 2.05 Hz, 1 H), 7.21 (d, J = 8.05 Hz, 1 H), 3.79 (s, 2 H), 3.48 (m, J = 7.90 Hz, 1 H), 3.05 (d, J = 7.32 Hz, 2 H), 2.43 (s, 3 H), 2.40 (m, 1 H), 2.24-2.31 (m, 1 H), 2.15 (s, 3 H), 2.12 (m, 1 H), 1.80-1.92 (m, 2 H), 1.45-1.59 (m, 2 H). | Rt (Peak 2) = 8.27 minutes Chiralcel OJ-H 4.6 x 250 mm column 15% MeOH @ 140 bar CO2, 3 mL/min. |
| 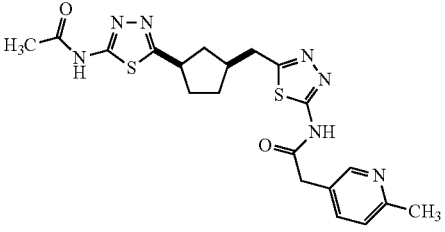 [SMILES: CC(=O)Nc1nnc([C@@H]2CC[C@H](Cc3nnc(NC(=O)Cc4ccc(C)nc4)s3)C2)s1]<br>(Scheme C)<br>N-[5-({(cis)-3-[5-(acetylamino)-1,3,4-thiadiazol-2-yl]cyclopentyl}methyl)-1,3,4-thiadiazol-2-yl]-2-(6-methylpyridin-3-yl)acetamide | 54* | 458.1 | (600 MHz, DMSO-d6) δ ppm 8.36 (s, 1 H), 7.60 (dd, J = 7.90, 2.05 Hz, 1 H), 7.21 (d, J = 8.05 Hz, 1 H), 3.79 (s, 2 H), 3.48 (m, J = 7.90 Hz, 1 H), 3.05 (d, J = 7.32 Hz, 2 H), 2.43 (s, 3 H), 2.40 (m, 1 H), 2.24-2.31 (m, 1 H), 2.15 (s, 3 H), 2.12 (m, 1 H), 1.80-1.92 (m, 2 H), 1.45-1.59 (m, 2 H). | Rt (Peak 1) = 6.64 minutes Chiralcel OJ-H 4.6 x 250 mm column 15% MeOH @ 140 bar CO2, 3 mL/min. |
| 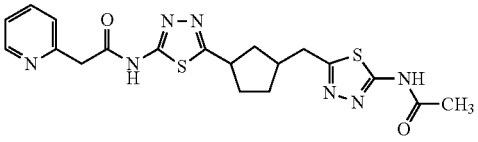 [SMILES: CC(=O)Nc1nnc(CC2CCC(c3nnc(NC(=O)Cc4ccccn4)s3)C2)s1]<br>(Scheme D)<br>(rac)-N-{5-[(cis)-3-{[5-(acetylamino)-1,3,4-thiadiazol-2-yl]methyl}cyclopentyl]-1,3,4-thiadiazol-2-yl}-2-(pyridin-2-yl)acetamide | 55 | 444.0 | (400 MHz, DMSO-d6) δ ppm 8.48 (d, J = 4.28 Hz, 1 H), 7.75 (d, J = 1.51 Hz, 1 H), 7.38 (d, J = 7.81 Hz, 1 H), 7.26 (dd, J = 7.05, 5.29 Hz, 1 H), 3.95 (s, 2 H), 3.50 (d, J = 9.32 Hz, 1 H), 3.05 (d, J = 7.30 Hz, 2 H), 2.36-2.46 (m, 1 H), 2.28 (d, J = 12.34 Hz, 1 H), 2.15 (s, 4 H), 1.80-1.94 (m, 2 H), 1.43-1.62 (m, 2 H). | Racemic Cis |
| 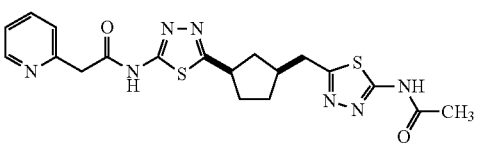 [SMILES: CC(=O)Nc1nnc(C[C@H]2CC[C@@H](c3nnc(NC(=O)Cc4ccccn4)s3)C2)s1]<br>(Scheme D)<br>N-{5-[(cis)-3-{[5-(acetylamino)-1,3,4-thiadiazol-2-yl]methyl}cyclopentyl]-1,3,4-thiadiazol-2-yl}-2-(pyridin-2-yl)acetamide | 56* | 444.0 | (400 MHz, DMSO-d6) δ ppm 8.48 (d, J = 4.28 Hz, 1 H), 7.75 (d, J = 1.51 Hz, 1 H), 7.38 (d, J = 7.81 Hz, 1 H), 7.26 (dd, J = 7.05, 5.29 Hz, 1 H), 3.95 (s, 2 H), 3.50 (d, J = 9.32 Hz, 1 H), 3.05 (d, J = 7.30 Hz, 2 H), 2.36-2.46 (m, 1 H), 2.28 (d, J = 12.34 Hz, 1 H), 2.15 (s, 4 H), 1.80-1.94 (m, 2 H), 1.43-1.62 (m, 2 H). | Rt (Peak 1) = 5.14 minutes Chiralpak AS-H 4.6 x 250 mm column 30% MeOH @ 140 bar CO2, 3 mL/min. |

TABLE 1-continued

| Example No. (Scheme) Structure and Compound Name | LRMS m/z [M + H]+ | 1H NMR | Chiral Separation Conditions (SFC) |
|---|---|---|---|
| 57* (Scheme D) N-{5-[(cis)-3-{[5-(acetylamino)-1,3,4-thiadiazol-2-yl]methyl}cyclopentyl]-1,3,4-thiadiazol-2-yl}-2-(pyridin-2-yl)acetamide | 444.0 | (400 MHz, DMSO-$d_6$) δ ppm 8.48 (d, J = 4.28 Hz, 1 H), 7.75 (d, J = 1.51 Hz, 1 H), 7.38 (d, J = 7.81 Hz, 1 H), 7.26 (dd, J = 7.05, 5.29 Hz, 1 H), 3.95 (s, 2 H), 3.50 (d, J = 9.32 Hz, 1 H), 3.05 (d, J = 7.30 Hz, 2 H), 2.36-2.46 (m, 1 H), 2.28 (d, J = 12.34 Hz, 1 H), 2.15 (s, 4 H), 1.80-1.94 (m, 2 H), 1.43-1.62 (m, 2 H). | Rt (Peak 2) = 6.82 minutes Chiralpak AS-H 4.6 x 250 mm column 30% MeOH @ 140 bar $CO_2$, 3 mL/min. |
| 58* (Scheme D) N-{5-[(cis)-3-{[5-(acetylamino)-1,3,4-thiadiazol-2-yl]methyl}cyclopentyl]-1,3,4-thiadiazol-2-yl}-2-(pyrimidin-5-yl)acetamide | 445.0 | (700 MHz, DMSO-$d_6$) δ ppm 9.09 (s, 1 H), 8.74 (s, 2 H), 3.91 (s, 2 H), 3.50 (dq, J = 10.4, 8.1 Hz, 1 H), 3.05 (d, J = 7.3 Hz, 2 H), 2.42 (dq, J = 10.0, 7.5 Hz, 1 H), 2.28 (dt, J = 13.6, 7.1 Hz, 1 H), 2.16 (s, 3 H), 2.08-2.13 (m, 1 H), 1.80-1.92 (m, 2 H), 1.44-1.58 (m, 2 H). | Rt (Peak 2) = 6.06 minutes Chiralcel OJ-H 4.6 x 250 mm column 20% MeOH @ 140 bar $CO_2$, 3 mL/min. |
| 59* (Scheme D) N-{5-[(cis)-3-{[5-(acetylamino)-1,3,4-thiadiazol-2-yl]methyl}cyclopentyl]-1,3,4-thiadiazol-2-yl}-2-(pyrimidin-5-yl)acetamide | 445.0 | (700 MHz, DMSO-$d_6$) δ ppm 9.09 (s, 1 H), 8.74 (s, 2 H), 3.91 (s, 2 H), 3.50 (dq, J = 10.4, 8.1 Hz, 1 H), 3.05 (d, J = 7.3 Hz, 2 H), 2.42 (dq, J = 10.0, 7.5 Hz, 1 H), 2.28 (dt, J = 13.6, 7.1 Hz, 1 H), 2.16 (s, 3 H), 2.08-2.13 (m, 1 H), 1.80-1.92 (m, 2 H), 1.44-1.58 (m, 2 H). | Rt (Peak 1) = 5.03 minutes Chiralcel OJ-H 4.6 x 250 mm column 20% MeOH @ 140 bar $CO_2$, 3 mL/min. |
| 60 (Scheme B) N,N'-{[-1,2,2-trimethylcyclopentane-1,3-diyl]di-1,3,4-thiadiazole-5,2-diyl}diacetamide | 395.1 | (400 MHz, DMSO-$d_6$) δ ppm 12.40 (s, 2 H), 3.77 (t, J = 9.72 Hz, 1 H), 2.85-2.97 (m, 1 H), 2.39-2.47 (m, 1 H), 2.31 (d, J = 10.51 Hz, 1 H), 2.17 (s, 6 H) 1.83-1.94 (m, 1 H), 1.46 (s, 3 H), 1.22 (s, 3 H), 0.38 (s, 3 H). | Racemic |

TABLE 1-continued

| Example No. (Scheme) Structure and Compound Name | | LRMS m/z [M + H]+ | 1H NMR | Chiral Separation Conditions (SFC) |
|---|---|---|---|---|
| (Scheme B) N,N'-(spiro[3.3]heptane-2,6-diyldi-1,3,4-thiadiazole-5,2-diyl)bis[2-(pyridin-2-yl)acetamide] | 61 | 533.0 | (400 MHz, DMSO-d$_6$) δ ppm 12.67 (br s, 2 H), 8.49 (d, J = 4.28 Hz, 2 H), 7.77 (t, J = 7.58 Hz, 2 H), 7.40 (d, J = 7.70 Hz, 2 H), 7.25-7.32 (m, 2 H), 4.01 (s, 4 H) 3.78 (quin, J = 8.38 Hz, 2 H), 2.62-2.71 (m, 2 H), 2.37-2.47 (m, 4 H), 2.25-2.34 (m, 2 H). | Racemic |
| (Scheme E) N-[5-({cis-3-[5-(acetylamino)-1,3,4-thiadiazol-2-yl]cyclobutyl}methyl)-1,3,4-thiadiazol-2-yl]acetamide | 62 | 352.4 | (400 MHz, DMSO-d$_6$) δ ppm 12.36 (br s, 2 H), 3.67-3.81 (m, 1 H), 3.12 (d, J = 6.97 Hz, 2 H), 2.63-2.77 (m, 1 H), 2.55 (d, J = 8.56 Hz, 2 H), 2.16 (s, 6 H), 2.07 (m, J = 9.40 Hz, 2 H). | Rt (Peak 1) = 2.61 minutes Chiralpak OJ-H 4.6 x 250 mm column 10% MeOH @ 140 bar CO$_2$, 3 mL/min (diastereomer separation). |
| (Scheme E) N-[5-({trans-3-[5-(acetylamino)-1,3,4-thiadiazol-2-yl]cyclobutyl}methyl)-1,3,4-thiadiazol-2-yl]acetamide | 63 | 352.4 | (400 MHz, DMSO-d$_6$) δ ppm 12.38 (br s, 2 H), 3.95 (t, J = 6.91 Hz, 1 H), 3.23 (d, J = 7.70 Hz, 2 H), 2.73-2.88 (m, 1 H), 2.38-2.48 (m, 2 H), 2.24-2.35 (m, 2 H), 2.16 (s, 6 H). | Rt (Peak 2) = 3.25 minutes Chiralpak OJ-H 4.6 x 250 mm column 10% MeOH (w. 0.1% DEA) @ 140 bar CO$_2$, 3 mL/min (diastereomer separation). |
| (Scheme D) N-(5-{(cis)-3-[(5-amino-1,3,4-thiadiazol-2-yl)methyl]cyclopentyl}-1,3,4-thiadiazol-2-yl)-2-phenylacetamide | 64* | 401.0 | (400 MHz, MeOH-d$_4$) δ ppm 7.30-7.38 (m, 5 H), 3.83 (s, 2 H), 3.52 (m, 1 H), 2.99 (d, J = 6.8 Hz, 2 H), 2.43-2.45 (m, 2 H), 2.23-2.30 (m, 1 H), 1.98-2.05 (m, 2 H), 1.61-1.63 (m, 2 H), 1.31-1.39 (m, 2 H). | Rt (Peak 1) = 4.85 minutes Chiralpak AS-H 4.6 x 250 mm column 40% MeOH @ 140 bar CO$_2$, 3 mL/min. |
| (Scheme D) N-(5-{(cis)-3-[(5-amino-1,3,4-thiadiazol-2-yl)methyl]cyclopentyl}-1,3,4-thiadiazol-2-yl)-2-phenylacetamide | 65* | 401.0 | (400 MHz, MeOH-d$_4$) δ ppm 7.30-7.38 (m, 5 H), 3.83 (s, 2 H), 3.52 (m, 1 H), 2.99 (d, J = 6.8 Hz, 2 H), 2.43-2.45 (m, 2 H), 2.23-2.30 (m, 1 H), 1.98-2.05 (m, 2 H), 1.61-1.63 (m, 2 H), 1.31-1.39 (m, 2 H). | Rt (Peak 2) = 5.73 minutes Chiralpak AS-H 4.6 x 250 mm column 40% MeOH @ 140 bar CO$_2$, 3 mL/min. |

| Example No. (Scheme) Structure and Compound Name | LRMS m/z [M + H]+ | 1H NMR | Chiral Separation Conditions (SFC) |
|---|---|---|---|
| (Scheme F) (rac)-N-[5-({(cis)-3-[5-(ethylamino)-1,3,4-thiadiazol-2-yl]cyclopentyl}methyl)-1,3,4-thiadiazol-2-yl]acetamide | 66  353.1 | (400 MHz, DMSO-d6) δ ppm 12.66 (s, 2 H), 6.72-7.88 (m, 10 H), 3.78 (d, J = 1.5 Hz, 4 H), 3.49 (dd, J = 10.0, 7.5 Hz, 1 H), 3.05 (d, J = 7.3 Hz, 2 H), 2.34-2.47 (m, 1 H), 2.26 (dt, J = 13.0, 6.9 Hz, 1 H), 2.03-2.17 (m, 1 H), 1.93-1.76 (m, 2 H), 1.41-1.60 (m, 2 H). | Racemic Cis |
| (Scheme D) (rac)-N-(5-{(cis)-3-[(5-amino-1,3,4-thiadiazol-2-yl)methyl]cyclopentyl}-1,3,4-thiadiazol-2-yl)-2-(pyridin-2-yl)acetamide | 67  402.1 | (400 MHz, DMSO-d6) δ ppm 12.65 (br s, 1 H), 8.49 (d, J = 4.52 Hz, 1 H), 7.77 (t, J = 7.52 Hz, 1 H), 7.39 (d, J = 7.58 Hz, 1 H), 7.22-7.33 (m, 1 H), 6.97 (s, 2 H), 4.00 (s, 2 H), 3.51 (br s, 1 H), 2.81-2.96 (m, 2 H), 2.21-2.44 (m, 2 H), 2.12 (d, J = 7.58 Hz, 1 H), 1.86 (d, J = 7.34 Hz, 2 H), 1.37-1.61 (m, 2 H). | Racemic Cis |
| (Scheme A) N-{5-[(cis)-3-{[6-(acetylamino)pyridazin-3-yl]methyl}cyclopentyl]-1,3,4-thiadiazol-2-yl}-2-(pyridin-2-yl)acetamide | 68*  438.2 | (400 MHz, DMSO-d6) δ ppm 12.59-12.69 (m, 1 H), 10.92-11.02 (m, 1 H), 8.45-8.52 (m, 1 H), 8.14-8.26 (m, 1 H), 7.71-7.82 (m, 1 H), 7.51-7.61 (m, 1 H), 7.36-7.44 (m, 1 H), 7.23-7.35 (m, 1 H), 3.96-4.04 (m, 2 H), 3.45-3.57 (m, 1 H), 2.88-2.98 (m, 2 H), 2.16-2.28 (m, 2 H), 2.13 (s, 4 H), 1.76-1.90 (m, 2 H), 1.43-1.61 (m, 2 H). | Rt (Peak 2) = 1.71 minutes Chiralpak AS-H 4.6 x 100 mm column 30% MeOH @ 120 bar CO2, 4 mL/min. |
| (Scheme A) N-{5-[(cis)-3-{[6-(acetylamino)pyridazin-3-yl]methyl}cyclopentyl]-1,3,4-thiadiazol-2-yl}-2-(pyridin-2-yl)acetamide | 69*  438.2 | (700 MHz, DMSO-d6) δ ppm 12.67 (s, 1 H), 11.00 (s, 1 H), 8.54-8.42 (m, 1 H), 8.20 (d, J = 9.1 Hz, 1 H), 7.77 (td, J = 7.7, 1.9 Hz, 1 H), 7.56 (d, J = 9.1 Hz, 1 H), 7.39 (d, J = 7.8 Hz, 1 H), 7.28 (ddd, J = 7.5, 4.8, 1.2 Hz, 1 H), 4.00 (s, 2 H), 3.49 (dq, J = 10.3, 8.2 Hz, 1 H), 2.93 (d, J = 7.4 Hz, 2 H), 2.43 (dt, J = 10.1, 7.5 Hz, 1 H), 2.20 (dt, J = 13.5, 7.1 Hz, 1 H), 2.12 (s, 4 H), 1.92-1.71 (m, 2 H), 1.60-1.41 (m, 2 H). | Rt (Peak 1) = 1.42 minutes Chiralpak AS-H 4.6 x 100 mm column 30% MeOH @ 120 bar CO2, 4 mL/min. |

TABLE 1-continued

| Example No. (Scheme) Structure and Compound Name | LRMS m/z [M + H]+ | 1H NMR | Chiral Separation Conditions (SFC) |
|---|---|---|---|
| 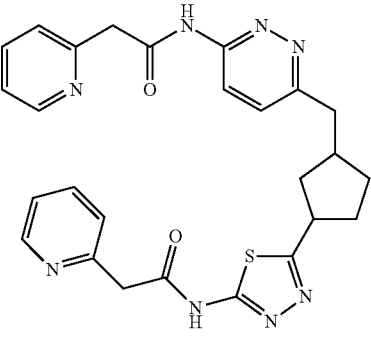 [SMILES: O=C(Cc1ccccn1)Nc1ccc(CC2CCC(c3nnc(NC(=O)Cc4ccccn4)s3)C2)nn1]<br>(Scheme A)<br>(rac)-2-(pyridin-2-yl)-N-{5-[(cis)-3-({6-[(pyridin-2-ylacetyl)amino]pyridazin-3-yl}methyl)cyclopentyl]-1,3,4-thiadiazol-2-yl}acetamide | 70   514.8 | (400 MHz, DMSO-d6) δ ppm 11.33 (m, 1 H), 8.51-8.56 (m, 2 H), 8.20 (d, J = 9.2 Hz, 1 H), 7.82-7.87 (m, 2 H), 7.59 (d, J = 9.2 Hz, 1 H), 7.44-7.50 (m, 2 H), 7.35-7.42 (m, 2 H), 4.02-4.03 (m, 4 H), 3.43-3.53 (m, 2 H), 2.95 (d, J = 7.6 Hz, 2 H), 2.19-2.22 (m, 2 H), 1.82-1.84 (m, 2 H), 1.50-1.56 (m, 2 H). | Racemic Cis |
| 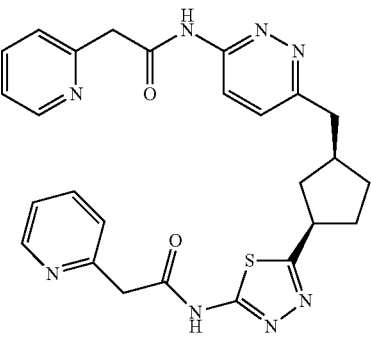 [SMILES: O=C(Cc1ccccn1)Nc1ccc(C[C@H]2CC[C@@H](c3nnc(NC(=O)Cc4ccccn4)s3)C2)nn1]<br>(Scheme A)<br>2-(pyridin-2-yl)-N-{5-[(cis)-3-({6-[(pyridin-2-ylacetyl)amino]pyridazin-3-yl}methyl)cyclopentyl]-1,3,4-thiadiazol-2-yl}acetamide | 71*   514.8 | (700 MHz, DMSO-d6) δ ppm 11.29 (s, 1 H), 8.48-8.52 (m, 2 H), 8.21 (d, J = 9.2 Hz, 1 H), 7.75-7.79 (m, 2 H), 7.58 (d, J = 9.6 Hz, 1 H), 7.38-7.42 (m, 2 H), 7.24-7.31 (m, 2 H), 4.01 (s, 3 H), 3.99 (s, 3 H), 3.46-3.56 (m, 2 H), 2.96 (d, J = 6.8 Hz, 2 H), 2.15-2.25 (m, 1 H), 2.07-2.15 (m, 1 H), 1.74-1.93 (m, 2 H), 1.48-1.61 (m, 2 H). | Rt (Peak 2) = 11.47 minutes Chiralpak OJ-H 4.6 x 150 mm column 40% MeOH @ 100 bar CO2, 3 mL/min. |
| 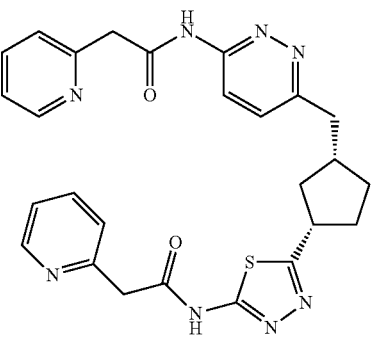 [SMILES: O=C(Cc1ccccn1)Nc1ccc(C[C@@H]2CC[C@H](c3nnc(NC(=O)Cc4ccccn4)s3)C2)nn1]<br>(Scheme A)<br>2-(pyridin-2-yl)-N-{5-[(cis)-3-({6-[(pyridin-2-ylacetyl)amino]pyridazin-3-yl}methyl)cyclopentyl]-1,3,4-thiadiazol-2-yl}acetamide | 72*   514.8 | (700 MHz, DMSO-d6) δ ppm 11.29 (s, 1 H), 8.48-8.52 (m, 2 H), 8.21 (d, J = 9.2 Hz, 1 H), 7.75-7.79 (m, 2 H), 7.58 (d, J = 9.6 Hz, 1 H), 7.38-7.42 (m, 2 H), 7.24-7.31 (m, 2 H), 4.01 (s, 3 H), 3.99 (s, 3 H), 3.46-3.56 (m, 2 H), 2.96 (d, J = 6.8 Hz, 2 H), 2.15-2.25 (m, 1 H), 2.07-2.15 (m, 1 H), 1.74-1.93 (m, 2 H), 1.48-1.61 (m, 2 H). | Rt (Peak 1) = 10.82 minutes Chiralpak OJ-H 4.6 x 150 mm column 40% MeOH @ 100 bar CO2, 3 mL/min. |

TABLE 1-continued

| Example No. (Scheme) Structure and Compound Name | | LRMS m/z [M + H]+ | 1H NMR | Chiral Separation Conditions (SFC) |
|---|---|---|---|---|
| 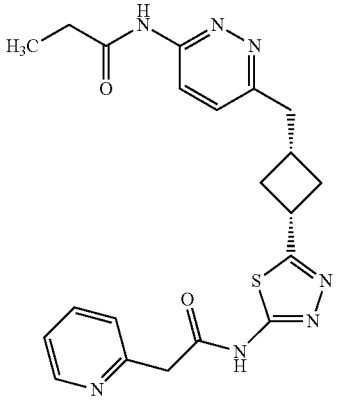 [SMILES: CCC(=O)Nc1ccc(C[C@H]2C[C@@H](c3nnc(NC(=O)Cc4ccccn4)s3)C2)nn1]<br>(Scheme A)<br>N-{6-[(cis-3-{5-[(pyridin-2-ylacetyl)amino]-1,3,4-thiadiazol-2-yl}cyclobutyl)methyl]pyridazin-3-yl}propanamide | 73 | 438.1 | (400 MHz, CDCl$_3$) δ ppm 12.63 (br s, 1 H), 8.68 (d, J = 4.8 Hz, 1 H), 8.49 (br s, 1 H), 8.39 (d, J = 9.2 Hz, 1 H), 7.73 (t, J = 7.6 Hz, 1 H), 7.27-7.32 (m, 2 H), 4.01 (s, 2 H), 3.73-3.78 (m, 1 H), 3.07 (d, J = 6.8 Hz, 2 H), 2.78-2.83 (m, 1 H), 2.60-2.72 (m, 2 H), 2.50 (q, J = 7.6 Hz, 2 H), 2.20 (q, J = 11.6 Hz, 2 H), 1.23 (t, J = 7.6 Hz, 3 H). | Single diastereomer |
| 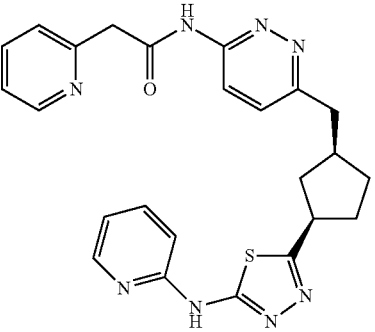 [SMILES: O=C(Cc1ccccn1)Nc1ccc(C[C@H]2CC[C@@H](c3nnc(Nc4ccccn4)s3)C2)nn1]<br>(Scheme A)<br>2-(pyridin-2-yl)-N-[6-({(cis)-3-[5-(pyridin-2-ylamino)-1,3,4-thiadiazol-2-yl]cyclopentyl}methyl)pyridazin-3-yl]acetamide | 74* | 474.0 | (400 MHz, DMSO-d$_6$) δ ppm 11.51 (br s, 1 H), 11.29 (s, 1 H), 8.49 (d, J = 4.4 Hz, 1 H), 8.28 (d, J = 3.2 Hz, 1 H), 8.21 (d, J = 9.2 Hz, 1 H), 7.72-7.76 (m, 1 H), 7.59 (d, J = 0.2 Hz, 1 H), 7.39 (d, J = 8 Hz, 1 H), 7.27 (t, J = 8 Hz, 1 H), 7.07 (d, J = 8.4 Hz, 1 H), 7.04 (t, J = 8 Hz, 1 H), 3.99 (s, 2 H), 3.44-3.46 (m, 2 H), 2.96 (d, J = 7.6 Hz, 2 H), 2.08-2.25 (m, 2 H), 1.75-1.93 (m, 2 H), 1.43-1.55 (m, 2 H). | Rt (Peak 1) = 1.72 minutes Chiralpak OJ-H 4.6 x 150 mm column 40% MeOH @ 100 bar CO$_2$, 4 mL/min. |
| 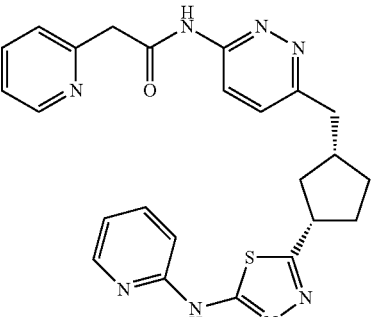<br>(Scheme A)<br>2-(pyridin-2-yl)-N-[6-({(cis)-3-[5-(pyridin-2-ylamino)-1,3,4-thiadiazol-2-yl]cyclopentyl}methyl)pyridazin-3-yl]acetamide | 75* | 474.0 | (400 MHz, DMSO-d$_6$) δ ppm 11.51 (br s, 1 H), 11.29 (s, 1 H), 8.49 (d, J = 4.4 Hz, 1 H), 8.28 (d, J = 3.2 Hz, 1 H), 8.21 (d, J = 9.2 Hz, 1 H), 7.72-7.76 (m, 1 H), 7.59 (d, J = 0.2 Hz, 1 H), 7.39 (d, J = 8 Hz, 1 H), 7.27 (t, J = 8 Hz, 1 H), 7.07 (d, J = 8.4 Hz, 1 H), 7.04 (t, J = 8 Hz, 1 H), 3.99 (s, 2 H), 3.44-3.46 (m, 2 H), 2.96 (d, J = 7.6 Hz, 2 H), 2.08-2.25 (m, 2 H), 1.75-1.93 (m, 2 H), 1.43-1.55 (m, 2 H). | Rt (Peak 2) = 1.86 minutes Chiralpak OJ-H 4.6 x 150 mm column 40% MeOH @ 100 bar CO$_2$, 4 mL/min. |

TABLE 1-continued

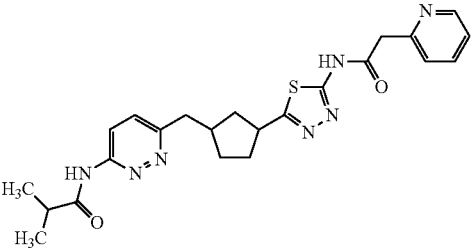 [SMILES: CC(C)C(=O)Nc1ccc(C[C@H]2CC[C@@H](c3nnc(NC(=O)Cc4ccccn4)s3)C2)nn1]

| Example No. (Scheme) Structure and Compound Name | LRMS m/z [M + H]+ | 1H NMR | Chiral Separation Conditions (SFC) |
|---|---|---|---|
| 76 (Scheme A) (rac)-2-methyl-N-(6-{[(cis)-3-{5-[(pyridin-2-ylacetyl)amino]-1,3,4-thiadiazol-2-yl}cyclopentyl]methyl}pyridazin-3-yl)propanamide | 466.2 | (400 MHz, DMSO-$d_6$) δ ppm 10.90-10.96 (m, 1 H), 8.44-8.55 (m, 1 H), 8.21 (s, 1 H), 7.71-7.83 (m, 1 H), 7.51-7.63 (m, 1 H), 7.34-7.45 (m, 1 H), 7.21-7.33 (m, 1 H), 3.96 (s, 2 H), 3.41-3.56 (m, 1 H), 2.94 (d, J = 7.55 Hz, 2 H), 2.72-2.86 (m, 1 H), 2.41-2.46 (m, 1 H), 2.02-2.28 (m, 2 H), 1.72-1.95 (m, 2 H), 1.40-1.64 (m, 2 H), 1.10 (d, J = 6.80 Hz, 6 H). | Racemic Cis |
| 77* (Scheme A) 2-methyl-N-(6-{[(cis)-3-{5-[(pyridin-2-ylacetyl)amino]-1,3,4-thiadiazol-2-yl}cyclopentyl]methyl}pyridazin-3-yl)propanamide | 466.2 | (400 MHz, DMSO-$d_6$) δ ppm 10.90-10.96 (m, 1 H), 8.44-8.55 (m, 1 H), 8.21 (s, 1 H), 7.71-7.83 (m, 1 H), 7.51-7.63 (m, 1 H), 7.34-7.45 (m, 1 H), 7.21-7.33 (m, 1 H), 3.96 (s, 2 H), 3.41-3.56 (m, 1 H), 2.94 (d, J = 7.55 Hz, 2 H), 2.72-2.86 (m, 1 H), 2.41-2.46 (m, 1 H), 2.02-2.28 (m, 2 H), 1.72-1.95 (m, 2 H), 1.40-1.64 (m, 2 H), 1.10 (d, J = 6.80 Hz, 6 H). | Rt (Peak 2) = 1.92 minutes Chiralpak AS-H 4.6 x 100 mm column 20% MeOH (w. 0.1% DEA) @ 120 bar $CO_2$, 4 mL/min. |
| 78* (Scheme A) 2-methyl-N-(6-{[(cis)-3-{5-[(pyridin-2-ylacetyl)amino]-1,3,4-thiadiazol-2-yl}cyclopentyl]methyl}pyridazin-3-yl)propanamide | 466.2 | (400 MHz, DMSO-$d_6$) δ ppm 10.90-10.96 (m, 1 H), 8.44-8.55 (m, 1 H), 8.21 (s, 1 H), 7.71-7.83 (m, 1 H), 7.51-7.63 (m, 1 H), 7.34-7.45 (m, 1 H), 7.21-7.33 (m, 1 H), 3.96 (s, 2 H), 3.41-3.56 (m, 1 H), 2.94 (d, J = 7.55 Hz, 2 H), 2.72-2.86 (m, 1 H), 2.41-2.46 (m, 1 H), 2.02-2.28 (m, 2 H), 1.72-1.95 (m, 2 H), 1.40-1.64 (m, 2 H), 1.10 (d, J = 6.80 Hz, 6 H). | Rt (Peak 1) = 2.30 minutes Chiralpak AS-H 4.6 x 100 mm column 20% MeOH (w. 0.1% DEA) @ 120 bar $CO_2$, 4 mL/min. |
| 79* (Scheme A) N-(6-{[(cis)-3-{5-[(pyridin-2-ylacetyl)amino]-1,3,4-thiadiazol-2-yl}cyclopentyl]methyl}pyridazin-3-yl)propanamide | 452.0 | (600 MHz, DMSO-$d_6$) δ ppm 10.97 (br s, 1 H), 8.51 (d, J = 4.8 Hz, 1 H), 8.23 (d, J = 9.2 Hz, 1 H), 7.78-7.80 (m, 1 H), 7.57 (d, J = 9.2 Hz, 1 H), 7.41 (d, J = 7.6 Hz, 1 H), 7.29 (t, J = 6 Hz, 1 H), 4.01 (s, 2 H), 3.46-3.53 (m, 1 H), 2.94 (d, J = 7.2 Hz, 2 H), 2.42 (q, J = 6.8 Hz, 2 H), 2.19-2.23 (m, 2 H), 1.80-1.89 (m, 2 H), 1.51-1.56 (m, 2 H), 1.08 (t, J = 7.2 Hz, 3 H). | Rt (Peak 2) = 4.21 minutes Chiralpak AS-H 4.6 x 100 mm column 35% EtOH (w. 0.1% $NH_3$) @ 100 bar $CO_2$, 3 mL/min. |

TABLE 1-continued

| Example No. (Scheme) Structure and Compound Name | LRMS m/z [M + H]+ | 1H NMR | Chiral Separation Conditions (SFC) |
|---|---|---|---|
| 80 (Scheme A) 2-phenyl-N-(6-{[(1R,3S)-3-{5-[(pyridin-2-ylacetyl)amino]-1,3,4-thiadiazol-2-yl}cyclopentyl]methyl}pyridazin-3-yl)acetamide | 514.2 | (400 MHz, DMSO-d6) δ ppm 12.63 (br s, 1 H), 11.22 (s, 1 H), 8.49 (d, J = 4.78 Hz, 1 H), 8.19 (d, J = 9.06 Hz, 1 H), 7.76 (td, J = 7.68, 1.76 Hz, 1 H), 7.56 (d, J = 9.32 Hz, 1 H), 7.19-7.43 (m, 7 H), 3.99 (s, 2 H), 3.76 (s, 2 H), 3.44-3.55 (m, 1 H), 2.94 (d, J = 7.30 Hz, 2 H), 1.74-1.91 (m, 2 H), 1.42-1.60 (m, 2 H). | Enantio-enriched (ca. 84% ee) |
| 81* (Scheme A) 2-phenyl-N-(6-{[(cis)-3-{5-[(pyridin-2-ylacetyl)amino]-1,3,4-thiadiazol-2-yl}cyclopentyl]methyl}pyridazin-3-yl)acetamide | 514.2 | (400 MHz, DMSO-d6) δ ppm 12.63 (br s, 1 H), 11.22 (s, 1 H), 8.49 (d, J = 4.78 Hz, 1 H), 8.19 (d, J = 9.06 Hz, 1 H), 7.76 (td, J = 7.68, 1.76 Hz, 1 H), 7.56 (d, J = 9.32 Hz, 1 H), 7.19-7.43 (m, 7 H), 3.99 (s, 2 H), 3.76 (s, 2 H), 3.44-3.55 (m, 1 H), 2.94 (d, J = 7.30 Hz, 2 H), 1.74-1.91 (m, 2 H), 1.42-1.60 (m, 2 H). | Rt (Peak 2) = 2.75 minutes Chiralpak OJ-H 4.6 x 150 mm column 40% MeOH @ 120 bar CO2, 4 mL/min. |
| 82 (Scheme A) 2-phenyl-N-(6-{[(cis)-3-{5-[(pyridin-2-ylacetyl)amino]-1,3,4-thiadiazol-2-yl}cyclopentyl]methyl}pyridazin-3-yl)acetamide | 514.2 | (400 MHz, DMSO-d6) δ ppm 12.63 (br s, 1 H), 11.22 (s, 1 H), 8.49 (d, J = 4.78 Hz, 1 H), 8.19 (d, J = 9.06 Hz, 1 H), 7.76 (td, J = 7.68, 1.76 Hz, 1 H), 7.56 (d, J = 9.32 Hz, 1 H), 7.19-7.43 (m, 7 H), 3.99 (s, 2 H), 3.76 (s, 2 H), 3.44-3.55 (m, 1 H), 2.94 (d, J = 7.30 Hz, 2 H), 1.74-1.91 (m, 2 H), 1.42-1.60 (m, 2 H). | Rt (Peak 1) = 2.40 minutes Chiralpak OJ-H 4.6 x 150 mm column 40% MeOH @ 120 bar CO2, 4 mL/min. |
| 83 (Scheme F) (rac)-2-(pyridin-2-yl)-N-[5-({(cis)-3-[5-(pyrimidin-2-ylamino)-1,3,4-thiadiazol-2-yl]cyclopentyl}methyl)-1,3,4-thiadiazol-2-yl]acetamide | 480.0 | (400 MHz, DMSO-d6) δ ppm 8.64-8.65 (m, 2 H), 8.51 (s, 1 H), 7.77-7.81 (m, 1 H), 7.41 (d, J = 7.2 Hz, 1 H), 7.31 (t, J = 6.4 Hz, 1 H) 7.08-7.12 (m, 1 H), 4.02 (s, 2 H), 3.58-3.61 (m, 1 H), 3.11 (d, J = 7.2 Hz, 2 H), 2.15-2.41 (m, 3 H), 1.81-1.91 (m, 2 H), 1.63-1.81 (m, 2 H). | Racemic Cis |

TABLE 1-continued

| Example No. (Scheme) Structure and Compound Name | LRMS m/z [M + H]+ | 1H NMR | Chiral Separation Conditions (SFC) |
|---|---|---|---|
| 84* (Scheme F) 2-(pyridin-2-yl)-N-[5-({(cis)-3-[5-(pyrimidin-2-ylamino)-1,3,4-thiadiazol-2-yl]cyclopentyl}methyl)-1,3,4-thiadiazol-2-yl]acetamide | 480.2 | (600 MHz, DMSO-d$_6$) δ ppm 8.63 (d, J = 4.83 Hz, 1 H), 8.49 (d, J = 4.39 Hz, 1 H), 7.77 (td, J = 7.68, 1.76 Hz, 1 H), 7.39 (d, J = 7.76 Hz, 1 H), 7.28 (dd, J = 6.95, 5.34 Hz, 1 H) 7.06 (t, J = 4.83 Hz, 1 H), 4.00 (s, 2 H), 3.42-3.56 (m, 1 H), 2.93-3.14 (m, 2 H), 2.36-2.46 (m, 1 H), 2.25-2.35 (m, 1H), 2.08-2.19 (m, 1 H), 1.83-1.97 (m, 2 H), 1.46-1.64 (m, 2 H). | Rt (Peak 2) = 1.61 minutes Chiralpak OJ-3 4.6 x 100 mm column 40% MeOH @ 120 bar CO$_2$, 4 mL/min. |
| 85* (Scheme F) 2-(pyridin-2-yl)-N-[5-({3-[5-(trans)(pyridin-2-ylamino)-1,3,4-thiadiazol-2-yl]cyclopentyl}methyl)-1,3,4-thiadiazol-2-yl]acetamide | 479.0 | (700 MHz, DMSO-d$_6$) δ ppm 12.61 (br s, 1 H), 11.37 (br s, 1 H), 8.42-8.45 (m, 1 H), 8.19-8.28 (m, 1 H), 7.64-7.71 (m, 2 H), 7.32-7.33 (m, 1 H), 7.21-7.22 (m, 1 H), 6.98-6.99 (m, 1 H), 6.87-6.88 (m, 1 H), 3.94 (s, 2 H), 3.50-3.54 (m, 1 H), 3.00 (d, J = 7.5 Hz, 2 H), 2.12-2.14 (m, 1 H), 1.96-2.00 (m, 1 H), 1.87-1.92 (m, 1 H), 1.75-1.83 (m, 3 H), 1.32-1.38 (m, 1 H). | Rt (Peak 4) = 3.76 minutes Chiralpak AS-3 4.6 x 100 mm column 40% MeOH (w. 0.1% DEA) @ 120 bar CO$_2$, 4 mL/min. |
| 86* (Scheme F) 2-(pyridin-2-yl)-N-[5-({(cis)-3-[5-(pyridin-2-ylamino)-1,3,4-thiadiazol-2-yl]cyclopentyl}methyl)-1,3,4-thiadiazol-2-yl]acetamide | 479.0 | (700 MHz, DMSO-d$_6$) δ ppm 12.68 (br s, 1 H), 11.46 (br s, 1 H), 8.49-8.52 (m, 1 H), 8.27-8.31 (m, 1 H), 7.71-7.78 (m, 2 H), 7.38-7.39 (m, 1 H), 7.25-7.29 (m, 1 H), 7.03-7.07 (m, 1 H), 6.92-6.95 (m, 1 H), 4.00 (s, 2 H), 3.57-3.61 (m, 1 H), 3.04-3.07 (m, 2 H), 2.16-2.24 (m, 1 H), 2.01-2.06 (m, 1 H), 1.93-1.98 (m, 1 H), 1.80-1.90 (m, 2 H), 1.39-1.44 (m, 1 H). | Rt (Peak 2) = 2.44 minutes Chiralpak AS-3 4.6 x 100 mm column 40% MeOH (w. 0.1% DEA) @ 120 bar CO$_2$, 4 mL/min. |
| 87 (Scheme F) (rac)-N-[5-({(cis)-3-[5-(pyrazin-2-ylamino)-1,3,4-thiadiazol-2-yl]cyclopentyl}methyl)-1,3,4-thiadiazol-2-yl]-2-(pyridin-2-yl)acetamide | 480.1 | (400 MHz, DMSO-d$_6$) δ ppm 8.52 (d, J = 4 Hz, 1 H), 8.47 (s, 1 H), 8.31 (s, 1 H), 8.17 (t, J = 2.8 Hz, 1 H), 7.82 (t, J = 6.4 Hz, 1 H), 7.43 (d, J = 8 Hz, 1 H), 7.33 (t, J = 7.2 Hz, 1 H), 4.03 (s, 2 H), 3.62-3.65 (m, 1 H), 3.07-3.11 (m, 2 H), 1.89-2.31 (m, 4 H), 1.46-1.60 (m, 2 H), 1.25-1.28 (m, 1 H). | Racemic Cis |

TABLE 1-continued

| Example No. (Scheme) Structure and Compound Name | | LRMS m/z [M + H]+ | 1H NMR | Chiral Separation Conditions (SFC) |
|---|---|---|---|---|
| 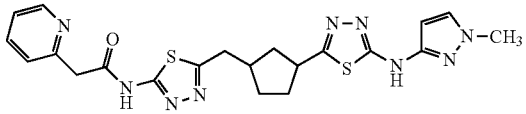 [SMILES: Cn1ccc(Nc2nnc(C3CCC(Cc4nnc(NC(=O)Cc5ccccn5)s4)C3)s2)n1]<br>(Scheme F)<br>(rac)-N-(5-{[(cis)-3-{5-[(1-methyl-1H-pyrazol-3-yl)amino]-1,3,4-thiadiazol-2-yl}cyclopentyl]methyl}-1,3,4-thiadiazol-2-yl)-2-(pyridin-2-yl)acetamide | 88** | 482.2 | (400 MHz, DMSO-$d_6$) δ ppm 12.66 (br s, 1 H), 10.66 (br s, 1 H), 8.49 (d, J = 4.16 Hz, 1 H), 7.77 (td, J = 7.64, 1.71 Hz, 1 H), 7.56 (d, J = 2.08 Hz, 1 H), 7.40 (d, J = 7.83 Hz, 1 H), 7.28 (dd, J = 7.09, 5.14 Hz, 1 H), 5.92 (d, J = 2.20 Hz, 1 H), 4.01 (s, 2 H), 3.74 (s, 3 H), 3.38-3.49 (m, 1 H), 3.06 (d, J = 1.00 Hz, 2 H), 2.36-2.46 (m, 1 H), 2.21-2.32 (m, 1 H), 2.09 (m, J = 13.70, 5.50 Hz, 1 H), 1.79-1.96 (m, 2 H), 1.41-1.61 (m, 2 H). | Racemic Cis |
| 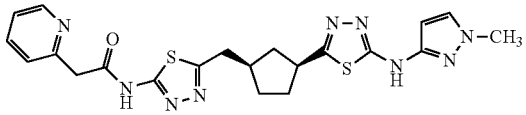 [SMILES: Cn1ccc(Nc2nnc([C@H]3CC[C@@H](Cc4nnc(NC(=O)Cc5ccccn5)s4)C3)s2)n1]<br>(Scheme F)<br>N-(5-{[(cis)-3-{5-[(1-methyl-1H-pyrazol-3-yl)amino]-1,3,4-thiadiazol-2-yl}cyclopentyl]methyl}-1,3,4-thiadiazol-2-yl)-2-(pyridin-2-yl)acetamide | 89* | 482.2 | (600 MHz, DMSO-$d_6$) δ ppm 10.66 (br s, 1 H), 8.48 (dt, J = 4.8, 0.9 Hz, 1 H), 7.76 (td, J = 7.6, 1.8 Hz, Hz, 1 H), 7.55-7.56 (m, 1 H), 7.39 (d, J = 7.9 Hz, 1 H), 7.27-7.29 (m, 1 H), 5.91 (d, J = 2.20 Hz, 1 H), 3.99 (s, 2 H), 3.73 (s, 3 H), 3.04-3.06 (m, 2 H), 2.37-2.41 (m, 1 H), 2.23-2.26 (m, 1 H), 2.04-2.09 (m, 1 H), 1.79-1.90 (m, 2 H), 1.45-1.55 (m, 2 H). | Rt (Peak 2) = 1.56 minutes Chiralpak OJ-3 4.6 x 100 mm column 40% MeOH @ 120 bar $CO_2$, 4 mL/min. |
| 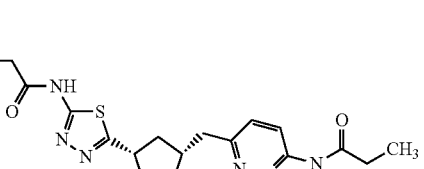<br>(Scheme A)<br>3-methoxy-N-{5-[(cis)-3-{[6-(propanoylamino)pyridazin-3-yl]methyl}cyclopentyl]-1,3,4-thiadiazol-2-yl}propanamide | 90* | 419.2 | (400 MHz, DMSO-$d_6$) δ ppm 10.97 (s, 1 H), 8.24 (d, J = 8.8 Hz, 1 H), 7.58 (d, J = 9.2 Hz, 1 H), 3.63 (t, J = 6 Hz, 2 H), 3.48-3.50 (m, 1 H), 3.23 (s, 3 H), 2.95 (d, J = 7.2 Hz, 2 H), 2.70 (t, J = 6.4 Hz, 2 H), 2.45-2.48 (m, 3 H), 2.05-2.23 (m, 2 H), 1.49-1.91 (m, 2 H), 1.42-1.53 (m, 2 H), 1.08 (t, J = 7.2 Hz, 3 H). | Rt (Peak 1) = 3.56 minutes Chiralpak AS-H 4.6 x 100 mm column 40% MeOH @ 100 bar $CO_2$, 3 mL/min. |
| 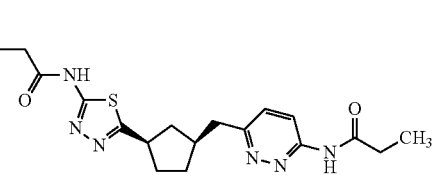<br>(Scheme A)<br>N-(6-{[(cis)-3-(5-{[(1-methyl-1H-pyrazol-3-yl)acetyl]amino}-1,3,4-thiadiazol-2-yl)cyclopentyl]methyl}pyridazin-3-yl)propanamide | 91* | 455.2 | (400 MHz, DMSO-$d_6$) δ ppm 10.97 (s, 1 H), 8.23 (d, J = 9.2 Hz, 1 H), 7.60 (d, J = 2 Hz, 1 H), 7.57 (d, J = 9.2 Hz, 1 H), 6.15 (d, J = 2 Hz, 1 H), 3.78 (s, 3 H), 3.75 (s, 2 H), 3.44-3.48 (m, 1 H), 2.94 (d, J = 7.6 Hz, 2 H), 2.44 (q, J = 7.6 Hz, 2 H), 2.02-2.23 (m, 2 H), 1.71-1.85 (m, 2 H), 1.43-1.52 (m, | Rt (Peak 2) = 2.19 minutes Chiralpak AS-H 4.6 x 100 mm column 40% MeOH @ 100 bar $CO_2$, 4 mL/min. |

TABLE 1-continued

| Example No. (Scheme) Structure and Compound Name | | LRMS m/z [M + H]+ | 1H NMR | Chiral Separation Conditions (SFC) |
|---|---|---|---|---|
| | | | 2 H), 1.08 (t, J = 7.6 Hz, 3 H). | |
| 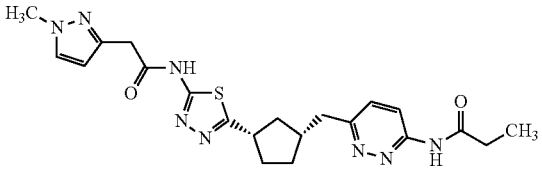 [SMILES: CCC(=O)Nc1ccc(C[C@@H]2CC[C@H](c3nnc(NC(=O)Cc4ccn(C)n4)s3)C2)nn1]<br>(Scheme A)<br>N-(6-{[(cis)-3-(5-{[(1-methyl-1H-pyrazol-3-yl)acetyl]amino}-1,3,4-thiadiazol-2-yl)cyclopentyl]methyl}pyridazin-3-yl)propanamide | 92* | 455.2 | (400 MHz, DMSO-d6) δ ppm 10.97 (s, 1 H), 8.23 (d, J = 9.2 Hz, 1 H), 7.60 (d, J = 2 Hz, 1 H), 7.57 (d, J = 9.2 Hz, 1 H), 6.15 (d, J = 2 Hz, 1 H), 3.78 (s, 3 H), 3.75 (s, 2 H), 3.44-3.48 (m, 2 H), 2.94 (d, J = 7.6 Hz, 2 H), 2.44 (q, J = 7.6 Hz, 2 H), 2.02-2.23 (m, 2 H), 1.71-1.85 (m, 2H), 1.43-1.52 (m, 2 H), 1.08 (t, J = 7.6 Hz, 3 H). | Rt (Peak 1) = 2.01 minutes Chiralpak AS-H 4.6 x 100 mm column 40% MeOH @ 100 bar CO2, 4 mL/min. |
| 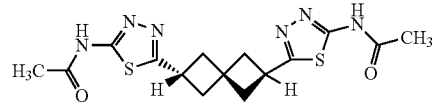<br>(Scheme B)<br>N,N'-(spiro[3.3]heptane-2,6-diyldi-1,3,4-thiadiazole-5,2-diyl)diacetamide | 93 | 379.1 | (600 MHz, DMSO-d6) δ ppm 12.39 (br s, 2 H), 3.78 (quin, J = 8.48 Hz 2 H) 2.64-2.71 (m, 2 H), 2.39-2.48 (m, 4 H), 2.30 (dd, J = 11.37, 8.80 Hz, 2 H), 2.17 (s, 6 H). | Rt (Peak 2) = 2.20 minutes Chiralpak AS-H 4.6 x column 20% MeOH @ 120 bar CO2, 4 mL/min. |
| <br>(Scheme B)<br>(rac)-N,N'-(spiro[3.3]heptane-2,6-diyldi-1,3,4-thiadiazole-5,2-diyl)bis(2-methylpropanamide) | 94 | 435.1 | (600 MHz, DMSO-d6) δ ppm 3.76 (quin, J = 8.45 Hz, 2 H), 2.74 (dt, J = 13.65, 6.86 Hz, 2 H), 2.62-2.68 (m, 2 H), 2.37-2.47 (m, 4 H), 2.28 (dd, J = 11.20, 8.85 Hz, 2 H), 1.10 (d, J = 6.88 Hz, 12 H). | Racemic |
| <br>(Scheme B)<br>N,N'-(spiro[3.3]heptane-2,6-diyldi-1,3,4-thiadiazole-5,2-diyl)bis(2-methylpropanamide) | 95 | 435.1 | (600 MHz, DMSO-d6) δ ppm 3.77 (quin, J = 8.45 Hz, 2 H), 2.75 (spt, J = 6.85 Hz, 2 H), 2.63-2.69 (m, 2 H), 2.38-2.48 (m, 4 H), 2.29 (dd, J = 11.27, 8.63 Hz, 2 H), 1.11 (d, J = 6.88 Hz, 12 H). | Single (S) Enantiomer |
| 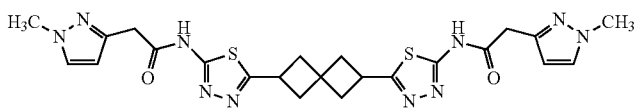<br>(Scheme B)<br>(rac)-N,N'-(spiro[3.3]heptane-2,6-diyldi-1,3,4-thiadiazole-5,2-diyl)bis[2-(1-methyl-1H-pyrazol-3-yl)acetamide] | 96 | 539.1 | (600 MHz, DMSO-d6) δ ppm 7.58 (d, J = 2.05 Hz, 2 H), 6.14 (d, J = 2.20 Hz, 2 H), 3.73-3.79 (m, 8 H), 3.73 (s, 4 H), 2.63-2.68 (m, 2 H), 2.41-2.46 (m, 2 H), 2.39 (dd, J = 10.83, 8.78 Hz, 2 H), 2.28 (dd, J = 11.27, 8.78 Hz, 2 H). | Racemic |

TABLE 1-continued

| Example No. (Scheme) Structure and Compound Name | LRMS m/z [M + H]+ | 1H NMR | Chiral Separation Conditions (SFC) |
|---|---|---|---|
| 97 (Scheme B) N,N'-(spiro[3.3]heptane-2,6-diyldi-1,3,4-thiadiazole-5,2-diyl)bis[2-(1-methyl-1H-pyrazol-3-yl)acetamide] | 539.1 | (600 MHz, DMSO-d6) δ ppm 7.57 (d, J = 2.05 Hz, 2 H), 6.13 (d, J = 2.20 Hz, 2 H), 3.73-3.79 (m, 8 H), 3.72 (s, 4 H), 2.62-2.67 (m, 2 H), 2.36-2.45 (m, 4 H), 2.27 (dd, J = 11.34, 8.71 Hz, 2 H). | Single (R) Enantiomer |
| 98 (Scheme B) N,N'-(spiro[3.3]heptane-2,6-diyldi-1,3,4-thiadiazole-5,2-diyl)bis[2-(1-methyl-1H-pyrazol-3-yl)acetamide] | 539.1 | (600 MHz, DMSO-d6) δ ppm 7.58 (d, J = 1.90 Hz, 2 H), 6.14 (d, J = 2.05 Hz, 2 H), 3.74-3.80 (m, 8 H), 3.73 (s, 4 H), 2.62-2.69 (m, 2 H), 2.37-2.47 (m, 4 H), 2.28 (dd, J = 11.20, 8.85 Hz, 2 H). | Single (S) Enantiomer |
| 99* (Scheme B) N,N'-(spiro[3.3]heptane-2,6-diyldi-1,3,4-thiadiazole-5,2-diyl)bis[2-(pyridin-2-yl)acetamide] | 533.2 | (400 MHz, DMSO-d6) δ ppm 12.67 (br s, 2 H), 8.49 (d, J = 4.28 Hz, 2 H), 7.77 (t, J = 7.58 Hz, 2 H), 7.40 (d, J = 7.70 Hz, 2 H), 7.25-7.32 (m, 2 H), 4.01 (s, 4 H), 3.78 (quin, J = 8.38 Hz, 2 H), 2.62-2.71 (m, 2 H), 2.37-2.47 (m, 4 H), 2.25-2.34 (m, 2 H). | Rt (Peak 1) = 1.08 minutes Chiralpak OJ-H 4.6 x 100 mm column 40% MeOH @ 120 bar CO2, 4 mL/min. |
| 100 (Scheme A) N-[6-({cis-3-[5-(ethylamino)-1,3,4-thiadiazol-2-yl]cyclobutyl}methyl)pyridazin-3-yl]-2-phenylacetamide | 409.0 | (400 MHz, CDCl3) δ ppm 9.04 (br s, 1 H), 8.40 (d, J = 8.8 Hz, 1 H), 7.34-7.41 (m, 5 H), 7.27 (d, J = 9.2 Hz, 1 H), 5.17 (br s, 1 H), 3.88 (s, 2 H), 3.53-3.62 (m, 1 H), 3.31-3.39 (m, 2 H), 3.03 (d, J = 7.2 Hz, 2 H), 2.65-2.77 (m, 1 H), 2.51-2.59 (m, 2 H), 2.10 (q, J = 9.6 Hz, 2 H), 1.29 (t, J = 7.2 Hz, 3 H). | Single diastereomer |

TABLE 1-continued

| Example No. (Scheme) Structure and Compound Name | LRMS m/z [M + H]+ | 1H NMR | Chiral Separation Conditions (SFC) |
|---|---|---|---|
| 101* (Scheme A) N-[6-({(cis)-3-[5-(ethylamino)-1,3,4-thiadiazol-2-yl]cyclopentyl}methyl)pyridazin-3-yl]-2-(pyridin-2-yl)acetamide | 424.1 | (400 MHz, CD$_3$OD) δ ppm 8.54 (br s, 1 H), 8.40( d, J = 9.2 Hz, 1 H), 7.82-7.89 (m, 1 H), 7.62 (d, J = 8.8 Hz, 1 H), 7.49 (d, J = 6.8 Hz, 1 H), 7.7 (t, J = 6.8 Hz, 1 H), 3.36-3.41 (m, 4 H), 3.02 (d, J = 6.4 Hz, 2 H), 2.49-2.50 (m, 1 H), 2.15-2.27 (m, 2 H), 1.88-1.92 (m, 2 H), 1.45-1.55 (m, 2 H), 1.26-1.36 (m, 4 H). | Rt (Peak 2) = 1.54 minutes Chiralpak OJ-H 4.6 x 100 mm column 40% MeOH @ 100 bar CO$_2$, 4 mL/min. |
| 102* (Scheme B) 2-(pyridin-2-yl)-N-{5-[(1-(cis)-3-{5-[(pyridin-2-ylacetyl)amino]-1,3,4-thiadiazol-2-yl}cyclobutyl)ethyl]-1,3,4-thiadiazol-2-yl}acetamide | 521.1 | (400 MHz, DMSO-d$_6$) δ ppm 12.66 (br s, 2 H), 8.48-8.49 (m, 2 H), 7.76 (td, J = 7.70, 1.30 Hz, 2 H), 7.39 (d, J = 7.80 Hz, 2 H), 7.28 (dd, J = 7.0, 5.2 Hz, 2 H), 4.00 (d, J = 1.5 Hz, 4 H), 3.67-3.73 (m, 1 H), 3.20-3.24 (m, 1 H), 2.51-2.63 (m, 2 H), 2.33-2.45 (m, 1 H), 2.05 (t, J = 10.5 Hz, 2 H), 1.25 (d, J = 6.8 Hz, 3 H). | Rt (Peak 2) = 0.97 minutes Chiralpak OJ-H 4.6 x 100 mm column 40% MeOH @ 120 bar CO$_2$, 4 mL/min. |
| 103* (Scheme B) 2-(pyridin-2-yl)-N-{5-[1-(cis)-3-{5-[(pyridin-2-ylacetyl)amino]-1,3,4-thiadiazol-2-yl}cyclobutyl)ethyl]-1,3,4-thiadiazol-2-yl}acetamide | 521.1 | (400 MHz, DMSO-d$_6$) δ ppm 12.67 (br s, 2 H), 8.49 (dd, J = 4.8, 0.8 Hz, 2 H), 7.77 (td, J = 7.70, 1.70 Hz, 2 H), 7.40 (d, J = 7.80 Hz, 2 H), 7.29 (dd, J = 7.2, 5.2 Hz, 2 H), 4.00 (d, J = 1.3 Hz, 4 H), 3.67-3.73 (m, 1 H), 3.20-3.24 (m, 1 H), 2.51-2.63 (m, 2 H), 2.33-2.45 (m, 1 H), 2.01-2.08 (m, 2 H), 1.26 (d, J = 7.0 Hz, 3H). | Rt (Peak 1) = 1.16 minutes Chiralpak OJ-H 4.6 x 100 mm column 40% MeOH @ 120 bar CO$_2$, 4 mL/min. |
| 104 (Scheme C) 2-methyl-N-{5-[(cis-3-{5-[(pyridin-2-ylacetyl)amino]-1,3,4-thiadiazol-2-yl}cyclobutyl)methyl]-1,3,4-thiadiazol-2-yl}propanamide | 458.1 | (600 MHz, DMSO-d$_6$) δ ppm 8.48 (d, J = 4.83 Hz, 1 H), 7.76 (td, J = 7.68, 1.76 Hz, 1 H), 7.39 (d, J = 7.76 Hz, 1 H), 7.28 (dd, J = 7.10, 5.19 Hz, 1 H), 3.99 (s, 2 H), 3.74 (t, J = 8.49 Hz, 1 H), 3.11 (d, J = 7.46 Hz, 2 H), 2.65-2.80 (m, 2 H), 2.52-2.61 (m, 2 H), 2.00-2.12 (m, 2 H), 1.10 | Rt (Peak 1) = 1.94 minutes Chiralpak OJ-H 4.6 x 100 mm column 20% MeOH @ 120 bar CO$_2$, 4 mL/min (diastereomer separation). |

TABLE 1-continued

| Example No. (Scheme) Structure and Compound Name | LRMS m/z [M + H]+ | 1H NMR | Chiral Separation Conditions (SFC) |
|---|---|---|---|
| | | (d, J = 6.88 Hz, 6 H). | |
| 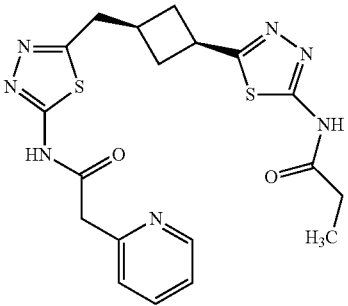 [SMILES: CCC(=O)Nc1nnc([C@H]2C[C@@H](Cc3nnc(NC(=O)Cc4ccccn4)s3)C2)s1]<br>(Scheme C)<br>N-{5-[cis-3-({5-[(pyridin-2-ylacetyl)amino]-1,3,4-thiadiazol-2-yl}methyl)cyclobutyl]-1,3,4-thiadiazol-2-yl}propanamide | 105  444.10 | (600 MHz, DMSO-d6) δ ppm 8.49 (d, J = 4.54 Hz, 1 H), 7.77 (t, J = 7.02 Hz, 1 H), 7.39 (d, J = 7.76 Hz, 1 H), 7.25-7.32 (m, 1 H), 4.00 (s, 2 H), 3.73 (dq, J = 9.00, 8.85 Hz, 1 H), 3.12 (d, J = 7.46 Hz, 2 H), 2.69 (ddd, J = 16.06, 8.41, 8.16 Hz, 1 H), 2.52-2.59 (m, 2 H), 2.45 (q, J = 7.51 Hz, 2 H), 2.01-2.11 (m, 2 H), 1.08 (t, J = 7.54 Hz, 3 H). | Rt (Peak 1) = 2.15 minutes Chiralpak OJ-3 4.6 x 100 mm column 20% MeOH @ 120 bar CO2, 4 mL/min (diastereomer separation). |
| 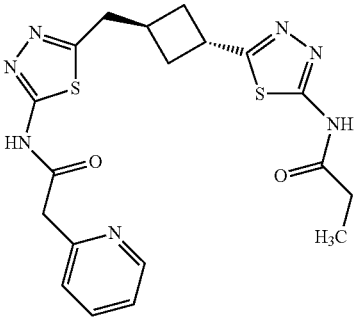 [SMILES: CCC(=O)Nc1nnc([C@H]2C[C@H](Cc3nnc(NC(=O)Cc4ccccn4)s3)C2)s1]<br>(Scheme C)<br>N-{5-[trans-3-({5-[(pyridin-2-ylacetyl)amino]-1,3,4-thiadiazol-2-yl}methyl)cyclobutyl]-1,3,4-thiadiazol-2-yl}propanamide | 106  444.10 | (600 MHz, DMSO-d6) δ ppm 8.48 (d, J = 4.83 Hz, 1 H), 7.77 (td, J = 7.65, 1.24 Hz, 1 H), 7.39 (d, J = 7.76 Hz, 1 H), 7.28 (dd, J = 7.10, 5.20 Hz, 1 H), 4.00 (s, 2 H), 3.94 (t, J = 7.39 Hz, 1 H), 3.23 (d, J = 7.76 Hz, 1 H), 2.71-2.87 (m, 1 H), 2.38-2.48 (m, 4 H), 2.20-2.34 (m, 2 H), 1.08 (t, J = 7.46 Hz, 3 H). | Rt (Peak 2) = 2.55 minutes Chiralpak OJ-3 4.6 x 100 mm column 20% MeOH @ 120 bar CO2, 4 mL/min (diastereomer separation). |
| 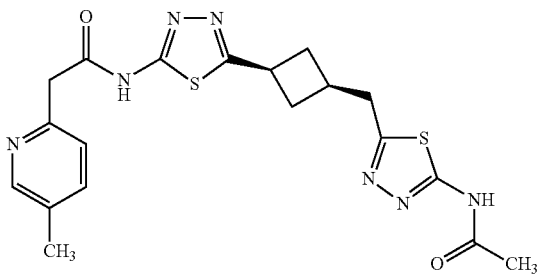 [SMILES: CC(=O)Nc1nnc(C[C@H]2C[C@@H](c3nnc(NC(=O)Cc4ccc(C)cn4)s3)C2)s1]<br>(Scheme C)<br>N-[5-(cis-3-{[5-(acetylamino)-1,3,4-thiadiazol-2-yl]methyl}cyclobutyl)-1,3,4-thiadiazol-2-yl]-2-(5-methylpyridin-2-yl)acetamide | 107  444.1 | (600 MHz, DMSO-d6) δ ppm 8.31 (s, 1 H), 7.57 (dd, J = 7.83, 1.83 Hz, 1 H), 7.27 (d, J = 7.90 Hz, 1 H), 3.92 (s, 2 H), 3.64-3.80 (m, 1 H), 3.10 (d, J = 7.32 Hz, 2 H) 2.68 (ddd, J = 16.17, 8.41, 8.20 Hz, 1 H), 2.51-2.58 (m, 2 H), 2.26 (s, 3 H), 2.15 (s, 3 H), 2.05 (q, J = 9.46 Hz, 2 H). | Rt (Peak 1) = 0.41 minutes Chiralpak OJ-3 4.6 x 100 mm column 20% MeOH @ 140 bar CO2, 4 mL/min (diastereomer separation). |

TABLE 1-continued

| Example No. (Scheme) Structure and Compound Name | LRMS m/z [M + H]+ | 1H NMR | Chiral Separation Conditions (SFC) |
|---|---|---|---|
| 108 (Scheme E) 2-(5-methylpyridin-2-yl)-N-(5-{[cis-3-(5-{[(5-methylpyridin-2-yl)acetyl]amino}-1,3,4-thiadiazol-2-yl)cyclobutyl]methyl}-1,3,4-thiadiazol-2-yl)acetamide | 535.0 | (700 MHz, DMSO-$d_6$) δ ppm 8.31 (s, 2 H), 7.57 (dd, J = 7.86, 1.54 Hz, 2 H), 7.27 (d, J = 7.86 Hz, 2 H), 3.94 (d, J = 3.42 Hz, 4 H), 3.74 (m, J = 8.90, 8.90 Hz, 1 H), 3.11 (d, J = 7.34 Hz, 2 H), 2.63-2.74 (m, 1 H), 2.54 (m, J = 8.90, 2.00 Hz, 2 H), 2.26 (s, 6 H), 1.97-2.11 (m, 2 H). | Rt (Peak 1) = 0.75 minutes Chiralpak OJ-3 4.6 x 100 mm column 20% MeOH @ 120 bar $CO_2$, 3 mL/min (diastereomer separation). |
| 109 (Scheme E) 2-(5-methylpyridin-2-yl)-N-(5-{[trans-3-(5-{[(5-methylpyridin-2-yl)acetyl]amino}-1,3,4-thiadiazol-2-yl)cyclobutyl]methyl}-1,3,4-thiadiazol-2-yl)acetamide | 535.0 | (700 MHz DMSO-$d_6$) δ ppm 12.64 (br s, 2 H), 8.31 (s, 2 H), 7.57 (d, J = 7.86 Hz, 2 H), 7.27 (d, J = 7.86 Hz, 2 H), 3.87-4.00 (m, 5 H), 3.22 (d, J = 7.69 Hz, 2 H), 2.73-2.83 (m, 1 H), 2.37-2.47 (m, 2 H), 2.21-2.33 (m, 8 H). | Rt (Peak 2) = 0.97 minutes Chiralpak OJ-3 4.6 x 100 mm column 20% MeOH @ 120 bar $CO_2$, 3 mL/min (diastereomer separation). |
| 110* (Scheme F) N-[6-({(cis)-3-[5-(cyclopropylamino)-1,3,4-thiadiazol-2-yl]cyclopentyl}methyl)pyridazin-3-yl]-2-(pyridin-2-yl)acetamide | 436.1 | (400 MHz, $CD_3OD$) δ ppm 8.54 (d, J = 4 Hz, 1 H), 8.42 (d, J = 8 Hz, 1 H), 7.85 (t, J = 4 Hz, 1 H), 7.63 (d, J = 8.8 Hz, 1 H), 7.49 (d, J = 7.6 Hz, 1 H), 7.37 (t, J = 6 Hz, 1 H), 4.03 (d, J = 8.4 Hz, 2 H), 3.44 (t, J = 8.8 Hz, 1 H), 3.03 (d, J = 7.6 Hz, 1 H), 2.65-2.68 (m, 1 H), 2.49-2.61 (m, 1 H), 2.12-2.32 (m, 2 H), 1.85-1.96 (m, 2H), 1.5-1.62 (m, 2 H), 0.79-0.82 (m, 2 H), 0.62 (br s, 2 H). | Rt (Peak 2) = 4.70 minutes Chiralpak AS-H 4.6 x 100 mm column 40% MeOH @ 100 bar $CO_2$, 3 mL/min. |
| 111 (Scheme C) 2-(5-methylpyridin-2-yl)-N-{5-[(cis-3-{5-[(pyridin-2-ylacetyl)amino]-1,3,4-thiadiazol-2-yl}cyclobutyl)methyl]-1,3,4-thiadiazol-2-yl}acetamide | 521.2 | (600 MHz, DMSO-$d_6$) δ ppm 8.72 (d, J = 4.83 Hz, 1 H), 8.55 (s, 1 H), 8.00 (td, J = 7.68, 1.46 Hz, 1 H), 7.81 (dd, J = 7.76, 1.46 Hz, 1 H), 7.63 (d, J = 7.76 Hz, 1 H), 7.46-7.56 (m, 2 H), 4.24 (s, 2 H), 4.18 (s, 2 H), 3.98 (t, J = 8.78 Hz, 1 H), 3.35 (d, J = 7.46 Hz, 1 H), 2.87-2.97 (m, 1 H), 2.75-2.82 (m, 2 H), 2.74 (s, 3 H), 2.24-2.34 (m, 2 H). | Rt (Peak 1) = 1.72 minutes Chiralpak OJ-3 4.6 x 100 mm column 30% MeOH @ 120 bar $CO_2$, 4 mL/min (diastereomer separation). |

TABLE 1-continued

| Example No. (Scheme) Structure and Compound Name | LRMS m/z [M + H]+ | 1H NMR | Chiral Separation Conditions (SFC) |
|---|---|---|---|
| 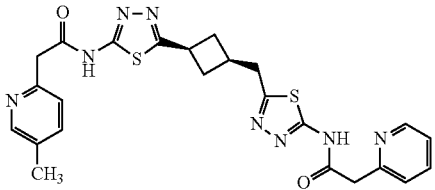 [SMILES: Cc1ccc(CC(=O)Nc2nnc([C@H]3C[C@@H](Cc4nnc(NC(=O)Cc5ccccn5)s4)C3)s2)nc1]<br>(Scheme C)<br>2-(5-methylpyridin-2-yl)-N-{5-[cis-3-({5-[(pyridin-2-ylacetyl)amino]-1,3,4-thiadiazol-2-yl}methyl)cyclobutyl]-1,3,4-thiadiazol-2-yl}acetamide | 112  521.2 | (700 MHz, DMSO-$d_6$) δ ppm 8.48 (d, J = 4.10 Hz, 1 H), 8.31 (s, 1 H), 7.76 (t, J = 7.60 Hz, 1 H), 7.57 (d, J = 7.69 Hz, 1 H), 7.39 (d, J = 7.86 Hz, 1 H), 7.24-7.30 (m, 2 H), 3.99 (s, 2 H), 3.94 (s, 2 H), 3.74 (m, J = 8.70, 8.70 Hz, 1 H), 3.11 (d, J = 7.34 Hz, 2 H), 2.62-2.73 (m, 1 H), 2.55 (q, J = 8.83 Hz, 2 H), 2.05 (q, J = 9.91 Hz, 2 H). | Rt (Peak 1) = 4.03 minutes Chiralpak OJ-3 4.6 × 100 mm column 20% MeOH @ 120 bar $CO_2$, 4 mL/min (dia-separation). stereomer |
| 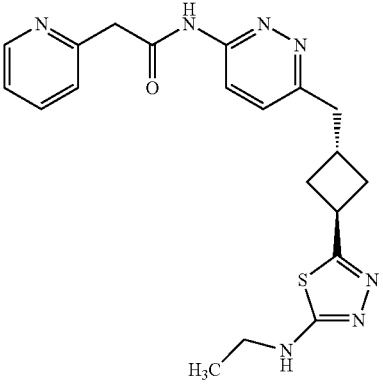 [SMILES: CCNc1nnc([C@H]2C[C@H](Cc3ccc(NC(=O)Cc4ccccn4)nn3)C2)s1]<br>(Scheme F)<br>N-[6-({trans-3-[5-(ethylamino)-1,3,4-thiadiazol-2-yl]cyclobutyl}methyl)pyridazin-3-yl]-2-(pyridin-2-yl)acetamide | 113  409.2 | (400 MHz, DMSO-$d_6$) δ ppm 11.26-11.36 (m, 1 H), 8.48-8.54 (m, 1 H), 8.17-8.26 (m, 1 H), 7.74-7.82 (m, 1 H), 7.54-7.65 (m, 2 H), 7.35-7.44 (m, 1 H), 7.24-7.33 (m, 1 H), 3.99 (s, 2 H), 3.75-3.84 1 H), 3.17-3.28 (m, 2 H), 3.03-3.13 (m, 2 H), 2.67-2.83 (m, 1 H), 2.13-2.37 (m, 5 H), 1.15 (t, J = 6.80 Hz, 4 H). | Single dia-stereomer |
| 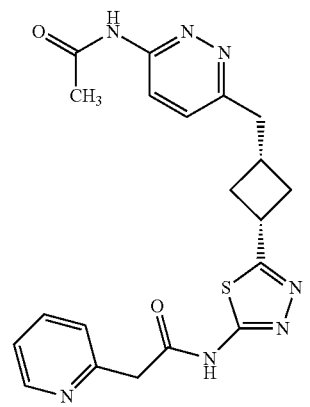 [SMILES: CC(=O)Nc1ccc(C[C@H]2C[C@@H](c3nnc(NC(=O)Cc4ccccn4)s3)C2)nn1]<br>(Scheme A)<br>N-[5-(cis-3-{[6-(acetylamino)pyridazin-3-yl]methyl}cyclobutyl)-1,3,4-thiadiazol-2-yl]-2-(pyridin-2-yl)acetamide | 114  409.2 | (400 MHz, DMSO-$d_6$) δ ppm 11.02 (s, 1 H), 8.50 (d, J = 4.02 Hz, 1 H), 8.21 (d, J = 9.03 Hz, 1 H), 7.78 (td, J = 7.59, 1.88 Hz, 1 H), 7.55 (d, J = 9.29 Hz, 1 H), 7.40 (d, J = 7.78 Hz, 1 H), 7.30 (dd, J = 7.03, 5.27 Hz, 1 H), 4.01 (s, 2 H), 3.73 (t, J = 8.41 Hz, 1 H), 2.99 (d, J = 7.53 Hz, 2 H), 2.65-2.78 (m, 1 H), 2.32-2.36 (m, 1 H), 2.13 (s, 3 H), 2.01-2.11 (m, 5 H). | Single dia-stereomer |

TABLE 1-continued

| Example No. (Scheme) Structure and Compound Name | LRMS m/z [M + H]+ | 1H NMR | Chiral Separation Conditions (SFC) |
|---|---|---|---|
| 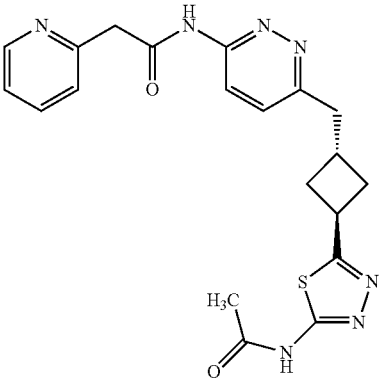 [SMILES: CC(=O)Nc1nnc([C@H]2C[C@H](Cc3ccc(NC(=O)Cc4ccccn4)nn3)C2)s1]<br>(Scheme A)<br>N-[6-({trans-3-[5-(acetylamino)-1,3,4-thiadiazol-2-yl]cyclobutyl}methyl)pyridazin-3-yl]-2-(pyridin-2-yl)acetamide | 115    423.2 | (400 MHz, DMSO-$d_6$) δ ppm 11.03 (s, 1 H), 8.49 (d, J = 4.02 Hz, 1 H), 8.22 (d, J = 9.29 Hz, 1 H), 7.78 (td, J = 7.65, 1.76 Hz, 1 H), 7.58 (d, J = 9.03 Hz, 1 H), 7.40 (d, J = 7.78 Hz, 1 H), 7.29 (dd, J = 6.90, 5.14 Hz, 1 H), 3.90-4.04 (m, 3 H), 3.11 (d, J = 7.78 Hz, 2 H), 2.77-2.89 (m, 1 H), 2.65-2.72 (m, 1 H), 2.23-2.43 (m, 5 H). | Single diastereomer |
| 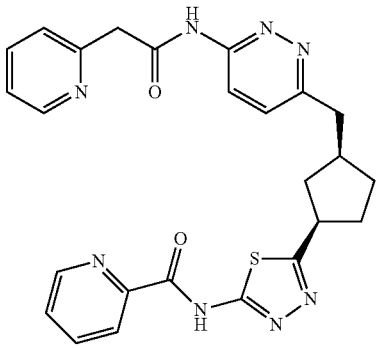 [SMILES: O=C(Cc1ccccn1)Nc1ccc(C[C@H]2CC[C@@H](c3nnc(NC(=O)c4ccccn4)s3)C2)nn1]<br>(Scheme A)<br>N-{5-[(cis)-3-({6-[(pyridin-2-ylacetyl)amino]pyridazin-3-yl}methyl)cyclopentyl]-1,3,4-thiadiazol-2-yl}pyridine-2-carboxamide | 116*    501.0 | (400 MHz, CDCl$_3$) δ ppm 8.75 (d, J = 4.8 Hz, 1 H), 8.70 (d, J = 4.4 Hz, 1 H), 8.57 (d, J = 9.6 Hz, 1 H), 8.28 (d, J = 7.6 Hz, 1 H), 7.96-8.01 (m, 2 H), 7.53-7.64 (m, 4 H), 4.29 (s, 2 H), 3.57-3.61 (m, 1 H), 3.07 (d, J = 7.2 Hz, 2 H), 2.42-2.56 (m, 1 H), 2.39-2.41 (m, 1 H), 2.25-2.27 (m, 1 H), 1.95-2.05 (m, 2 H), 1.71-1.73 (m, 1 H), 1.61-1.63 (m, 1 H). | Rt (Peak 2) = 2.50 minutes Chiralpak OJ-3 4.6 x 50 mm column 5-40% MeOH (w. 0.05% DEA) @ 100 bar CO$_2$, 4 mL/min. |
| 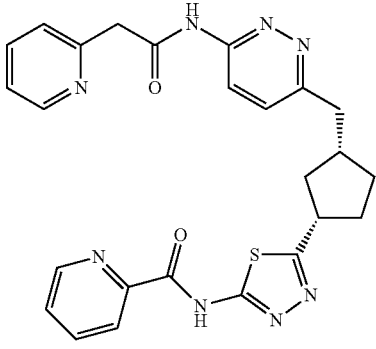 [SMILES: O=C(Cc1ccccn1)Nc1ccc(C[C@@H]2CC[C@H](c3nnc(NC(=O)c4ccccn4)s3)C2)nn1]<br>(Scheme A)<br>N-{5-[(cis)-3-({6-[(pyridin-2-ylacetyl)amino]pyridazin-3-yl}methyl)cyclopentyl]-1,3,4-thiadiazol-2-yl}pyridine-2-carboxamide | 117*    501.0 | (400 MHz, CDCl$_3$) δ ppm 8.75 (d, J = 5.2 Hz, 1 H), 8.70 (d, J = 4.0 Hz, 1 H), 8.55 (d, J = 5.6 Hz, 1 H), 8.28 (d, J = 8.0 Hz, 1 H), 7.96-8.00 (m, 2 H), 7.56-7.61 (m, 2 H), 7.49-7.52 (m, 2 H), 4.26 (s, 2 H), 3.56-3.61 (m, 1 H), 3.06 (d, J = 7.6 Hz, 2 H), 2.55-2.57 (m, 1 H), 2.40-2.42 (m, 1 H), 2.24-2.26 (m, 1 H), 1.94-2.04 (m, 2 H), 1.61-1.73 (m, 2 H). | Rt (Peak 1) = 2.26 minutes Chiralpak OJ-3 4.6 x 50 mm column 5-40% MeOH (w. 0.05% DEA) @ 100 bar CO$_2$, 4 mL/min. |

TABLE 1-continued

| Example No. (Scheme) Structure and Compound Name | LRMS m/z [M + H]+ | 1H NMR | Chiral Separation Conditions (SFC) |
|---|---|---|---|
| 118 (Scheme A) 2-phenyl-N-{6-[(cis-3-{5-[(pyridin-2-ylacetyl)amino]-1,3,4-thiadiazol-2-yl}cyclobutyl)methyl]pyridazin-3-yl}acetamide | 431.1 | (400 MHz, DMSO-$d_6$) δ ppm 9.04 (s, 1 H), 8.39-8.42 (m, 1 H), 7.27-7.41 (m, 6 H), 5.17 (br s, 1 H), 3.88 (s, 1 H), 3.56-3.61 (m, 1 H), 3.34-3.35 (m, 2 H), 3.02-3.04 (m, 2 H), 2.72-2.76 (m, 1 H), 2.55-2.60 (m, 2 H), 1.28-1.31 (m, 3 H). | Single diastereomer |
| 119 (Scheme A) N-{5-[(1S,3R)-3-({6-[(pyridin-2-ylacetyl)amino]pyridazin-3-yl}methyl)cyclopentyl]-1,3,4-thiadiazol-2-yl}propanamide | 474.0 [M + Na]+ | (400 MHz, CDCl$_3$) δ ppm 8.62 (s, 1 H), 8.31 (d, J = 9.2 Hz, 1 H), 7.61-7.63 (m, 1 H), 7.24-7.26 (m, 5 H), 3.90 (s, 2 H), 3.46-3.51 (m, 1 H), 2.95 (d, J = 6.8 Hz, 2 H), 2.61 (d, J = 6.8 Hz, 2 H), 2.14-2.60 (m, 4 H), 1.89-2.01 (m, 2 H), 1.58-1.61 (m, 1 H), 1.21-1.19 (t, J = 6.8 Hz, 3 H). | Rt = 4.13 minutes Chiralpak AS-H 4.6 x 150 mm column 5-40% EtOH (w. 0.05% DEA) @ 100 bar CO$_2$, 3 mL/min. |
| 120 (Scheme A) 2-methyl-N-{5-[(1S,3R)-3-({6-[(pyridin-2-ylacetyl)amino]pyridazin-3-yl}methyl)cyclopentyl]-1,3,4-thiadiazol-2-yl}propanamide | 465.9 | (400 MHz, CDCl$_3$) δ ppm 8.67 (s, 1 H), 8.36 (d, J = 8.8 Hz, 1 H), 7.67-7.69 (m, 1 H), 7.24-7.26 (m, 5 H), 3.95 (s, 2 H), 3.49-3.52 (m, 1 H), 2.89-3.01 (m, 3 H), 2.19-2.55 (m, 4 H), 1.92-1.94 (m, 2 H), 1.58-1.61 (m, 1 H), 1.27 (d, J = 6.4 Hz, 6H). | Rt = 3.92 minutes Chiralpak AS-H 4.6 x 150 mm column 5-40% EtOH (w. 0.05% DEA) @ 100 bar CO$_2$, 3 mL/min. |

TABLE 1-continued

| Example No. (Scheme) Structure and Compound Name | LRMS m/z [M + H]+ | 1H NMR | Chiral Separation Conditions (SFC) |
|---|---|---|---|
| 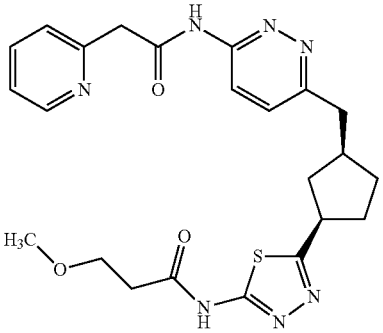 [SMILES: COCCC(=O)Nc1nnc([C@@H]2CC[C@H](Cc3ccc(NC(=O)Cc4ccccn4)nn3)C2)s1]<br>(Scheme A)<br>3-methoxy-N-{5-[(cis)-3-({6-[(pyridin-2-ylacetyl)amino]pyridazin-3-yl}methyl)cyclopentyl]-1,3,4-thiadiazol-2-yl}propanamide | 121* 482.2 | (400 MHz, CDCl$_3$) δ ppm 10.90 (br s, 1 H), 10.52 (br s, 1 H), 8.69 (d, J = 4.4 Hz, 1 H), 8.38 (d, J = 9.2 Hz, 1 H), 7.69-7.73 (m, 1 H), 7.29-7.31 (m, 3 H), 3.95 (s, 2H), 3.73-3.76 (m, 2 H), 3.51-3.54 (m, 1 H), 3.46 (s, 3 H), 3.02 (d, J = 6.8 Hz, 2 H), 2.79-2.82 (m, 2 H), 2.51-2.53 (m, 1 H), 2.36-2.39 (m, 1 H), 2.21-2.24 (m, 1 H), 1.94-1.99 (m, 2 H), 1.63-1.66 (m, 2 H). | Rt (Peak 2) = 1.08 minutes Chiralpak AS-3 4.6 x 50 mm column 60% IPA w. 0.05% DEA) @ 100 bar CO$_2$, 3 mL/min. |
| 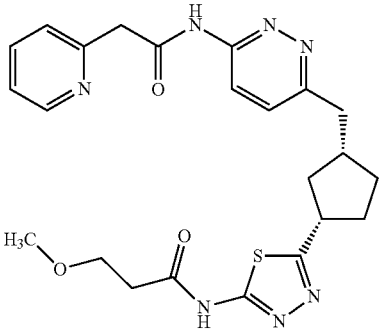 [SMILES: COCCC(=O)Nc1nnc([C@H]2CC[C@@H](Cc3ccc(NC(=O)Cc4ccccn4)nn3)C2)s1]<br>(Scheme A)<br>3-methoxy-N-{5-[(cis)-3-({6-[(pyridin-2-ylacetyl)amino]pyridazin-3-yl}methyl)cyclopentyl]-1,3,4-thiadiazol-2-yl}propanamide | 122* 482.2 | (400 MHz, MeOD-d$_4$) δ ppm 8.54 (d, J = 4.4 Hz, 1 H), 8.40 (d, J = 9.2 Hz, 1 H), 7.85-7.87 (m, 1 H), 7.63 (d, J = 9.6 Hz, 1 H), 7.49 (d, J = 7.6 Hz, 1 H), 7.35-7.38 (m, 1 H), 3.74-3.77 (m, 2 H), 3.55-3.57 (m, 1 H), 3.37 (s, 3 H), 3.05 (d, J = 7.6 Hz, 2 H), 2.74-2.77 (m, 2 H), 2.55-2.57 (m, 2 H), 2.25-2.31 (m, 2 H), 1.96-1.98 (m, 2 H), 1.64-1.67 (m, 2 H). | Rt (Peak 1) = 0.68 minutes Chiralpak AS-3 4.6 x 50 mm column 60% IPA w. 0.05% DEA) @ 100 bar CO$_2$, 3 mL/min. |
| 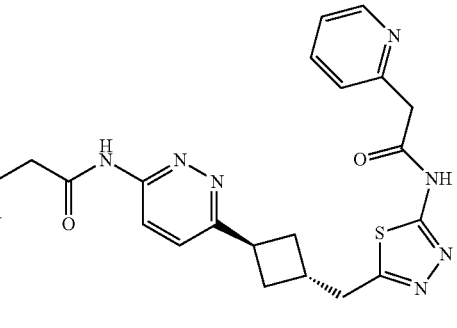<br>(Scheme A)<br>2-(pyridin-2-yl)-N-{5-[(trans-3-{6-[(pyridin-2-ylacetyl)amino]pyridazin-3-yl}cyclobutyl)methyl]-1,3,4-thiadiazol-2-yl}acetamide | 123 523.1 [M + Na]+ | (400 MHz, DMSO-d$_6$) δ ppm 11.33 (s, 1 H), 8.50 (t, J = 5.40 Hz, 2 H), 8.22 (d, J = 9.29 Hz, 1 H), 7.77 (td, J = 7.78, 1.76 Hz, 2 H), 7.63 (d, J = 9.29 Hz, 1 H), 7.41 (d, J = 7.78 Hz, 2 H), 7.25-7.33 (m, 2 H), 4.00 (s, 4 H), 3.86 (s, 1 H), 3.27 (d, J = 7.78 Hz, 2 H), 2.68 (d, J = 1.76 Hz, 1 H), 2.41-2.48 (m, 2 H), 2.16-2.28 (m, 2 H). | Single diastereomer |

TABLE 1-continued

| Example No. (Scheme) Structure and Compound Name | LRMS m/z [M + H]+ | 1H NMR | Chiral Separation Conditions (SFC) |
|---|---|---|---|
| 124 (Scheme A) 2-(pyridin-2-yl)-N-{5-[(cis-3-{6-[(pyridin-2-ylacetyl)amino]pyridazin-3-yl}cyclobutyl)methyl]-1,3,4-thiadiazol-2-yl}acetamide | 523.1 [M + Na]+ | (400 MHz, DMSO-$d_6$) δ ppm 11.31-11.35 (m, 1 H), 8.47-8.53 (m, 2 H), 8.20-8.25 (m, 1 H), 7.75-7.81 (m, 2 H), 7.62-7.67 (m, 1 H), 7.38-7.44 (m, 2 H), 7.26-7.32 (m, 2 H), 3.97-4.02 (m, 4 H), 3.60-3.67 (m, 1 H), 3.41-3.44 (m, 1 H), 3.11-3.16 (m, 2 H), 2.65-2.70 (m, 2 H), 2.32-2.36 (m, 1 H), 2.03-2.11 (m, 1 H). | Single diastereomer |
| 125 (Scheme A) 2-methyl-N-{6-[cis-3-({5-[(pyridin-2-ylacetyl)amino]-1,3,4-thiadiazol-2-yl}methyl)cyclobutyl]pyridazin-3-yl}propanamide | 474.0 [M + Na]+ | (400 MHz, DMSO-$d_6$) δ ppm 10.96-11.02 (m, 1 H), 8.47-8.54 (m, 1 H), 8.22-8.30 (m, 1 H), 7.73-7.82 (m, 1 H), 7.59-7.67 (m, 1 H), 7.38-7.45 (m, 1 H), 7.26-7.33 (m, 1 H), 4.01 (s, 2 H), 3.83-3.90 (m, 1 H), 3.23-3.30 (m, 3 H), 2.77-2.85 (m, 1 H), 2.64-2.72 (m, 1 H), 2.40-2.45 (m, 2 H), 2.32-2.37 (m, 1 H), 2.17-2.28 (m, 1 H), 1.11 (d, J = 6.78 Hz, 6 H). | Single diastereomer |
| 126* (Scheme A) 2-(1-methyl-1H-pyrazol-3-yl)-N-{5-[(cis)-3-({6-[(pyridin-2-ylacetyl)amino]pyridazin-3-yl}methyl)cyclopentyl]-1,3,4-thiadiazol-2-yl}acetamide | 518.1 | (400 MHz, MeOD-$d_4$) δ ppm 8.54 (d, J = 8.8 Hz, 1 H), 8.39 (d, J = 8.8 Hz, 1 H), 8.25-8.26 (m, 1 H), 7.85-7.87 (m, 1 H), 7.62 (d, J = 9.2 Hz, 1 H), 7.55 (s, 1 H), 7.48 (d, J = 8.0 Hz, 1 H), 7.35-7.38 (m, 1 H), 6.26 (s, 1 H), 3.88 (s, 3 H), 3.84 (s, 2 H), 3.54-3.58 (m, 1 H), 3.40-3.41 (m, 2 H), 3.03-3.05 (d, J = 7.2 Hz, 2 H), 2.54-2.56 (m, 1 H), 2.32-2.53 (m, 1 H), 2.22-2.26 (m, 1 H), 1.95-1.97 (m, 2 H), 1.60-1.66 (m, 2 H). | Rt (Peak 2) = 5.91 minutes Chiralpak OJ-H 4.6 x 250 mm column 40% MeOH (w. 0.05% DEA) @ 100 bar $CO_2$, 2.4 mL/min. |

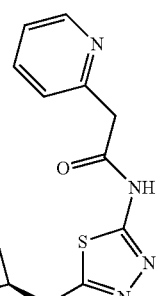

TABLE 1-continued

| Example No. (Scheme) Structure and Compound Name | | LRMS m/z [M + H]+ | 1H NMR | Chiral Separation Conditions (SFC) |
|---|---|---|---|---|
| 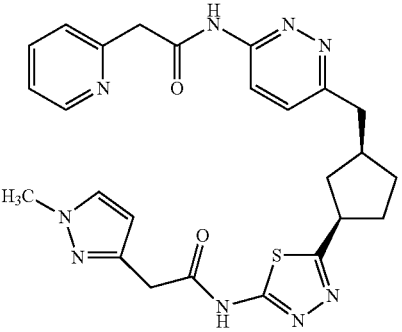 [SMILES: Cn1ccc(CC(=O)Nc2nnc([C@@H]3CC[C@H](Cc4ccc(NC(=O)Cc5ccccn5)nn4)C3)s2)n1]<br>(Scheme A)<br>2-(1-methyl-1H-pyrazol-3-yl)-N-{5-[(cis)-3-({6-[(pyridin-2-ylacetyl)amino]pyridazin-3-yl}methyl)cyclopentyl]-1,3,4-thiadiazol-2-yl}acetamide | 127* | 518.1 | (400 MHz, MeOD-d$_4$) δ ppm 8.54 (d, J = 8.8 Hz, 1 H), 8.39 (d, J = 8.8 Hz, 1 H), 8.25-8.26 (m, 1 H), 7.85-7.87 (m, 1 H), 7.62 (d, J = 9.2 Hz, 1 H), 7.55 (s, 1 H), 7.48 (d, J = 8.0 Hz, 1 H), 7.35-7.38 (m, 1 H), 6.26 (s, 1 H), 3.88 (s, 3 H), 3.84 (s, 2 H), 3.54-3.58 (m, 1 H), 3.40-3.41 (m, 2 H), 3.03-3.05 (d, J = 7.2 Hz, 2 H), 2.54-2.56 (m, 1 H), 2.32-2.53 (m, 1 H), 2.22-2.26 (m, 1 H), 1.95-1.97 (m, 2 H), 1.60-1.66 (m, 2 H). | Rt (Peak 1) = 4.98 minutes Chiralpak OJ-H 4.6 x 250 mm column 40% MeOH (w. 0.05% DEA) @ 100 bar CO$_2$, 2.4 mL/min. |
| 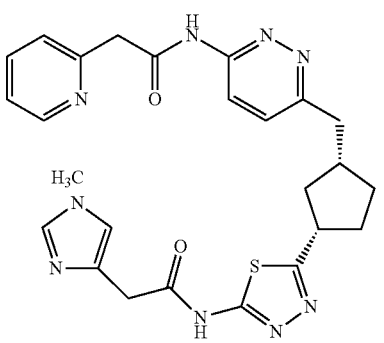<br>(Scheme A)<br>2-(1-methyl-1H-imidazol-4-yl)-N-{5-[(cis)-3-({6-[(pyridin-2-ylacetyl)amino]pyridazin-3-yl}methyl)cyclopentyl]-1,3,4-thiadiazol-2-yl}acetamide | 128* | 518.0 | (400 MHz, CDCl$_3$) δ ppm 10.98 (s, 1 H), 8.67 (d, J = 4.8 Hz, 1 H), 8.37(d, J = 9.2 Hz, 1 H), 7.68-7.72 (m, 1 H), 7.50 (s, 1 H), 7.24-7.31 (m, 4 H), 6.83 (s, 1 H), 3.98 (s, 2 H), 3.79 (s, 2 H), 3.69 (s, 3 H), 3.48 v 3.50 (m, 1 H), 2.99-3.00 (d, J = 6.8 Hz, 2 H), 2.53-2.55 (m, 1 H), 2.33-2.36 (m, 1 H), 2.18 (m, 1 H), 1.88-1.96 (m, 2 H), 1.58-1.63 (m, 2 H). | Rt (Peak 1) = 1.65 minutes Chiralpak OJ-3 4.6 x 50 mm column 5-40% MeOH (w. 0.05% DEA) @ 100 bar CO$_2$, 4 mL/min. |
| 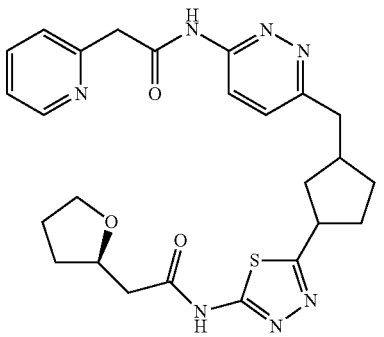 [SMILES: O=C(Cc1ccccn1)Nc1ccc(CC2CCC(c3nnc(NC(=O)C[C@H]4CCCO4)s3)C2)nn1]<br>(Scheme A)<br>(rac)-2-(pyridin-2-yl)-N-(6-{[(cis)-3-(5-{[(2R)-tetrahydrofuran-2-ylacetyl]amino}-1,3,4-thiadiazol-2-yl)cyclopentyl]methyl}pyridazin-3-yl)acetamide | 129 | 508.1 | (400 MHz, MeOD-d$_6$) δ ppm 8.54-8.55 (m, 1 H), 8.40 (d, J = 8.8 Hz, 1 H), 7.83-7.85 (m, 1 H), 7.61-7.63 (m, 1 H), 7.48-7.50 (m, 1 H), 7.35-7.37 (m, 1 H), 4.39 (s, 1 H), 3.90 (s, 2 H), 3.75-3.77 (m, 1 H), 3.55-3.56 (m, 1 H), 3.33-3.35 (m, 2 H), 3.03-3.04 (m, 1 H), 2.70-2.72 (m, 1 H), 2.53-2.55 (m, 1 H), 2.33-2.35 (m, 1 H), 2.22-2.25 (m, 1 H), 2.13-2.15 (m, 1 H), 1.95-1.97 (m, 4 H), 1.63-1.68 (m, 3 H). | Racemic Cis |

TABLE 1-continued

| Example No. (Scheme) Structure and Compound Name | LRMS m/z [M + H]+ | 1H NMR | Chiral Separation Conditions (SFC) |
|---|---|---|---|
| 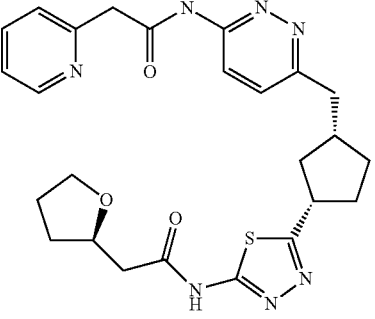<br>(Scheme A)<br>2-(pyridin-2-yl)-N-(6-{[(cis)-3-(5-{[(2R)-tetrahydrofuran-2-ylacetyl]amino}-1,3,4-thiadiazol-2-yl)cyclopentyl]methyl}pyridazin-3-yl)acetamide | 130* 508.2 | (400 MHz, MeOD-d₆) δ ppm 8.54-8.55 (m, 1 H), 8.40 (d, J = 8.8 Hz, 1 H), 7.83-7.85 (m, 1 H), 7.61-7.63 (m, 1 H), 7.48-7.50 (m, 1 H), 7.35-7.37 (m, 1 H), 4.39 (s, 1 H), 3.90 (s, 2 H), 3.75-3.77 (m, 1 H), 3.55-3.56 (m, 1 H), 3.33-3.35 (m, 2 H), 3.03-3.04 (m, 1 H), 2.70-2.72 (m, 1 H), 2.53-2.55 (m, 1 H), 2.33-2.35 (m, 1 H), 2.22-2.25 (m, 1 H), 2.13-2.15 (m, 1 H), 1.95-1.97 (m, 4 H), 1.63-1.68 (m, 3 H). | Rt (Peak 2) = 1.19 minutes Chiralpak AS-3 4.6 x 50 mm column 60% IPA w. 0.05% DEA) @ 100 bar CO₂, 3 mL/min. |
| 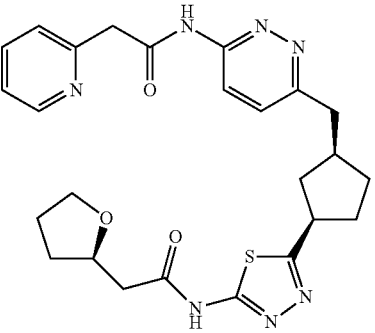 [SMILES: O=C(Cc1ccccn1)Nc1ccc(C[C@H]2CC[C@@H](c3nnc(NC(=O)C[C@H]4CCCO4)s3)C2)nn1]<br>(Scheme A)<br>2-(pyridin-2-yl)-N-(6-{[(cis)-3-(5-{[(2R)-tetrahydrofuran-2-ylacetyl]amino}-1,3,4-thiadiazol-2-yl)cyclopentyl]methyl}pyridazin-3-yl)acetamide | 131* 508.2 | (400 MHz, MeOD-d₆) δ ppm 8.54-8.55 (m, 1 H), 8.40 (d, J = 8.8 Hz, 1 H), 7.83-7.85 (m, 1 H), 7.61-7.63 (m, 1 H), 7.48-7.50 (m, 1 H), 7.35-7.37 (m, 1 H), 4.39 (s, 1 H), 3.90 (s, 2 H), 3.75-3.77 (m, 1 H), 3.55-3.56 (m, 1 H), 3.33-3.35 (m, 2 H), 3.03-3.04 (m, 1 H), 2.70-2.72 (m, 1 H), 2.53-2.55 (m, 1 H), 2.33-2.35 (m, 1 H), 2.22-2.25 (m, 1 H), 2.13-2.15 (m, 1 H), 1.95-1.97 (m, 4 H), 1.63-1.68 (m, 3 H). | Rt (Peak 1) = 0.91 minutes Chiralpak AS-3 4.6 x 50 mm column 60% IPA w. 0.05% DEA) @ 100 bar CO₂, 3 mL/min. |
| 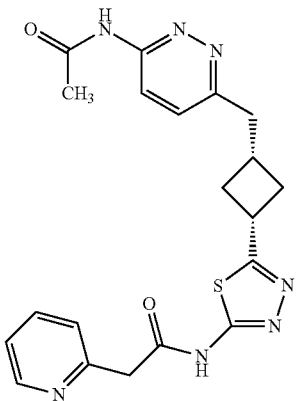 [SMILES: CC(=O)Nc1ccc(C[C@H]2C[C@@H](c3nnc(NC(=O)Cc4ccccn4)s3)C2)nn1]<br>(Scheme A)<br>N-[6-({cis-3-[5-(acetylamino)-1,3,4-thiadiazol-2-yl]cyclobutyl}methyl)pyridazin-3-yl]-2-phenylacetamide | 132 445.0 | (400 MHz, DMSO-d₆) δ ppm 12.35 (br s, 1 H), 11.28 (s, 1 H), 8.22-8.19 (m, 1 H), 7.55-7.60 (m, 1 H), 7.26-7.37 (m, 5 H), 3.96-3.98 (m, 1 H), 3.72-3.74 (m, 2 H), 3.34-3.36 (m, 1 H), 3.10-3.12 (m, 1 H), 2.99-3.01 (m, 1 H), 2.68-2.69 (m, 1 H), 2.17-2.38 (m, 3 H), 2.09-2.13 (m, 3 H). | Single diastereomer |

TABLE 1-continued

| Example No. (Scheme) Structure and Compound Name | LRMS m/z [M + H]+ | 1H NMR | Chiral Separation Conditions (SFC) |
|---|---|---|---|
| 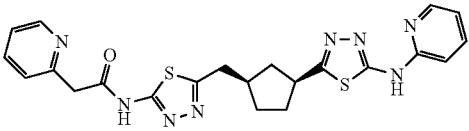 [SMILES: O=C(Cc1ccccn1)Nc1nnc(C[C@@H]2CC[C@H](c3nnc(Nc4ccccn4)s3)C2)s1]<br>(Scheme C)<br>2-(pyridin-2-yl)-N-[5-({(cis)-3-[5-(pyridin-2-ylamino)-1,3,4-thiadiazol-2-yl]cyclopentyl}methyl)-1,3,4-thiadiazol-2-yl]acetamide | 133* 479.2 | (700 MHz, DMSO-d₆) δ ppm 11.41 (br s, 1 H), 8.48-8.49 (m, 1 H), 8.27-8.28 (1 H), 7.76 (t, J = 7.7 Hz, 1H), 7.74 (t, J = 7.7 Hz, 1H), 7.39 (d, J = 7.5 Hz, 1 H), 7.27-7.29 (m, 1 H), 7.05 (dd, J = 8.3, 0.8 Hz, 1 H), 6.95 (t, J = 6.1 Hz, 1 H), 3.47 (quin, J = 8.5 Hz, 1H), 3.08 (d, J = 7.3 Hz, 2 H), 2.42 (dt, J = 15, 7.5 Hz, 2 H), 2.25-2.32 (m, 2 H), 2.09-2.16 (m, 2 H), 1.86-1.92 (m, 2 H), 1.46-1.60 (m, 2 H). | Rt (Peak 1) = 2.38 minutes Chiralpak AS-3 4.6 x 100 mm column 40% MeOH (w. 0.1% DEA) @ 120 bar CO₂, 4 mL/min |
| <br>(Scheme B)<br>N,N'-(spiro[3.3]heptane-2,6-diyldi-1,3,4-thiadiazole-5,2-diyl)dipropanamide | 134 407.1 | (600 MHz, DMSO-d₆) δ ppm 3.76 (quin, J = 8.45 Hz, 2 H), 2.63-2.69 (m, 2 H), 2.38-2.48 (m, 8 H), 2.29 (dd, J = 11.27, 8.78 Hz, 2 H), 1.08 (t, J = 7.46 Hz, 6 H). | Single (S) Enantiomer |
| 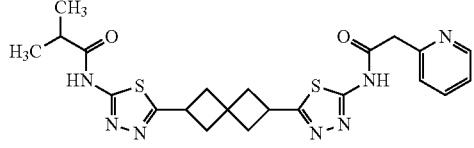 [SMILES: CC(C)C(=O)Nc1nnc(C2CC3(CC(c4nnc(NC(=O)Cc5ccccn5)s4)C3)C2)s1]<br>(Scheme D)<br>2-methyl-N-[5-(6-{5-[(pyridin-2-ylacetyl)amino]-1,3,4-thiadiazol-2-yl}spiro[3.3]hept-2-yl)-1,3,4-thiadiazol-2-yl]propanamide | 135 484.1 | (600 MHz, DMSO-d₆) δ ppm 8.47 (d, J = 4.39 Hz, 1 H), 7.76 (td, J = 7.68, 1.61 Hz, 1 H), 7.38 (d, J = 7.9 Hz, 1 H), 7.28 (dd, J = 6.88, 5.12 Hz, 1 H), 3.99 (s, 2 H), 3.71-3.80 (m, 2 H), 2.73 (quin, J = 6.88 Hz, 1 H), 2.62-2.68 (m, 2 H), 2.35-2.46 (m, 4 H), 2.24-2.30 (m, 2 H), 1.09 (d, J = 6.88 Hz, 6 H). | Racemic |
| 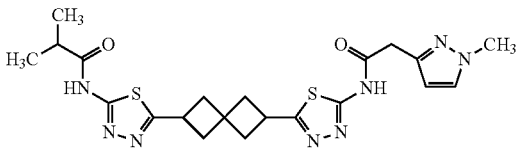 [SMILES: CC(C)C(=O)Nc1nnc(C2CC3(CC(c4nnc(NC(=O)Cc5ccn(C)n5)s4)C3)C2)s1]<br>(Scheme B)<br>2-methyl-N-{5-[6-(5-{[(1-methyl-1H-pyrazol-3-yl)acetyl]amino}-1,3,4-thiadiazol-2-yl)spiro[3.3]hept-2-yl]-1,3,4-thiadiazol-2-yl}propanamide | 136 487.1 | (600 MHz, DMSO-d₆) δ ppm 7.57 (s, 1 H), 6.14 (d, J = 1.90 Hz, 1 H), 3.71-3.80 (m, 7 H), 2.74 (dt, J = 13.61, 6.80 Hz, 1 H), 2.63-2.68 (m, 2 H), 2.36-2.47 (m, 4 H), 2.25-2.31 (m, 2 H), 1.10 (d, J = 6.88 Hz, 6 H). | Racemic |

*Compounds are single enantiomers, however, absolute stereochemistry is unknown. (stereochemistry is depicted based on the biological activity of a compound of known absolute stereochemistry).
**Compounds are racemates containing two cis enantiomers.

TABLE 2

| Example No. (Scheme) Structure and Compound Name | Observed MW | LCMS Rt (min) | Method |
|---|---|---|---|
| 137** (Scheme C) 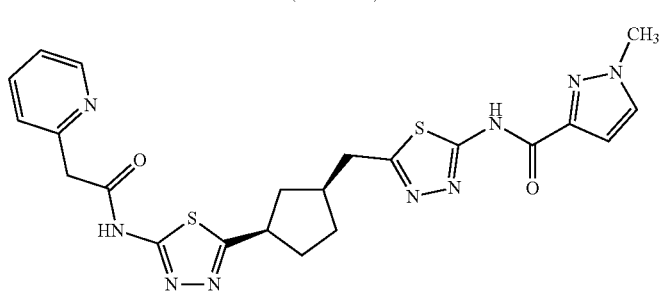 (rac)-1-methyl-N-(5-{[(cis)-3-{5-[(pyridin-2-ylacetyl)amino]-1,3,4-thiadiazol-2-yl}cyclopentyl]methyl}-1,3,4-thiadiazol-2-yl)-1H-pyrazole-3-carboxamide | 510.0 | 2.435 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive. |
| 138*** (Scheme B) 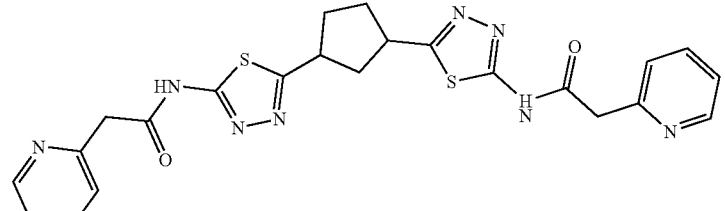 N,N'-[cyclopentane-1,3-diyldi-1,3,4-thiadiazole-5,2-diyl]bis[2-(pyridin-2-yl)acetamide] | 507 | 1.733 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive. |
| 139*** (Scheme B) 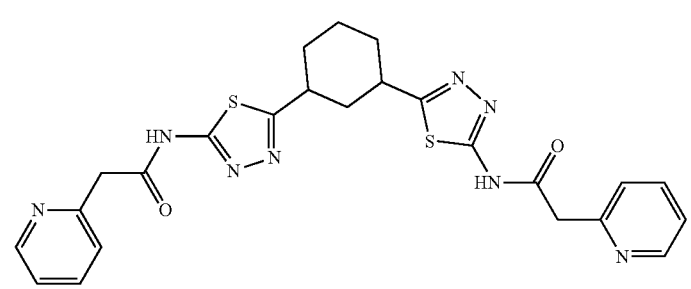 [SMILES: O=C(Cc1ccccn1)Nc1nnc(C2CCCC(c3nnc(NC(=O)Cc4ccccn4)s3)C2)s1] N,N'-[cyclohexane-1,3-diyldi-1,3,4-thiadiazole-5,2-diyl]bis[2-(pyridin-2-yl)acetamide] | 521 | 1.695 | Xbridge C18 2.1 × 50 mm (5 μm). 40° C. Mobile phase A: Water (w. 0.05% NH4OH). B: MeCN (w. 0.1875% TFA). Initial 5% B over 0.5 mins to 100% B after 3.4 mins. Flow rate 0.8 mL/min. API-ES positive. |

TABLE 2-continued

| Example No. (Scheme) Structure and Compound Name | Observed MW | LCMS Rt (min) | Method |
|---|---|---|---|
| 140*** (Scheme B) 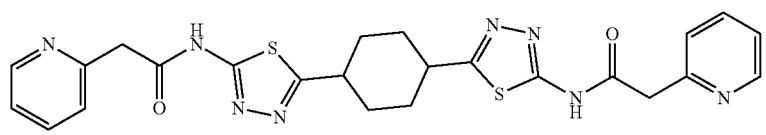 [SMILES: O=C(Cc1ccccn1)Nc1nnc(C2CCC(c3nnc(NC(=O)Cc4ccccn4)s3)CC2)s1] N,N'-(cyclohexane-1,4-diyldi-1,3,4-thiadiazole-5,2-diyl)bis[2-(pyridin-2-yl)acetamide] | 521 | 1.695 | Xbridge C18 2.1 × 50 mm (5 μm). 40° C. Mobile phase A: Water (w. 0.05% NH$_4$OH). B: MeCN (w. 0.1875% TFA). Initial 5% B over 0.5 mins to 100% B after 3.4 mins. Flow rate 0.8 mL/min. API-ES positive. |
| 141*** (Scheme B) 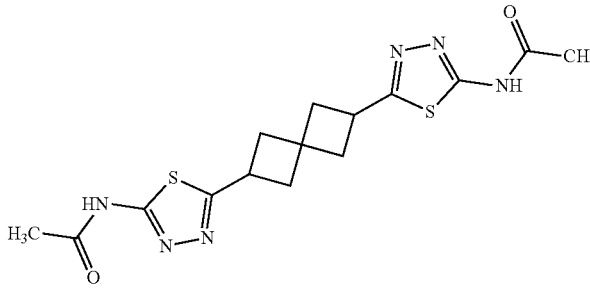 [SMILES: CC(=O)Nc1nnc(C2CC3(C2)CC(c2nnc(NC(C)=O)s2)C3)s1] N,N'-(spiro[3.3]heptane-2,6-diyldi-1,3,4-thiadiazole-5,2-diyl)diacetamide | 379 | 1.744 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive. |
| 142** (Scheme C) 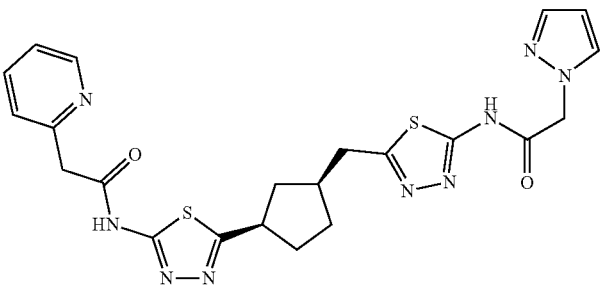 [SMILES: O=C(Cn1cccn1)Nc1nnc(C[C@H]2CC[C@@H](c3nnc(NC(=O)Cc4ccccn4)s3)C2)s1] (rac)-2-(1H-pyrazol-1-yl)-N-(5-{[(cis)-3-{5-[(pyridin-2-ylacetyl)amino]-1,3,4-thiadiazol-2-yl}cyclopentyl]methyl}-1,3,4-thiadiazol-2-yl)acetamide | 510 | 2.370 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive. |

TABLE 2-continued

| Example No. (Scheme) Structure and Compound Name | Observed MW | LCMS Rt (min) | Method |
|---|---|---|---|
| 143** (Scheme C) 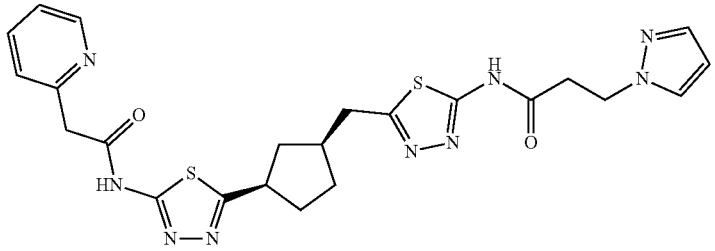 [SMILES: O=C(CCn1cccn1)Nc1nnc(C[C@H]2CC[C@@H](c3nnc(NC(=O)Cc4ccccn4)s3)C2)s1] (rac)-3-(1H-pyrazol-1-yl)-N-(5-{[(cis)-3-{5-[(pyridin-2-ylacetyl)amino]-1,3,4-thiadiazol-2-yl}cyclopentyl]methyl}-1,3,4-thiadiazol-2-yl)propanamide | 524 | 2.414 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive. |
| 144** (Scheme C) 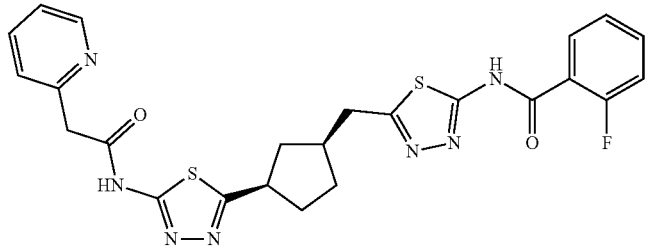 [SMILES: O=C(Cc1ccccn1)Nc1nnc([C@@H]2CC[C@H](Cc3nnc(NC(=O)c4ccccc4F)s3)C2)s1] (rac)-2-fluoro-N-(5-{[(cis)-3-{5-[(pyridin-2-ylacetyl)amino]-1,3,4-thiadiazol-2-yl}cyclopentyl]methyl}-1,3,4-thiadiazol-2-yl)benzamide | 524 | 2.648 | Xbridge C18 2.1 × 50 mm (5 μm). 40° C. Mobile phase A: Water (w 0.375% TFA). B: MeCN (w 0.1875% TFA). 1 to 5% B over 0.6 mins to 100% B after 4 mins. Flow rate 0.8 mL/min. API-ES positive. |
| 145** (Scheme C) 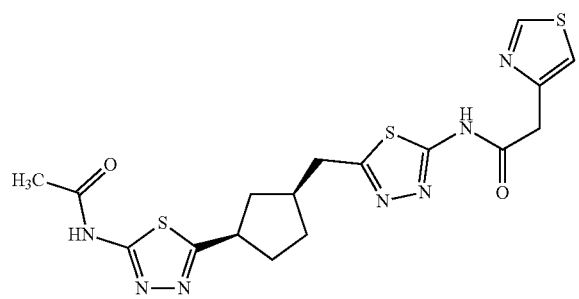 [SMILES: CC(=O)Nc1nnc([C@@H]2CC[C@H](Cc3nnc(NC(=O)Cc4cscn4)s3)C2)s1] (rac)-N-[5-({(cis)-3-[5-(acetylamino)-1,3,4-thiadiazol-2-yl]cyclopentyl}methyl)-1,3,4-thiadiazol-2-yl]-2-(1,3-thiazol-4-yl)acetamide | 450 | 2.514 | Xbridge C18 2.1 × 50 mm (5 μm). 40° C. Mobile phase A: Water (w 0.375% TFA). B: MeCN (w 0.1875% TFA). 1 to 5% B over 0.6 mins to 100% B after 4 mins. Flow rate 0.8 mL/min. API-ES positive. |

TABLE 2-continued

| Example No. (Scheme) Structure and Compound Name | Observed MW | LCMS Rt (min) | Method |
|---|---|---|---|
| 146** (Scheme C) 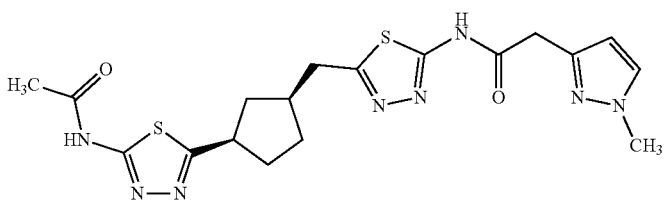 [SMILES: CC(=O)Nc1nnc([C@@H]2CC[C@H](Cc3nnc(NC(=O)Cc4ccn(C)n4)s3)C2)s1] (rac)-N-[5-({(cis)-3-[5-(acetylamino)-1,3,4-thiadiazol-2-yl] cyclopentyl}methyl)-1,3,4-thiadiazol-2-yl]-2-(1-methyl-1H-pyrazol-3-yl)acetamide | 447 | 2.049 | Xbridge C18 2.1 × 50 mm (5 μm). 40° C. Mobile phase A: Water (w. 0.05% NH4OH). B: MeCN (w. 0.1875% TFA). Initial 5% B over 0.5 mins to 100% B after 3.4 mins. Flow rate 0.8 mL/min. API-ES positive. |
| 147** (Scheme C) 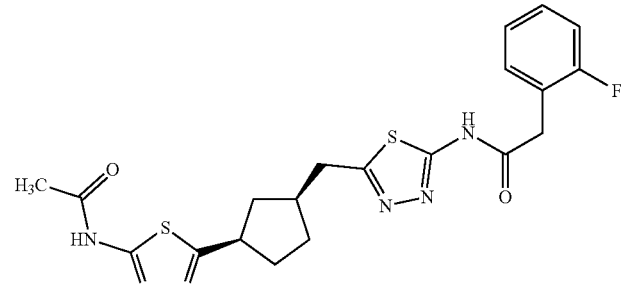 (rac)-N-[5-({(cis)-3-[5-(acetylamino)-1,3,4-thiadiazol-2-yl] cyclopentyl}methyl)-1,3,4-thiadiazol-2-yl]-2-(1-methyl-1H-pyrazol-3-yl)acetamide | 461 | 2.851 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive. |
| 148** (Scheme C) 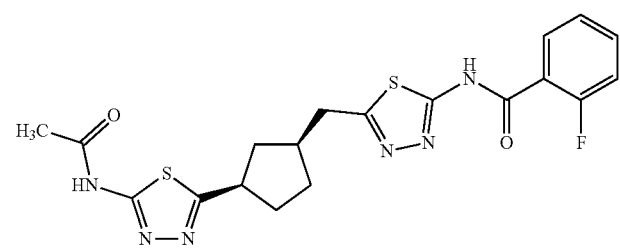 [SMILES: CC(=O)Nc1nnc([C@@H]2CC[C@H](Cc3nnc(NC(=O)c4ccccc4F)s3)C2)s1] (rac)-N-[5-({(cis)-3-[5-(acetylamino)-1,3,4-thiadiazol-2-yl] cyclopentyl}methyl)-1,3,4-thiadiazol-2-yl]-2-fluorobenzamide | 447 | 2.090 | Xbridge C18 2.1 × 50 mm (5 μm). 40° C. Mobile phase A: Water (w. 0.05% NH4OH). B: MeCN. 5% B for 0.5 mins to 100% B after 3.4 mins holding at 100% until 4.2 mins. Flow rate 0.8 mL/min. API-ES positive. |

TABLE 2-continued

| Example No. (Scheme) Structure and Compound Name | Observed MW | LCMS Rt (min) | Method |
|---|---|---|---|
| 149** (Scheme C) 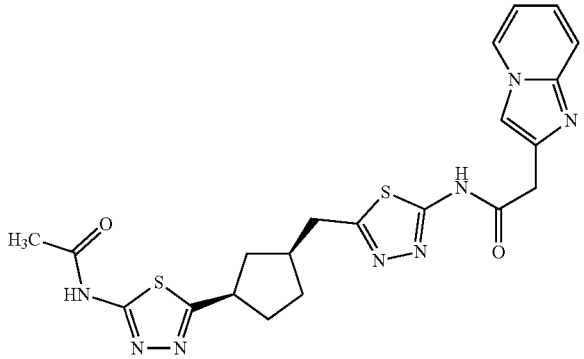 [SMILES: CC(=O)Nc1nnc([C@@H]2CC[C@H](Cc3nnc(NC(=O)Cc4cn5ccccc5n4)s3)C2)s1] (rac)-N-[5-({(cis)-3-[5-(acetylamino)-1,3,4-thiadiazol-2-yl]cyclopentyl}methyl)-1,3,4-thiadiazol-2-yl]-2-(imidazo[1,2-a]pyridin-2-yl)acetamide | 469 | 2.277 | Xbridge C18 2.1 × 50 mm (5 µm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive. |
| 150** (Scheme C) 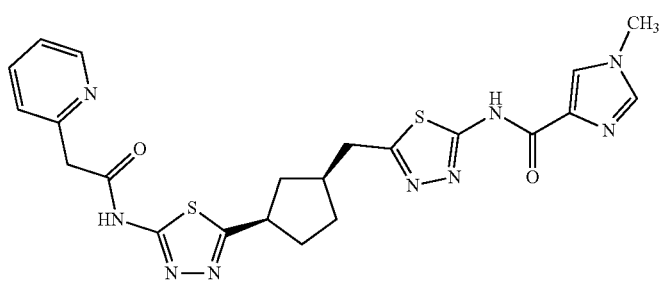 [SMILES: Cn1cnc(C(=O)Nc2nnc(C[C@H]3CC[C@@H](c4nnc(NC(=O)Cc5ccccn5)s4)C3)s2)c1] (rac)-1-methyl-N-(5-{[(cis)-3-{5-[(pyridin-2-ylacetyl)amino]-1,3,4-thiadiazol-2-yl}cyclopentyl]methyl}-1,3,4-thiadiazol-2-yl)-1H-imidazole-4-carboxamide | 510 | 2.272 | Xbridge C18 2.1 × 50 mm (5 µm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive. |
| 151** (Scheme C) 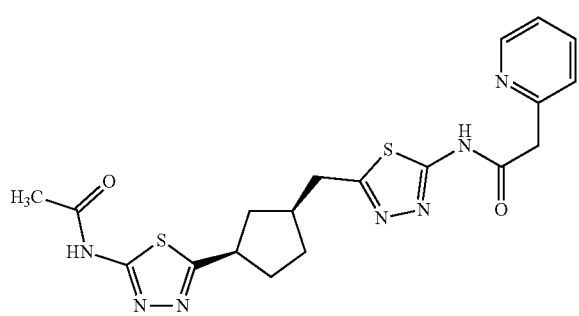 [SMILES: CC(=O)Nc1nnc([C@@H]2CC[C@H](Cc3nnc(NC(=O)Cc4ccccn4)s3)C2)s1] (rac)-N-[5-({(cis)-3-[5-(acetylamino)-1,3,4-thiadiazol-2-yl]cyclopentyl}methyl)-1,3,4-thiadiazol-2-yl]-2-(pyridin-2-yl)acetamide | 444 | 2.071 | Xbridge C18 2.1 × 50 mm (5 µm). 40° C. Mobile phase A: Water (w 0.05% NH₄OH). B: MeCN. 5% B for 0.5 mins to 100% B after 3.4 mins. Flow rate 0.8 mL/min. API-ES positive. |

TABLE 2-continued

| Example No. (Scheme) Structure and Compound Name | Observed MW | LCMS Rt (min) | Method |
|---|---|---|---|
| 152** (Scheme B) 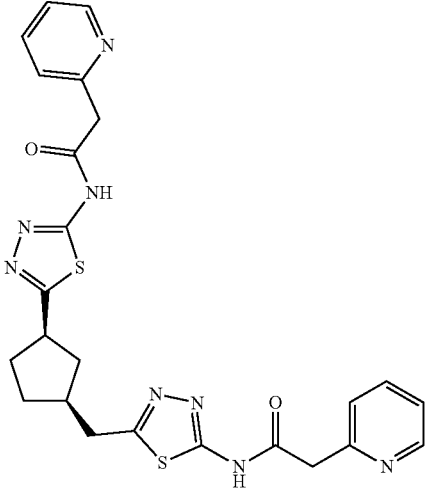 [SMILES: O=C(Cc1ccccn1)Nc1nnc(C[C@H]2CC[C@@H](c3nnc(NC(=O)Cc4ccccn4)s3)C2)s1] 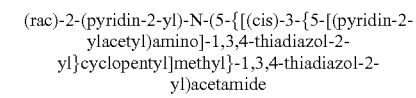 (rac)-2-(pyridin-2-yl)-N-(5-{[(cis)-3-{5-[(pyridin-2-ylacetyl)amino]-1,3,4-thiadiazol-2-yl}cyclopentyl]methyl}-1,3,4-thiadiazol-2-yl)acetamide | 521 | 2.193 | Xbridge C18 2.1 × 50 mm (5 μm). 40° C. Mobile phase A: Water (w. 0.375% TFA). B: MeCN (w. 0.1875% TFA). 1 to 5% B over 0.6 mins to 100% B after 4 mins. Flow rate 0.8 mL/min. API-ES positive. |

**Compounds are racemates containing two cis enantiomers.
***Compounds are racemic, or mixtures of diastereomers obtained from commercial diacids.

Cancer Cell Lysate Total L-Glutamate Assay

Cancer cell lines (BT20, HCT116, SKOV3, HCC70, SUM149, MDA-MB-231, etc.) were plated in 96 well plates and were used for the total L-glutamate assay when the monolayer was ca. 80% confluent. The media was changed and fresh media containing L-glutamine was added to the 96 well plates, just before incubation of the cells with test compound. The test compound was diluted in 100% DMSO using a two-fold or three-fold serial dilution. Small volumes of the dilutions of test compound were added to the 96 well plates so the final DMSO concentration was 0.5% v/v in the cell culture medium. The cells were incubated at 37° C., 5% $CO_2$, and 95% air for 2 hours. Following the 2 hour incubation, the cells were washed with water 2 times. After the last water wash, 100 μL of 50 mM Tris-HCl pH 7.4 and 0.01% Tween-20 was added to each well and the plate was frozen at −80° C. The 96 well plate was frozen and thawed a total of 3 times and then sonicated for 5 min at 4° C. in a bath sonicator. Following sonication, the 96 well plate was centrifuged for 5 min at 1000 rpm and 10 μL of the supernatant was transferred to a 384 well assay plate.

Total L-glutamate (L-glutamic acid) in the cell lysis supernatant was detected using glutamate oxidase, horseradish peroxidase and Amplex Red reagent (10-acetyl-3,7-dihydroxy phenoxazine, Invitrogen # A22177). In this assay, L-glutamate was oxidized by glutamate oxidase to produce alpha-ketoglutarate (2-oxopentane dioic acid), $NH_3$ and $H_2O2$. The $H_2O_2$ (hydrogen peroxide) was used by horseradish peroxidase (HRP) to oxidize the Amplex Red Reagent to resorufin which is a fluorescent molecule. When resorufin is excited with light with a wavelength 530-560 nm, it emits light at approximately 585 nm. For detection of total L-glutamate in 10 μL of lysate, 15 μL of an enzyme mixture was added to each well of the 384 well assay plate. The enzyme mixture consisted of 50 mM Tris-HCl pH 7.4, 0.01% Tween-20, 50 μM Amplex Red reagent (final concentration), 0.04 U/mL L-glutamate oxidase (final concentration), and 0.125 U/mL HRP (final concentration). The 384 well assay plate was incubated at room temperature for 5 min and then the fluorescence intensity of each well was measured at 585 nm using a 530-560 nm excitation wavelength in a plate based fluorimeter such as an LJL Analyst or a Tecan Infinite plate reader. Standard curves were constructed for this assay using dilutions of a L-glutamate standard. $IC_{50}$ were calculated by plotting the relative fluorescent units vs log of the inhibitor concentration and fitting the data to the four parameter logistic equation.

Reference: Chapman J. and Zhou M. (1999) Microplate-based fluorometric methods for the enzymatic determination of l-glutamate: application in measuring l-glutamate in food samples. *Analytica Chim Acta* 402:47-52.

The assay results for the compounds tested are listed in Table 3.

TABLE 3

| Example No. | BT20 Cell IC50 (nM) |
|---|---|
| 1 | 0.7 |
| 2 | 1.0 |
| 3 | 6.4 |
| 4 | 21.6 |
| 5 | 104.4 |
| 6 | N/D |
| 7 | 3359.7 |
| 8 | 1.4 |

TABLE 3-continued

| Example No. | BT20 Cell IC50 (nM) |
|---|---|
| 9 | 17.0 |
| 10 | 33.3 |
| 11 | 47.9 |
| 12 | >50000.0 |
| 13 | 23.8 |
| 14 | 3.1 |
| 15 | 10.6 |
| 16 | 398.7 |
| 17 | 12.2 |
| 18 | 79.7 |
| 19 | 1467.4 |
| 20 | 136.7 |
| 21 | >6650.5 |
| 22 | 1.4 |
| 23 | 9.9 |
| 24 | 78.9 |
| 25 | 1.0 |
| 26 | 1.3 |
| 27 | 241.9 |
| 28 | 3017.2 |
| 29 | 166.6 |
| 30 | 1.9 |
| 31 | 638.9 |
| 32 | 200.9 |
| 33 | 7.0 |
| 34 | 941.5 |
| 35 | 50.7 |
| 36 | 284.0 |
| 37 | 19.4 |
| 38 | 136.0 |
| 39 | N/D |
| 40 | 4576.2 |
| 41 | >40442.6 |
| 42 | 2373.8 |
| 43 | 94.4 |
| 44 | 5.5 |
| 45 | 294.7 |
| 46 | 349.0 |
| 47 | 511.5 |
| 48 | 989.3 |
| 49 | 788.8 |
| 50 | 8749.3 |
| 51 | 64.5 |
| 52 | 29.8 |
| 53 | 6.8 |
| 54 | 1276.4 |
| 55 | 391.1 |
| 56 | 2701.6 |
| 57 | 21.4 |
| 58 | 276.1 |
| 59 | 7758.6 |
| 60 | 274.3 |
| 61 | 1.6 |
| 62 | 38.5 |
| 63 | 109.8 |
| 64 | 71.2 |
| 65 | 1821.0 |
| 66 | 1287.9 |
| 67 | N/D |
| 68 | 7.1 |
| 69 | 2.5 |
| 70 | 0.2 |
| 71 | 2.7 |
| 72 | 0.9 |
| 73 | 0.7 |
| 74 | 3.4 |
| 75 | 1.1 |
| 76 | 3.0 |
| 77 | 0.4 |
| 78 | 3.0 |
| 79 | 1.1 |
| 80 | 0.1 |
| 81 | 4.5 |
| 82 | 0.1 |
| 83 | 2.4 |
| 84 | 0.5 |
| 85 | 8.2 |
| 86 | 4.8 |
| 87 | 7.5 |
| 88 | 13.0 |
| 89 | 3.9 |
| 90 | 1.3 |
| 91 | 1.5 |
| 92 | 0.2 |
| 93 | 10.4 |
| 94 | 8.5 |
| 95 | 1.4 |
| 96 | 0.3 |
| 97 | 2.7 |
| 98 | 0.5 |
| 99 | 0.3 |
| 100 | 2.4 |
| 101 | 338.7 |
| 102 | 2.0 |
| 103 | 0.8 |
| 104 | 8.6 |
| 105 | 9.5 |
| 106 | 13.7 |
| 107 | 10.1 |
| 108 | 0.3 |
| 109 | 1.3 |
| 110 | 2.3 |
| 111 | 1.2 |
| 112 | 0.2 |
| 113 | 5.6 |
| 114 | 6.5 |
| 115 | 2.0 |
| 116 | 5.9 |
| 117 | 1.4 |
| 118 | 0.2 |
| 119 | 0.2 |
| 120 | 0.4 |
| 121 | 4.0 |
| 122 | 0.4 |
| 123 | 1.8 |
| 124 | 4.7 |
| 125 | 3.1 |
| 126 | 0.5 |
| 127 | 0.7 |
| 128 | 2.0 |
| 129 | 2.2 |
| 130 | 1.8 |
| 131 | 3.1 |
| 132 | 1.7 |
| 133 | 1.7 |
| 134 | 1.3 |
| 135 | 2.1 |
| 136 | 1.9 |
| 137 | 4.4 |
| 138 | 120.3 |
| 139 | 195.5 |
| 140 | 380.3 |
| 141 | 297.6 |
| 142 | 13.2 |
| 143 | 4.2 |
| 144 | 0.7 |
| 145 | 7.1 |
| 146 | 6.9 |
| 147 | 0.5 |
| 148 | 12.6 |
| 149 | 6.9 |
| 150 | 1.5 |
| 151 | 4.6 |
| 152 | 2.8 |

We claim:
1. A compound selected from the group consisting of
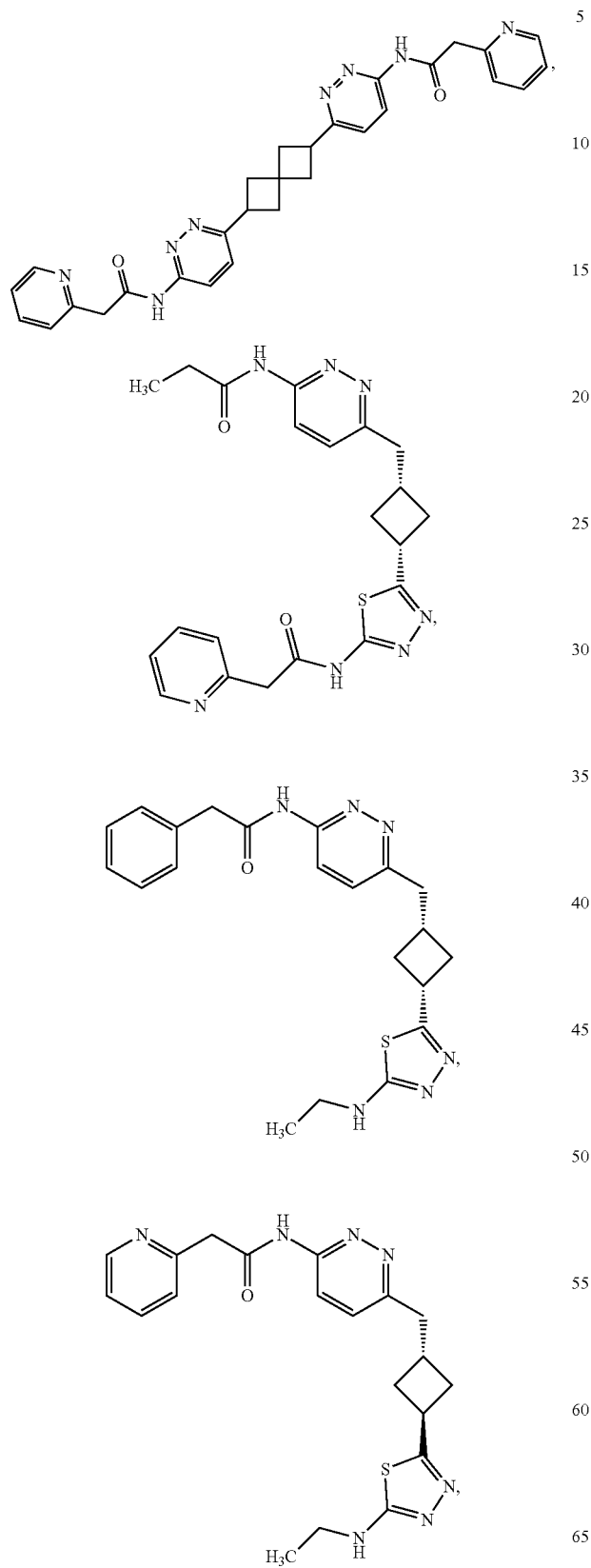
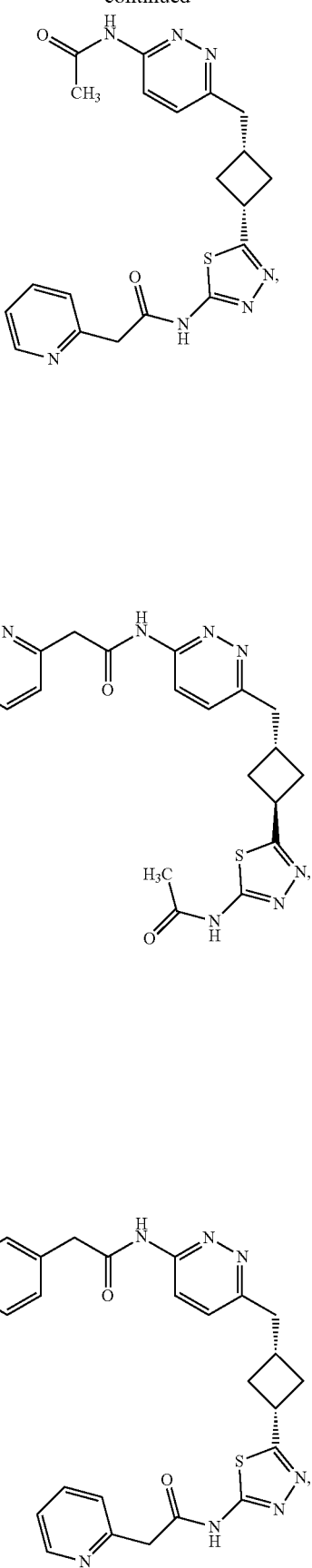

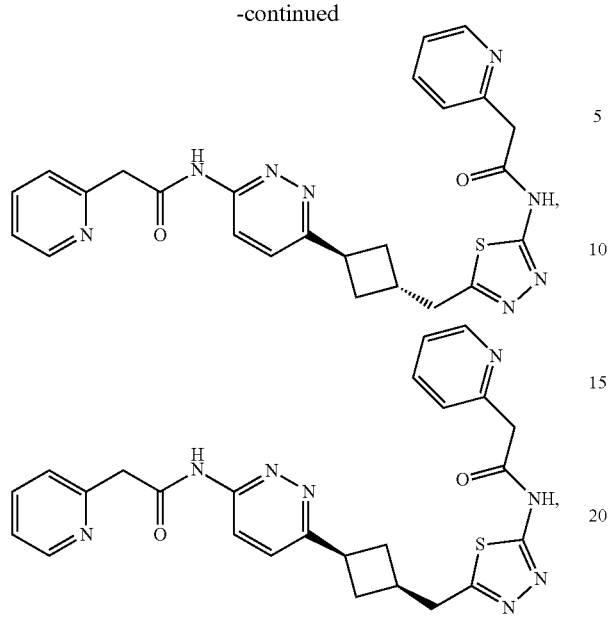
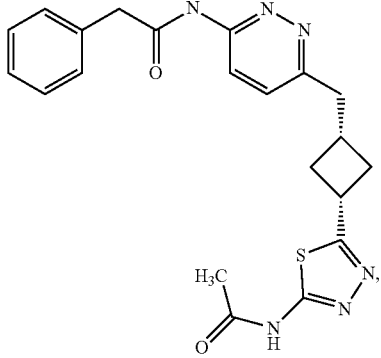
or a pharmaceutically acceptable salt thereof.
2. A pharmaceutical formulation comprising at least one compound of claim 1, or a pharmaceutically acceptable salt thereof, and at least one pharmaceutically acceptable carrier, diluent, or excipient.
* * * * *